(12) United States Patent
Fensholdt et al.

(10) Patent No.: US 9,487,494 B2
(45) Date of Patent: Nov. 8, 2016

(54) CYCLIC HYDROCARBON COMPOUNDS FOR THE TREATMENT OF DISEASES

(75) Inventors: Jef Fensholdt, Stenløse (DK); Sophie Elisabeth Havez, Valby (DK); Bjarne Nørremark, Stenløse (DK)

(73) Assignee: LEO PHARMA A/S, Ballerup (DK)

( * ) Notice: Subject to any disclaimer, the term of this patent is extended or adjusted under 35 U.S.C. 154(b) by 495 days.

(21) Appl. No.: 12/744,137

(22) PCT Filed: Nov. 20, 2008

(86) PCT No.: PCT/DK2008/000410
§ 371 (c)(1),
(2), (4) Date: Jul. 9, 2010

(87) PCT Pub. No.: WO2009/065406
PCT Pub. Date: May 28, 2009

(65) Prior Publication Data
US 2010/0317582 A1 Dec. 16, 2010

Related U.S. Application Data

(60) Provisional application No. 60/989,856, filed on Nov. 23, 2007, provisional application No. 60/092,553, filed on Aug. 28, 2008.

(51) Int. Cl.
| | | |
|---|---|---|
| *C07D 295/182* | (2006.01) | |
| *C07C 211/35* | (2006.01) | |
| *C07C 211/36* | (2006.01) | |
| *C07C 211/48* | (2006.01) | |
| *C07C 215/28* | (2006.01) | |
| *C07C 217/52* | (2006.01) | |

(Continued)

(52) U.S. Cl.
CPC ......... *C07D 295/182* (2013.01); *C07C 211/35* (2013.01); *C07C 211/36* (2013.01); *C07C 211/48* (2013.01); *C07C 215/28* (2013.01); *C07C 217/52* (2013.01); *C07C 217/74* (2013.01); *C07C 233/05* (2013.01); *C07C 233/41* (2013.01); *C07C 237/24* (2013.01); *C07C 237/30* (2013.01); *C07C 237/32* (2013.01); *C07C 237/34* (2013.01); *C07C 237/36* (2013.01); *C07C 237/40* (2013.01); *C07C 239/14* (2013.01); *C07C 255/03* (2013.01); *C07C 255/32* (2013.01); *C07C 255/50* (2013.01); *C07C 257/18* (2013.01); *C07C 259/10* (2013.01); *C07C 259/18* (2013.01); *C07C 271/44* (2013.01); *C07C 309/15* (2013.01); *C07C 311/05* (2013.01); *C07C 311/08* (2013.01); *C07C 311/37* (2013.01); *C07C 311/51* (2013.01); *C07C 317/32* (2013.01); *C07D 205/04* (2013.01); *C07D 207/08* (2013.01); *C07D 207/12* (2013.01); *C07D 207/16* (2013.01); *C07D 207/27* (2013.01); *C07D 209/08* (2013.01); *C07D 209/12* (2013.01); *C07D 209/20* (2013.01); *C07D 211/46* (2013.01); *C07D 211/60* (2013.01); *C07D 211/62* (2013.01); *C07D 213/30* (2013.01); *C07D 213/38* (2013.01); *C07D 213/40* (2013.01); *C07D 213/80* (2013.01); *C07D 231/12* (2013.01); *C07D 231/40* (2013.01); *C07D 233/61* (2013.01); *C07D 233/90* (2013.01); *C07D 263/22* (2013.01); *C07D 271/06* (2013.01); *C07D 295/088* (2013.01); *C07D 295/13* (2013.01); *C07D 295/135* (2013.01); *C07D 295/192* (2013.01); *C07D 295/195* (2013.01); *C07D 295/26* (2013.01); *C07D 305/08* (2013.01); *C07D 307/12* (2013.01); *C07D 307/52* (2013.01); *C07D 307/68* (2013.01); *C07D 307/79* (2013.01); *C07D 309/10* (2013.01); *C07D 319/18* (2013.01); *C07D 333/38* (2013.01); *C07D 333/40* (2013.01); *C07D 333/58* (2013.01); *C07D 413/04* (2013.01); *C07D 413/06* (2013.01); *C07D 417/06* (2013.01); *C07C 2101/08* (2013.01); *C07C 2101/14* (2013.01); *C07C 2101/18* (2013.01)

(58) Field of Classification Search
CPC .................................................. C07C 2102/00
See application file for complete search history.

(56) References Cited

U.S. PATENT DOCUMENTS 6,069,176 A 5/2000 Tsuchiya et al.
6,143,749 A * 11/2000 Bhagwat et al. .......... 514/262.1
(Continued)

FOREIGN PATENT DOCUMENTS

DE 4438055 * 5/1996 ........... C07C 233/23
EP 0 940 387 A1 9/1999
(Continued)

OTHER PUBLICATIONS

Sharan. Indian Journal of Medicine Research, 2008, 127, 274-286.*
(Continued)

*Primary Examiner* — Andrew D Kosar
*Assistant Examiner* — John S Kenyon
(74) *Attorney, Agent, or Firm* — Birch, Stewart, Kolasch & Birch, LLP

(57) ABSTRACT

The invention relates to novel cyclic hydrocarbon compounds and derivatives thereof, processes for the preparation thereof, to said compounds for use as a medicament, to said compounds for use in therapy, to pharmaceutical compositions comprising said compounds, to methods of treating diseases with said compounds, and to the use of said compounds in the manufacture of medicaments.

22 Claims, 4 Drawing Sheets

(51) Int. Cl.

| | | |
|---|---|---|
| C07C 217/74 | (2006.01) | |
| C07C 233/05 | (2006.01) | |
| C07C 233/41 | (2006.01) | |
| C07C 237/24 | (2006.01) | |
| C07C 237/30 | (2006.01) | |
| C07C 237/32 | (2006.01) | |
| C07C 237/34 | (2006.01) | |
| C07C 237/36 | (2006.01) | |
| C07C 237/40 | (2006.01) | |
| C07C 239/14 | (2006.01) | |
| C07C 255/03 | (2006.01) | |
| C07C 255/32 | (2006.01) | |
| C07C 255/50 | (2006.01) | |
| C07C 257/18 | (2006.01) | |
| C07C 259/10 | (2006.01) | |
| C07C 259/18 | (2006.01) | |
| C07C 271/44 | (2006.01) | |
| C07C 309/15 | (2006.01) | |
| C07C 311/05 | (2006.01) | |
| C07C 311/08 | (2006.01) | |
| C07C 311/37 | (2006.01) | |
| C07C 311/51 | (2006.01) | |
| C07C 317/32 | (2006.01) | |
| C07D 205/04 | (2006.01) | |
| C07D 207/08 | (2006.01) | |
| C07D 207/12 | (2006.01) | |
| C07D 207/16 | (2006.01) | |
| C07D 207/27 | (2006.01) | |
| C07D 209/08 | (2006.01) | |
| C07D 209/12 | (2006.01) | |
| C07D 209/20 | (2006.01) | |
| C07D 211/46 | (2006.01) | |
| C07D 211/60 | (2006.01) | |
| C07D 211/62 | (2006.01) | |
| C07D 213/30 | (2006.01) | |
| C07D 213/38 | (2006.01) | |
| C07D 213/40 | (2006.01) | |
| C07D 213/80 | (2006.01) | |
| C07D 231/12 | (2006.01) | |
| C07D 231/40 | (2006.01) | |
| C07D 233/61 | (2006.01) | |
| C07D 233/90 | (2006.01) | |
| C07D 263/22 | (2006.01) | |
| C07D 271/06 | (2006.01) | |
| C07D 295/088 | (2006.01) | |
| C07D 295/13 | (2006.01) | |
| C07D 295/135 | (2006.01) | |
| C07D 295/192 | (2006.01) | |
| C07D 295/195 | (2006.01) | |
| C07D 295/26 | (2006.01) | |
| C07D 305/08 | (2006.01) | |
| C07D 307/12 | (2006.01) | |
| C07D 307/52 | (2006.01) | |
| C07D 307/68 | (2006.01) | |
| C07D 307/79 | (2006.01) | |
| C07D 309/10 | (2006.01) | |
| C07D 319/18 | (2006.01) | |
| C07D 333/38 | (2006.01) | |
| C07D 333/40 | (2006.01) | |
| C07D 333/58 | (2006.01) | |
| C07D 413/04 | (2006.01) | |
| C07D 413/06 | (2006.01) | |
| C07D 417/06 | (2006.01) | |

(56) References Cited

U.S. PATENT DOCUMENTS

| | | | |
|---|---|---|---|
| 6,211,244 B1 | 4/2001 | Van Wagenen et al. | |
| 2005/0209297 A1* | 9/2005 | Sanner et al. | 514/406 |
| 2012/0122941 A1* | 5/2012 | Marumoto et al. | 514/381 |

FOREIGN PATENT DOCUMENTS

| | | | | |
|---|---|---|---|---|
| GB | 1242109 | * | 8/1971 | ............. C07C 87/28 |
| WO | 9824754 | * | 6/1998 | ........... C07D 211/35 |
| WO | WO 00/76972 A1 | | 12/2000 | |
| WO | WO 00/76973 A1 | | 12/2000 | |
| WO | WO 01/46199 A1 | | 6/2001 | |
| WO | WO 2005/067502 A2 | | 7/2005 | |
| WO | WO 2010/021351 | | 2/2010 | |

OTHER PUBLICATIONS

Hutton. Journal of the Chemical Society [Section] A: Inorganic, Physical, Theoretical, 1966, (11), 1573-9.*
"Treatment", http://medical-dictionary.thefreedictionary.com/treatment, accessed Aug. 28, 2013.*
Paul E. Fink et al., "Preparation of Amino Acid N-cyclopentyl Modulators of Chemokine Receptor Activity" XP002537431.
Paul E. Fink et al., "Preparation of Amino Acid N-cyclopentyl Modulators of Chemokine Receptor Activity" XP002537220.
Sun-Young Sung et al., "Asymmetric Synthesis and Structure-Activity Relationship of the Four Stereoisomers of the Antibiotic Amidinomycin. Part 1. The Synthesis" Archiv Der Pharmazie 1996, pp. 291-300, XP-002537265.
Timothy J. Peelen et al., "Synthesis of 4,4-Disubstituted 2-Aminocyclopentanecarboxylic Acid Derivatives and Their Incorporation into 12-Helical .beta.-Peptides" Organic Letters 2004 pp. 4411-4414, XP-002537266.
Costero et al., "Chiral cyclohexane based fluorescent chemosensors for enantiomeric discrimination of aspartate" Tetrahedron, Elsevier Science Publishers, Amsterdam, vol. 64 No. 14, Jan. 30, 2008 pp. 3217-3224.
Magdaline Koutsaplis et al., "A new diastereoselective aza-allyl conjugate addition—Michael addition—ring closure reaction sequence and its application in the construction of six contiguous stereogenic centers" Chemical Communications 2007, (34), pp. 3580-3582.
Kim et al., "New Insight into Modeling Non-Covalently Imprinted Polymers," J. Am. Chem. Soc., vol. 125, No. 37, 2003, pp. 11269-11275.

* cited by examiner

CYCLIC HYDROCARBON COMPOUNDS FOR THE TREATMENT OF DISEASES

This application is a National Phase of PCT/DK2008/000410 filed on Nov. 20, 2008, which claims priority under 35 U.S.C. 119(e) to U.S. Provisional Application No. 60/989,856 filed on Nov. 23, 2007 and 61/092,553 filed on Aug. 28, 2008, both of which are hereby incorporated by reference into the present application.

FIELD OF THE INVENTION

This invention relates to novel cyclic hydrocarbon compounds and derivatives thereof, processes for the preparation thereof, to said compounds for use as a medicament, to said compounds for use in therapy, to pharmaceutical compositions comprising said compounds, to methods of treating diseases with said compounds, and to the use of said compounds in the manufacture of medicaments.

BACKGROUND OF THE INVENTION

The calcium-sensing receptor (CaSR) is a G-protein-coupled receptor (GPCR) that signals through the activation of phospholipase C, increasing levels of inositol 1,4,5-triphosphate and cytosolic calcium. The CaSR belongs to the subfamily C of the GPCR superfamily, which also includes receptors for glutamate, gamma aminobutyric acid (GABA), pheromones and odorants that all possess a very large extracellular domain. This domain is highly negatively charged and is involved in binding of calcium and other positively charged molecules. The CaSR is found in the parathyroid glands but has also been identified in the brain, intestine, pituitary, thyroid glands, bone tissue and kidneys. In the parathyroid glands, the CaSR is activated by small increases in extracellular ionized calcium, which inhibits parathyroid hormone (PTH) release from within the stored intracellular granules [Brown, E. M. Calcium-Sensing Receptor. *Primer of the Metabolic Bone Diseases and Disorders of Mineral Metabolism Fifth Edition*, 2003 by American Society for Bone and Mineral Research, Chapter 17, p. 111.; Drueke, T. E. *Nephrol Dial Transplant* (2004) 19, v20-v26].

In addition to endogenous ligands, small molecule allosteric activators of the CaSR ("calcimimetics") have been developed [Urena, P.; Frazao, J. M. Calcimimetic agents: Review and perspectives. *Kidney International* (2003), 63, pp. s91-s96; Soudijn, W. et al. Allosteric modulation of G protein-coupled receptors: perspectives and recent developments. *DDT* (2004), 9, 752-758].

The binding site of known calcimimetics is believed to be located in the seven-transmembrane domain of the receptor [Petrel, C. et al. *Journal of Biological Chemistry* (2004), 279, 18990-18997].

Calcimimetics have already been shown to be commercially useful for the treatment of hyperparathyroidism (HPT): The calcimimetic compound Cinacalcet® [Balfour, J. A. B. et al. *Drugs* (2005) 65(2), 271-281; Linberg et. al. *J. Am. Soc. Nephrol* (2005), 16, 800-807, Clinical Therapeutics (2005), 27(11), 1725-1751] has recently been launched for the treatment of secondary HPT in chronic kidney disease patients on dialysis and for the treatment of primary HPT in patients with parathyroid carcinoma.

Thus, proof of concept for activators of calcium sensing receptor (CaSR) in humans has been achieved and the clinical relevance is already well established.

In chronic kidney disease hypocalcemia results from a disturbance in renal phosphorus handling and decreased formation of 1,25(OH)-2-VitD. In response, the PTH secretion is increased resulting in a condition referred to as secondary HPT. Primary HPT is a hypercalcemic disorder that results from excessive secretion of PTH usually caused by parathyroid adenoma or primary parathyroid hyperplasia.

Other calcimimetic compounds were for example described in WO 94/018959, WO98/001417, WO05/065050, WO03/099814, WO03/099776, WO00/21910, WO01/34562, WO01/090069, WO97/41090, U.S. Pat. No. 6,001,884, WO96/12697, EP1203761, WO95/11221, WO93/04373, EP1281702, WO02/12181, WO04/069793, US2004242602, WO04/106296 and WO05/115975.

The calcimimetic activity corresponds to the ability to produce or induce biological responses observed through variations in the concentration of extracellular calcium ions $(Ca^{2+})_e$ and extracellular magnesium ions $(Mg^{2+})_e$.

$(Ca^{2+})_e$ and $(Mg^{2+})_e$ ions play a major role in the body since they regulate calcium homeostasis on which the vital functions of the body depend. Thus, hypo- and hypercalcemia, that is to say conditions in which $(Ca^{2+})_e$ ions are below or above the mean threshold, have a major effect on many functions, such as cardiac, renal or intestinal functions. They deeply affect the central nervous system [Chattopadhyay et al. *Endocr. Review*, (1998)].

CaSRs are proteins which are sensitive to $(Ca^{2+})_e$ and $(Mg^{2+})_e$ ions, and are present in the parathyroid and thyroid glands, the kidney, the intestine, the lungs, bone cells, the brain, the spinal cord, the pituitary gland, the stomach and keratinocytes [Brown et al, *Nature*, (1993); Ruat et al, *Proc. Natl. Acad. Sci.*, USA, (1995); Brown et al, *Ann. Rev. Med.*, (1998)]. These proteins are encoded by a single gene isolated from various animal species. They belong to the family of G protein-coupled receptors with seven transmembrane domains, and exhibit structural homologies with metabotropic glutamate receptors, GABA receptors, and hypothetical pheromone and taste receptors. Activating or inhibitory mutations of the genes in humans are responsible for extremely serious genetic diseases which cause hypocalcemia or hypercalcemia [Pollack et al, *Cell*, (1993); Pollack et al, *Nature Genetic*, (1994); Brown et al, *Ann. Rev. Med.*, (1998)]. The functions associated with the expression of these proteins in tissues are not yet all known and are the subject of a very great deal of research activity, particularly with regard to the CaSRs present in the parathyroid and thyroid glands, the kidney, the intestine, the spinal cord, the brain and bone cells.

In the parathyroid gland, the CaSRs modulate the secretion of parathyroid hormone (PTH), which is the main regulator of calcium homeostasis: an increase in $(Ca^{2+})_e$ ions in the serum will activate the CaSRs present on the cells of the parathyroid gland and decrease secretion of the PTH hormone.

The complementary DNA encoding rat CaSR has been isolated from a rat striatum cDNA library [Ruat et al, *Proc. Natl. Acad. Sci.*, (1995)]. This receptor is identical, in terms of its amino acid sequence, to that expressed in the other tissues. Transfected Chinese hamster ovary (CHO) cells expressing rat CaSR(CHO(CaSR)) have been characterized and the chemical signals (second messengers) induced by activation of this receptor have been analyzed. Thus, a biochemical test for measuring the accumulation of tritiated inositol phosphates, [$^3$H]IPs, in response to activation of the receptor has been developed [Ruat et al, *J. Biol. Chem.*, (1996); Ferry et al, *Biochem. Biophys. Res. Common.*, (1997)].

It has been shown that $Ca^{2+}$ and $Mg^{2+}$ ions, but also $Ba^{2+}$ ions, within millimolar concentration ranges, stimulate CaSRs. Activation of CaSRs might be induced in the brain by β-amyloid peptides, which are involved in neurodegenerative diseases such as Alzheimer's disease [Ye et al, *J. Neurosci. Res.* (1997)].

Disturbance of CaSR activity is associated with biological disorders such as primary and secondary hyperparathyroidism, osteoporosis, cardiovascular, gastrointestinal, endocrine and neurodegenerative diseases, or certain cancers in which $(Ca^{2+})_e$ ions are abnormally high.

Secondary hyperparathyroidism is observed in chronic renal failure and is characterized by hyperplasia of the parathyroid glands and an increase in circulating PTH. The renal failure is also accompanied by renal osteodystrophy, e.g. osteitis fibrosa, osteomalacia, adynamic bone disease, or osteoporosis. The disorders are characterized by either high or low bone turnover.

Osteoporosis is a multifactor disease which depends in particular on age and sex. While menopausal women are very greatly affected, osteoporosis is increasingly proving to be a problem in elderly men, and, for the moment, no really satisfactory treatments exist. Its social cost may become even heavier in the years to come, particularly in our European society where life expectancy is becoming longer. Osteoporosis is currently treated with estrogens, calcitonin or biphosphonates which prevent bone resorption without stimulating bone growth. More recent data demonstrate that intermittent increases in PTH or in derivatives thereof are effective in the treatment of osteoporosis and make it possible to remodel bone by stimulating bone formation [Whitfield et al, *Drugs & Aging*, (1999), Whitfield et al, *Calc. Tissue Int.*, (1999)]. This new therapeutic approach for treatment of osteoporosis appears to be very advantageous, although major problems are associated with the use of PTH hormone, such as the route of injection, but also the appearance of tumors, observed recently during clinical trials in humans. Intermittent secretion of endogenous PTH can be obtained by blocking the calcium sensing receptor. The blocking of PTH secretion with CaSR agonists may be followed by a rapid increase in PTH (rebound effect), which is then beneficial in the treatment of osteoporosis.

SUMMARY OF THE INVENTION

The present invention provides novel cyclic hydrocarbon compounds having advantageous calcium sensing receptor (CaSR) modulating effects. It has surprisingly been found that cyclic hydrocarbon compounds of the present invention are modulators, e.g. activators or agonists of the human calcium sensing receptor (CaSR) and may thus be useful in the treatment or prophylaxis of a number of diseases or physiological disorders involving modulation of CaSR activity.

The cyclic hydrocarbon compounds of the present invention may for example be useful in the treatment of complications associated with chronic kidney disease, such as hyperparathyroidism, e.g. primary and/or secondary hyperparathyroidism, or tertiary hyperparathyroidism. Other complications associated with chronic kidney disease are anemia, cardiovascular diseases, podocyte-related dysfunction, such as proteinuria, tubular atrophy or podocytopenia, and the compounds of the present invention are also believed to have a beneficial effect on these diseases. The cyclic hydrocarbon compounds of the present invention may furthermore be useful for promoting osteogenesis and treating or preventing osteoporosis, such as steroid induced, senile and post menopausal osteoporosis; osteomalacia and related bone disorders, or for the prevention of bone loss post renal transplantation, or in rescue therapy pre-parathyroidectomy.

It is presently believed that the cyclic hydrocarbon compounds of the present invention may have advantageous pharmacokinetic or pharmacodynamic properties, such as oral bioavailability, in comparison to known structurally related compounds.

Accordingly, the present invention relates to a compound of general formula I

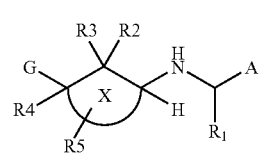

wherein

represents cycloalkyl comprising 4-7 carbon atoms optionally being substituted with one or more, same of different substitutents selected from $R_2$, $R_3$, $R_4$ or $R_5$;

A represents $C_{1-10}$heteroaryl, $C_{6-14}$aryl or $C_{6-10}$heterocloalkylaryl, each of which are optionally substituted with one or more, same or different substituents represented by halogen, hydroxy, mercapto, trifluoromethyl, cyano, carboxy, $—NH_2$, $—C(O)NH_2$, nitro, oxo, $—S(O)_2NH_2$, $C_{1-4}$alkyl, $C_{2-4}$alkenyl, $C_{2-4}$alkynyl, $C_{1-4}$hydroxyalkyl, $C_{1-6}$haloalkyl, $C_{1-4}$alkoxy, $C_{1-4}$alkoxycarbonyl, $C_{1-4}$alkylcarbonyloxy, $C_{1-4}$alkoxycarbonyloxy, $C_{1-4}$alkoxysulfonyloxy, $C_{1-4}$alkoxycarbamoyl, $C_{1-4}$-aminocarbonyl, $C_{1-4}$alkylthio, $C_{3-8}$cycloalkyl, $C_{3-8}$cycloalkenyl, $C_{1-6}$-amino, iminomethyl, $C_{1-4}$-aminosulfonyl, $C_{1-4}$-aminocarbonyloxy, $C_{1-4}$alkylsulfonylamino, hydroxyiminomethyl, $C_{1-4}$alkylcarbonylamino, $C_{1-4}$alkylsulfonyl, $C_{1-6}$heterocycloalkyl, $C_{1-6}$heterocycloalkenyl, $C_{1-10}$heteroaryl or $C_{6-14}$aryl,
wherein said $C_{1-4}$alkyl, $C_{2-4}$alkenyl, $C_{2-4}$alkynyl, $C_{1-4}$hydroxyalkyl, $C_{1-4}$alkoxy, $C_{1-4}$alkoxycarbonyl, $C_{1-4}$alkylcarbonyloxy, $C_{1-4}$alkoxycarbonyloxy, $C_{1-4}$alkoxysulfonyloxy, $C_{1-4}$alkoxycarbamoyl, $C_{1-4}$-aminocarbonyl, $C_{1-4}$alkylthio, $C_{3-6}$cycloalkyl, $C_{3-6}$cycloalkenyl, $C_{1-6}$-amino, iminomethyl, $C_{1-4}$-aminosulfonyl, $C_{1-4}$aminocarbonyloxy, $C_{1-4}$alkylsulfonylamino, hydroxyiminomethyl, $C_{1-4}$alkylcarbonylamino, $C_{1-4}$alkylsulfonyl, $C_{1-6}$heterocycloalkyl, $C_{1-6}$heterocycloalkenyl, $C_{1-10}$heteroaryl or $C_{6-14}$aryl,
are optionally further substituted with one or more, same or different substituents selected from halogen, hydroxy, $—NH_2$, mercapto, trifluoromethyl, cyano, carboxy, $—C(O)NH_2$, nitro, oxo, $—S(O)_2NH_2$, $C_{1-4}$alkyl, $C_{1-6}$haloalkyl, $C_{1-3}$alkoxy or $C_{1-3}$hydroxyalkyl;

$R_1$ is $C_{1-6}$alkyl, $C_{2-6}$alkenyl, $C_{2-6}$alkynyl, $C_{1-6}$hydroxyalkyl, $C_{1-6}$haloalkyl, $C_{1-6}$alkylamino, $C_{3-6}$cycloalkyl, or $C_{1-6}$heterocycloalkyl,
each of which are optionally substituted with one or more, same or different substituents selected from halogen, hydroxy, mercapto, trifluoromethyl, cyano, carboxy, $NH_2$, $—C(O)NH_2$, nitro, oxo, $C_{1-3}$alkyl, $C_{2-4}$alkenyl, $C_{1-3}$hydroxyalkyl, $C_{1-3}$haloalkyl, $C_{1-4}$alkoxy, $C_{1-4}$alkoxycarbonyl or $C_{1-4}$amino;

$R_2$ and $R_3$ independently of each other represent hydrogen, cyano, halogen, carboxy, —C(O)NH$_2$, $C_{1-4}$alkyl, $C_{2-6}$alkenyl, $C_{2-6}$alkynyl, $C_{1-6}$hydroxyalkyl, amino$C_{1-6}$alkyl, $C_{3-6}$cycloalkyl, $C_{1-6}$heterocycloalkyl, $C_{1-6}$alkoxy, $C_{1-6}$aminocarbonyl, $C_{6-10}$aryloxycarbonyl, $C_{1-6}$amino, $C_{6-10}$arylamino, $C_{1-4}$alkoxycarbonylamino, $C_{1-4}$alkylcarbonylamino, $C_{2-4}$alkenylcarbonylamino, $C_{3-6}$cycloalkylcarbonylamino or $C_{1-6}$heterocycloalkylcarbonylamino, wherein said —C(O)NH$_2$, $C_{2-6}$alkenyl, $C_{2-6}$alkynyl, $C_{1-6}$hydroxyalkyl, $C_{1-6}$haloalkyl, amino$C_{1-6}$alkyl, $C_{3-6}$cycloalkyl, $C_{1-6}$heterocycloalkyl, $C_{1-6}$alkoxy, $C_{1-6}$aminocarbonyl, $C_{6-10}$aryloxycarbonyl, $C_{1-6}$amino, $C_{6-10}$arylamino, $C_{1-4}$alkoxycarbonylamino, $C_{1-4}$alkylcarbonylamino, $C_{2-4}$alkenylcarbonylamino, $C_{3-4}$cycloalkylcarbonylamino or $C_{1-6}$heterocycloalkylcarbonylamino, are optionally substituted with one or more, same or different substituents represented by halogen, hydroxy, mercapto, trifluoromethyl, cyano, carboxy, —NH$_2$, —C(O)NH$_2$, nitro, $C_{1-3}$alkyl, $C_{2-4}$alkenyl, $C_{1-3}$hydroxyalkyl, $C_{1-3}$haloalkyl, $C_{1-4}$alkoxycarbonyl or $C_{1-4}$amino;

$R_4$ represents hydrogen, halogen, hydroxy, carboxy, —NH$_2$, —C(O)NH$_2$, $C_{1-6}$alkyl, $C_{2-6}$alkenyl, $C_{2-6}$alkynyl, $C_{1-6}$hydroxyalkyl, $C_{1-6}$haloalkyl, amino$C_{1-6}$alkyl, $C_{3-6}$cycloalkyl, $C_{1-6}$heterocycloalkyl, $C_{1-6}$alkoxycarbonyl, $C_{1-6}$aminocarbonyl, $C_{6-10}$aryloxycarbonyl, $C_{1-10}$heteroaryloxycarbonyl, $C_{1-6}$amino, $C_{6-10}$arylamino, $C_{1-6}$heteroarylamino, $C_{6-10}$aryl$C_{1-6}$amino, $C_{1-4}$alkoxycarbonylamino, $C_{1-4}$alkylcarbonylamino, $C_{2-4}$alkenylcarbonylamino, $C_{3-6}$cycloalkylcarbonylamino or $C_{1-6}$heterocycloalkylcarbonylamino, wherein said —C(O)NH$_2$, $C_{1-6}$alkyl, $C_{2-6}$alkenyl, $C_{2-6}$alkynyl, $C_{1-6}$hydroxyalkyl, $C_{1-6}$haloalkyl, amino$C_{1-6}$alkyl, $C_{3-6}$cycloalkyl, $C_{1-6}$heterocycloalkyl, $C_{1-6}$alkoxy, $C_{1-6}$alkoxycarbonyl, $C_{1-6}$aminocarbonyl, $C_{6-10}$aryloxycarbonyl, $C_{1-10}$heteroaryloxycarbonyl, $C_{1-6}$amino, $C_{6-10}$arylamino, $C_{1-10}$heteroarylamino, $C_{6-10}$aryl$C_{1-6}$amino, $C_{1-4}$alkoxycarbonylamino, $C_{1-4}$alkylcarbonylamino, $C_{2-4}$alkenylcarbonylamino, $C_{3-6}$cycloalkylcarbonylamino or $C_{1-6}$heterocycloalkylcarbonylamino, are optionally substituted with one or more, same or different substituents represented by halogen, hydroxy, mercapto, trifluoromethyl, cyano, carboxy, —NH$_2$, hydroxyiminomethyl, —C(O)NH$_2$, nitro, $C_{1-3}$alkyl, $C_{2-4}$alkenyl, $C_{1-3}$hydroxyalkyl, $C_{1-3}$haloalkyl, $C_{1-4}$alkoxy, $C_{1-4}$alkoxycarbonyl or $C_{1-4}$amino;

each of $R_5$ represents independently one or more same or different substituents represented by hydrogen, halogen, hydroxy, carboxy, —NH$_2$, —C(O)NH$_2$, $C_{1-6}$alkyl, $C_{2-6}$alkenyl, $C_{2-6}$alkynyl, $C_{1-6}$hydroxyalkyl, $C_{3-6}$cycloalkyl, $C_{1-6}$heterocycloalkyl, $C_{1-6}$alkoxy, $C_{1-4}$alkoxycarbonyl, $C_{1-6}$aminocarbonyl, $C_{6-10}$aryloxycarbonyl, $C_{1-10}$heteroaryloxycarbonyl, $C_{1-6}$amino, $C_{6-10}$aryl, $C_{6-10}$arylamino, $C_{1-10}$heteroarylamino, $C_{6-10}$arylcarbonylamino, $C_{1-4}$alkoxycarbonylamino, $C_{6-10}$arylsulfonylamino, $C_{1-4}$alkylcarbonylamino, $C_{2-4}$alkenylcarbonylamino, $C_{3-6}$cycloalkylcarbonylamino or $C_{1-6}$heterocycloalkylcarbonylamino, wherein said $C_{1-6}$alkyl, $C_{2-6}$alkenyl, $C_{2-6}$alkynyl, $C_{1-6}$hydroxyalkyl, $C_{1-6}$haloalkyl, $C_{3-6}$cycloalkyl, $C_{1-6}$heterocycloalkyl, $C_{1-6}$alkoxy, $C_{1-4}$alkoxycarbonyl, $C_{1-6}$aminocarbonyl, $C_{6-10}$aryloxycarbonyl, $C_{1-10}$heteroaryloxycarbonyl, $C_{1-6}$amino, $C_{6-10}$aryl, $C_{6-10}$arylamino, $C_{1-10}$heteroarylamino, $C_{6-10}$arylcarbonylamino, $C_{1-4}$alkoxycarbonylamino, $C_{6-10}$arylsulfonylamino, $C_{1-4}$alkylcarbonylamino, $C_{2-4}$alkenylcarbonylamino, $C_{3-6}$cycloalkylcarbonylamino or $C_{1-6}$heterocycloalkylcarbonylamino, are optionally further substituted with one or more, same or different substituents selected from halogen, hydroxy, mercapto, cyano, trifluoromethyl, carboxy, —NH$_2$, —C(O)NH$_2$, nitro, oxo, $C_{1-3}$alkyl, $C_{2-4}$alkenyl, $C_{1-3}$hydroxyalkyl, $C_{1-3}$haloalkyl, $C_{1-4}$alkoxy, $C_{1-4}$alkoxycarbonyl, iminomethyl or hydroxyiminomethyl;

G represents hydrogen, —C(O)H, —C(O)NH$_2$, —O—C(O)NH$_2$, $C_{1-6}$alkyl, $C_{2-6}$alkenyl, $C_{2-6}$alkynyl, $C_{1-6}$hydroxyalkyl, $C_{1-6}$haloalkyl, $C_{1-6}$amino, $C_{3-8}$cycloalkyl, $C_{1-6}$heterocycloalkyl, $C_{1-6}$heterocycloalkenyl, $C_{3-8}$cycloalkenyl, $C_{6-14}$aryl, $C_{1-10}$heteroaryl, $C_{6-10}$arylamino, hydroxyaminocarbonyl, $C_{6-10}$arylaminocarbonyl, $C_{1-4}$aminocarbonyl, $C_{1-6}$heterocycloalkylcarbonyl, $C_{1-10}$heteroarylaminocarbonyl, $C_{6-10}$arylsulfonylaminocarbonyl, $C_{6-14}$aryloxy, $C_{6-10}$heteroaryloxy, $C_{1-4}$alkoxy, $C_{1-4}$alkoxycarbonyl, $C_{1-4}$alkylcarbonyloxy, $C_{1-4}$alkoxycarbonyloxy, $C_{1-6}$aminocarbonyloxy, $C_{1-10}$heteroarylamino, $C_{1-3}$alkylcarbonylamino, $C_{6-10}$arylcarbonylamino, $C_{3-6}$cycloalkylcarbonylamino, $C_{1-4}$alkoxycarbonylamino, $C_{1-6}$heterocycloalkylcarbonylamino or ureido, wherein said —C(O)H, —C(O)NH$_2$, —O—C(O)NH$_2$, $C_{1-6}$alkyl, $C_{2-6}$alkenyl, $C_{2-6}$alkynyl, $C_{1-6}$hydroxyalkyl, $C_{1-6}$haloalkyl, $C_{1-6}$amino, $C_{3-8}$cycloalkyl, $C_{1-6}$heterocycloalkyl, $C_{1-6}$heterocycloalkenyl, $C_{3-8}$cycloalkenyl, $C_{6-14}$aryl, $C_{1-10}$heteroaryl, $C_{6-10}$arylamino, hydroxyaminocarbonyl, $C_{6-10}$arylaminocarbonyl, $C_{1-4}$aminocarbonyl, $C_{1-6}$heterocycloalkylcarbonyl, $C_{1-10}$heteroarylaminocarbonyl, $C_{1-10}$arylsulfonylaminocarbonyl, $C_{6-14}$aryloxy, $C_{1-10}$heteroaryloxy, $C_{1-4}$alkoxy, $C_{1-4}$alkoxycarbonyl, $C_{1-4}$alkylcarbonyloxy, $C_{1-4}$alkoxycarbonyloxy, $C_{1-6}$aminocarbonyloxy, $C_{1-10}$heteroarylamino, $C_{1-3}$alkylcarbonylamino, $C_{6-10}$arylcarbonylamino, $C_{3-6}$cycloalkylcarbonylamino, $C_{1-4}$alkoxycarbonylamino, $C_{1-6}$heterocycloalkylcarbonylamino or ureido, are optionally further substituted with one or more, same or different substituents represented by halogen, cyano, carboxy, —NH$_2$, $C_{1-6}$amino, iminomethyl, hydroxyiminomethyl, amidino, hydroxy, mercapto, —C(O)H, —C(O)NH$_2$, nitro, oxo, trifluoromethyl, $C_{2-4}$alkenyl, $C_{2-4}$alkynyl, $C_{1-4}$hydroxyalkyl, amino$C_{1-3}$alkyl, $C_{1-6}$haloalkyl, $C_{1-4}$alkoxy, $C_{1-4}$alkoxycarbonyl, $C_{1-4}$alkylcarbonyl, $C_{1-4}$aminocarbonyl, hydroxyaminocarbonyl, $C_{3-6}$cycloalkylaminocarbonyl, $C_{1-6}$heterocycloalkylaminocarbonyl, $C_{3-6}$cycloalkyl, $C_{3-6}$cycloalkenyl, $C_{1-6}$cycloalkylamino, $C_{1-6}$heterocycloalkyl, $C_{1-6}$heterocycloalkenyl, $C_{1-6}$heterocycloalkylcarbonyl, $C_{6-14}$aryl, carboxy$C_{6-10}$aryl, $C_{1-6}$heteroaryl, $C_{1-6}$heteroarylaminocarbonyl, —S(O)$_2$NH$_2$, $C_{1-6}$ureido, $C_{1-6}$thioureido, $C_{1-4}$alkylcarbonyloxy, $C_{1-4}$alkoxycarbonyloxy, $C_{1-4}$alkoxysulfonyloxy, $C_{1-6}$heterocycloalkyloxy, $C_{1-4}$aminosulfonyl, $C_{1-4}$aminocarbonyloxy, $C_{1-4}$alkylsulfonylamino, $C_{6-10}$arylamino, $C_{6-10}$arylaminocarbonyl, $C_{6-10}$aryloxycarbonyl, $C_{1-4}$alkoxycarbamoyl, $C_{6-10}$arylcarbonylamino, $C_{6-10}$arylsulfonylamino, $C_{1-4}$alkylcarbonylamino, $C_{1-4}$alkenylcarbonylamino, $C_{3-6}$cycloalkenylcarbonylamino, $C_{1-6}$cycloalkylcarbonylamino, $C_{1-4}$alkoxycarbonylamino, $C_{1-6}$heterocycloalkylcarbonylamino, $C_{1-4}$alkylsulfonyl, $C_{1-6}$heterocycloalkylsulfonyl or $C_{1-3}$alkylsulfonylaminocarbonyl, wherein said carboxy, $C_{1-6}$amino, iminomethyl, hydroxyiminomethyl, C(O)NH$_2$, $C_{1-6}$alkyl, $C_{2-4}$alkenyl, $C_{2-4}$alkenyl, $C_{2-4}$alkynyl, $C_{1-4}$hydroxyalkyl, amino$C_{1-3}$alkyl, $C_{1-6}$haloalkyl, $C_{1-4}$alkoxy, $C_{1-4}$alkoxycarbonyl, $C_{1-4}$alkylcarbonyl, $C_{1-4}$aminocarbonyl, hydroxyaminocarbonyl, $C_{3-6}$cycloalkylaminocarbonyl, $C_{1-6}$heterocycloalkylaminocarbonyl, $C_{3-6}$cycloalkyl, $C_{3-6}$cycloalkenyl, $C_{1-6}$cycloalkylamino, $C_{1-6}$heterocycloalkyl, $C_{1-6}$heterocycloalkenyl, $C_{1-6}$heterocycloalkylcarbonyl, $C_{6-14}$aryl, carboxy$C_{6-10}$aryl, $C_{1-6}$heteroaryl, $C_{1-6}$heteroarylaminocarbonyl, —S(O)$_2$NH$_2$, $C_{1-6}$ureido, $C_{1-6}$thioureido, $C_{1-4}$alkylcarbonyloxy, $C_{1-4}$alkoxycarbonyloxy, $C_{1-4}$alkoxysulfonyloxy, $C_{1-6}$heterocycloalkyloxy, $C_{1-4}$alkylthio, $C_{1-4}$aminosulfonyl, $C_{1-4}$aminocarbonyloxy, $C_{1-4}$alkylsulfonylamino, $C_{6-10}$arylamino, $C_{6-10}$arylaminocarbonyl, $C_{6-10}$aryloxycarbonyl, $C_{1-4}$alkoxycarbamoyl, $C_{6-10}$arylcarbonylamino, $C_{6-10}$arylsulfonylamino, $C_{1-4}$alkylcarbonylamino, $C_{1-4}$alkenylcarbonylamino, $C_{3-6}$cycloalkenylcarbonylamino, $C_{3-6}$cycloalkylcarbonylamino, $C_{1-4}$alkoxycarbonylamino, $C_{1-6}$heterocycloalkylcarbonylamino, $C_{1-4}$alkylsulfonyl, $C_{1-6}$heterocycloalkylsulfonyl or $C_{1-3}$alkylsulfonylaminocarbonyl,
are optionally further substituted with one or more, same or different substituents selected from hydroxy, —NH$_2$, $C_{1-6}$amino, iminomethyl, hydroxyiminomethyl, carboxy, trifluoromethyl, halogen, oxo, mercapto, cyano, —C(O)NH$_2$, nitro, $C_{1-6}$alkyl, $C_{2-4}$alkenyl, $C_{2-4}$alkynyl, $C_{1-4}$hydroxyalkyl, $C_{1-6}$haloalkyl, $C_{1-3}$alkoxy, $C_{1-4}$alkoxycarbonyl, $C_{1-4}$alkylcarbonyl, $C_{3-8}$cycloalkyl, $C_{3-8}$cycloalkenyl, $C_{1-6}$heterocycloalkyl, $C_{6-12}$aryl, $C_{1-10}$heteroaryl, $C_{1-3}$alkoxy$C_{6-10}$aryl, $C_{1-10}$heterocycloalkylaryl, $C_{1-6}$heterocycloalkenyl, —S(O)$_2$NH$_2$, —S(O)$_2$OH, —S(O)$_2$CH$_3$, $C_{1-6}$ureido, $C_{1-6}$thioureido, $C_{1-4}$alkylcarbonyloxy, $C_{1-4}$alkoxycarbonyloxy, $C_{1-4}$alkoxysulfonyloxy, $C_{1-4}$alkoxycarbamoyl, $C_{1-4}$aminocarbonyl, $C_{1-6}$heterocycloalkylcarbonyl, $C_{1-4}$alkylthio, $C_{1-4}$aminosulfonyl, $C_{1-4}$aminocarbonyloxy, $C_{1-4}$alkylsulfonylamino, $C_{6-14}$arylsulfonyl, $C_{6-10}$arylsulfonylamino, hydroxyiminomethyl, $C_{1-4}$alkylcarbonylamino or $C_{1-4}$alkylsulfonyl,
wherein said —C(O)NH$_2$, $C_{1-6}$amino, $C_{1-6}$alkyl, $C_{2-4}$alkenyl, $C_{2-4}$alkynyl, $C_{1-4}$hydroxyalkyl, $C_{1-6}$haloalkyl, $C_{1-3}$alkoxy, $C_{1-4}$alkoxycarbonyl, $C_{3-8}$cycloalkyl, $C_{3-8}$cycloalkenyl, $C_{1-6}$heterocycloalkyl, $C_{6-12}$aryl, $C_{1-10}$heteroaryl, $C_{1-3}$alkoxy$C_{6-10}$aryl, $C_{1-10}$heterocycloalkylaryl, $C_{1-6}$heterocycloalkenyl, —S(O)$_2$NH$_2$, —S(O)$_2$OH, $C_{1-6}$ureido, $C_{1-6}$thioureido, $C_{1-4}$alkylcarbonyloxy, $C_{1-4}$alkoxycarbonyloxy, $C_{1-4}$alkoxysulfonyloxy, $C_{1-4}$alkoxycarbamoyl, $C_{1-4}$aminocarbonyl, $C_{1-6}$heterocycloalkylcarbonyl, $C_{1-4}$alkylthio, $C_{1-4}$aminosulfonyl, $C_{1-4}$aminocarbonyloxy, $C_{1-4}$alkylsulfonylamino, $C_{6-14}$arylsulfonyl, $C_{6-10}$arylsulfonylamino, hydroxyiminomethyl, $C_{1-4}$alkylcarbonylamino or $C_{1-4}$alkylsulfonyl, are optionally further substituted with one or more, same or different substituents selected from hydroxy, oxo, cyano, halogen, trifluoromethyl, $C_{1-3}$alkoxy, $C_{1-3}$alkoxy$C_{1-3}$alkoxy, $C_{1-6}$amino, mercapto, carboxy, —C(O)NH$_2$, nitro, $C_{1-6}$alkyl, $C_{1-3}$hydroxyalkyl, $C_{1-4}$alkoxycarbonyl, $C_{1-3}$alkylcarbonylamino, $C_{1-6}$heterocycloalkyl, $C_{6-12}$aryl, $C_{1-6}$heteroaryl, —S(O)$_2$NH$_2$ or —S(O)$_2$OH;
or G, together with R$_4$, forms an oxo group;
provided that the compound is not
N-cyclopentyl-α-methyl-benzenemethanamine,
N-cyclohexyl-α-methyl-benzenemethanamine,
3-[3-[(1-phenylethyl)amino]cyclohexyl]-phenol,
2-[3-[3-[(1-phenylethyl)amino]cyclohexyl]phenoxy]-ethylester acetic acid,
N-[3-(3-methoxyphenyl)cyclohexyl]-α-methyl-2-naphthalenemethanamine,
N-[3-(3-methoxyphenyl)cyclohexyl]-α-methyl-benzenemethanamine,
N-cyclohexyl-α-methyl-1-naphthalenennethanamine,
3-methoxy-α-methyl-N-(2-phenylcyclohexyl)-benzenemethanamine,
3-methoxy-α-methyl-N-(3-phenylcyclohexyl)-benzenemethanamine,
3-methoxy-α-methyl-N-(4-phenylcyclohexyl)-benzenemethanamine,
4-chloro-N-cyclohexyl-α-methyl-benzenemethanamine,
N-(1-phenylethyl)-cycloheptanamine,
or a pharmaceutically acceptable salt, solvate or in vivo hydrolysable ester thereof.

In another aspect, the present invention relates to a compound of formula I as defined herein for use as a medicament in therapy.

In yet another aspect, the present invention relates to a compound of formula I as defined herein or compound
N-cyclopentyl-α-methyl-benzenemethanamine,
N-cyclohexyl-α-methyl-benzenemethanamine,
3-[3-[(1-phenylethyl)amino]cyclohexyl]-phenol,
2-[3-[3-[(1-phenylethyl)amino]cyclohexyl]phenoxy]-, ethyl ester, acetic acid,
N-[3-(3-methoxyphenyl)cyclohexyl]-α-methyl-2-naphthalenemethanamine,
N-[3-(3-methoxyphenyl)cyclohexyl]-α-methyl-benzenemethanamine,
N-cyclohexyl-α-methyl-1-naphthalenemethanamine,
4-chloro-N-cyclohexyl-α-methyl-benzenemethanamine, or
N-(1-phenylethyl)-cycloheptanamine,
for use in the treatment, amelioration or prophylaxis of physiological disorders or diseases associated with disturbances of CaSR activity, such as hyperparathyroidism.

In a further aspect, the invention relates to the use of a compound of general formula I as defined herein or compound
N-cyclopentyl-α-methyl-benzenemethanamine,
N-cyclohexyl-α-methyl-benzenemethanamine,
3-[3-[(1-phenylethyl)amino]cyclohexyl]-phenol,
2-[3-[3-[(1-phenylethyl)amino]cyclohexyl]phenoxy]-, ethyl ester, acetic acid,
N-[3-(3-methoxyphenyl)cyclohexyl]-α-methyl-2-naphthalenemethanamine,
N-[3-(3-methoxyphenyl)cyclohexyl]-α-methyl-benzenemethanamine,
N-cyclohexyl-α-methyl-1-naphthalenemethanamine,
4-chloro-N-cyclohexyl-α-methyl-benzenemethanamine, or
N-(1-phenylethyl)-cycloheptanamine,
for the manufacture of a medicament for the prophylaxis, treatment or amelioration of physiological disorders or diseases associated with disturbances of CaSR activity, such as hyperparathyroidism.

In a still further aspect, the invention relates to a pharmaceutical composition comprising a compound of formula I as defined herein or a pharmaceutically acceptable salt, solvate, or in vivo hydrolysable ester thereof together with a pharmaceutically acceptable excipient or vehicle.

In a still further aspect, the invention relates to a method of preventing, treating or ameliorating parathyroid carcinoma, parathyroid adenoma, primary parathyroid hyperplasia, cardiac, renal or intestinal disfunctions, diseases of the central nervous system, chronic renal failure, chronic kidney disease, primary hyperparathyroidism, secondary hyperparathyroidism, tertiary hyperparathyroidism, anemia, cardiovascular diseases, osteitis fibrosa, adynamic bone disease, osteoporosis, steroid induced osteoporosis, senile osteoporosis, post menopausal osteoporosis, osteomalacia and related bone disorders, bone loss post renal transplantation, gastrointestinal diseases, endocrine and neurodegenerative diseases, cancer, Alzheimer's disease, hypercalcemia, or renal bone diseases, the method comprising administering to a patient in need thereof an effective amount of a compound of general formula I as defined herein, optionally in combination or as supplement with an active vitamin-D sterol or vitamin-D derivative, such as 1-α-hydroxycholecalciferol, ergocalciferol, cholecalciferol, 25-hydroxycholecalciferol, 1-α-25-dihydroxycholecalciferol, or in combination or as supplement with phosphate binders, estrogens, calcitonin or biphosphonates.

DETAILED DESCRIPTION OF THE INVENTION

Definitions

Figure 1:
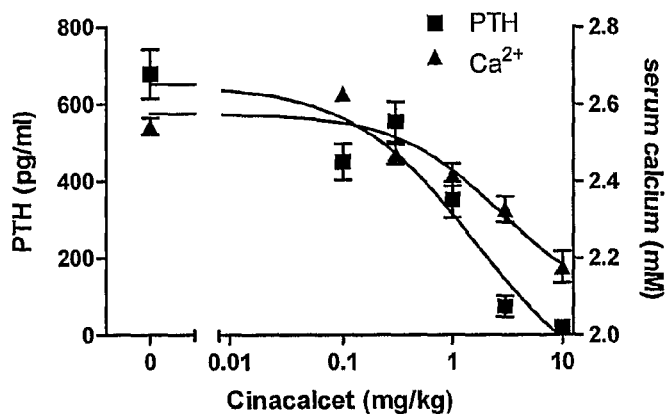
FIG. 1 shows a dose-response curve for suppression of serum PTH and serum calcium levels by Cinacalcet.
Figure 2:
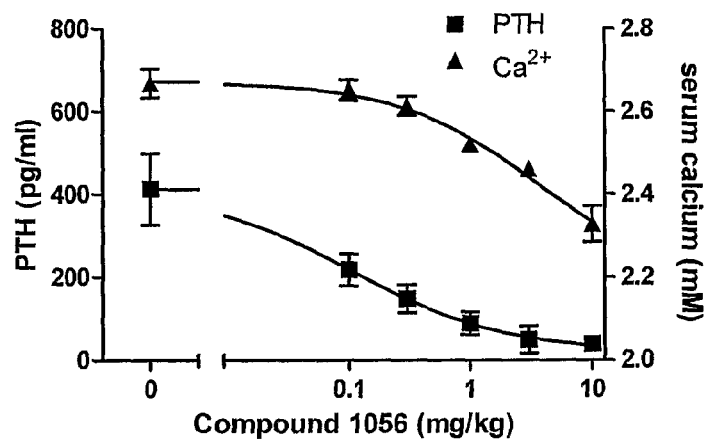
FIG. 2 shows a dose-response curve for suppression of serum PTH and serum calcium levels by Compound 1056.
Figure 3:
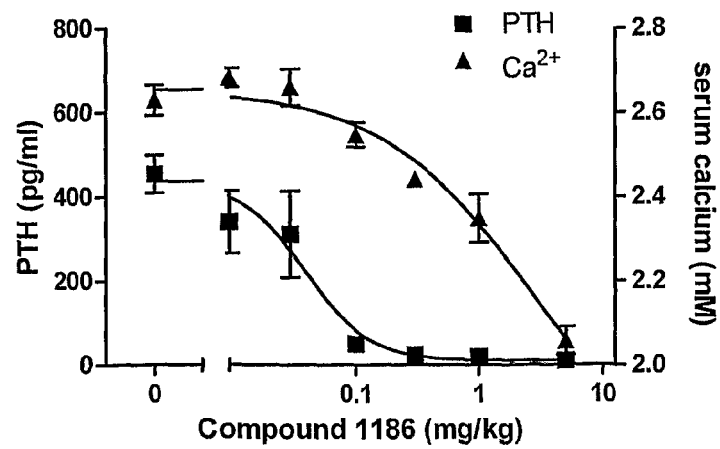
FIG. 3 shows a dose-response curve for suppression of serum PTH and serum calcium levels by Compound 1186.
Figure 4:
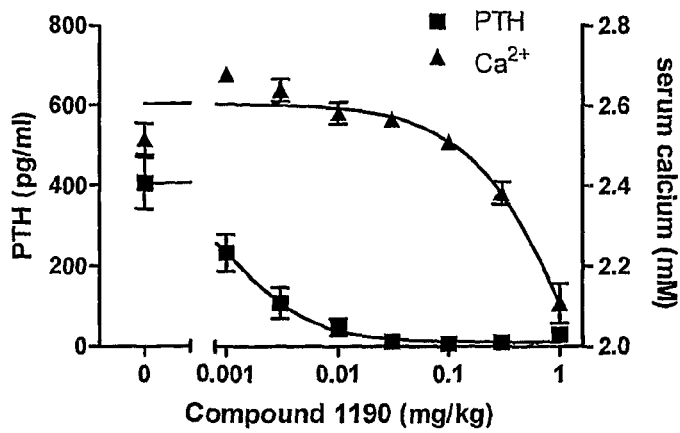
FIG. 4 shows a dose-response curve for suppression of serum PTH and serum calcium levels by Compound 1190.
Figure 5:
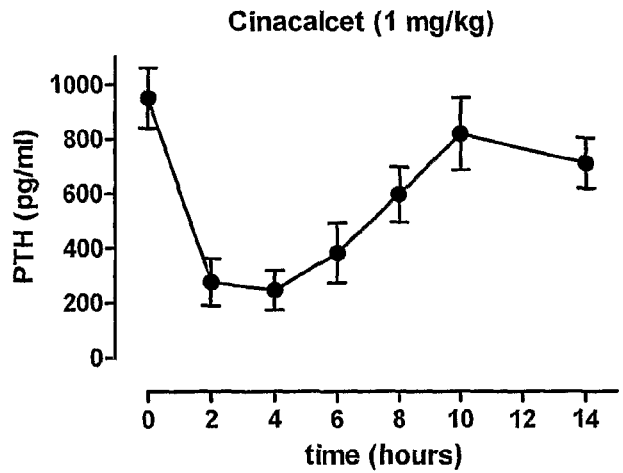
FIG. 5 shows a graph for suppression of serum PTH levels over time by Cinacalcet.
Figure 6:
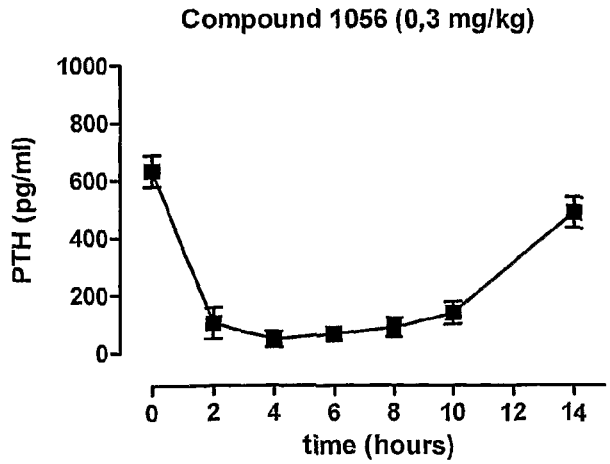
FIG. 6 shows a graph for suppression of serum PTH levels over time by Compound 1056.
Figure 7:
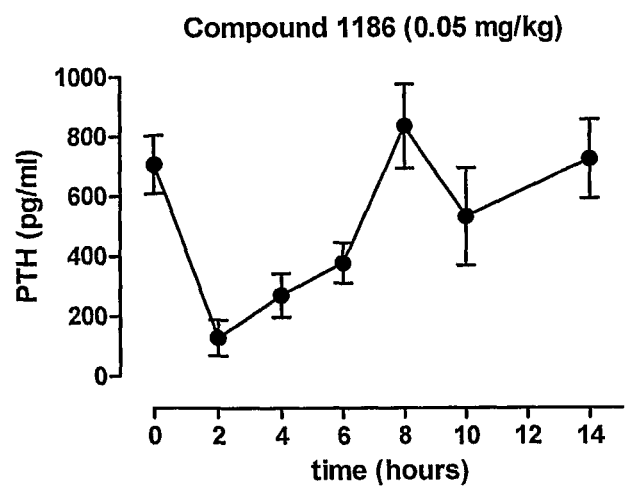
FIG. 7 shows a graph for suppression of serum PTH levels over time by Compound 1186.
Figure 8:
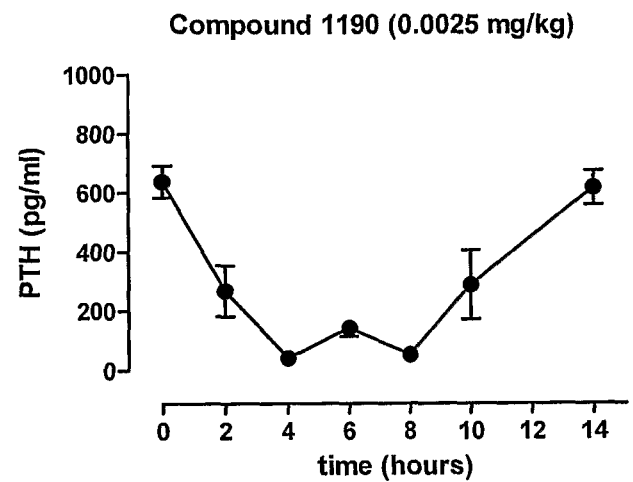
FIG. 8 shows a graph for suppression of serum PTH levels over time by Compound 1190.

The term "cycloalkyl" is intended to indicate a saturated cycloalkane radical, comprising 3-8 carbon atoms, such as 4-7 or 3-6 carbon atoms, such as 4-6 or preferably 5-6 carbon atoms, e.g. cyclopropyl, cyclobutyl, cyclopentyl, cyclohexyl or cycloheptyl.

The term

is intended to indicate a saturated cycloalkane radical, comprising 4-7 carbon atoms, such as 4-6 or 5-6 carbon atoms, preferably 5 carbon atoms or 6 carbon atoms, e.g. cyclobutyl, cyclopentyl, cyclohexyl or cycloheptyl.

The term "cycloalkenyl" is intended to indicate a mono-, or di- unsaturated non-aromatic cyclic hydrocarbon radical, comprising 3-8 carbon atoms, such as 4-7, such as 3-6 carbon atoms, such as 4-6 or preferably 5-6 carbon atoms, e.g. cyclobutenyl, cyclopentenyl, or cyclohexenyl.

The term "heterocycloalkyl" is intended to include a cycloalkyl radical as defined above, comprising 1-7 carbon atoms, such as 1-6 carbon atoms, in particular a 4-, 5- or 6-membered ring, comprising 2-5 carbon atoms and 1-5 hetero atoms (selected from O, S and N), such as 3-5 carbon atoms and 1-3 hetero atoms, preferably 4-5 carbon atoms and 1-2 hetero atoms selected from O, S, or N, e.g. morpholino, morpholinyl, pyrrolidinyl, oxo-pyrrolidinyl, piperidino, azetidinyl, tetrahydro-furyl, tetrahydro-pyranyl, oxo-tetrahydro-furyl, oxo-oxazolidinyl, oxetanyl, dioxoimidazolidinyl, piperidyl or piperazinyl.

The term "heterocycloalkenyl" is intended to indicate a cycloalkenyl radical as defined above, comprising 1-7 carbon atoms, such as 1-6 carbon atoms, in particular a 5- or 6-membered ring, comprising 1-5 carbon atoms and 1-5 hetero atoms (selected from O, S and N), such as 3-5 carbon atoms and 1-3 hetero atoms, preferably 4-5 carbon atoms and 1-2 hetero atoms selected from O, S, or N.

The term "heterocycloalkyloxy" is intended to include a radical of the formula —OR, wherein R represents heterocycloalkyl as defined above, e.g. oxo-dihydro-furyloxy.

The term "heterocycloalkylaryl" is intended to include radicals of (a) heterocycloalkyl ring(s), in particular 5- or 6-membered ring, comprising 1-5 carbon atoms and 1-4 heteroatoms, selected from O, N or S, such as 1-5 carbon atoms and 1-3 heteroatoms, preferably 2-5 carbon atoms and 1-2 heteroatoms, the heterocycloalkyl ring being fused or annelated with one or more aromatic carbocyclic rings comprising 6-10 carbon atoms, such as phenyl or naphthyl.

The term "aryl" is intended to indicate a radical of (an) aromatic carbocyclic ring(s) comprising 6-20 carbon atoms, such as 6-14 carbon atoms, preferably 6-10 carbon atoms, in particular 6-membered rings, optionally fused or annelated carbocyclic rings with at least one aromatic ring, e.g. phenyl, naphthyl, 1-naphthyl or indanyl.

The term "heteroaryl" is intended to include radicals of (a) heterocyclic aromatic ring(s), comprising 1-4 heteroatoms (selected from O, S and N) and 1-10 carbon atoms, such as 1-3 heteroatoms and 1-6 carbon atoms, such as 1-3 heteroatoms and 2-5 carbon atoms, such as 1-2 heteroatoms and 3-5 carbon atoms, preferably 5- or 6-membered rings with 1-3 heteroatoms and 2-5 carbon atoms or 1-3 heteroatoms and 2-4 carbon atoms selected from O, S and N, e.g. pyridyl, thiazolyl, imidazolyl, isoxadiazolyl, [1,2,4]oxadiazolyl, oxazolyl, pyrazolyl, indolyl, thienyl, furyl, 1-benzo[b] thiophenyl, 2,3-dihydro-benzo[1,4]dioxinyl, or 2,3-dihydrobenzofuryl.

The term "halogen" is intended to indicate a substituent from the 7$^{th}$ main group of the periodic table, preferably fluoro, chloro, iodo or bromo.

In the present context, the term "alkyl" is intended to indicate the radical obtained when one hydrogen atom is removed from a hydrocarbon. Said alkyl comprises 1-6, preferably 1-4 or 1-3, such as 2-4 or 1-2 carbon atoms. The term includes the subclasses normal alkyl (n-alkyl), secondary and tertiary alkyl, such as methyl, ethyl, n-propyl, isopropyl, n-butyl, isobutyl, sec-butyl, tert-butyl, pentyl, isopentyl, hexyl or isohexyl.

The term "alkenyl" is intended to indicate a mono-, di-, or triunsaturated hydrocarbon radical comprising 2-6 carbon atoms, in particular 2-4 carbon atoms, such as 2-3 carbon atoms, e.g. vinyl, allyl, propenyl, butenyl, pentenyl or hexenyl.

The term "alkynyl" is intended to indicate a hydrocarbon radical comprising 1-4 C—C triple bonds, e.g. 1, 2 or 3 triple bonds and 2-6 carbon atoms, the alkane chain typically comprising 2-5 carbon atoms, in particular 2-4 carbon atoms, such as 2-3 carbon atoms, e.g. ethynyl, propynyl, butynyl or pentynyl.

The term "hydroxyalkyl" is intended to indicate an alkyl radical as defined above, wherein one, two, three or more hydrogen atoms are replaced by hydroxy, e.g. hydroxymethyl, hydroxyethyl, hydroxypropyl, hydroxybutyl etc.

The term "haloalkyl" is intended to indicate an alkyl radical as defined above, wherein one, two, three or more hydrogen atoms are replaced by halogen, same or different, such as iodo, chloro, bromo and/or fluoro, e.g. fluoroethyl, difluoroethyl, difluoromethyl or trifluoromethyl.

The term "aminoalkyl" in intended to indicate an alkyl radical as defined above wherein one or two hydrogen atoms are replaced by —NH$_2$, e.g. aminomethyl, aminoethyl or aminopropyl.

The term "aminocarbonyl" is intended to indicate a radical of the formula —C(O)—NRR', wherein R and R' independently represents hydrogen, alkyl, cycloalkyl or alkenyl as indicated above, e.g. aminocarbonyl, methylaminocarbonyl, ethylaminocarbonyl, propylaminocarbonyl, tert-butylaminocarbonyl, cyclopropylaminocarbonyl, isopropylaminocarbonyl, sec-butylaminocarbonyl, methylethylaminocarbonyl, dimethylaminocarbonyl or diethylaminocarbonyl.

The term "alkylcarbonyl" is intended to indicate a radical of the formula —C(O)—R, wherein R represents alkyl as indicated above, e.g. methylcarbonyl, ethylcarbonyl.

The term "alkoxy" is intended to indicate a radical of the formula —OR, wherein R is alkyl or alkenyl as indicated above, e.g. methoxy, ethoxy, n-propoxy, isopropoxy, butoxy, tert-butoxy, etc.

The term "alkoxyalkoxy" is intended to indicate a radical of the formula —OR—OR, wherein R is alkyl or alkenyl as indicated above, e.g. methoxymethoxy, methoxyethoxy, ethoxymethoxy, ethoxyethoxy, etc.

The term "alkoxycarbonyl" is intended to indicate a radical of the formula —C(O)—O—R, wherein R is alkyl as indicated above, e.g. methoxycarbonyl, ethoxycarbonyl, n-propoxycarbonyl, isopropoxycarbonyl, tert-butoxycarbonyl etc.

The term "alkylcarbonyloxy" is intended to indicate a radical of the formula —O—C(O)—R, wherein R is alkyl as indicated above, e.g. methylcarbonyloxy, or ethylcarbonyloxy.

The term "alkoxycarbamoyl" is intended to indicate a radical of the formula —C(O)NR'—O—R, wherein R' is hydrogen or alkyl as indicated above, and R is alkyl as indicated above, e.g. methoxycarbamoyl, tert-butoxycarbamoyl.

The term "amino" is intended to indicate a radical of the formula —NRR', wherein R and R' independently represent hydrogen, alkyl or alkenyl, as indicated above, e.g. —NH$_2$, methylamino, ethylamino, propylamino, dimethylamino, diethylamino, isopropylamino, sec-butylamino, tert-butylamino or ethylmethylamino.

The term "cycloalkylamino" is intended to indicate a radical of the formula —NRR', wherein R represents hydrogen or alkyl and R' represents cycloalkyl as indicated above, e.g. cyclopropylamino.

The term "arylamino" is intended to indicate a radical of the formula —NRR', wherein R represents hydrogen or alkyl as inducated above and R' represents aryl as indicated above, e.g. phenylamino or indalylamino.

The term "alkoxyaryl" is intended to indicate a radical of the formula —Ar—O—R, wherein Ar represents aryl as indicated above and R represents alkyl as indicated above, e.g. methoxyphenyl or ethoxyphenyl.

The term "carboxyaryl" is intended to indicate a radical of the formula —Ar—C(O)OH, wherein Ar represents aryl as indicated above, e.g. carboxyphenyl.

The term "heteroarylamino" is intended to indicate a radical of the formula —NRR', wherein R represents hydrogen or alkyl as indicated above, and R' represents heteroaryl as indicated above.

The term "heterocycloalkylcarbonyl" is intended to indicate a radical of the formula —C(O)—R, wherein R is heterocycloalkyl as indicated below, e.g. piperidylcarbonyl, morpholinocarbonyl, morpholinylcarbonyl, piperazinylcarbonyl, pyrrolidinylcarbonyl, oxo-pyrrolidinylcarbonyl, piperidinylcarbonyl or azetidinylcarbonyl.

The term "aminocarbonyl" is intended to indicate a radical of the formula —C(O)—NR'$_2$, wherein each R' is independently hydrogen, alkyl, alkenyl or cycloalkyl as indicated above, e.g. carbamoyl, methylaminocarbonyl, ethylaminocarbonyl, dimethylaminocarbonyl, diethylaminocarbonyl, ethylmethylaminocarbonyl, methylethylaminocarbonyl, propylaminocarbonyl, isopropylaminocarbonyl, butylaminocarbonyl, sec-butylaminocarbonyl, tert-butylaminocarbonyl, cyclopropylaminocarbonyl or cyclohexylaminocarbonyl.

The term "hydroxyaminocarbonyl" is intended to indicate a radical of the formula —C(O)—NR'—OH, wherein R' is independently hydrogen or alkyl as indicated above.

The term "arylaminocarbonyl" is intended to indicate a radical of the formula —C(O)—NR'-aryl, wherein R' is independently hydrogen or alkyl as indicated above and aryl is as indicated above, e.g. phenylaminocarbonyl, indanylaminocarbonyl.

The term "heteroarylaminocarbonyl" is intended to indicate a radical of the formula —C(O)—NR'-heteroaryl, wherein R' is independently hydrogen or alkyl as indicated above and heteroaryl is as indicated above, e.g. pyrazolylaminocarbonyl, pyridylaminocarbonyl.

The term "cycloalkylaminocarbonyl" is intended to indicate a radical of the formula —C(O)—NR'-cycloalkyl, wherein R' is independently hydrogen or alkyl as indicated above and cycloalkyl is as indicated above, e.g. cyclopropylaminocarbonyl, cyclobutylaminocarbonyl, cyclopentylaminocarbonyl or cyclohexylaminocarbonyl.

The term "heterocycloalkylaminocarbonyl" is intended to indicate a radical of the formula —C(O)—NR'-heterocycloalkyl, wherein R' is independently hydrogen or alkyl as indicated above and heterocycloalkyl is as indicated above, e.g. tetrahydrofurylaminocarbonyl or oxo-tetrahydrofurylaminocarbonyl.

The term "alkylsulfonylaminocarbonyl" is intended to indicate a radical of the formula —C(O)—NR'—S(O)$_2$—R, wherein R' is independently hydrogen, alkyl or cycloalkyl as indicated above and R is alkyl as indicated above, e.g. methylsulfonylaminocarbonyl.

The term "aryloxy" is intended to indicate a radical of the formula —O—R, wherein R is aryl as indicated above, e.g. phenyloxy.

The term "aryloxycarbonyl" is intended to indicate a radical of the formula —C(O)—O—R wherein R is aryl as indicated above, e.g. phenyloxycarbonyl.

The term "heteroaryloxy" is intended to indicate a radical of the formula —O—R, wherein R is heteroaryl as indicated above.

The term "heteroaryloxycarbonyl" is intended to indicate a radical of the formula —C(O)—O—R, wherein R is heteroaryl as indicated above.

The term "alkylthio" is intended to indicate a radical of the formula —S—R, wherein R is alkyl as indicated above.

The term "iminomethyl" is intended to indicate the radical —CH=NH.

The term "hydroxyiminomethyl" is intended to indicate the radical —CH=N—(OH).

The term "aminosulfonyl" is intended to indicate a radical of the formula —S(O)$_2$—NR$_2$, wherein each R independently represents hydrogen, or alkyl as indicated above, e.g. ethylaminosulfonyl.

The term "alkylsulfonyl" is intended to indicate a radical of the formula —S(O)$_2$—R, wherein R is alkyl as indicated above.

The term "arylsulfonyl" is intended to indicate a radical of the formula —S(O)$_2$—R, wherein R is aryl as indicated above, e.g. phenylsulfonyl.

The term "heterocycloalkylsulfonyl" is intended to indicate a radical of the formula —S(O)$_2$—R, wherein R is a heterocycloalkyl as indicated above, e.g. morpholinesulfonyl.

The term "aminocarbonyloxy" is intended to indicate a radical of the formula —O—C(O)—NRR', wherein R and R' independently represent hydrogen or alkyl as indicated above.

The term "alkylcarbonylamino" is intended to indicate a radical of the formula —NR'—C(O)—R, wherein R' is hydrogen or alkyl as indicated above, and R is alkyl as indicated above, e.g. methylcarbonylamino.

The term "alkoxycarbonylamino" is intended to indicate a radical of the formula —NR'—C(O)—O—R, wherein R' is hydrogen or alkyl as indicated above, and R is alkyl as indicated above.

The term "alkylsulfonylamino" is intended to indicate a radical of the formula —NR'—S(O)$_2$—R, wherein R is alkyl as indicated above, and R' is hydrogen or alkyl as indicated above, e.g. methylsulfonylamino, ethylsulfonylamino, propylsulfonylamino or butylsulfonylamino.

The term "arylsulfonylamino" is intended to indicate a radical of the formula —NR'—S(O)$_2$—R, wherein R is aryl as indicated above, and R' is hydrogen, or alkyl as indicated above, e.g. phenylsulfonylamino.

The term "alkoxysulfonyloxy" is intended to represent a radical of the formula —O—S(O)$_2$—O—R, wherein R is alkyl as indicated above.

The term "arylsulfonylaminocarbonyl" is intended to indicate a radical of the formula —C(O)—NR'—S(O)$_2$—R, wherein R is aryl as indicated above, and R' is hydrogen or alkyl as indicated above, e.g. phenylsulfonylaminocarbonyl.

The term "arylcarbonylamino" is intended to indicate a radical of the formula —NR'—C(O)—R, wherein R' is hydrogen or alkyl as indicated above, and R is aryl as indicated above e.g. phenylcarbonylamino.

The term "alkenylcarbonylamino" is intended to indicate a radical of the formula —NR'—C(O)—R, wherein R' is hydrogen or alkyl as indicated above, and R is alkenyl as indicated above.

The term "cycloalkylcarbonylamino" is intended to indicate a radical of the formula —NR'—C(O)—R, wherein R' is hydrogen or alkyl as indicated above, and R is cycloalkyl as indicated above.

The term "cycloalkenylcarbonylamino" is intended to indicate a radical of the formula —NR'—C(O)—R, wherein R' is hydrogen or alkyl as indicated above, and R is cycloalkenyl as indicated above.

The term "heterocycloalkylcarbonylamino" is intended to indicate a radical of the formula —NR'—C(O)—R, wherein R' is hydrogen or alkyl as indicated above, and R is heterocycloalkyl as indicated above.

The term "ureido" is intended to indicate a radical of the formula "—NR'—C(O)—NH—R, wherein R' is hydrogen or alkyl as indicated above, and R is hydrogen, alkyl, alkenyl, alkynyl, cycloalkyl or aryl as indicated above.

The term "thioureido" is intended to indicate a radical of the formula "—NR'—C(S)—NH—R, wherein R' is hydrogen or alkyl as indicated above, and R is hydrogen, alkyl, or cycloalkyl as indicated above.

The term "pharmaceutically acceptable salt" is intended to indicate salts prepared by reacting a compound of formula I with a suitable inorganic or organic acid, such as hydrochloric, hydrobromic, hydroiodic, sulfuric, nitric, phosphoric, formic, acetic, 2,2-dichloroacetic, choline, adipic, ascorbic, L-aspartic, L-glutamic, galactaric, lactic, maleic, L-malic, phthalic, citric, propionic, benzoic, glutaric, gluconic, D-glucuronic, methanesulfonic, salicylic, succinic, malonic, tartaric, benzenesulfonic, ethane-1,2-disulfonic, 2-hydroxy ethanesulfonic acid, toluenesulfonic, sulfamic or fumaric acid. Pharmaceutically acceptable salts of compounds of formula I may also be prepared by reaction with a suitable base such as sodium hydroxide, potassium hydroxide, magnesium hydroxide, calcium hydroxide, ammonia, or suitable non-toxic amines, such as lower alkylamines, for example triethylamine, hydroxy-lower alkylamines, for example 2-hydroxyethylamine, bis-(2-hydroxyethyl)-amine, cycloalkylamines, for example dicyclohexylamine, or benzylamines, for example N,N'-dibenzylethylene-diamine, and dibenzylamine, or L-arginine or L-lysine.

The term "solvate" is intended to indicate a species formed by interaction between a compound, e.g. a compound of formula I, and a solvent, e.g. alcohol, glycerol or water, wherein said species are in a solid form. When water is the solvent, said species is referred to as a hydrate.

The term "pharmaceutically acceptable in vivo hydrolysable ester" is intended to indicate easily in vivo hydrolysable esters, i.e. in vivo hydrolysable esters of the compounds of formula I such as alkanoyloxyalkyl, aralkanoyloxyalkyl, aroyloxyalkyl, e.g. acetoxymethyl, pivaloyloxymethyl, benzoyloxymethyl esters and the corresponding 1'-oxyethyl derivatives, or alkoxycarbonyloxyalkyl esters, e.g. methoxycarbonyloxymethyl esters and ethoxycarbonyloxymethyl esters and the corresponding 1'-oxyethyl derivatives, or lactonyl esters, e.g. phthalidyl esters, or dialkylaminoalkyl esters, e.g. dimethylaminoethyl esters. Such esters may be prepared by conventional methods known to persons skilled in the art, such as method disclosed in GB patent No. 1 490 852 incorporated herein by reference.

Compounds of formula I may comprise asymmetrically substituted (chiral) carbon atoms and carbon-carbon double bonds which may give rise to the existence of isomeric forms, e.g. enantiomers, diastereomers and geometric isomers. The present invention includes all such isomers, either in pure form or as mixtures thereof. Pure stereoisomeric forms of the compounds and the intermediates of this invention may be obtained by the application of procedures known in the art. Diastereomers may be separated by physical separation methods such as selective crystallization and chromatographic techniques, e.g. liquid chromatography using chiral stationary phases. Enantiomers may be separated from each other by the selective crystallization of their diastereomeric salts with optically active acids. Alternatively, enantiomers may be separated by chromatographic techniques using chiral stationary phases. Said pure stereoisomeric forms may also be derived from the corresponding pure stereoisomeric forms of the appropriate starting materials, provided that the reaction occurs stereoselectively or stereospecifically. Preferably, if a specific stereoisomer is desired, said compound will be synthesized by stereoselective or stereospecific methods of preparation. These methods will advantageously employ chirally pure starting materials. Likewise, pure geometric isomers may be obtained from the corresponding pure geometric isomers of the appropriate starting materials. A mixture of geometric isomers will typically exhibit different physical properties, and they may thus be separated by standard chromatographic techniques well-known in the art.

The present invention further includes prodrugs of compounds of general formula I, such as esters, ethers, complexes or other derivatives which undergo a biotransformation in vivo before exhibiting their pharmacological effects.

The compounds of formula I may be obtained in crystalline form either directly by concentration from an organic solvent or by crystallisation or recrystallisation from an organic solvent or mixture of said solvent and a cosolvent that may be organic or inorganic, such as water. The crystals may be isolated in essentially solvent-free form or as a solvate, such as a hydrate. The invention covers all crystalline modifications and forms and also mixtures thereof.

EMBODIMENTS

In one embodiment of the present invention, compound I represents:

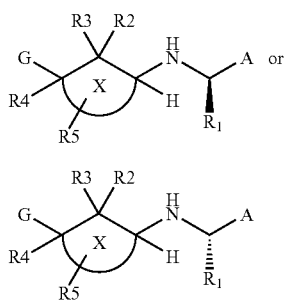

In one embodiment of the present invention,

represents:

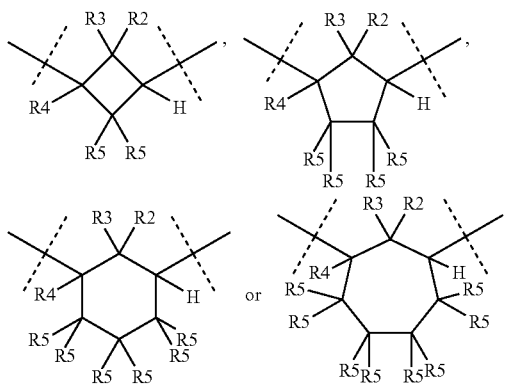

In another embodiment of the present invention $R_2$ and $R_3$ represent hydrogen.

In another embodiment of the present invention A represents 1-naphthyl.

In another embodiment of the present invention G represents —C(O)—$R_6$, wherein $R_6$ represents —$NH_2$, $C_{1-6}$amino, hydroxy, mercapto, —C(O)$NH_2$, trifluoromethyl, carboxy, $C_{1-6}$alkyl, $C_{2-4}$alkenyl, $C_{2-4}$alkynyl, $C_{1-4}$hydroxyalkyl, $C_{1-6}$haloalkyl, $C_{1-4}$alkoxy, $C_{1-4}$alkoxycarbonyl, $C_{1-4}$aminocarbonyl, $C_{3-6}$cycloalkyl, $C_{3-6}$cycloalkenyl, $C_{1-6}$heterocycloalkenyl, $C_{3-6}$cycloalkylamino, $C_{1-6}$heterocycloalkyl, $C_{1-6}$heterocycloalkylcarbonyl, $C_{6-14}$aryl, $C_{1-6}$heteroaryl, $C_{6-10}$arylamino, carboxy$C_{6-10}$aryl, $C_{1-4}$alkylcarbonyloxy, $C_{1-4}$alkoxycarbonyloxy, $C_{1-4}$alkoxysulfonyloxy, $C_{1-4}$alkylthio, $C_{1-4}$aminocarbonyloxy, $C_{1-4}$alkylsulfonylamino, $C_{1-4}$alkylcarbonylamino, $C_{1-4}$alkenylcarbonylamino, $C_{3-6}$cycloalkenylcarbonylamino, $C_{3-6}$cycloalkylcarbonylamino, $C_{1-4}$alkoxycarbonylamino, $C_{6-10}$arylcarbonylamino or $C_{6-10}$arylsulfonylamino, wherein said $C_{1-6}$amino, $C_{1-6}$alkyl, $C_{2-4}$alkenyl, $C_{2-4}$alkynyl, $C_{1-4}$hydroxyalkyl, $C_{1-6}$haloalkyl, $C_{1-4}$alkoxy, $C_{1-4}$alkoxycarbonyl, $C_{1-4}$aminocarbonyl, $C_{3-6}$cycloalkyl, $C_{3-6}$cycloalkenyl, $C_{1-6}$heterocycloalkenyl, $C_{3-6}$cycloalkylamino, $C_{1-6}$heterocycloalkyl, $C_{1-6}$heterocycloalkylcarbonyl, $C_{6-14}$aryl, $C_{1-6}$heteroaryl, $C_{6-10}$arylamino, carboxy$C_{6-10}$aryl, $C_{1-4}$alkylcarbonyloxy, $C_{1-4}$alkoxycarbonyloxy, $C_{1-4}$alkoxysulfonyloxy, $C_{1-4}$alkylthio, $C_{1-4}$aminocarbonyloxy, $C_{1-4}$alkylsulfonylamino, $C_{1-4}$alkylcarbonylamino, $C_{1-4}$alkenylcarbonylamino, $C_{3-6}$cycloalkenylcarbonylamino, $C_{3-6}$cycloalkylcarbonylamino, $C_{1-4}$alkoxycarbonylamino, $C_{6-10}$arylcarbonylamino or $C_{6-10}$arylsulfonylamino, may further be optionally substituted with one or more same or different substituents represented by hydroxy, halogen, $C_{1-4}$alkyl, $C_{1-3}$alkoxy, $C_{1-4}$alkoxycarbonyl, $C_{1-6}$heterocycloalkyl, $C_{6-12}$aryl or oxo, wherein said $C_{1-4}$alkyl, $C_{1-3}$alkoxy, $C_{1-4}$alkoxycarbonyl, $C_{1-6}$heterocycloalkyl or $C_{6-12}$aryl are optionally further substituted with trifluoromethyl, halogen, $C_{1-4}$alkyl, $C_{1-3}$alkoxy or $C_{1-4}$alkoxycarbonyl.

In yet another embodiment of the present invention G represents —C(O)$NH_2$, $C_{1-4}$aminocarbonyl, $C_{4-5}$heterocycloalkylcarbonyl, $C_{6-10}$arylaminocarbonyl, $C_{6-10}$arylsulfonylaminocarbonyl, wherein said $C_{1-4}$aminocarbonyl, $C_{4-5}$heterocycloalkylcarbonyl, $C_{6-10}$arylaminocarbonyl or $C_{6-10}$arylsulfonylaminocarbonyl are optionally substituted with one or more, same or different substituents selected from oxo, hydroxy, $C_{1-4}$alkyl, $C_{1-3}$alkoxy, $C_{1-3}$alkoxycarbonyl, $C_{4-5}$heterocycloalkyl, $C_{6-10}$aryl, wherein said $C_{1-4}$alkyl, $C_{1-3}$alkoxy, $C_{1-3}$alkoxycarbonyl, $C_{4-5}$heterocycloalkyl or $C_{6-10}$aryl are optionally substituted with one or more, same or different substituents represented by halogen, trifluoromethyl, $C_{1-3}$alkoxy or $C_{1-3}$alkoxycarbonyl.

In yet another embodiment of the present invention G represents methylpiperazinylcarbonyl, cyclopropylaminocarbonyl, isopropylaminocarbonyl, propylaminocarbonyl, morpholinocarbonyl, dimethylaminocarbonyl, isobutylaminocarbonyl, ethylaminocarbonyl, N-methoxy-N-methylaminocarbonyl, methoxycarbonylmethyleneaminocarbonyl, methoxyethyleneaminocarbonyl, ethoxycarbonylphenyleneaminocarbonyl, dimethylmorpholinocarbonyl, morpholinopropylaminocarbonyl, ethoxycarbonylpiperidinocarbonyl, chlorobenzylaminocarbonyl, phenylhydroxyethylaminocarbonyl, ethoxycarbonylethyleneaminocarbonyl, trifluoromethylphenylenepiperazinylcarbonyl, hydroxyindanylaminocarbonyl, phenylmethoxycarbonylmethyleneaminocarbonyl, methoxyethylenepiperazinylcarbonyl, trifluorobenzylaminocarbonyl, methoxycarbonylbenzylaminocarbonyl, methylphenylenesulfonylaminocarbonyl or carboxyphenylmethyleneaminocarbonyl.

In yet another embodiment of the present invention G represents phenyl optionally substituted with one or more, same or different substituents selected from —C(O)H, —C(O)$NH_2$, hydroxy, halogen, cyano, nitro, amidino, carboxy, trifluoromethyl, $C_{1-6}$alkyl, $C_{2-4}$alkenyl, $C_{2-4}$alkynyl, $C_{1-4}$hydroxyalkyl, $C_{1-6}$amino, amino$C_{1-3}$alkyl, iminomethyl, hydroxyiminomethyl, $C_{1-6}$haloalkyl, $C_{1-4}$alkoxy, $C_{1-4}$alkoxycarbonyl, $C_{1-3}$alkoxycarbamoyl, $C_{1-4}$aminocarbonyl, $C_{1-3}$alkylsulfonylaminocarbonyl, hydroxyaminocarbonyl, $C_{1-6}$heterocycloalkyloxy, $C_{1-6}$heterocycloalkylaminocarbonyl, $C_{3-6}$cycloalkylaminocarbonyl, $C_{6-10}$arylaminocarbonyl, $C_{1-10}$heteroarylaminocarbonyl, $C_{3-6}$cycloalkyl, $C_{1-6}$heterocycloalkyl, $C_{1-6}$heterocycloalkenyl, $C_{1-6}$heterocycloalkylcarbonyl, $C_{1-4}$alkylcarbonyloxy, $C_{1-4}$alkoxycarbonyloxy, $C_{1-4}$alkoxysulfonyloxy, $C_{1-4}$alkylthio, $C_{3-6}$cycloalkenyl, $C_{1-4}$aminosulfonyl, $C_{1-4}$aminocarbonyloxy, $C_{1-4}$alkylsulfonylamino, $C_{1-10}$heteroaryl, $C_{6-10}$arylamino, $C_{6-10}$aryloxycarbonyl, $C_{6-10}$arylcarbonylamino, $C_{6-10}$arylsulfonylamino, $C_{1-4}$alkylcarbonylamino, $C_{1-4}$alkenylcarbonylamino, $C_{3-6}$cycloalkenylcarbonylamino, $C_{3-6}$cycloalkylcarbonylamino, $C_{1-4}$alkoxycarbonylamino, $C_{1-6}$heterocycloalkylcarbonylamino, $C_{1-4}$alkylsulfonyl or $C_{1-6}$heterocycloalkylsulfonyl, wherein said $C(O)NH_2$, $C_{2-4}$alkenyl, $C_{2-4}$alkynyl, $C_{1-4}$hydroxyalkyl, $C_{1-6}$amino, amino$C_{1-3}$alkyl, iminomethyl, hydroxyiminomethyl, $C_{1-4}$alkoxy, $C_{1-4}$alkoxycarbonyl, $C_{1-3}$alkoxycarbamoyl, $C_{1-4}$aminocarbonyl, $C_{1-3}$alkylsulfonylaminocarbonyl, hydroxyaminocarbonyl, $C_{1-6}$heterocycloalkyloxy, $C_{1-6}$heterocycloalkylaminocarbonyl, $C_{3-6}$cycloalkylaminocarbonyl, $C_{6-10}$arylaminocarbonyl, $C_{1-10}$heteroarylaminocarbonyl, $C_{3-6}$cycloalkyl, $C_{1-6}$heterocycloalkyl, $C_{1-6}$heterocycloalkenyl, $C_{1-6}$heterocycloalkylcarbonyl, $C_{1-4}$alkylcarbonyloxy, $C_{1-4}$alkoxycarbonyloxy, $C_{1-4}$alkoxysulfonyloxy, $C_{1-4}$alkylthio, $C_{3-6}$cycloalkenyl, $C_{1-4}$aminosulfonyl, $C_{1-4}$aminocarbonyloxy, $C_{1-4}$alkylsulfonylamino, $C_{1-10}$heteroaryl, $C_{6-10}$arylamino, $C_{6-10}$aryloxycarbonyl, $C_{6-10}$arylcarbonylamino, $C_{6-10}$arylsulfonylamino, $C_{1-4}$alkylcarbonylamino, $C_{1-4}$alkenylcarbonylamino, $C_{3-6}$cycloalkenylcarbonylamino, $C_{3-6}$cycloalkylcarbonylamino, $C_{1-4}$alkoxycarbonylamino, $C_{1-6}$heterocycloalkylcarbonylamino, $C_{1-4}$alkylsulfonyl, or $C_{1-6}$heterocycloalkylsulfonyl are optionally further substituted with one or more, same or different substituents selected from the group consisting of hydroxy, —$NH_2$, $C_{1-6}$amino, iminomethyl, hydroxyiminomethyl, carboxy, trifluoromethyl, halogen, oxo, mercapto, cyano, —$C(O)NH_2$, nitro, $C_{1-6}$alkyl, $C_{2-4}$alkenyl, $C_{2-4}$alkynyl, $C_{1-4}$hydroxyalkyl, $C_{1-3}$alkoxy, $C_{1-4}$alkoxycarbonyl, $C_{1-6}$heterocycloalkylcarbonyl, $C_{3-6}$cycloalkyl, $C_{3-6}$cycloalkenyl, $C_{1-6}$heterocycloalkyl, $C_{6-12}$aryl, $C_{1-10}$heteroaryl, $C_{1-3}$alkoxy$C_{6-10}$aryl, $C_{1-10}$heterocycloalkylaryl, $C_{1-6}$heterocycloalkenyl, —$S(O)_2NH_2$, —$S(O)_2OH$, $C_{1-6}$ureido, $C_{1-6}$thioureido, $C_{1-4}$alkylcarbonyloxy, $C_{1-4}$alkoxycarbonyloxy, $C_{1-4}$alkoxysulfonyloxy, $C_{1-4}$alkoxycarbamoyl, $C_{1-4}$aminocarbonyl, $C_{1-4}$alkylthio, $C_{1-4}$aminosulfonyl, $C_{1-4}$aminocarbonyloxy, $C_{1-4}$alkylsulfonylamino, $C_{6-12}$arylsulfonyl, $C_{6-10}$arylsulfonylamino, $C_{1-4}$alkylcarbonylamino or $C_{1-4}$alkylsulfonyl, wherein said $C_{3-6}$cycloalkyl, $C_{1-6}$alkyl, $C_{1-3}$alkoxy, $C_{1-4}$alkoxycarbonyl, $C_{1-6}$heterocycloalkyl, $C_{6-10}$aryl or $C_{1-10}$heteroaryl may be further substituted with carboxy, halogen, hydroxy, cyano, $C_{1-6}$heterocycloalkyl, one or more $C_{1-6}$alkyl, $C_{1-3}$alkoxy, $C_{1-3}$alkoxy$C_{1-3}$alkoxy $C_{1-4}$alkoxycarbonyl, $C_{1-3}$hydroxyalkyl or $C_{6-10}$aryl.

In yet another embodiment of the present invention G represents phenyl substituted with one or more same or different substituents selected from cyano, carboxy, —$C(O)H$, —$C(O)NH_2$, hydroxyl, halogen, amidino, iminomethyl, hydroxyiminomethyl, $C_{1-6}$alkyl, $C_{2-4}$alkynyl, amino$C_{1-3}$alkyl, $C_{1-3}$alkoxy, $C_{1-3}$alkoxycarbonyl, $C_{1-4}$alkoxycarbamoyl, $C_{1-3}$aminosulfonyl, $C_{3-6}$cycloalkyl, $C_{1-6}$heterocycloalkyl, $C_{1-6}$heterocycloalkylcarbonyl, $C_{1-6}$heterocycloalkyloxy, $C_{1-3}$aminocarbonyloxy, $C_{1-10}$heteroaryl, $C_{6-10}$arylamino, $C_{6-10}$aryloxycarbonyl, $C_{1-3}$alkylsulfonylaminocarbonyl, hydroxyaminocarbonyl, $C_{1-3}$alkylsulfonyl, $C_{1-6}$heterocycloalkylsulfonyl, $C_{1-6}$heterocycloalkylaminocarbonyl, $C_{3-6}$cycloalkylaminocarbonyl, $C_{6-10}$arylaminocarbonyl, $C_{1-3}$aminosulfonyl, $C_{1-10}$heteroarylaminocarbonyl, $C_{1-3}$alkylcarbonylamino, $C_{1-3}$alkylsulfonylamino or $C_{6-10}$arylsulfonylamino, each of which is optionally substituted with one or more same or different substituents selected from hydroxy, —$NH_2$, $C_{1-3}$amino, iminomethyl, carboxy, trifluoromethyl, cyano, fluoro, chloro, iodo, oxo, mercapto, $C_{1-4}$alkyl, $C_{1-3}$hydroxyalkyl, $C_{1-2}$alkoxy, $C_{1-4}$alkoxycarbonyl, $C_{3-6}$cycloalkyl, $C_{3-5}$heterocycloalkyl, $C_{1-6}$heterocycloalkylcarbonyl, $C_{6-10}$aryl, $C_{1-10}$heteroaryl, $C_{1-2}$alkoxy$C_{6-10}$aryl, $C_{1-3}$alkylsulfonylamino, —$S(O)_2OH$ or $C_{1-3}$alkylcarbonylamino, wherein said $C_{3-6}$cycloalkyl, $C_{1-4}$alkyl, $C_{1-2}$alkoxy, $C_{1-4}$alkoxycarbonyl, $C_{1-6}$heterocycloalkyl, $C_{6-10}$aryl or $C_{1-10}$heteroaryl are optionally further substituted with carboxy, halogen, hydroxy, cyano, $C_{1-6}$heterocycloalkyl, one or more $C_{1-6}$alkyl, $C_{1-3}$alkoxy, $C_{1-3}$alkoxy$C_{1-3}$alkoxy, $C_{1-4}$alkoxycarbonyl, $C_{1-3}$hydroxyalkyl or $C_{6-10}$aryl, such as hydroxymethylpyrrolidinylcarbonyl, ethylaminocarbonyl, dimethylaminoethylmethylaminocarbonyl, pyrrolidinyliminomethyl, amidino, aminohydroxyiminomethyl, methoxycarbonyl, ethoxycarbonyl, hydroxyethylaminocarbonyl, N-hydroxyethyl-N-methylaminocarbonyl, N-hydroxyethyl-N-propylaminocarbonyl, bishydroxyethylaminocarbonyl, dihydroxytert-butylaminocarbonyl, N-hydroxyethyl-N-ethylaminocarbonyl, cyanoethylaminocarbonyl, morpholinoethylaminocarbonyl, fluoroethylaminocarbonyl, difluoroethylaminocarbonyl, methoxycarbonylethylaminocarbonyl, N-pyridylmethyl-N-methylaminocarbonyl, benzyloxycarbamoyl, methylcarbonylaminoethylaminocarbonyl, iodophenyleneoxycarbonyl, methoxyethylaminocarbonyl, mercaptoethylaminocarbonyl, ethoxycarbonylmethylaminocarbonyl, sulfoethylaminocarbonyl, dimethylaminocarbonyl, dimethylaminoethylaminocarbonyl, dimethylaminopropylaminocarbonyl, piperidinocarbonyl, methylpiperazinylcarbonyl, hydroxyethylpiperazinylcarbonyl, morpholinocarbonyl, hydroxypiperidinocarbonyl, imidazolylpropylaminocarbonyl, carboxymethylaminocarbonyl, tert-butoxycabonylmethoxycarbonylethylaminocarbonyl, tert-butoxycarbonylcarboxyethylaminocarbonyl, methoxycarbonylphenylethylaminocarbonyl, carboxyphenylethylaminocarbonyl, methoxycarbonylindolylethylaminocarbonyl, carboxyindolylethylaminocarbonyl, N-ethoxycarbonylmethyl-N-cyclohexylaminocarbonyl, diethoxycarbonylmethylaminocarbonyl, tert-butoxycarbonylhydroxyethylaminocarbonyl, carboxypyridylaminocarbonyl, carboxyphenylaminocarbonyl, methoxyethoxycarbonylphenylaminocarbonyl, N,N-dicarboxymethylaminocarbonyl, carboxycyclopentylmethylaminocarbonyl, carboxyethylaminocarbonyl, carboxymethylcyclohexylaminocarbonyl, ethylcarboxycyclopropylaminocarbonyl, carboxycyclopropylaminocarbonyl, carboxyisopropylaminocarbonyl, carboxyazetidinylcarbonyl, N-methyl-N-carboxymethylaminocarbonyl, carboxypropylaminocarbonyl, ethoxycarbonylpiperidylcarbocyl, carboxypiperidylcarbonyl, N-carboxymethyl-N-cyclohexylaminocarbonyl, oxotetrahydrofurylaminocarbonyl, cyanomethylaminocarbonyl, cyanopyrazolaminocarbonyl, phenylmethoxycarbonylhydroxyethylaminocarbonyl, methoxycarbonylhydroxyethylaminocarbonyl, ethoxycarbonylhydroxyethylaminocarbonyl, carboxyhydroxyethylaminocarbonyl, carboxyhydroxypropylaminocarbonyl, tert-butoxyaminocarbonyl, methoxyaminocarbonyl, tetrahydrofurylmethoxyaminocarbonyl, N-methoxy-N-methylaminocarbonyl, phenylmethoxyaminocarbonyl, hydroxyaminocarbonyl, morpholinocarbonylmethoxyaminocarbonyl, methylsulfonylaminocarbonyl, methoxycarbonylhydroxypyrrolidinylcarbonyl, carboxyhydroxypyrrolidinylcarbonyl, ethoxycarbonylmethoxy, methoxycarbonylethyl, carboxymethoxy or carboxyethyl.

In one embodiment when G represents phenyl being further substituted the substituent is attached to the phenylene ring in the meta or para position from where the phenyl ring is attached to the cycloalkyl representing

In another embodiment when G represents phenyl being further substituted, the substituent is attached to the phenylene ring in the ortho position from where the phenyl ring is attached to the cycloalkyl representing

In yet another embodiment of the present invention G represents $C_{1-10}$heteroaryl or $C_{1-6}$heterocycloalkyl and wherein said $C_{1-10}$heteroaryl or $C_{1-6}$heterocycloalkyl is optionally substituted with carboxy, $C_{1-6}$alkyl, $C_{6-10}$aryl, $C_{1-3}$alkoxycarbonyl, which may further be optionally substituted with trifluoromethyl, halogen, $C_{1-3}$alkyl, $C_{1-3}$alkoxy, $C_{1-10}$heteroaryl, wherein $C_{1-10}$heteroaryl may further be substituted with $C_{1-3}$alkyl or oxo, such as fluorophenylene[1,2,4]oxadiazolyl, phenyl[1,2,4]oxadiazolyl, isopropyl[1,2,4]oxadiazolyl, trifluoromethylphenylene[1,2,4]oxadiazolyl, methyl[1,2,4]oxadiazolyl, methylthiazolylmethylene[1,2,4]oxadiazolyl, propyl[1,2,4]oxadiazolyl, oxopyridinylmethylene[1,2,4]oxadiazolyl, methoxyphenylene[1,2,4]oxadiazolyl, methylcarboxylmidazolyl, ethoxycarbonylthienyl, ethoxycarbonylfuryl, pyridyl, carboxythienyl or carboxyfuryl.

In yet another embodiment of the present invention G represents phenylamino or phenyloxy, optionally substituted with cyano, carboxy, $C_{1-4}$alkoxycarbonyl or trifluoromethyl.

In yet another embodiment of the present invention A represents 1-naphthyl, 2-naphthyl or phenyl, each of which is optionally substituted as defined above for the substitution of $C_{6-14}$aryl representing A.

In yet another embodiment of the present invention $R_4$ represents hydrogen, hydroxy, halogen or $C_{1-6}$alkyl.

In yet another embodiment of the present invention $R_5$ represents hydrogen or $C_{1-6}$alkyl.

In yet another embodiment of the present invention $R_2$, $R_3$, $R_4$ and $R_5$ represent hydrogen.

In yet another embodiment of the present invention $R_1$ represents methyl, ethyl or n-propyl, optionally substituted with halogen or hydroxy, such as methyl.

In yet another embodiment, the present invention relates to compounds of general formula I, wherein G represents $C_{6-10}$aryl, $C_{1-3}$aminocarbonyl$C_{6-10}$aryl or $C_{1-4}$alkyl$C_{6-10}$aryl optionally substituted with carboxy, $C_{1-3}$alkoxy or $C_{1-3}$alkoxycarbonyl, A represents 1-naphthyl, $R_2$, $R_3$, $R_4$ and $R_5$ represent hydrogen and $R_1$ represents methyl.

Specific examples of compounds of formula I may be selected from the group consisting of 3-((R)-1-naphthalen-1-yl-ethylamino)-cyclobutanecarboxylic acid (compound 1000),
cyclobutyl-((R)-1-naphthalen-1-yl-ethyl)-amine, hydrochloride (compound 1001),
3-((R)-1-naphthalen-1-yl-ethylamino)-cyclobutanecarboxylic acid dimethylamide (compound 1002),
3-((R)-1-naphthalen-1-yl-ethylamino)-cyclobutanecarboxylic acid amide (compound 1003),
(4-Methyl-piperazin-1-yl)-[3-((R)-1-naphthalen-1-yl-ethylamino)-cyclobutyl]-methanone; hydrochloride (compound 1004),
3-((R)-1-naphthalen-1-yl-ethylamino)-cyclobutanecarboxylic acid cyclopropylamide (compound 1005),
3-((R)-1-naphthalen-1-yl-ethylamino)-cyclobutanecarboxylic acid isopropylamide (compound 1006),
3-((R)-1-naphthalen-1-yl-ethylamino)-cyclobutanecarboxylic acid propylamide (compound 1007),
Morpholin-4-yl-[3-((R)-1-naphthalen-1-yl-ethylamino)-cyclobutyl]-methanone (compound 1008),
3-((R)-1-naphthalen-1-yl-ethylamino)-cyclobutanecarboxylic acid tert-butylamide (compound 1009),
3-((R)-1-naphthalen-1-yl-ethylamino)-cyclobutanecarboxylic acid ethylamide (compound 1010),
3-((R)-1-naphthalen-1-yl-ethylamino)-cyclobutanecarboxylic acid methoxy-methyl-amide; hydrochloride (compound 1011),
[3-(3-Isopropyl-[1,2,4]oxadiazol-5-yl)-cyclobutyl]-((R)-1-naphthalen-1-yl-ethyl)-amine; hydrochloride (compound 1012),
((R)-1-Naphthalen-1-yl-ethyl)-{3-[3-(3-trifluoromethyl-phenyl)-[1,2,4]oxadiazol-5-yl]-cyclobutyl}-amine; hydrochloride (compound 1013),
[3-(3-Methyl-[1,2,4]oxadiazol-5-yl)-cyclobutyl]-((R)-1-naphthalen-1-yl-ethyl)-amine; hydrochloride (compound 1014),
((R)-1-Naphthalen-1-yl-ethyl)-[3-(3-phenyl-[1,2,4]oxadiazol-5-yl)-cyclobutyl]-amine; hydrochloride (compound 1015),
((R)-1-Naphthalen-1-yl-ethyl)-{3-[3-(4-trifluoromethyl-phenyl)-[1,2,4]oxadiazol-5-yl]-cyclobutyl}-amine; hydrochloride (compound 1016),
{3-(3-[3-(4-Methoxy-phenyl)-[1,2,4]oxadiazol-5-yl]-cyclobutyl}-((R)-1-naphthalen-1-yl-ethyl)-amine; hydrochloride (compound 1017),
3-((R)-1-Naphthalen-1-yl-ethylamino)-cyclobutanecarboxylic acid 4-chloro-benzylamide (compound 1018),
{[3-((R)-1-Naphthalen-1-yl-ethylamino)-cyclobutanecarbonyl]-amino}-acetic acid methyl ester (compound 1019),
3-((R)-1-Naphthalen-1-yl-ethylamino)-cyclobutanecarboxylic acid (2-methoxy-ethyl)-amide (compound 1020),
4-{[3-((R)-1-Naphthalen-1-yl-ethylamino)-cyclobutanecarbonyl]-amino}-benzoic acid ethyl ester (compound 1021),
(2,6-Dimethyl-morpholin-4-yl)-[3-((R)-1-naphthalen-1-yl-ethylamino)-cyclobutyl]-methanone (compound 1022),
3-((R)-1-Naphthalen-1-yl-ethylamino)-cyclobutanecarboxylic acid (3-morpholin-4-yl-propyl)-amide (compound 1023),
1-[3-((R)-1-Naphthalen-1-yl-ethylamino)-cyclobutanecarbonyl]-piperidine-4-carboxylic acid ethyl ester (compound 1024),
3-((R)-1-Naphthalen-1-yl-ethylamino)-cyclobutanecarboxylic acid (2-hydroxy-2-phenyl-ethyl)-amide (compound 1025),
3-{[3-((R)-1-Naphthalen-1-yl-ethylamino)-cyclobutanecarbonyl]-amino}-propionic acid ethyl ester (compound 1026),

[3-((R)-1-Naphthalen-1-yl-ethylamino)-cyclobutyl]-[4-(3-trifluoromethyl-phenyl)-piperazin-1-yl]-methanone (compound 1027),
{[3-((R)-1-Naphthalen-1-yl-ethylamino)-cyclobutanecarbonyl]-amino}-phenyl-acetic acid methyl ester (compound 1028),
3-((R)-1-Naphthalen-1-yl-ethylamino)-cyclobutanecarboxylic acid (2-hydroxy-indan-1-yl)-amide (compound 1029),
[4-(2-Methoxy-ethyl)-piperazin-1-yl]-[3-((R)-1-Naphthalen-1-yl-ethylamino)-cyclobutyl]-methanone (compound 1030),
3-((R)-1-Naphthalen-1-yl-ethylamino)-cyclobutanecarboxylic acid 2,3,6-trifluoro-benzylamide (compound 1031),
3-({[3-((R)-1-Naphthalen-1-yl-ethylamino)-cyclobutanecarbonyl]-amino}-methyl)-benzoic acid methyl ester (compound 1032),
4-({[3-((R)-1-Naphthalen-1-yl-ethylamino)-cyclobutanecarbonyl]-amino}-methyl)-benzoic acid methyl ester (compound 1033),
{[3-((R)-1-Naphthalen-1-yl-ethylamino)-cyclobutanecarbonyl]-amino}-phenyl-acetic acid (compound 1034),
((R)-1-Naphthalen-1-yl-ethyl)-(3-phenyl-cyclobutyl)-amine (compound 1035 and compound 1036),
{3-[3-(4-Fluoro-phenyl)-[1,2,4]oxadiazol-5-yl]-cyclopentyl}-((R)-1-naphthalen-1-yl-ethyl)-amine; hydrochloride (compound 1037),
((R)-1-Naphthalen-1-yl-ethyl)-[3-(3-phenyl-[1,2,4]oxadiazol-5-yl)-cyclopentyl]-amine; hydrochloride (compound 1038),
[3-(3-Isopropyl-[1,2,4]oxadiazol-5-yl)-cyclopentyl]-(R)-1-naphthalen-1-yl-ethyl)-amine; hydrochloride (compound 1039),
((R)-1-Naphthalen-1-yl-ethyl)-{3-[3-(4-trifluoromethyl-phenyl)-[1,2,4]oxadiazol-5-yl]-cyclopentyl}-amine; hydrochloride (compound 1040),
[3-(3-Methyl-[1,2,4]oxadiazol-5-yl)-cyclopentyl]-((R)-1-naphthalen-1-yl-ethyl)-amine; hydrochloride (compound 1041),
{3-[3-(5-Methyl-thiazol-2-ylmethyl)-[1,2,4]oxadiazol-5-yl]-cyclopentyl}-((R)-1-naphthalen-1-yl-ethyl)-amine (compound 1042),
((R)-1-naphthalen-1-yl-ethyl)-[3-(3-propyl-[1,2,4]oxadiazol-5-yl)-cyclopentyl]-amine; hydrochloride (compound 1043a and 1043b),
1-{5-[3-((R)-1-Naphthalen-1-yl-ethylamino)-cyclopentyl]-[1,2,4]oxadiazol-3-ylmethyl}-1H-pyridin-2-one; hydrochloride (compound 1044),
{3-[3-(4-Methoxy-phenyl)-[1,2,4]oxadiazol-5-yl]-cyclopentyl}-((R)-1-naphthalen-1-yl-ethyl)-amine; hydrochloride (compound 1045),
3-((R)-1-Naphthalen-1-yl-ethylamino)-cyclopentanecarboxylic acid amide (compound 1046),
4-Methyl-N-[3-((R)-1-naphthalen-1-yl-ethylamino)-cyclopentane carbonyl]-benzenesulfonamide (compound 1047a, compound 1047b, compound 1047c and compound 1047d),
4-[3-((R)-1-Naphthalen-1-yl-ethylamino)-cyclohexyl]-benzonitrile (compounds 1048/1049/1050),
N-Hydroxy-4-[3-((R)-1-naphthalen-1-yl-ethylamino)-cyclohexyl]-benzamidine (compound 1051),
N-Hydroxy-4-[3-((R)-1-naphthalen-1-yl-ethylamino)-cyclohexyl]-benzamidine (compound 1052),
N-Hydroxy-4-[3-((R)-1-naphthalen-1-yl-ethylamino)-cyclohexyl]-benzamidine (compound 1053a and compound 1053b),
{3-[4-(Imino-pyrrolidin-1-yl-methyl)-phenyl]-cyclohexyl}-((R)-1-naphthalen-1-yl-ethyl)-amine (compound 1054),
4-[3-((R)-1-naphthalen-1-yl-ethylamino)-cyclohexyl]-benzamidine (compound 1055),
4-[3-((R)-1-naphthalen-1-yl-ethylamino)-cyclohexyl]-benzoic acid (compound 1056),
4-[3-((R)-1-naphthalen-1-yl-ethylamino)-cyclohexyl]-benzoic acid (compound 1057),
4-[3-((R)-1-naphthalen-1-yl-ethylamino)-cyclohexyl]-benzoic acid (compound 1058, 1058a),
3-[3-((R)-1-naphthalen-1-yl-ethylamino)-cyclohexyl]-benzoic acid ethyl ester (compound 1059),
N-(2-Hydroxy-ethyl)-3-[3-((R)-1-naphthalen-1-yl-ethylamino)-cyclohexyl]-benzamide (compound 1060),
3-[3-((R)-1-naphthalen-1-yl-ethylamino)-cyclohexyl]-benzoic acid (compounds 1061/1062),
((R)-1-Naphthalen-1-yl-ethyl)-(3 (S)-phenyl-cyclohexyl)-amine (compound 1063),
((R)-1-Naphthalen-1-yl-ethyl)-(3 (R)-phenyl-cyclohexyl)-amine (compound 1064),
N—((R)-1-Naphthalen-1-yl-ethyl)-N'-phenyl-cyclohexane-1,3-diamine (compound 1065),
N—((R)-1-Naphthalen-1-yl-ethyl)-N'-(3-trifluoromethyl-phenyl)-cyclohexane-1,3-diamine (compound 1066),
4-[3-((R)-1-Naphthalen-1-yl-ethylamino)-cyclohexylamino]-benzonitrile (compound 1067),
(3-Morpholin-4-yl-cyclohexyl)-((R)-1-naphthalen-1-yl-ethyl)-amine (compound 1068),
((R)-1-Naphthalen-1-yl-ethyl)-(3-pyridin-2-yl-cyclohexyl)-amine (compounds 1069/1070),
5-[3-((R)-1-Naphthalen-1-yl-ethylamino)-cyclohexyl]-thiophene-2-carboxylic acid ethyl ester (compound 1071),
5-[3-((R)-1-Naphthalen-1-yl-ethylamino)-cyclohexyl]-thiophene-2-carboxylic acid (compound 1072),
5-[3-((R)-1-Naphthalen-1-yl-ethylamino)-cyclohexyl]-furan-2-carboxylic acid ethyl ester (compound 1073),
5-[3-((R)-1-Naphthalen-1-yl-ethylamino)-cyclohexyl]-furan-2-carboxylic acid (compound 1074a, compound 1074b and compound 1074c),
{3-[3-(4-Fluoro-phenyl)-[1,2,4]oxadiazol-5-yl]-cyclohexyl}-((R)-1-naphthalen-1-yl-ethyl)-amine (compound 1075),
((R)-1-Naphthalen-1-yl-ethyl)-{3-[3-(4-trifluoromethyl-phenyl)-[1,2,4]oxadiazol-5-yl]-cyclohexyl}-amine (compound 1076),
((R)-1-Naphthalen-1-yl-ethyl)-[3-(3-phenyl-[1,2,4]oxadiazol-5-yl)-cyclohexyl]-amine (compound 1077),
4-[3-((R)-1-Naphthalen-1-yl-ethylamino)-cyclohexyl]-benzamide (compound 1078),
N-Benzyloxy-4-[3-((R)-1-naphthalen-1-yl-ethylamino)-cyclohexyl]-benzamide (compound 1079),
4-[3-((R)-1-Naphthalen-1-yl-ethylamino)-cyclohexyl]-benzoic acid 4-iodo-phenyl ester (compound 1080),
2-{4-[3-((R)-1-Naphthalen-1-yl-ethylamino)-cyclohexyl]-benzoylamino}-ethanesulfonic acid (compound 1081),
N—((R)-1-Hydroxymethyl-propyl)-4-[3-((R)-1-naphthalen-1-yl-ethylamino)-cyclohexyl]-benzamide (compound 1082),
N—((S)-1-Hydroxymethyl-propyl)-4-[3-((R)-1-naphthalen-1-yl-ethylamino)-cyclohexyl]-benzamide (compound 1083),
N-(2-Cyano-ethyl)-4-[3-((R)-1-naphthalen-1-yl-ethylamino)-cyclohexyl]-benzamide (compound 1084),
N-(2-Morpholin-4-yl-ethyl)-4-[3-((R)-1-naphthalen-1-yl-ethylamino)-cyclohexyl]-benzamide (compound 1085),
N-(2-Fluoro-ethyl)-4-[3-((R)-1-naphthalen-1-yl-ethylamino)-cyclohexyl]-benzamide (compound 1086), N-(2,2-Difluoro-ethyl)-4-[3-((R)-1-naphthalen-1-yl-ethyl-amino)-cyclohexyl]-benzamide (compound 1087),
3-{4-[3-((R)-1-Naphthalen-1-yl-ethylamino)-cyclohexyl]-benzoylamino}-propionic acid methyl ester (compound 1088),
N-Methyl-4-[3-((R)-1-naphthalen-1-yl-ethylamino)-cyclohexyl]-N-pyridin-4-ylmethyl-benzamide (compound 1089),
N-(2-Dimethylamino-ethyl)-N-methyl-4-[3-((R)-1-naphthalen-1-yl-ethylamino)-cyclohexyl]-benzamide (compound 1090),
(2-Hydroxymethyl-pyrrolidin-1-yl)-{4-[3-(1-naphthalen-1-yl-ethylamino)-cyclohexyl]-phenyl}-methanone (compound 1091),
N-(2-Acetylamino-ethyl)-4-[3-((R)-1-naphthalen-1-yl-ethylamino)-cyclohexyl]-benzamide (compound 1092),
N-Ethyl-4-[3-((R)-1-naphthalen-1-yl-ethylamino)-cyclohexyl]-benzamide (compound 1093),
N-(2-Hydroxy-ethyl)-4-[3-((R)-1-naphthalen-1-yl-ethyl-amino)-cyclohexyl]-benzamide (compound 1094),
N-(2-Hydroxy-1-hydroxymethyl-1-methyl-ethyl)-4-[3-((R)-1-naphthalen-1-yl-ethylamino)-cyclohexyl]-benzamide (compound 1095),
N-(2-Methoxy-ethyl)-4-[3-((R)-1-naphthalen-1-yl-ethyl-amino)-cyclohexyl]-benzamide (compound 1096),
N-(2-Mercapto-ethyl)-4-[3-((R)-1-naphthalen-1-yl-ethyl-amino)-cyclohexyl]-benzamide (compound 1097),
{4-[3-((R)-1-Naphthalen-1-yl-ethylamino)-cyclohexyl]-benzoylamino}-acetic acid ethyl ester (compound 1098),
N,N-Dimethyl-4-[3-((R)-1-naphthalen-1-yl-ethylamino)-cyclohexyl]-benzamide (compound 1099),
N-(2-Hydroxy-ethyl)-N-methyl-4-[3-((R)-1-naphthalen-1-yl-ethylamino)-cyclohexyl]-benzamide (compound 1100),
N-Ethyl-N-(2-hydroxy-ethyl)-4-[3-((R)-1-naphthalen-1-yl-ethylamino)-cyclohexyl]-benzamide (compound 1101),
N,N-Bis-(2-hydroxy-ethyl)-4-[3-((R)-1-naphthalen-1-yl-ethylamino)-cyclohexyl]-benzamide (compound 1102),
N-(2-Dimethylamino-ethyl)-4-[3-((R)-1-naphthalen-1-yl-ethylamino)-cyclohexyl]-benzamide (compound 1103),
N-(3-Dimethylamino-propyl)-4-[3-((R)-1-naphthalen-1-yl-ethylamino)-cyclohexyl]-benzamide (compound 1104),
{4-[3-((R)-1-Naphthalen-1-yl-ethylamino)-cyclohexyl]-phenyl}-piperidin-1-yl-methanone (compound 1105),
(4-Methyl-piperazin-1-yl)-{4-[3-((R)-1-naphthalen-1-yl-ethylamino)-cyclohexyl]-phenyl}-methanone (compound 1106),
[4-(2-Hydroxy-ethyl)-piperazin-1-yl]-{4-[3-((R)-1-naphthalen-1-yl-ethylamino)-cyclohexyl]-phenyl}-methanone (compound 1107),
Morpholin-4-yl-{4-[3-((R)-1-naphthalen-1-yl-ethylamino)-cyclohexyl]-phenyl}-methanone (compound 1108),
(4-Hydroxy-piperidin-1-yl)-{4-[3-((R)-1-naphthalen-1-yl-ethylamino)-cyclohexyl]-phenyl}-methanone (compound 1109),
N-(3-Imidazol-1-yl-propyl)-4-[3-((R)-1-naphthalen-1-yl-ethylamino)-cyclohexyl]-benzamide (compound 1110),
3-((R)-1-naphthalen-1-yl-ethylamino)-cyclopentanecarboxylic acid (compound 1111),
(S)-2-{4-[(1S,3S)-3-((R)-1-Naphthalen-1-yl-ethylamino)-cyclohexyl]-benzoylamino}-succinic acid 4-tert-butyl ester 1-methyl ester (compound 1116),
(S)-2-{4-[(1S,3S)-3-((R)-1-Naphthalen-1-yl-ethylamino)-cyclohexyl]-benzoylamino}-succinic acid 4-tert-butyl ester (compound 1117),
(R)-2-{4-[(1S,3S)-3-((R)-1-Naphthalen-1-yl-ethylamino)-cyclohexyl]-benzoylamino}-3-phenyl-propionic acid methyl ester (compound 1118),
(R)-2-{4-[(1S,3S)-3-((R)-1-Naphthalen-1-yl-ethylamino)-cyclohexyl]-benzoylamino}-3-phenyl-propionic acid (compound 1119),
(S)-2-{4-[(1S,3S)-3-((R)-1-Naphthalen-1-yl-ethylamino)-cyclohexyl]-benzoylamino}-3-phenyl-propionic acid methyl ester (compound 1120),
(S)-2-{4-[(1S,3S)-3-((R)-1-Naphthalen-1-yl-ethylamino)-cyclohexyl]-benzoylamino}-3-phenyl-propionic acid; hydrochloride (compound 1121),
(S)-3-(1H-Indol-3-yl)-2-{4-[(1S,3S)-3-((R)-1-naphthalen-1-yl-ethylamino)-cyclohexyl]-benzoylamino}-propionic acid methyl ester (compound 1122),
(S)-3-(1H-Indol-3-yl)-2-{4-[(1S,3S)-3-((R)-1-naphthalen-1-yl-ethylamino)-cyclohexyl]-benzoylamino}-propionic acid (compound 1123),
(R)-3-(1H-Indol-3-yl)-2-{4-[(1S,3S)-3-((R)-1-naphthalen-1-yl-ethylamino)-cyclohexyl]-benzoylamino}-propionic acid methyl ester (compound 1124),
(R)-3-(1H-Indol-3-yl)-2-{4-[(1S,3S)-3-((R)-1-naphthalen-1-yl-ethylamino)-cyclohexyl]-benzoylamino}-propionic acid (compound 1125),
(Cyclohexyl-{4-[3-(1-naphthalen-1-yl-ethylamino)-cyclohexyl]-benzoyl}-amino)-acetic acid ethyl ester (compound 1126),
2-{4-[3-((R)-1-Naphthalen-1-yl-ethylamino)-cyclohexyl]-benzoylamino}-malonic acid diethyl ester (compound 1127),
(S)-3-Hydroxy-2-{4-[(1S,3S)-3-((R)-1-naphthalen-1-yl-ethylamino)-cyclohexyl]-benzoylamino}-propionic acid tert-butyl ester (compound 1128),
5-{4-[(1S,3S)-3-((R)-1-Naphthalen-1-yl-ethylamino)-cyclohexyl]-benzoylamino}-nicotinic acid (compound 1129),
4-{4-[(1S,3S)-3-((R)-1-Naphthalen-1-yl-ethylamino)-cyclohexyl]-benzoylamino}-benzoic acid (compound 1130),
4-Methoxy-3-{4-[(1S,3S)-3-((R)-1-naphthalen-1-yl-ethyl-amino)-cyclohexyl]-benzoylamino}-benzoic acid methyl ester; hydrochloride (compound 1131),
2-{4-[(1S,3S)-3-((R)-1-Naphthalen-1-yl-ethylamino)-cyclohexyl]-benzoylamino}-benzoic acid; hydrochloride (compound 1132),
(Carboxymethyl-{4-[(1S,3S)-3-((R)-1-naphthalen-1-yl-ethylamino)-cyclohexyl]-benzoyl}-amino)-acetic acid; hydrochloride (compound 1133),
1-({4-[(1S,3S)-3-((R)-1-Naphthalen-1-yl-ethylamino)-cyclohexyl]-benzoylamino}-methyl)-cyclopentanecarboxylic acid (compound 1134),
1-{4-[(1S,3S)-3-((R)-1-Naphthalen-1-yl-ethylamino)-cyclohexyl]-benzoylamino}-cyclopentanecarboxylic acid; hydrochloride (compound 1135),
3-{4-[(1S,3S)-3-((R)-1-Naphthalen-1-yl-ethylamino)-cyclohexyl]-benzoylamino}-propionic acid; hydrochloride (compound 1136),
(1-{4-[(1S,3S)-3-((R)-1-Naphthalen-1-yl-ethylamino)-cyclohexyl]-benzoylamino}-cyclohexyl)-acetic acid; hydrochloride (compound 1137),
1-{4-[(1S,3S)-3-((R)-1-Naphthalen-1-yl-ethylamino)-cyclohexyl]-benzoylamino}-cyclopropanecarboxylic acid ethyl ester (compound 1138),
1-{4-[(1S,3S)-3-((R)-1-Naphthalen-1-yl-ethylamino)-cyclohexyl]-benzoylamino}-cyclopropanecarboxylic acid (compound 1139), 1-({4-[(1S,3S)-3-((R)-1-Naphthalen-1-yl-ethylamino)-cyclohexyl]-benzoylamino}-methyl)-cyclopropanecarboxylic acid (compound 1140), 2-Methyl-2-{4-[(1S,3S)-3-((R)-1-naphthalen-1-yl-ethylamino)-cyclohexyl]-benzoylamino}-propionic acid (compound 1141), 1-{4-[(1S,3S)-3-((R)-1-Naphthalen-1-yl-ethylamino)-cyclohexyl]-benzoyl}-azetidine-3-carboxylic acid (compound 1142), (Methyl-{4-[(1S,3S)-3-((R)-1-naphthalen-1-yl-ethylamino)-cyclohexyl]-benzoyl}-amino)-acetic acid (compound 1143), 4-{4-[(1S,3S)-3-((R)-1-Naphthalen-1-yl-ethylamino)-cyclohexyl]-benzoylamino}-butyric acid (compound 1144), 1-{4-[(1S,3S)-3-((R)-1-Naphthalen-1-yl-ethylamino)-cyclohexyl]-benzoyl}-piperidine-4-carboxylic acid ethyl ester (compound 1145), 1-{4-[(1S,3S)-3-((R)-1-Naphthalen-1-yl-ethylamino)-cyclohexyl]-benzoyl}-piperidine-4-carboxylic acid (compound 1146), (Cyclohexyl-{4-[3-((R)-1-naphthalen-1-yl-ethylamino)-cyclohexyl]-benzoyl}-amino)-acetic acid ethyl ester (compound 1147), (Cyclohexyl-{4-[3-((R)-1-naphthalen-1-yl-ethylamino)-cyclohexyl]-benzoyl}-amino)-acetic acid (compound 1148), 4-[(1S,3S)-3-((R)-1-Naphthalen-1-yl-ethylamino)-cyclohexyl]-N—((R)-2-oxo-tetrahydro-furan-3-yl)-benzamide (compound 1149), N-Cyanomethyl-4-[(1S,3S)-3-((R)-1-naphthalen-1-yl-ethylamino)-cyclohexyl]-benzamide (compound 1150), N-(4-Cyano-1H-pyrazol-3-yl)-4-[(1S,3S)-3-((R)-1-naphthalen-1-yl-ethylamino)-cyclohexyl]-benzamide (compound 1151), (R)-3-Hydroxy-2-{4-[(1S,3S)-3-((R)-1-naphthalen-1-yl-ethylamino)-cyclohexyl]-benzoylamino}-propionic acid benzyl ester (compound 1152), (S)-3-Hydroxy-2-{4-[(1S,3S)-3-((R)-1-naphthalen-1-yl-ethylamino)-cyclohexyl]-benzoylamino}-propionic acid benzyl ester (compound 1153), (S)-3-Hydroxy-2-{4-[(1S,3S)-3-((R)-1-naphthalen-1-yl-ethylamino)-cyclohexyl]-benzoylamino}-propionic acid methyl ester (compound 1154), (R)-3-Hydroxy-2-{4-[(1S,3S)-3-((R)-1-naphthalen-1-yl-ethylamino)-cyclohexyl]-benzoylamino}-propionic acid methyl ester (compound 1155), (S)-3-Hydroxy-2-{4-[(1S,3S)-3-((R)-1-naphthalen-1-yl-ethylamino)-cyclohexyl]-benzoylamino}-propionic acid ethyl ester; hydrochloride (compound 1156), 3-Hydroxy-2-{4-[3-((R)-1-naphthalen-1-yl-ethylamino)-cyclohexyl]-benzoylamino}-propionic acid; hydrochloride (compound 1157), (R)-4-Hydroxy-2-{4-[(1S,3S)-3-((R)-1-naphthalen-1-yl-ethylamino)-cyclohexyl]-benzoylamino}-butyric acid (compound 1158), N-tert-Butoxy-4-[(1S,3S)-3-((R)-1-naphthalen-1-yl-ethylamino)-cyclohexyl]-benzamide; formiate (compound 1159), N-tert-Butoxy-4-[3-((R)-1-naphthalen-1-yl-ethylamino)-cyclohexyl]-benzamide; formiate (compound 1160), N-Methoxy-4-[(1S,3S)-3-((R)-1-naphthalen-1-yl-ethylamino)-cyclohexyl]-benzamide; formiate (compound 1161), N-Methoxy-4-[3-((R)-1-naphthalen-1-yl-ethylamino)-cyclohexyl]-benzamide; formiate (compound 1162), 4-[(1S,3S)-3-((R)-1-Naphthalen-1-yl-ethylamino)-cyclohexyl]-N-(tetrahydro-furan-3-ylmethoxy)-benzamide (compound 1163), 4-[3-((R)-1-Naphthalen-1-yl-ethylamino)-cyclohexyl]-N-(tetrahydro-furan-3-ylmethoxy)-benzamide (compound 1164), N-Methoxy-N-methyl-4-[(1S,3S)-3-((R)-1-naphthalen-1-yl-ethylamino)-cyclohexyl]-benzamide; bis formate (compound 1165), N-Methoxy-N-methyl-4-[3-((R)-1-naphthalen-1-yl-ethylamino)-cyclohexyl]-benzamide (compound 1166), N-Benzyloxy-4-[(1S,3S)-3-((R)-1-naphthalen-1-yl-ethylamino)-cyclohexyl]-benzamide (compound 1167), N-Benzyloxy-4-[3-((R)-1-naphthalen-1-yl-ethylamino)-cyclohexyl]-benzamide (compound 1168), N-Hydroxy-4-[3-((R)-1-naphthalen-1-yl-ethylamino)-cyclohexyl]-benzamide (compound 1169), N-Hydroxy-4-[(1S,3S)-3-((R)-1-naphthalen-1-yl-ethylamino)-cyclohexyl]-benzamide (compound 1170), N-(2-Morpholin-4-yl-2-oxo-ethoxy)-4-[(1S,3S)-3-((R)-1-naphthalen-1-yl-ethylamino)-cyclohexyl]-benzamide (compound 1171), N-(2-Morpholin-4-yl-2-oxo-ethoxy)-4-[3-((R)-1-naphthalen-1-yl-ethylamino)-cyclohexyl]-benzamide (compound 1172), N-{4-[(1S,3S)-3-((R)-1-Naphthalen-1-yl-ethylamino)-cyclohexyl]-benzoyl}-methanesulfonamide (compound 1173), 4R-Hydroxy-1-{4-[(1S,3S)-3-((R)-1-naphthalen-1-yl-ethylamino)-cyclohexyl]-benzoyl}-pyrrolidine-2S-carboxylic acid methyl ester (compound 1174), 4R-Hydroxy-1-{4-[(1S,3S)-3-((R)-1-naphthalen-1-yl-ethylamino)-cyclohexyl]-benzoyl}-pyrrolidine-2S-carboxylic acid (compound 1175), N-{4-[3-((R)-1-Naphthalen-1-yl-ethylamino)-cyclohexyl]-benzoyl}-methanesulfonamide; hydrochloride (compound 1176), {4-[3-((R)-1-Naphthalen-1-yl-ethylamino)-cyclopentyl]-phenoxy}-acetic acid ethyl ester (compound 1177/1178), {4-[3-((R)-1-Naphthalen-1-yl-ethylamino)-cyclopentyl]-phenoxy}-acetic acid ethyl ester (compound 1179/1180), 3-{4-[(3S)-3-((R)-1-Naphthalen-1-yl-ethylamino)-cyclopentyl]-phenyl}-propionic acid methyl ester (compounds 1181/1182/1183/1184), {4-[3-((R)-1-Naphthalen-1-yl-ethylamino)-cyclopentyl]-phenoxy}-acetic acid (compound 1185), {4-[(1R,3S)-3-((R)-1-Naphthalen-1-yl-ethylamino)-cyclopentyl]-phenoxy}-acetic acid (compound 1186), {4-[3-((R)-1-Naphthalen-1-yl-ethylamino)-cyclopentyl]-phenoxy}-acetic acid (compound 1187), {4-[3-((R)-1-Naphthalen-1-yl-ethylamino)-cyclopentyl]-phenoxy}-acetic acid (compound 1188), 3-{4-[3-((R)-1-Naphthalen-1-yl-ethylamino)-cyclopentyl]-phenyl}-propionic acid (compound 1189), 3-{4-[(1S,3S)-3-((R)-1-Naphthalen-1-yl-ethylamino)-cyclopentyl]-phenyl}-propionic acid; hydrochloride (compound 1190), 3-{4-[3-((R)-1-Naphthalen-1-yl-ethylamino)-cyclopentyl]-phenyl}-propionic acid (compound 1191), 3-{4-[3-((R)-1-Naphthalen-1-yl-ethylamino)-cyclopentyl]-phenyl}-propionic acid (compound 1192), {3-[3-((R)-1-Naphthalen-1-yl-ethylamino)-cyclopentyl]-phenoxy}-acetic acid ethyl ester (compounds 1193/1194/1195/1196), 3-{3-[3-((R)-1-Naphthalen-1-yl-ethylamino)-cyclopentyl]-phenyl}-propionic acid ethyl ester (compounds 1197/1198/1199/1200), {3-[3-((R)-1-Naphthalen-1-yl-ethylamino)-cyclopentyl]-phenoxy}-acetic acid hydrochloride (compound 1201), {3-[3-((R)-1-Naphthalen-1-yl-ethylamino)-cyclopentyl]-phenoxy}-acetic acid (compound 1202),
{3-[3-((R)-1-Naphthalen-1-yl-ethylamino)-cyclopentyl]-phenoxy}-acetic acid (compound 1203),
3-{3-[3-((R)-1-Naphthalen-1-yl-ethylamino)-cyclopentyl]-phenyl}-propionic acid hydrochloride (compound 1204),
3-{3-[3-((R)-1-Naphthalen-1-yl-ethylamino)-cyclopentyl]-phenyl}-propionic acid (compound 1205),
3-{3-[3-((R)-1-Naphthalen-1-yl-ethylamino)-cyclopentyl]-phenyl}-propionic acid (compound 1206),
3-{3-[3-((R)-1-Naphthalen-1-yl-ethylamino)-cyclopentyl]-phenyl}-propionic acid (compound 1207),
3-{3-[3-((R)-1-Naphthalen-1-yl-ethylamino)-cyclopentyl]-phenyl}-propionic acid hydrochloride (compound 1208),
[3-(4-Iodo-phenyl)-cyclohexyl]-((R)-1-naphthalen-1-yl-ethyl)-amine (compound 1209),
1-{4-[3-((R)-1-Naphthalen-1-yl-ethylamino)-cyclohexyl]-phenyl}-pyrrolidin-2-one (compound 1210),
3-{4-[3-((R)-1-Naphthalen-1-yl-ethylamino)-cyclohexyl]-phenyl}-oxazolidin-2-one (compound 1211),
N-{4-[3-((R)-1-Naphthalen-1-yl-ethylamino)-cyclohexyl]-phenyl}-acetamide (compound 1212),
4-{4-[3-((R)-1-Naphthalen-1-yl-ethylamino)-cyclohexyl]-phenyl}-tetrahydro-pyran-4-ol (compound 1213),
[3-(4-Imidazol-1-yl-phenyl)-cyclohexyl]-((R)-1-naphthalen-1-yl-ethyl)-amine (compound 1214),
1-{4-[3-((R)-1-Naphthalen-1-yl-ethylamino)-cyclohexyl]-phenyl}-cyclopentanol (compound 1215),
1-{4-[3-((R)-1-Naphthalen-1-yl-ethylamino)-cyclohexyl]-phenyl}-ethanone (compound 1216),
4-{4-[3-((R)-1-Naphthalen-1-yl-ethylamino)-cyclohexyl]-phenyl}-tetrahydro-pyran-4-ol hydrochloride (compound 1217),
{4-[3-((R)-1-Naphthalen-1-yl-ethylamino)-cyclohexyl]-phenyl}-methanol (compound 1218),
1-{4-[3-((R)-1-Naphthalen-1-yl-ethylamino)-cyclohexyl]-phenyl}-cyclobutanol (compound 1219),
2-{4-[3-((R)-1-Naphthalen-1-yl-ethylamino)-cyclohexyl]-phenyl}-malonic acid diethyl ester (compound 1220),
{4-[3-((R)-1-Naphthalen-1-yl-ethylamino)-cyclohexyl]-phenyl}-acetic acid ethyl ester (compound 1221),
{4-[3-((R)-1-Naphthalen-1-yl-ethylamino)-cyclohexyl]-phenyl}-acetic acid (compound 1222),
3-{4-[3-((R)-1-Naphthalen-1-yl-ethylamino)-cyclohexyl]-phenyl}-oxetan-3-ol (compound 1223),
{3-[4-(3-Fluoro-oxetan-3-yl)-phenyl]-cyclohexyl}-((R)-1-naphthalen-1-yl-ethyl)-amine (compound 1224),
{3-[4-(3-Amino-3-methyl-but-1-ynyl)-phenyl]-cyclohexyl}-((R)-1-naphthalen-1-yl-ethyl)-amine (compound 1225),
{3-[4-(5-Cyclopropyl-[1,2,4]oxadiazol-3-yl)-phenyl]-cyclohexyl}-((R)-1-naphthalen-1-yl-ethyl)-amine (compound 1226),
{3-[4-(5-Cyclopentyl-[1,2,4]oxadiazol-3-yl)-phenyl]-cyclohexyl}-((R)-1-naphthalen-1-yl-ethyl)-amine (compound 1227),
{3-[4-(5-Methyl-[1,2,4]oxadiazol-3-yl)-phenyl]-cyclohexyl}-((R)-1-naphthalen-1-yl-ethyl)-amine (compound 1228),
{3-[4-(5-Isopropyl-[1,2,4]oxadiazol-3-yl)-phenyl]-cyclohexyl}-((R)-1-naphthalen-1-yl-ethyl)-amine (compound 1229),
{3-[4-(5-tert-Butyl-[1,2,4]oxadiazol-3-yl)-phenyl]-cyclohexyl}-((R)-1-naphthalen-1-yl-ethyl)-amine (compound 1230),
{3-[4-(5-Cyclohexyl-[1,2,4]oxadiazol-3-yl)-phenyl]-cyclohexyl}-((R)-1-naphthalen-1-yl-ethyl)-amine (compound 1231),
(3-{4-[5-(3-Methyl-butyl)-[1,2,4]oxadiazol-3-yl]-phenyl}-cyclohexyl)-((R)-1-naphthalen-1-yl-ethyl)-amine (compound 1232),
5-(3-{4-[3-((R)-1-Naphthalen-1-yl-ethylamino)-cyclohexyl]-phenyl}-[1,2,4]oxadiazol-5-ylmethyl)-imidazolidine-2,4-dione (compound 1233),
(3-{4-[5-(4-Methyl-oxazol-5-yl)-[1,2,4]oxadiazol-3-yl]-phenyl}-cyclohexyl)-((R)-1-naphthalen-1-yl-ethyl)-amine (compound 1234),
(3-{4-[5-(2,5-Dimethyl-oxazol-4-yl)-[1,2,4]oxadiazol-3-yl]-phenyl}-cyclohexyl)-((R)-1-naphthalen-1-yl-ethyl)-amine (compound 1235),
2-Methyl-2-{4-[3-((R)-1-naphthalen-1-yl-ethylamino)-cyclohexyl]-phenyl}-propionitrile (compound 1236/1237),
2-Methyl-2-{4-[3-((R)-1-naphthalen-1-yl-ethylamino)-cyclohexyl]-phenyl}-propionic acid (compound 1238),
2-Methyl-2-{4-[3-((R)-1-naphthalen-1-yl-ethylamino)-cyclohexyl]-phenyl}-propionic acid (compound 1239),
[3-(4-Methanesulfonyl-phenyl)-cyclohexyl]-((R)-1-naphthalen-1-yl-ethyl)-amine (compounds 1240),
2-Fluoro-4-[3-((R)-1-naphthalen-1-yl-ethylamino)-cyclohexyl]-benzoic acid methyl ester (compound 1241),
{4-[3-((R)-1-Naphthalen-1-yl-ethylamino)-cyclohexyl]-phenyl}-methanol (compound 1242),
N-{4-[3-((R)-1-Naphthalen-1-yl-ethylamino)-cyclohexyl]-benzyl}-methanesulfonamide (compound 1243),
{3-[4-(Morpholine-4-sulfonyl)-phenyl]-cyclohexyl}-((R)-1-naphthalen-1-yl-ethyl)-amine (compound 1244/1245),
N-{4-[3-((R)-1-Naphthalen-1-yl-ethylamino)-cyclohexyl]-benzyl}-acetamide (compounds 1246/1247),
3-Fluoro-4-[3-((R)-1-naphthalen-1-yl-ethylamino)-cyclohexyl]-benzoic acid methyl ester (compound 1248),
N-{4-[3-((R)-1-Naphthalen-1-yl-ethylamino)-cyclohexyl]-phenyl}-methanesulfonamide (compound 1249/1250),
N-{3-[3-((R)-1-Naphthalen-1-yl-ethylamino)-cyclohexyl]-phenyl}-methanesulfonamide (compound 1251),
N-(2-Hydroxy-ethyl)-4-[3-((R)-1-naphthalen-1-yl-ethylamino)-cyclohexyl]-benzenesulfonamide (compounds 1252/1253),
3-{4-[3-((R)-1-Naphthalen-1-yl-ethylamino)-cyclohexyl]-phenyl}-propionic acid (compound 1254),
{4-[3-((R)-1-Naphthalen-1-yl-ethylamino)-cyclohexyl]-phenoxy}-acetic acid (compound 1255),
[3-(4-Methanesulfonyl-phenyl)-cyclopentyl]-((R)-1-naphthalen-1-yl-ethyl)-amine (compounds 1256/1257),
N-{3-[3-((R)-1-Naphthalen-1-yl-ethylamino)-cyclopentyl]-phenyl}-methanesulfonamide (compounds 1258/1259),
N-{4-[3-((R)-1-Naphthalen-1-yl-ethylamino)-cyclopentyl]-phenyl}-acetamide (compounds 1260/1261),
N-{4-[3-((R)-1-Naphthalen-1-yl-ethylamino)-cyclopentyl]-benzyl}-acetamide (compound 1262/1263),
N-{4-[3-((R)-1-Naphthalen-1-yl-ethylamino)-cyclopentyl]-benzyl}-methanesulfonamide (compounds 1264/1265),
N-{4-[3-((R)-1-Naphthalen-1-yl-ethylamino)-cyclopentyl]-phenyl}-methanesulfonamide (compounds 1266/1267),
[3-(4-Methanesulfonyl-phenyl)-cycloheptyl]-((R)-1-naphthalen-1-yl-ethyl)-amine (compound 1268),
2-Fluoro-4-[3-((R)-1-naphthalen-1-yl-ethylamino)-cycloheptyl]-benzoic acid methyl ester (compound 1269),
N-{3-[3-((R)-1-Naphthalen-1-yl-ethylamino)-cycloheptyl]-phenyl}-methanesulfonamide (compound 1270),
N-{4-[3-((R)-1-Naphthalen-1-yl-ethylamino)-cycloheptyl]-phenyl}-acetamide (compound 1271/1272), N-{4-[3-((R)-1-Naphthalen-1-yl-ethylamino)-cycloheptyl]-benzyl}-acetamide (compounds 1273/1274), N-{4-[3-((R)-1-Naphthalen-1-yl-ethylamino)-cycloheptyl]-benzyl}-methanesulfonamide (compounds 1275/1276), {4-[3-((R)-1-Naphthalen-1-yl-ethylamino)-cycloheptyl]-phenoxy}-acetic acid ethyl ester (compound 1277), 3-{4-[3-((R)-1-Naphthalen-1-yl-ethylamino)-cycloheptyl]-phenyl}-propionic acid methyl ester (compounds 1278/1279), N-{4-[3-((R)-1-Naphthalen-1-yl-ethylamino)-cycloheptyl]-phenyl}-methanesulfonamide (compounds 1280/1281), {3-[4-(Morpholine-4-sulfonyl)-phenyl]-cycloheptyl}-((R)-1-naphthalen-1-yl-ethyl)-amine (compound 1282), {4-[3-((R)-1-Naphthalen-1-yl-ethylamino)-cycloheptyl]-phenyl}-methanol (compound 1283), 4-[3-((R)-1-Naphthalen-1-yl-ethylamino)-cyclohexyl]-benzoic acid methyl ester (compound 1284), 4-[3-((R)-1-Naphthalen-1-yl-ethylamino)-cyclohexyl]-benzoic acid ethyl ester (compound 1285), 4-[3-((R)-1-Naphthalen-1-yl-ethylamino)-cyclohexyl]-benzoic acid 2-morpholin-4-yl-ethyl ester dihydrochloride (compound 1286), 4-[3-((R)-1-Naphthalen-1-yl-ethylamino)-cyclohexyl]-benzoic acid 2-(2-methoxy-ethoxy)-ethyl ester hydrochloride (compound 1287), 4-[3-((R)-1-Naphthalen-1-yl-ethylamino)-cyclohexyl]-benzoic acid 2-[2-(2-methoxy-ethoxy)-ethoxy]-ethyl ester hydrochloride (compound 1288), 4-[3-((R)-1-Naphthalen-1-yl-ethylamino)-cyclohexyl]-benzoic acid 2-[2-(2-ethoxy-ethoxy)-ethoxy]-ethyl ester hydrochloride (compound 1289), 4-[3-((R)-1-Naphthalen-1-yl-ethylamino)-cyclohexyl]-benzoic acid 2,3-dihydroxy-propyl ester hydrochloride (compound 1290), 4-[3-((R)-1-Naphthalen-1-yl-ethylamino)-cyclohexyl]-benzoic acid tetrahydro-furan-2-ylmethyl ester hydrochloride (compound 1291), 4-[(1R,3S)-3-((R)-1-Naphthalen-1-yl-ethylamino)-cyclopentyl]-phenol (compound 1292), 2-{4-[(1R,3S)-3-((R)-1-Naphthalen-1-yl-ethylamino)-cyclopentyl]-phenoxy}-butyric acid ethyl ester (compound 1293), 2-{4-[(1R,3S)-3-((R)-1-Naphthalen-1-yl-ethylamino)-cyclopentyl]-phenoxy}-butyric acid (compound 1294), 2-{4-[(1R,3S)-3-((R)-1-Naphthalen-1-yl-ethylamino)-cyclopentyl]-phenoxy}-propionic acid (compound 1295), 3-{4-[(1R,3S)-3-((R)-1-Naphthalen-1-yl-ethylamino)-cyclopentyl]-phenoxy}-dihydro-furan-2-one (compound 1296), (S)-{3R-[4-(2-Ethoxy-ethoxy)-phenyl]-cyclopentyl}-((R)-1-naphthalen-1-yl-ethyl)-amine (compound 1297), 3-{4-[(1R,3S)-3-((R)-1-Naphthalen-1-yl-ethylamino)-cyclopentyl]-phenoxy}-propionic acid ethyl ester (compound 1298), 4-{4-[(1R,3S)-3-((R)-1-Naphthalen-1-yl-ethylamino)-cyclopentyl]-phenoxymethyl}-benzonitrile (compound 1299), (S)—((R)-1-Naphthalen-1-yl-ethyl)-{3R-[4-(pyridin-3-yl-methoxy)-phenyl]-cyclopentyl}-amine (compound 1300), (S)—((R)-1-Naphthalen-1-yl-ethyl)-{3R-[4-(2-pyrazol-1-yl-ethoxy)-phenyl]-cyclopentyl}-amine (compound 1301), (S)-(3R-{4-[2-(1H-Indol-3-yl)-ethoxy]-phenyl}-cyclopentyl)-((R)-1-naphthalen-1-yl-ethyl)-amine (compound 1302), 2-Methyl-2-{4-[(1R,3S)-3-((R)-1-naphthalen-1-yl-ethylamino)-cyclopentyl]-phenoxy}-propionic acid hydrochloride (compound 1303), 4-Hydroxy-2-{4-[(1R,3S)-3-((R)-1-naphthalen-1-yl-ethylamino)-cyclopentyl]phenoxy}-butyric acid (compound 1304), 2-{4-[(1R,3S)-3-((R)-1-Naphthalen-1-yl-ethylamino)-cyclopentyl]-phenoxy}-propionic acid hydrochloride (compound 1305), {4-[(1R,3S)-3-((R)-1-Naphthalen-1-yl-ethylamino)-cyclopentyl]-phenoxy}-phenyl-acetic acid hydrochloride (compound 1306), 2-Methyl-1-{4-[(1R,3S)-3-((R)-1-naphthalen-1-yl-ethylamino)-cyclopentyl]-phenoxy}-propan-2-ol (compound 1307), 3-{4-[(1R,3S)-3-((R)-1-Naphthalen-1-yl-ethylamino)-cyclopentyl]-phenoxymethyl}-pentan-3-ol (compound 1308), Dimethyl-carbamic acid 4-[(1R,3S)-3-((R)-1-naphthalen-1-yl-ethylamino)-cyclopentyl]-phenyl ester (compound 1309), 3-Ethyl-1-{4-[(1S,3S)-3-((R)-1-naphthalen-1-yl-ethylamino)-cyclopentyl]-phenyl}-pentan-3-ol (compound 1310), 2-Methyl-4-{4-[(1S,3S)-3-((R)-1-naphthalen-1-yl-ethylamino)-cyclopentyl]-phenyl}-butan-2-ol (compound 1311), 3-{4-[(1R,3S)-3-((R)-1-Naphthalen-1-yl-ethylamino)-cyclopentyl]-phenoxy}-propane-1,2-diol (compound 1312), (2-Fluoro-phenyl)-{4-[(1R,3S)-3-((R)-1-naphthalen-1-yl-ethylamino)-cyclopentyl]-phenoxy}-acetic acid hydrochloride (compound 1313), 2-{4-[(1R,3S)-3-((R)-1-Naphthalen-1-yl-ethylamino)-cyclopentyl]-phenoxy}-ethanol formiate (compound 1314), (1-{4-[3-((R)-1-Naphthalen-1-yl-ethylamino)-cyclohexyl]-benzyl}-pyrrolidin-2-yl)-methanol (compound 1315), 1-{4-[3-((R)-1-Naphthalen-1-yl-ethylamino)-cyclohexyl]-benzyl}-pyrrolidin-3-ol (compound 1316), 1-{4-[3-((R)-1-Naphthalen-1-yl-ethylamino)-cyclohexyl]-benzyl}-piperidine-3-carboxylic acid ethyl ester (compound 1317),

[3-(4-{[Methyl-(tetrahydro-furan-2-ylmethyl)-amino]-methyl}-phenyl)-cyclohexyl]-((R)-1-naphthalen-1-yl-ethyl)-amine (compound 1318), 3-(4-{(1S,3S)-3-[(R)-1-(4-Fluoro-3-methoxy-phenyl)-ethylamino]-cyclopentyl}-phenyl)-propionic acid ethyl ester (compound 1319), 3-(4-{(1S,3S)-3-[(R)-1-(3-Cyano-phenyl)-ethylamino]-cyclopentyl}-phenyl)-propionic acid ethyl ester (compound 1320), 3-{4-[(1S,3S)-3-((R)-1-Benzo[b]thiophen-3-yl-ethylamino)-cyclopentyl]-phenyl}-propionic acid ethyl ester (compound 1321), 3-(4-{(1S,3S)-3-[(R)-1-(2,3-Dihydro-benzo[1,4]dioxin-6-yl)-ethylamino]-cyclopentyl}-phenyl)-propionic acid ethyl ester (compound 1322), 3-{4-[(1S,3S)-3-((R)-1-Phenyl-ethylamino)-cyclopentyl]-phenyl}-propionic acid ethyl ester (compound 1323), 3-(4-{(1S,3S)-3-[(R)-1-(2,3-Dihydro-benzofuran-5-yl)-ethylamino]-cyclopentyl}-phenyl)-propionic acid ethyl ester (compound 1324), 3-(4-{(1S,3S)-3-[(R)-1-(1H-Indol-7-yl)-ethylamino]-cyclopentyl}-phenyl)-propionic acid hydroformiate (compound 1325), 3-(4-{(1S,3S)-3-[(R)-1-(2,3-Dihydro-benzo[1,4]dioxin-5-yl)-ethylamino]-cyclopentyl}-phenyl)-propionic acid hydroformiate (compound 1326), 3-(4-{(1S,3S)-3-[(R)-1-(1H-Indol-4-yl)-ethylamino]-cyclopentyl}-phenyl)-propionic acid hydroformiate (compound 1327),
3-(4-{(1S,3S)-3-[(R)-1-(3-Cyano-phenyl)-ethylamino]-cyclopentyl}-phenyl)-propionic acid, hydroformiate (compound 1328),
3-(4-{(1S,3S)-3-[(R)-1-(3-Pyrrolidin-1-yl-phenyl)-ethylamino]-cyclopentyl}-phenyl)-propionic acid hydroformiate (compound 1329),
3-(4-{(1S,3S)-3-[(R)-1-(2,3-Dihydro-benzofuran-5-yl)-ethylamino]-cyclopentyl}-phenyl)-propionic acid hydroformiate (compound 1330),
3-(4-{(1S,3S)-3-[(R)-1-(2,3-Dihydro-benzo[1,4]dioxin-6-yl)-ethylamino]-cyclopentyl}-phenyl)-propionic acid (compound 1331),
3-(4-{(1S,3S)-3-[(R)-1-(4-fluoro-3-methoxy-1-yl-phenyl)-ethylamino]-cyclopentyl}-phenyl)-propionic acid (compound 1332),
3-{4-[(1S,3S)-3-((R)-1-Benzo[b]thiophen-3-yl-ethylamino)-cyclopentyl]-phenyl}-propionic acid, hydrochloride (compound 1333),
3-{4-[(1S,3S)-3-((R)-1-Phenyl-ethylamino)-cyclopentyl]-phenyl}-propionic acid (compound 1334),
4-[3-((R)-1-Naphthalen-1-yl-ethylamino)-cyclopentyl]-benzoic acid ethyl ester (compound 1335/1336),
4-[3-((R)-1-Naphthalen-1-yl-ethylamino)-cyclopentyl]-benzoic acid (compound 1337),
4-[3-((R)-1-Naphthalen-1-yl-ethylamino)-cyclopentyl]-benzoic add (compound 1338),
3-{4-[3-((R)-1-Naphthalen-1-yl-ethylamino)-cyclopentyl]-benzoylamino}-propionic acid methyl ester (compound 1339),
1-{4-[3-((R)-1-Naphthalen-1-yl-ethylamino)-cyclopentyl]-benzoyl}-piperidine-4-carboxylic acid hydrochloride (compound 1340),
3-{4-[3-((R)-1-Naphthalen-1-yl-ethylamino)-cyclopentyl]-benzoylamino}-propionic acid hydrochloride (compound 1341),
4-[3-((R)-1-Naphthalen-1-yl-ethylamino)-cyclopentyloxy]-benzoic acid methyl ester (compound 1342),
4-[3R—((R)-1-Naphthalen-1-yl-ethylamino)-cyclopentyloxy]-benzoic acid formiate (compound 1343),
5-Methyl-3-[3-((R)-1-naphthalen-1-yl-ethylamino)-cyclopentyl]-3H-imidazole-4-carboxylic acid (compound 1344),
(3S,4S-Diphenyl-cyclopentyl)-((R)-1-naphthalen-1-yl-ethyl)-amine (compound 1345),
5-(4-ethoxy-phenyl)-2-propyl-cyclohexyl]-(R)-1-naphthalen-1-yl-ethyl)-amine (compound 1346)
[2-(4-Fluoro-phenyl)-5-((R)-1-naphthalen-1-yl-ethylamino)-cyclopentyl]-acetic acid hydrochloride (compound 1347), or
3-{4-[3-((R)-1-Naphthalen-1-yl-ethylamino)-cyclopentyl]-phenyl}-propan-1-ol (compound 1348).

Specific examples of intermediates for the preparation of compounds of formula I may be selected from the group consisting of
3-[3-(3-trifluoromethyl-phenyl)-[1,2,4]oxadiazol-5-yl]-cyclobutanone (compound 1112),
4-methyl-N-(3-oxo-cyclopentanecarbonyl)-benzenesulfonamide (compound 1113),
3-(3-trifluoromethylphenyl)amino-cyclohexanone (compound 1114),
3-((R)-1-Naphthalen-1-yl-ethylamino)-cyclohexanecarboxylic acid (preparation 4),
3-(4-Iodophenyl)-cyclohexan-1-one (preparation 5),
4-(3-Oxo-cyclohexyl)-benzaldehyde (preparation 7),
3-[4-((1S)-3-Oxo-cyclopentyl)-phenyl]-propionic acid ethyl ester (preparation 8),
3-[4-((1S,3R)-3-Acetoxy-cyclopentyl)-phenyl]-propionic acid ethyl ester (preparation 9),
3-[4-((1S,3R)-3-Hydroxy-cyclopentyl)-phenyl]-propionic acid ethyl ester (preparation 10),
3-[4-((1S,3R)-3-Methanesulfonyloxy-cyclopentyl)-phenyl]-propionic acid ethyl ester (preparation 11),
4-((1S,4S)-4-Acetoxy-cyclopent-2-enyloxy)-benzoic acid methyl ester (preparation 13),
4-((1S,4S)-4-Hydroxy-cyclopent-2-enyloxy)-benzoic acid methyl ester (preparation 14),
4-((1S,4R)-4-Chloro-cyclopent-2-enyloxy)-benzoic acid methyl ester (preparation 15),
4-[(1S,4S)-4-((R)-1-Naphthalen-1-yl-ethylamino)-cyclopent-2-enyloxy]-benzoic acid methyl ester (preparation 16),
3-((1S,4S)-4-Acetoxy-cyclopent-2-enyl)-5-methyl-3H-imidazole-4-carboxylic acid ethyl ester (preparation 17),
3-((1S,4S)-4-Hydroxy-cyclopent-2-enyl)-5-methyl-3H-imidazole-4-carboxylic acid ethyl ester (preparation 18),
3-((1S,4R)-4-Chloro-cyclopent-2-enyl)-5-methyl-3H-imidazole-4-carboxylic acid ethyl ester (preparation 19) or
5-Methyl-3-[(1S,4S)-4-((R)-1-naphthalen-1-yl-ethylamino)-cyclopent-2-enyl]-3H-imidazole-4-carboxylic acid ethyl ester (preparation 20).

Pharmaceutical Compositions

For use in therapy, compounds of the present invention are typically in the form of a pharmaceutical composition. The invention therefore relates to a pharmaceutical composition, both for veterinary (including mammals such as horses, cattle, sheep, pigs, dogs and cats) and for human medical use, comprising a compound of formula I, optionally together with one or more other therapeutically active compound(s), together with a pharmaceutically acceptable excipient or vehicle. The excipient must be "acceptable" in the sense of being compatible with the other ingredients of the composition and not deleterious to the recipient thereof.

Conveniently, the active ingredient comprises from 0.05-99.9% by weight of the formulation, e.g. 0.5-90%, such as 5-85%, such as 15-45%, preferably 20-30%.

Pharmaceutical compositions of the invention may be in unit dosage form such as tablets, pills, capsules, powders, granules, elixirs, syrups, emulsions, ampoules, suppositories or parenteral solutions or suspensions; for oral, parenteral, opthalmic, transdermal, intra-articular, topical, pulmonal, nasal, buccal or rectal administration or in any other manner appropriate for the formulation of compounds used in nephrology and in accordance with accepted practices such as those disclosed in *Remington: The Science and Practice of Pharmacy*, 21$^{St}$ ed., 2005, Lippincott Williams & Wilkins. In the composition of the invention, the active component may be present in an amount of from about 0.01 to about 99%, such as 0.1% to about 10% by weight of the composition.

For oral administration in the form of a tablet or capsule, a compound of formula I may suitably be combined with an oral, non-toxic, pharmaceutically acceptable carrier such as ethanol, glycerol, water or the like. Furthermore, suitable binders, lubricants, disintegrating agents, flavouring agents and colourants may be added to the mixture, as appropriate. Suitable binders include, e.g., lactose, glucose, starch, gelatin, acacia gum, tragacanth gum, sodium alginate, carboxymethylcellulose, polyethylene glycol, waxes or the like. Lubricants include, e.g., sodium oleate, sodium stearate, magnesium stearate, sodium benzoate, sodium acetate, sodium chloride or the like. Disintegrating agents include, e.g., starch, methyl cellulose, agar, bentonite, xanthan gum or the like. Additional excipients for capsules include macrogols or lipids.

For the preparation of solid compositions such as tablets, the active compound of formula I is mixed with one or more excipients, such as the ones described above, and other pharmaceutical diluents such as water to make a solid preformulation composition containing a homogenous mixture of a compound of formula I. The term "homogenous" is understood to mean that the compound of formula I is dispersed evenly throughout the composition so that the composition may readily be subdivided into equally effective unit dosage forms such as tablets or capsules. The preformulation composition may then be subdivided into unit dosage forms containing from about 0.05 to about 1000 mg, in particular from about 0.1 to about 500 mg, e.g. 10-200 mg, such as 30-180 mg, such as 20-50 mg of the active compound of the invention.

In the form of a dosage unit, the compound may be administered one or more times a day at appropriate intervals, always depending, however, on the condition of the patient, and in accordance with the prescription made by the medical practitioner. Conveniently, a dosage unit of a formulation contain between 0.1 mg and 1000 mg, preferably between 1 mg and 100 mg, such as 5-50 mg of a compound of formula I.

A suitable dosage of the compound of the invention will depend, inter alia, on the age and condition of the patient, the severity of the disease to be treated and other factors well known to the practising physician. The compound may be administered either orally, parenterally or topically according to different dosing schedules, e.g. daily or with weekly intervals. In general a single dose will be in the range from 0.01 to 400 mg/kg body weight. The compound may be administered as a bolus (i.e. the entire daily dosis is administered at once) or in divided doses two or more times a day.

If the treatment involves administration of another therapeutically active compound it is recommended to consult Goodman & Gilman's The Pharmacological Basis of Therapeutics, 9$^{th}$ Ed., J. G. Hardman and L. E. Limbird (Eds.), McGraw-Hill 1995, for useful dosages of said compounds. The administration of a compound of the present invention with one or more other active compounds may be either concomitantly or sequentially.

Liquid formulations for either oral or parenteral administration of the compound of the invention include, e.g., aqueous solutions, syrups, aqueous or oil suspensions and emulsion with edible oils such as cottonseed oil, sesame oil, coconut oil or peanut oil. Suitable dispersing or suspending agents for aqueous suspensions include synthetic or natural gums such as tragacanth, alginate, acacia, dextran, sodium carboxymethylcellulose, gelatin, methylcellulose or polyvinylpyrolidone.

For parenteral administration, e.g. intramuscular, intraperitoneal, subcutaneous or intravenous injection or infusion, the pharmaceutical composition preferably comprises a compound of formula I dissolved or solubilised in an appropriate, pharmaceutically acceptable solvent. For parenteral administration, the composition of the invention may include a sterile aqueous or non-aqueous solvent, in particular water, isotonic saline, isotonic glucose solution, buffer solution or other solvent conventionally used for parenteral administration of therapeutically active substances. The composition may be sterilised by, for instance, filtration through a bacteria-retaining filter, addition of a sterilising agent to the composition, irradiation of the composition, or heating the composition. Alternatively, the compound of the invention may be provided as a sterile, solid preparation, e.g. a freeze-dried powder, which is dissolved in sterile solvent immediately prior to use.

The composition intended for parenteral administration may additionally comprise conventional additives such as stabilisers, buffers or preservatives, e.g. antioxidants such as methylhydroxybenzoate or the like.

Compositions for rectal administration may be in the form of a suppository incorporating the active ingredient and a carrier such as cocoa butter, or in the form of an enema.

Compositions suitable for intra-articular administration may be in the form of a sterile aqueous preparation of the active ingredient which may be in microcrystalline form, for example, in the form of an aqueous microcrystalline suspension. Liposomal formulations or biodegradable polymer systems may also be used to present the active ingredient for both intra-articular and ophthalmic administration.

Compositions suitable for topical administration, including ophthalmic treatment, include liquid or semi-liquid preparations such as liniments, lotions, gels, applicants, oil-in-water or water-in-oil emulsions such as creams, ointments or pastes; or solutions or suspensions such as drops. For topical administration, the compound of formula I may typically be present in an amount of from 0.01 to 20% by weight of the composition, such as 0.1% to about 10%, but may also be present in an amount of up to about 50% of the composition.

Compositions for ophthalmic treatment may preferably additionally contain a cyclodextrin.

Compositions suitable for administration to the nasal or buccal cavity or for inhalation include powder, self-propelling and spray formulations, such as aerosols and atomizers. Such compositions may comprise a compound of formula I in an amount of 0.01-20%, e.g. 2%, by weight of the composition.

The composition may additionally comprise one or more other active components conventionally used in the treatment of physiological disorders or diseases associated with disturbances of CaSR activity, such as hyperparathyroidism.

A suitable dosage of the compound of the invention will depend, inter alia, on the age and condition of the patient, the severity of the disease to be treated and other factors well known to the practising physician. The compound may be administered orally, parenterally or topically according to different dosing schedules, e.g. daily or with weekly intervals. In general a single dose will be in the range from 0.01 to 400 mg/kg body weight. The compound may be administered as a bolus (i.e. the entire daily dosis is administered at once) or in divided doses two or more times a day.

Pharmacological Methods

The calcium sensing receptor (CaSR) and its use in identifying or screening for calcimimetic compounds has been described in EP637237, EP1296142, EP1100826, EP1335978 and EP1594446.

In vitro and vivo methods for testing the compounds of the present invention are well established and may be found in the references listed above, or e.g. in Journal of Biological Chemistry (2004), 279(8), 7254-7263 or in U.S. Pat. No. 5,858,684 and references cited therein.

Biological Assay for Analysis of In Vitro Activity

The assay investigates a compound's functional ability to act as a biological positive modulator on the human CaSR. Activation of the receptor expressed on CHO-K1 cells is detected through the G alpha q pathway, the activation of phospholipase C and the accumulation of intracellular inositol phosphate (IP) as described earlier [Sandrine Ferry, Bruno Chatel, Robert H. Dodd, Christine Lair, Danielle Gully, Jean-Pierre Maffrand, and Martial Ruat, Effects of Divalent Cations and of a Calcimimetic on Adrenocorticotropic Hormone Release in Pituitary Tumor Cells. *Biochemical and biophysical research communications* 238, 866-873 (1997)]. The human CaSR is stably expressed on a CHO-K1 cell clone, stimulated with a basal level of calcium and challenged with the tested compound. The level of IP1 is determined using the IP-One htrf kit (Cisbio, France). CHO-K1 cells not transfected with the CaSR fail to elicit an IP1 response upon calcium and/or compound stimulation.

Cloning of the Human CaSR Gene

The ORF coding for the human CaSR (genebank: NM_000388) was acquired from Invitrogen Corp, USA and subsequently cloned into the mammalian expression vector pCDA3.1.

Generation of Cell Line Expressing CaSR

CHO-K1 cells were transfected using Lipofectamine according to manufacturer's protocol (400,000 cells/well were seeded in a 6-well plate and transfected after 24 hours using 2 μg DNA and 5 μl lipofectamine). After another 24 hours the cells were detached, seeded and subjected to 1 mg/ml of G-418. Following 7 days growth single clones were picked, the CaSR expression evaluated using the 5C10 antibody against CaSR, the clones with the highest expression were selected and tested for functional response. The preferred clone was continuously cultured according to standard procedures described in ATCC (American Type Culture Collection) protocols for CHO-K1 with the addition of 500 μg/ml G-418.

As described above, the compounds described in the present invention are modulators of CaSR activity. The CaSR can be found in the parathyroid gland, the thyroid, bone cells, the stomach, the lung, the kidney, pituitary gland, the brain, the hypothalamus, the olfactory areas or the hippocampus. Compounds according to the present invention may preferably be more selective, in their use, with respect to the receptors of the parathyroid compared with those of the thyroid gland.

The compounds according to the invention, and the pharmaceutical compositions comprising them, may be used as a medicinal product, in particular for the treatment of physiological disorders or diseases associated with disturbances of CaSR activity. Even more particularly, these physiological disorders or diseases of the type including primary or secondary hyperparathyroidism, osteoporosis, cardiovascular, gastrointestinal, endocrine or neurodegenerative diseases or certain cancers in which $(Ca^{2+})_e$ ions are abnormally high. The secondary hyperparathyroidism is more particularly observed in chronic renal failure.

The following preparations and non-limiting examples are given in order to enable a person skilled in the art to understand and to carry out the invention.

The examples described in further detail in the following non-limiting examples are not in any way intended to limit the scope of the invention as claimed but are merely considered as being illustrative and representative thereof.

Methods of Preparation

The compounds of general formula I can be prepared in a number of ways well known to those skilled in the art of organic synthesis. The compounds of formula I can be synthesised using the methods outlined below, together with methods known in the art of synthetic organic chemistry, or variations thereof as appreciated by those skilled in the art. Preferred methods include, but are not limited to, those described below.

The compounds of formula I can be prepared by techniques and procedures readily available to one of ordinary skill in the art, for example by following the procedures as set forth in the following schemes. The reactions are performed in solvents appropriate to the reagents and materials employed and suitable for the transformations being effected. Also, in the synthetic methods described below, it is to be understood that all proposed reaction conditions, including choice of solvent, reaction atmosphere, reaction temperature, duration of experiment and work-up procedures, are chosen to be conditions of standard for that reaction, which should be readily recognised by one skilled in the art. It is understood by one skilled in the art of organic synthesis that the functionalities present on various portions of the starting molecules in a reaction must be compatible with the reagents and reactions proposed. Not all compounds of formula I falling into a given class may be compatible with some of the reaction conditions required in some of the methods described. Such restrictions to the substituents which are compatible with the reaction conditions will be readily apparent to one skilled in the art and alternative methods can be used.

The schemes described in this section are not intended to limit the scope of the invention in any way. All substituents, unless otherwise indicated, are previously defined. The reagents and starting materials are either available from commercial suppliers or prepared by methods known to one of ordinary skilled in the art following procedures set forth in references such as *Fieser and Fieser's Reagents for Organic Synthesis*, Volumes 1-22 (John Wiley and Sons, 2004); *Rodd's Chemistry of Carbon Compounds*, Volumes 1-5 and Supplements (Elsevier Science Publishers, 2000); *Organic Reactions*, Volumes 1-64 (John Wiley and Sons, 2004); *March's Advanced Organic Chemistry* (John Wiley and Sons, $5^{th}$ Edition) and *Larock's Comprehensive Organic Transformations* (VCH Publishers Inc., 1999). These schemes are merely illustrative of some methods by which the compounds of this invention can be synthesised, and various modifications to these schemes can be made and will be suggested to one skilled in the art having referred to this disclosure. The starting materials and the intermediates of the reactions may be isolated and purified if desired using conventional techniques, including but not limited to filtration, distillation, crystallisation, chromatography and the like. Such materials may be characterised using conventional means, including physical constants and spectral data.

Compounds of general formula I may be obtained by reductive amination between a cyclic ketone of general formula II and an amine of general formula III. The reaction between ketone II and amine III may be carried out either by one-pot reductive amination or with isolation of the imine followed by reduction.

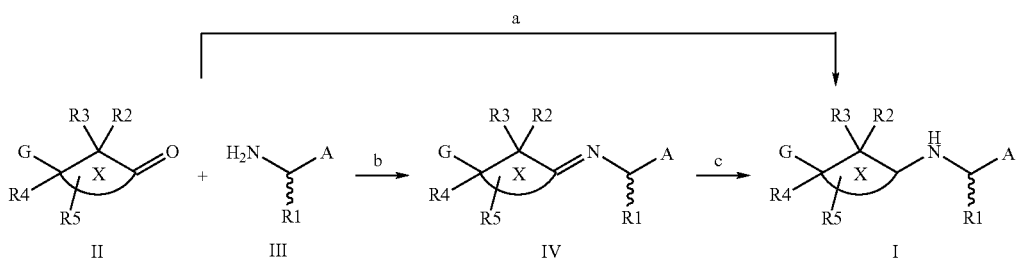

a. The formation of the intermediate iminium IV may be promoted by addition of a protic or aprotic acid such as, but not limited to acetic acid and Ti(Oi-Pr)$_4$ respectively. The reducing agent may be but is not limited to Na(CN)BH$_3$, NaBH$_4$, Na(OAc)$_3$BH (for other non-limiting conditions see *Org. React.* 2002, 59, 1-714 and references cited therein).

b. The formation of the imine is promoted either by Lewis acids such as TiCl$_4$, ZnCl$_2$, AlCl$_3$ or by bases such as pyridine, eventually in the presence of a drying agent such as TiCl$_4$ or molecular sieve (see *Comprehensive Organic Functionnal Group Transformations* 3, 403 (1995) Pergamon).

c. Reduction may be performed by hydrogenation in the presence of a catalyst such as Pd/C, Pt/C or a chiral rhodium complex to perform the reaction in a stereoselective manner or by hydride transfer from a reducing agent such as BH$_3$, NaBH$_4$, NaBH$_3$CN, LiAlH$_4$, L-selectride (see Larock R. C. *Comprehensive Organic Transformations* 1989, VCH; *Comprehensive Organic Functionnal Group Transformations* 2, 268-269 (2005) Pergamon and references cited therein).

Compounds of general formula I may also be prepared through alkylation of the amine III.

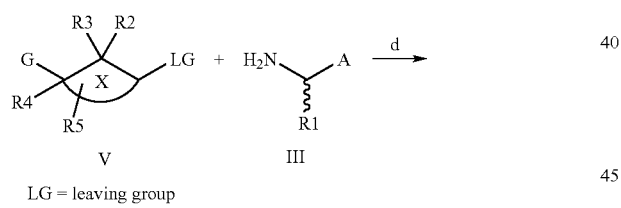

LG = leaving group d. When LG is a leaving group such as chloride, bromide, iodide, tosylate or triflate, alkylation is performed in the presence of a base such as NEt$_3$, DIPEA, NaH, NaOH, KOH, carbonates in an appropriate solvent such as DMF, pyridine, DMSO, CH$_3$CN, acetone, toluene. Alternatively reaction with an alcohol (LG=OH) may also be considered. Such Mitsunobu-like reaction is performed in the presence of a phosphine such as PBu$_3$, PPh$_3$ and the like, an azodicarboxylate or an azodicarboxamide in an aprotic solvent, typically THF. For this purpose the amine III is protected/activated as a carbamate or a sulphonamide. The resulting compound is deprotected using standard conditions (*Protective Groups in Organic Synthesis*, T. W. Greene and P. G. M. Wuts, John Wiley and Sons, 3$^{rd}$ Edition 1999 and reference sited therein) to afford I. The ketone II may be prepared in various manners:

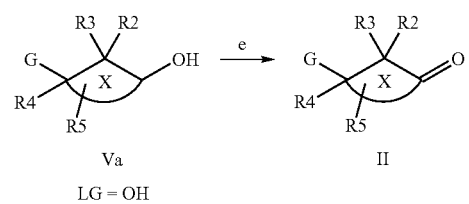

LG = OH e. An alcohol Va may be oxidised to afford II. Oxidation may be performed with many different reagents. A few of them are H$_2$Cr$_2$O$_7$, Al$_2$O$_3$, MnO$_2$, periodinanes, DMSO in combination with DCC, acetic anhydride, oxalyl chloride and the like.

Substituents G may be introduced through different pathways:

Cycloalkenones may be used as starting materials.

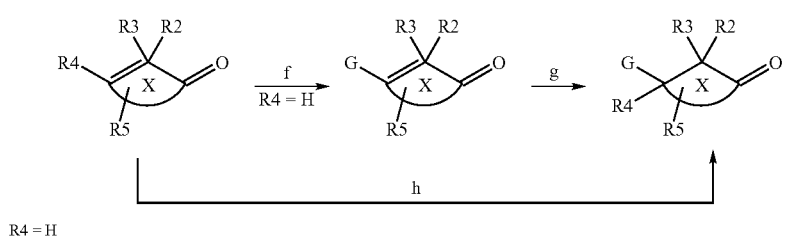

f. Coupling reaction with an aryl/heteroaryl halide or pseudo halide such as triflate in the presence of a palladium source such as Pd(OAc)$_2$, PdCl$_2$(PPh$_3$)$_2$, a base such as NEt$_3$, K$_2$CO$_3$, NaHCO$_3$, eventually with a phosphine such PPh$_3$, P(o-Tol)$_3$, 1,3-bis(diphenylphosphino)propane (dppp), eventually in the presence of a salt like NBu$_4$Cl, AgNO$_3$ in a solvent such as DMF or acetonitrile. Alternatively a decarboxylative Heck-type coupling may be performed using an aryl/heteroaryl carboxylic acid (*Org. Lett.* 2004, 6, 433).

g. Chemospecific reduction of the double bond may be performed under numerous conditions. The hydrogen source may be H$_2$, water, Hantzsch esters. Metal-based catalysts such as Pd/C, Pd(PPh$_3$)$_4$, supported PdCl$_2$, Rh-, Co-, Cu-, Ir-based catalysts may be used. Stereoselectivity may be achieved by addition of a chiral auxiliary such as but not limited to enantiopure binaphtol phosphate derivatives/valine, imidazolidinone iminiums, bidentate phosphines.

Alternatively cycloalkenones may be subjected to 1,4-addition.

h. Reaction with an aryl/heteroaryl metal in which the metal may be Li, Mg halide, trialkyltin, boronic acid eventually in the presence of a metal complex such as PdCl$_2$, Pd(OAc)$_2$, Pd(PPh$_3$)$_4$, (acac)Rh(CO)$_2$, Ni(acac)$_2$, (COD)Rh(1,4-dihydroquinone)BF$_4$ with a ligand typically phosphine-based such as PBu$_3$, PPh$_3$, 1,3-bis(diphenylphosphino)propane (dppp), 1,3-hydroquinone or 1,4-hydroquinone in solvents such as DMF, THF, water, toluene, dioxane, dimethoxyethane. In the presence of a chiral ligand as a pure enantiomer such as BINAP, phosphoramidite, Me-DuPHOS and the like the reaction may be performed stereoselectively.

1,4-Addition of heteroatom nucleophiles leads to compounds of general formula I. The reaction may be catalysed by reagents such as but not limited to NEt$_3$, ScCl$_3$, CAN, RuCl$_3$, PtCl$_4$ in solvents like CH$_2$Cl$_2$, CH$_3$CN, DMF, toluene.

Cycloalkan-1,3-diones may be used as starting materials.

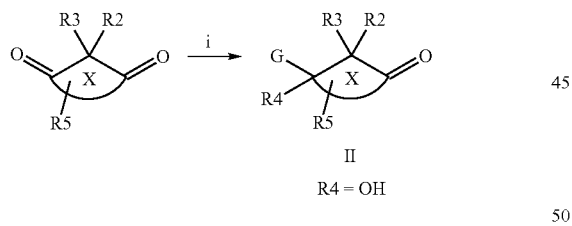

II
R4 = OH i. Addition of an organometallic species such as GLi or GMgHal (Hal=Cl, Br) affords a ketoalcohol II (R4=OH). Alternatively addition of GBr under indium catalysis may lead to analogous ketoalcohols II (R4=OH).

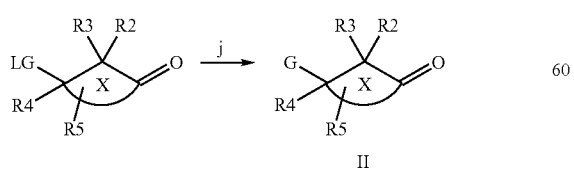

II j. Substitution of a leaving group (LG) such as chloride, bromide, iodide, tosylate or triflate by a nuceophile such as an amine or an alcohol optionally in the presence of a base such as NEt$_3$, NaH, NaOH, KOH, carbonates in an appropriate solvent such as DMF, pyridine, DMSO, CH$_3$CN, acetone, toluene.

Cycloalkan-3-one carboxylates (II, G=CO-Q) are starting materials for various compounds of general formula I where the carboxylic group is transformed into amides or heterocycles. Some non-limiting examples are depicted below.

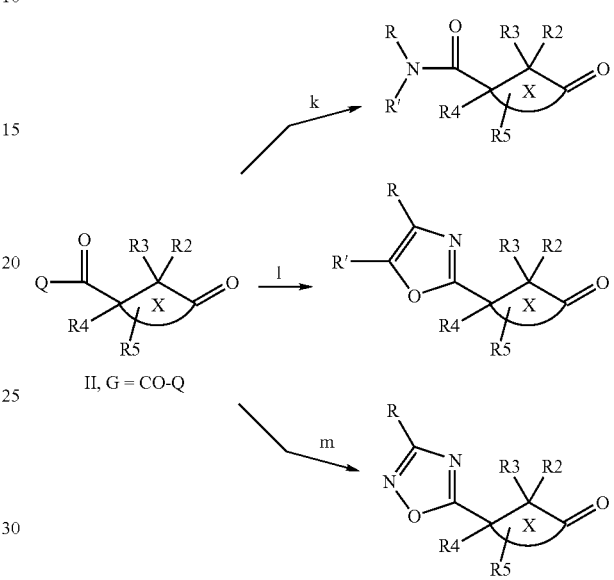

II, G = CO-Q k. The amide may be formed using an amine and a carboxylic acid (II, G=COOH) in the presence of coupling agents such as 1,1'-carbonyldiimidazole (CDI), diphenylphosphinic chloride (DPP-Cl), benzotriazol-yloxy-tripyrrolidinophosphonium hexafluorophosphate (PyBOP), benzotriazol-1-yloxy-tris(dimethylamino)-phosphonium hexafluorophosphate (BOP), pentafluorophenyl diphenylphosphinate (fdpp), N-[(dimethylamino)-1H-1,2,3-triazolo[4,5-b]pyridine-1-yl-methylene]-N-methylmethanaminium hexafluorophosphate N-oxide (HATU), bromotripyrrolidinophosphonium hexafluorophosphate (PyBroP), N,N'-dicyclohexylcarbodiimide (DCC), or 1-ethyl-3-(3-dimethylaminopropyl)-carbodiimide; hydrochloride (EDCI). The reaction may be performed in solvents such as diethylether, dichloromethane, 1,2-dichloro-ethane, tetrahydrofuran, 1-methyl-2-pyrrolidinone, dimethylsulfoxyde or dimethylformamide. The reactions are generally carried out in the presence of a base such as NEt$_3$, DIPEA, collidine or Bu$_3$N and preferably in the presence of an activator such as HOBt (for example where HOBt is used to improve reactions rates, see Windridge, G. C.; Jorgensen, *E. C. JACS* 1971, 93, 6318) or HOAt. The amide may also be formed through the reaction of the amine III and a carboxylic acid chloride (II, G=COCl). The carboxylic acid chloride may be prepared by reaction of the carboxylic acid (II, G=COOH) with chlorinating agents such as thionyl chloride or oxalyl chloride.

l. Carboxylic moiety may be converted into oxazoles by reaction with 1,2-aminoalcohols, 1,2-aminoketones or 1,2-hydroxyketones in the presence of a nitrogen source such as NH$_4$OAc typically through formation of an amide (see condition k) followed by cyclodehydration using reagents such as polyphosphoric acid, p-toluenesulfonic acid, DBU/CBrCl$_3$ or DDQ in solvents such as CCl$_4$, CH$_2$Cl$_2$, THF, dioxane or DMF.

m. Conversion to 1,2,4-oxadiazole may be achieved through reaction with N-hydroxyamidines under amide-bond formation condition (see k) followed by cyclodehydration in the presence of dehydrating agents such as CDI. Alternatively reaction of carboxylic esters (II, G=COOMe or COOEt) with N-hydroxyamidines in presence of a base such as K$_2$CO$_3$ leads to 1,2,4-oxadiazole. If not commercially available the N-hydroxyamidines may be prepared by reacting N-hydroxylamine:hydrochloride with nitriles in the presence of a base such as K$_2$CO$_3$, NaHCO$_3$, NEt$_3$, KOH or MeONa.

If specific substitution patterns are needed on the carbocycle, synthesis of the carbocycles themselves may be considered. Many general methods are available among them are the Diels-Alder reaction, the Robinson annulation, the Birch reduction of aromatics the Pauson-Khand reaction, cyclopropanation of 1-methoxycycloalkene followed by ring expansion, rearrangement of furans. For a comprehensive list see comprehensive organic synthesis works cited earlier in this section.

A compound of general formula I may be obtained from another compound of general formula I by the mean of functional group interconversion well-known to one skilled in the art of organic synthesis. This is if any of R1 to R5 or a substituent on G or on A may be converted to another functional group. These interconversions may be but are not limited to reduction of a nitrile to an amine, hydrolysis of a nitrile to an amide or to an acid or hydrolysis of an ester.

Many of the general methods described above may be used in a different order whenever appropriate.

EXAMPLES

General

For $^1$H nuclear magnetic resonance (NMR) spectra (300 MHz) and $^{13}$C NMR (75.6 MHz) chemical shift values (δ) (in ppm) are quoted for dimethyl-d$_6$ sulfoxide (DMSO-d$_6$) or CDCl$_3$ solutions relative to internal tetramethylsilane (δ=0) standard. The value of a multiplet, either defined (doublet (d), triplet (t), quartet (q)) or not (m) at the approximate mid point is given unless a range is quoted, (bs) indicates a broad singlet. The ES mass spectra were obtained on a VG Quattro II triple quadrapole mass spectrometer (Micromass, Manchester, UK) operating in either positive or negative electrospray mode with a cone voltage of 30V.

The microwave oven used was the model Initiator™ from Biotage.

The organic solvents used were anhydrous unless otherwise specified. Flash chromatography was performed on silica gel from Fluka Chemie GmbH, Switzerland. The phase separation cartridges used were Chromabond® from Macherey-Nagel GmbH.

Chemicals unless otherwise noted were from commercial sources, e.g. Aldrich, Maybridge Chemical, Fluka or ABCR.

ABBREVIATIONS acac acetylacetonate
aq. aqueous
BINAP 2,2'-bis(diphenylphosphino)-1,1'-binaphthyl
Boc tert-butoxycarbonyl
Bu$_3$N tributylamine
CAN ceric ammonium nitrate
CDI 1,1'-carbonyldiimidazole
COD 1,5-cyclooctadiene
DBU 1,8-Diazabicyclo[5.4.0]undec-7-ene
DCC N,N'-dicyclohexylcarbodiimide
DCE 1,2-dichloroethane
DCM dichloromethane
DDQ 2,3-dicyano-5,6-dichloro-parabenzoquinone
DIAD diisopropyl azodicarboxylate
DIPEA ethyl diisopropylamine
DMAP dimethyl aminopyridine
DMF N,N-Dimethylformamide
DME 1,2-dimethoxyethane
DMSO dimethyl sulfoxide
EDAC 1-(3-dimethylaminopropyl)-3-ethylcarbodiimide; hydrochloride
eq. equivalent(s)
ES Electro Spray
EtOAc ethyl acetate
h hour(s)
HOAt 1-hydroxy-7-aza-benzotriazole
HOBt hydroxybenzotriazole
mCPBA meta-chloro perbenzoic acid
Me-DuPhos 1,2-Bis[2,5-dimethylphospholano]benzene
MTBE methyl tert-butyl ether
nbd norbornadiene
NBu$_4$Cl tetrabutylammoniumchloride
NEt$_3$ triethylamine
NMR nuclear magnetic resonance
PBu$_3$ tributylphosphin
PE petroleum ether (low boiling point)
P(o-Tol)$_3$ tri(o-tolyl)-phosphin
r.t. room temperature
RT retention time
sat. saturated
THF tetrahydrofuran
Ti(Oi-Pr)$_4$ titanium tetraisopropoxide
TLC thin layer chromatography
TMSCl chloro trimethylsilane LC/MS Method A Analytical HPLC/MS was performed on a Dionex APS-system with a P680A analytical pump and a Thermo MSQ Plus mass spectrometer (ionisation mode: ES+/ES−). Column: Waters XTerra C-18, 150 mm×4.6 mm, 5 μm; mobile phase: A=water (0.1% formic acid) and B=acetonitrile (0.1% formic acid); flow rate=1.0 mL/min; method (10 min): Linear gradient method going from 10% B to 100% in 6.6 minutes and staying at 100% B for another 1.5 minutes.

LC/MS Method B

Analytical HPLC/MS was performed on a Waters 2795 Alliance-system with a Waters 996 DAD analytical pump and a Waters ZQ Mass spectrometer (ionisation mode: ES+/ES−). Column: Waters Waters XBridge RP18 3.0×50 mm, 5 μm; mobile phase: A=H$_2$O+0.05% HCOOH and B=CH$_3$CN+0.05% HCOOH; flow rate=1.0 mL/min; method (8 min): Linear gradient method going from 5% B to 95% B in 6 minutes and staying at 95% B for another 1 minute. Retention time in UV chromatogram (RT) is given in minutes.

General Procedure A

To a solution of ketone (1 eq.) in 1,2-dichlorethane (0.38M) were added the amine (1 eq.), glacial AcOH (1 eq.) and NaBH(OAc)$_3$ (1.4 eq.). The mixture was stirred at r.t. overnight, filtered and concentrated in vacuo. If necessary, purification was performed by continuous gradient flash chromatography.

Example 1

Cyclobutyl-((R)-1-naphthalen-1-yl-ethyl)-amine, hydrochloride (Compound 1001)

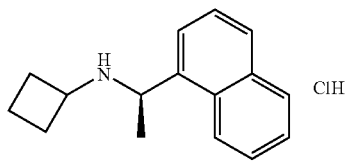 [SMILES: C[C@@H](NC1CCC1)c1cccc2ccccc12 ; Cl]

General procedure A was followed using cyclobutanone (488 mg, 1.2 eq.) and (+)-(R)-1-naphthalen-1-yl-ethylamine (1 g). The solution was stirred for 10 min before addition of 3 Å molecular sieves, glacial AcOH and NaBH(OAc)$_3$. After removal of the solvent the residue was taken in MeCN (20 mL) and treated with aq. 2N NaOH (10 mL), filtered and concentrated in vacuo. The residue was dissolved in EtOAc, washed with water, filtered and concentrated in vacuo. Chromatography (EtOAc-MeOH 100:0 to 80:20) afforded the title compound. $^{13}$C NMR (75.5 MHz, DMSO) δ: 134.58, 133.71, 130.61, 129.29, 129.25, 127.27, 126.48, 125.86, 125.06, 122.82, 50.43, 50.16, 26.90, 20.63, 15.19.

General Procedure B

To a solution or a suspension of acid (1 eq.) in DMF (1M) under argon was added CDI (1.2 eq.). The mixture was stirred at r.t. for 3 h before addition of the amine (6 eq.). DIPEA (6 eq.) was added if the amine was furnished as the hydrochloride. Stirring was continued overnight at r.t. DMF was removed in vacuo. If necessary, purification was performed by continuous gradient flash chromatography.

Preparation 1: 3-((R)-1-naphthalen-1-yl-ethylamino)-cyclobutanecarboxylic acid (Compound 1000)

To a solution of 3-oxo-1-cyclobutane carboxylic acid (4.0 g) in 1,2-dichlorethane (180 mL) were added (+)-(R)-1-naphthalen-1-yl-ethylamine (6.0 g), glacial AcOH (1 eq., 2.1 mL) and NaBH(OAc)$_3$ (1.5 eq., 11.1 g). The mixture was stirred at r.t. for 48 h before removal of the solvent. The residue was treated with 1N NaOH (ca 100 mL) and pH was adjusted to 7 by addition of 4N HCl. The oily precipitate was extracted with EtOAc. The solid formed upon extraction was filtered and washed with EtOAc to afford the title compound.

Example 2

3-((R)-1-naphthalen-1-yl-ethylamino)-cyclobutanecarboxylic acid dimethylamide (Compound 1002)

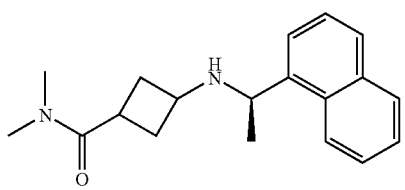 [SMILES: C[C@@H](NC1CC(C(=O)N(C)C)C1)c1cccc2ccccc12]

General procedure B was followed using 3-((R)-1-naphthalen-1-yl-ethylamino)-cyclobutanecarboxylic acid (preparation 1, 100 mg) and dimethylamine; hydrochloride (181 mg). Chromatography (CH$_2$Cl$_2$-MeOH/1% NEt$_3$ 100:0 to 70:30) afforded the title compound as an oil (mixture of 2 isomers. $^{13}$C NMR (75.5 MHz, DMSO) major isomer δ: 174.53, 140.84, 133.98, 131.12, 129.02, 127.40, 125.87, 125.69, 125.36, 123.06, 122.79, 51.12, 49.31, 36.71, 35.48, 33.38, 32.84, 31.59, 23.35.

Example 3

3-((R)-1-naphthalen-1-yl-ethylamino)-cyclobutanecarboxylic acid amide (Compound 1003)

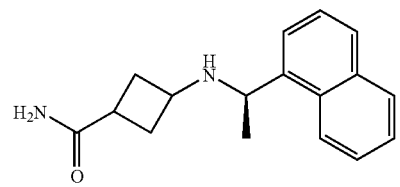 [SMILES: C[C@@H](NC1CC(C(N)=O)C1)c1cccc2ccccc12]

General procedure B was followed using 3-((R)-1-naphthalen-1-yl-ethylamino)-cyclobutanecarboxylic acid (preparation 1, 155 mg) and aq. NH$_3$ (2.5 mL). Chromatography (CH$_2$Cl$_2$-MeOH 90:10 to 70:30) afforded the title compound.

LC-MS (method B): RT=1.53, [M+H]$^+$=269.3, [M−H]$^-$=267.4.

Example 4

(4-Methyl-piperazin-1-yl)-[3-((R)-1-naphthalen-1-yl-ethylamino)-cyclobutyl]-methanone; hydrochloride (Compound 1004)

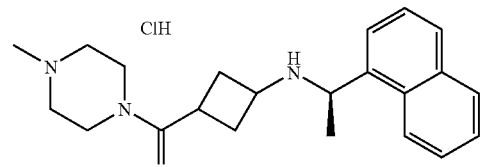

General procedure B was followed using 3-((R)-1-naphthalen-1-yl-ethylamino)-cyclobutanecarboxylic acid (preparation 1, 100 mg) and N-methylpiperazine (3 eq.). An extractive work-up (EtOAc and water) was performed before chromatography (CH$_2$Cl$_2$-MeOH 95:5 to 70:30). The resulting oil was treated with HCl. The precipitate was filtered to afford the title compound.

LC-MS (method B): RT=1.37, [M+H]$^+$=352.3.

Example 5

3-((R)-1-naphthalen-1-yl-ethylamino)-cyclobutan-ecarboxylic acid cyclopropylamide (Compound 1005)

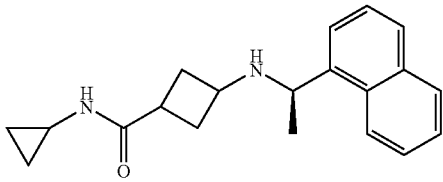 [SMILES: C[C@@H](NC1CC(C(=O)NC2CC2)C1)c1cccc2ccccc12]

General procedure B was followed using 3-((R)-1-naphthalen-1-yl-ethylamino)-cyclobutanecarboxylic acid (preparation 1, 100 mg) and cyclopropylamine. Chromatography (CH$_2$Cl$_2$-MeOH/1% NEt$_3$ 100:0 to 70:30) afforded the title compound. LC-MS (method B): RT=2.2, [M+H]$^+$=309.3.

Example 6

3-((R)-1-naphthalen-1-yl-ethylamino)-cyclobutan-ecarboxylic acid isopropylamide (Compound 1006)

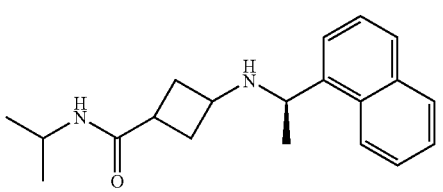 [SMILES: CC(C)NC(=O)C1CC(N[C@H](C)c2cccc3ccccc23)C1]

General procedure B was followed using 3-((R)-1-naphthalen-1-yl-ethylamino)-cyclobutanecarboxylic acid (preparation 1, 100 mg) and isopropylamine. Chromatography (CH$_2$Cl$_2$-MeOH/1% NEt$_3$ 100:0 to 70:30) afforded the title compound. LC-MS (method B): RT=2.3, [M+H]$^+$=311.3.

Example 7

3-((R)-1-naphthalen-1-yl-ethylamino)-cyclobutan-ecarboxylic acid propylamide (Compound 1007)

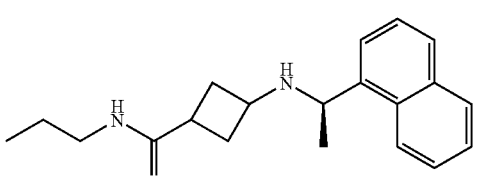

General procedure B was followed using 3-((R)-1-naphthalen-1-yl-ethylamino)-cyclobutanecarboxylic acid (preparation 1, 100 mg) and propylamine. Chromatography (CH$_2$Cl$_2$-MeOH/1% NEt$_3$ 100:0 to 70:30) afforded the title compound. LC-MS (method B): RT=2.3, [M+H]$^+$=311.1.

Example 8

Morpholin-4-yl-[3-((R)-1-naphthalen-1-yl-ethyl-amino)-cyclobutyl]-methanone (Compound 1008)

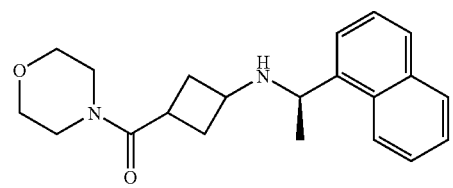 [SMILES: C[C@@H](NC1CC(C(=O)N2CCOCC2)C1)c1cccc2ccccc12]

General procedure B was followed using 3-((R)-1-naphthalen-1-yl-ethylamino)-cyclobutanecarboxylic acid (preparation 1, 100 mg) and morpholine. Chromatography (CH$_2$Cl$_2$-MeOH/1% NEt$_3$ 100:0 to 70:30) afforded the title compound as an oil. LC-MS (method B): RT=2.16, [M+H]$^+$=339.3.

Example 9

3-((R)-1-naphthalen-1-yl-ethylamino)-cyclobutan-ecarboxylic acid tert-butylamide (Compound 1009)

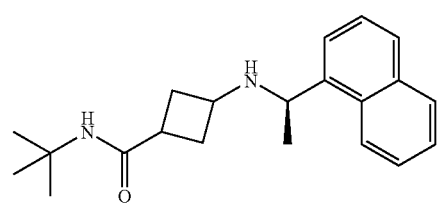 [SMILES: C[C@@H](NC1CC(C(=O)NC(C)(C)C)C1)c1cccc2ccccc12]

General procedure B was followed using 3-((R)-1-naphthalen-1-yl-ethylamino)-cyclobutanecarboxylic acid (preparation 1, 100 mg) and tert-butylamine. Chromatography (CH$_2$Cl$_2$-MeOH/1% NEt$_3$ 100:0 to 70:30) afforded the title compound as an oil. LC-MS (method B): RT=2.6, [M+H]$^+$=325.3.

Example 10

3-((R)-1-naphthalen-1-yl-ethylamino)-cyclobutan-ecarboxylic acid ethylamide (Compound 1010)

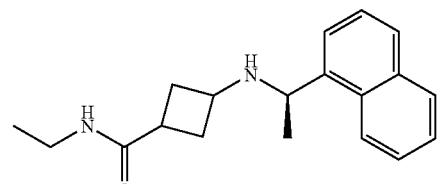

General procedure B was followed using 3-((R)-1-naphthalen-1-yl-ethylamino)-cyclobutanecarboxylic acid (preparation 1, 100 mg) and ethylamine. Chromatography (CH$_2$Cl$_2$-MeOH/1% NEt$_3$ 100:0 to 70:30) afforded the title compound as an oil. LC-MS (method B): RT=2.13, [M+H]$^+$=297.2.

Example 11

3-((R)-1-naphthalen-1-yl-ethylamino)-cyclobutanecarboxylic acid methoxy-methyl-amide; hydrochloride (Compound 1011)

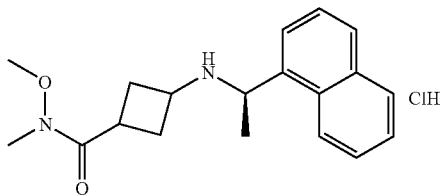 [SMILES: CON(C)C(=O)C1CC(N[C@H](C)c2cccc3ccccc23)C1 ; Cl]

General procedure B was followed using 3-((R)-1-naphthalen-1-yl-ethylamino)-cyclobutanecarboxylic acid (preparation 1, 100 mg) and N,O-dimethylhydroxyl-amine; hydrochloride. Chromatography (CH$_2$Cl$_2$-MeOH/1% NEt$_3$ 100:0 to 70:30) afforded the title compound as an oil. LC-MS (method B): RT=2.17/2.31, [M+H]$^+$=313.2.

General Procedure C

To a solution or a suspension of acid (1 eq.) in DMF (1M) under argon was added CDI (1.2 eq.). The mixture was stirred at r.t. for ×h before addition of the N-hydroxyamidine (1.2 eq.). Stirring was continued at r.t. for y h. CDI (1.2 eq.) was added and the mixture was heated to 115° C. for 1.5 h. The mixture was cooled to r.t., washed with water, NaHCO$_3$ and brine, dried over MgSO$_4$, filtered and concentrated in vacuo. If necessary, purification was performed by continuous gradient flash chromatography.

Example 12

[3-(3-Isopropyl-[1,2,4]oxadiazol-5-yl)-cyclobutyl]-((R)-1-naphthalen-1-yl-ethyl)-amine; hydrochloride (Compound 1012)

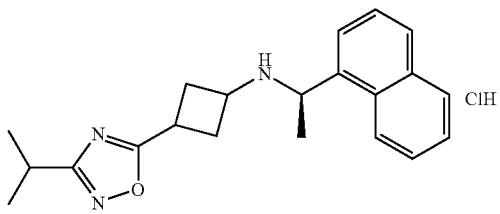 [SMILES: CC(C)c1noc(C2CC(N[C@H](C)c3cccc4ccccc34)C2)n1 ; Cl]

General procedure C was followed using 3-((R)-1-naphthalen-1-yl-ethylamino)-cyclobutanecarboxylic acid (preparation 1, 150 mg) and N'-hydroxy-2-methylpropaninnidamide (x=3 h, y=48 h). Chromatography (PE-EtOAc 100:0 to 40:60) afforded an oil which was treated with 4N HCl in dioxane. Precipitation occurred upon addition of Et$_2$O. The light-yellow precipitate was filtered and dried in vacuo to afford the title compound. $^{13}$C NMR (150.9 MHz, DMSO) δ: 180.68, 174.28, 133.70, 133.25, 130.19, 129.05, 128.86, 126.90, 126.13, 125.43, 124.68, 122.45, 50.23, 48.16, 39.97, 30.09, 25.92, 25.72, 20.09.

Example 13

((R)-1-Naphthalen-1-yl-ethyl)-{3-[3-(3-trifluoromethyl-phenyl)-[1,2,4]oxadiazol-5-yl]-cyclobutyl}-amine; hydrochloride (Compound 1013)

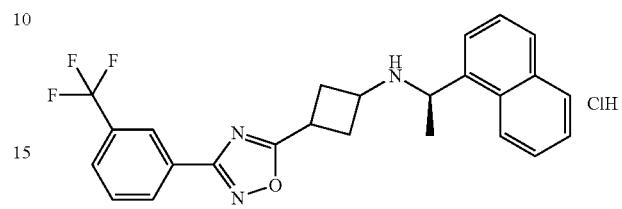

General procedure C was followed using 3-oxo-1-cyclobutane carboxylic acid (1.41 g, 12.4 mmol) and 3-trifluoromethyl-N-hydroxy-benzamidine (x=1 h, y=17 h). Chromatography (PE-EtOAc 80:20 to 70:30) afforded 3-[3-(3-trifluoromethyl-phenyl)-[1,2,4]oxadiazol-5-yl]-cyclobutanone (compound 1112).

General procedure A was followed using 3-[3-(3-trifluoromethyl-phenyl)-[1,2,4]oxadiazol-5-yl]-cyclobutanone (690 mg) and (+)-(R)-1-naphthalen-1-yl-ethylamine. The mixture was worked up as follows. Et$_2$O was added to the reaction mixture. The organic phase was washed with aq. NaOH (1N), water and brine, dried over MgSO$_4$, filtered and concentrated in vacuo. Chromatography (PE-EtOAc 80:20 to 60:40) afforded an oil which was treated with 4N HCl in dioxane. Precipitation occurred upon addition of Et$_2$O and trituration. The colourless precipitate was filtered and dried in vacuo to afford the title compound. LC-MS (method B): RT=3.28, [M+H]$^+$=438.2.

Example 14

[3-(3-Methyl-[1,2,4]oxadiazol-5-yl)-cyclobutyl]-((R)-1-naphthalen-1-yl-ethyl)-amine; hydrochloride (Compound 1014)

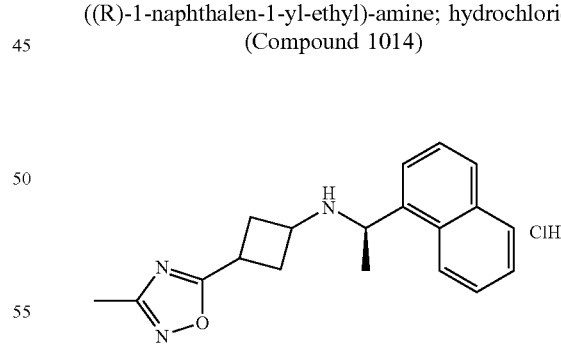

General procedure C was followed using 3-((R)-1-naphthalen-1-yl-ethylamino)-cyclobutanecarboxylic acid (preparation 1, 150 mg) and N'-hydroxy-ethanimidamide (x=2 h, y=48 h). Chromatography (PE-EtOAc 100:0 to 40:60) afforded an oil which was treated with 4N HCl in dioxane. Precipitation occurred upon addition of Et$_2$O and trituration. The light-yellow precipitate was filtered and dried in vacuo to afford the title compound. LC-MS (method B): RT=2.31, [M+H]$^+$=308.2.

Example 15

((R)-1-Naphthalen-1-yl-ethyl)-[3-(3-phenyl-[1,2,4]oxadiazol-5-yl)-cyclobutyl]-amine; hydrochloride (Compound 1015)

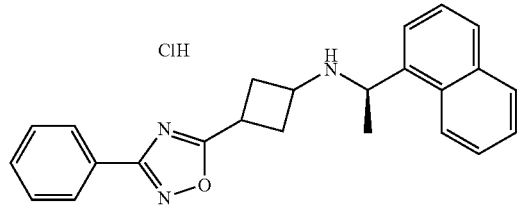 [SMILES: C[C@@H](NC1CC(c2nc(-c3ccccc3)no2)C1)c1cccc2ccccc12 ; Cl]

General procedure C was followed using 3-((R)-1-naphthalen-1-yl-ethylamino)-cyclobutanecarboxylic acid (preparation 1, 150 mg) and benzamidoxime (x=2 h, y=22 h). Chromatography (PE-EtOAc 100:0 to 50:50) afforded a light yellow oil which was treated with 4N HCl in dioxane. Precipitation occurred upon addition of Et$_2$O. The precipitate was filtered and dried in vacuo to afford the title compound. LC-MS (method B): RT=3.04, [M+H]$^+$=370.3.

Example 16

((R)-1-Naphthalen-1-yl-ethyl)-{3-[3-(4-trifluoromethyl-phenyl)-[1,2,4]oxadiazol-5-yl]-cyclobutyl}-amine; hydrochloride (Compound 1016)

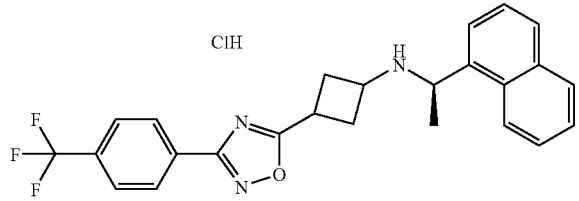 [SMILES: C[C@@H](NC1CC(c2nc(-c3ccc(C(F)(F)F)cc3)no2)C1)c1cccc2ccccc12 ; Cl]

General procedure C was followed using 3-((R)-1-naphthalen-1-yl-ethylamino)-cyclobutanecarboxylic acid (preparation 1, 150 mg) and 4-trifluoromethylbenzamidoxime (x=2 h, y=22 h). Chromatography (PE-EtOAc 100:0 to 50:50) afforded an oil which was treated with 4N HCl in dioxane. Precipitation occurred upon addition of Et$_2$O. The precipitate was filtered and dried in vacuo to afford the title compound. LC-MS (method B): RT=3.52, [M+H]$^+$=438.2.

Example 17

{3-[3-(4-Methoxy-phenyl)-[1,2,4]oxadiazol-5-yl]-cyclobutyl}-((R)-1-naphthalen-1-yl-ethyl)-amine; hydrochloride (Compound 1017)

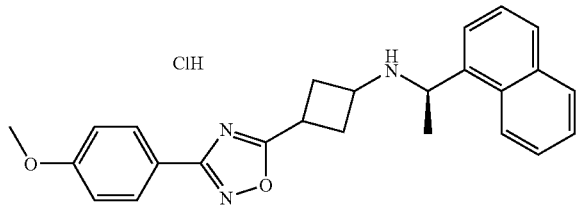 [SMILES: COc1ccc(-c2noc(C3CC(N[C@H](C)c4cccc5ccccc45)C3)n2)cc1 ; Cl]

General procedure C was followed using 3-((R)-1-naphthalen-1-ylethylamino)-cyclobutanecarboxylic acid (preparation 1, 150 mg) and 4-methoxybenzamidoxime (x=1 h, y=22 h). Chromatography (PE-EtOAc 100:0 to 40:60) afforded an oil which was treated with 4N HCl in dioxane. Precipitation occurred upon addition of Et$_2$O. The precipitate was filtered and dried in vacuo to afford the title compound. LC-MS (method B): RT=3.14, [M+H]$^+$=400.3.

Preparation 2: 3-Oxocyclobutane carbonyl chloride

Oxalylchloride (1.5 eq.) was added dropwise to a solution of 3-oxocyclobutane carboxylic acid (56 mmol) in CH$_2$Cl$_2$ and DMF (1 drop) under argon. The solution was stirred at r.t. for 30 min before being concentrated in vacuo to afford the crude 3-oxocyclobutane carbonyl chloride used without further purification.

General Procedure D

To a solution of the acid chloride (preparation 2, 1.2 mmol) in 1,2-dichloroethane (0.5 mL) was added the amine (1.2 mmol) as a CH$_2$Cl$_2$-solution (1 mL) and NEt$_3$ (1.5 eq.). The mixture was shaken at r.t. overnight. 0.5M aq. HCl (0.5 mL) was added and the mixture was shaken at r.t. for 2 h. Filtration through a phase separation cartridge afforded the organic phase which was concentrated in vacuo to give a crude amide used without further purification.

To a solution of the amide (1.2 mmol) in 1,2-dichloroethane (1 mL) were added (+)-(R)-1-naphthalen-1-yl-ethylamine (1 eq.) and glacial AcOH (2 eq.). The mixture was shaken for 2 h before addition of NaHB(OAc)$_3$ (1.5 eq.). Shaking was continued at r.t. overnight before filtration and concentration in vacuo. The residue was dissolved in DMSO (1 mL). 0.1 mL of this solution was purified by preparative HPLC-MS, re-analysed by HPLC-MS method A.

Example 18

3-((R)-1-Naphthalen-1-yl-ethylamino)-cyclobutanecarboxylic acid 4-chloro-benzylamide (Compound 1018)

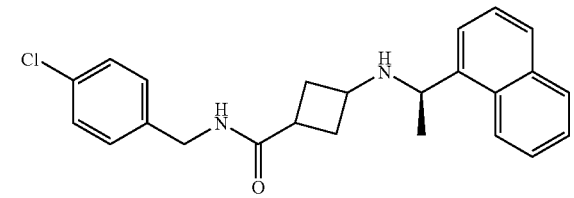 [SMILES: C[C@@H](NC1CC(C(=O)NCc2ccc(Cl)cc2)C1)c1cccc2ccccc12]

General procedure D was followed using 4-chlorobenzylamine to afford the title compound as a mixture of 2 isomers in almost equal amount. LC/MS (METHOD A): (m/z) 393.1 (MH+); RT (UV)=5.11 min. $^1$H NMR (500 MHz, DMSO) δ$_H$ 8.26 (t, 1H), 8.14-8.20 (m, 1H), 7.91 (d, 1H), 7.78 (d, 1H), 7.67 (t, 1H), 7.42-7.56 (m, 3H), 7.33 (dd, 2H), 7.19 (dd, 2H), 4.49-4.64 (m, 1H), 4.18 (dd, 1H), 2.80-3.03 (m, 2H), 1.79-2.24 (m, 4H), 1.36 (d, 3H) (one CH hidden by water-signal). LC-MS (method B): RT=5.11, [M+H]$^+$=393.1.

Example 19

{[3-((R)-1-Naphthalen-1-yl-ethylamino)-cyclobutan-ecarbonyl]-amino}-acetic acid methyl ester (Compound 1019)

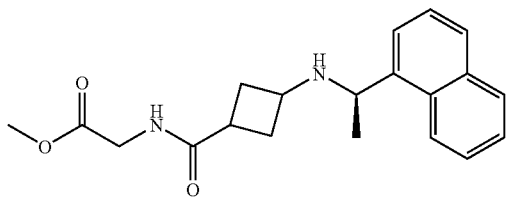 [SMILES: COC(=O)CNC(=O)C1CC(N[C@H](C)c2cccc3ccccc23)C1]

General procedure D was followed using 2-aminoacetic acid methyl ester;
hydrochloride. LC-MS (method B): RT=4.32, [M+H]$^+$=341.0.

Example 20

3-((R)-1-Naphthalen-1-yl-ethylamino)-cyclobutan-ecarboxylic acid (2-methoxy-ethyl)-amide (Compound 1020)

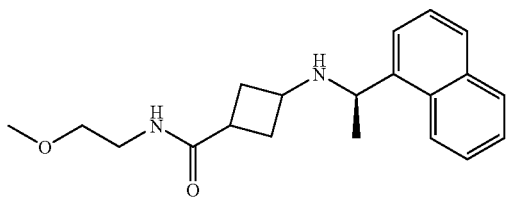 [SMILES: COCCNC(=O)C1CC(N[C@H](C)c2cccc3ccccc23)C1]

General procedure D was followed using 2-methoxyethylamine. LC-MS (method B): RT=4.12, [M+H]$^+$=327.1.

Example 21

4-{[3-((R)-1-Naphthalen-1-yl-ethylamino)-cyclobutanecarbonyl]-amino}-benzoic acid ethyl ester (Compound 1021)

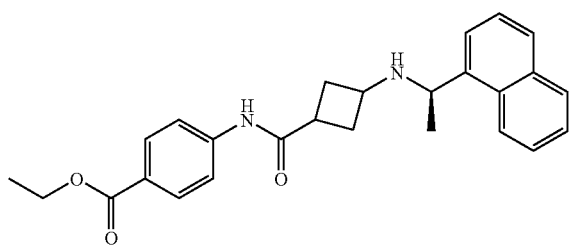 [SMILES: CCOC(=O)c1ccc(NC(=O)C2CC(N[C@H](C)c3cccc4ccccc34)C2)cc1]

General procedure D was followed using 4-aminobenzoic acid ethyl ester. LC-MS (method B): RT=5.12, [M+H]$^+$=417.2.

Example 22

(2,6-Dimethyl-morpholin-4-yl)-[3-((R)-1-naphthalen-1-yl-ethyl amino)-cyclobutyl]-methanone (Compound 1022)

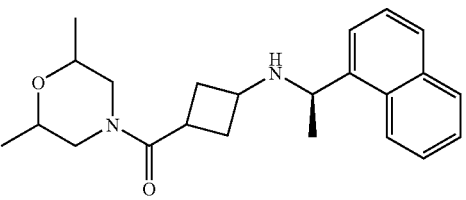 [SMILES: CC1CN(C(=O)C2CC(N[C@H](C)c3cccc4ccccc34)C2)CC(C)O1]

General procedure D was followed using 2,6-dimethyl-morpholine. LC-MS (method B): RT=4.56, [M+H]$^+$=367.1.

Example 23

3-((R)-1-Naphthalen-1-yl-ethylamino)-cyclobutan-ecarboxylic acid (3-morpholin-4-yl-propyl)-amide (Compound 1023)

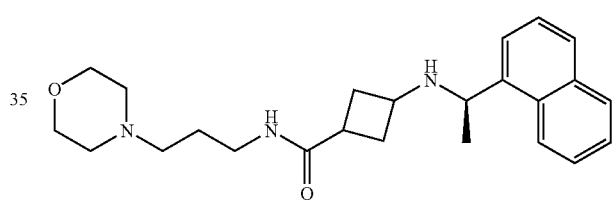

General procedure D was followed using 1-morpholino-3-aminopropane. LC-MS (method B): RT=3.54, [M+H]$^+$=396.2.

Example 24

1-[3-((R)-1-Naphthalen-1-yl-ethylamino)-cyclobutanecarbonyl]-piperidine-4-carboxylic acid ethyl ester (Compound 1024)

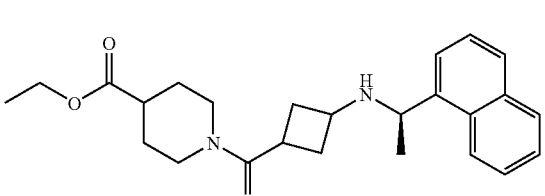

General procedure D was followed using piperidine-4-carboxylic acid ethyl ester. LC-MS (method B): RT=4.81, [M+H]$^+$=409.2.

Example 25

3-((R)-1-Naphthalen-1-yl-ethylamino)-cyclobutan-ecarboxylic acid (2-hydroxy-2-phenyl-ethyl)-amide (Compound 1025)

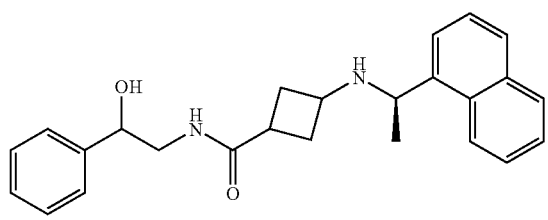 [SMILES: C[C@@H](NC1CC(C(=O)NCC(O)c2ccccc2)C1)c1cccc2ccccc12]

General procedure D was followed using 2-hydroxy-2-phenyl-ethylamine. LC-MS (method B): RT=4.59, [M+H]$^+$=389.1.

Example 26

3-{[3-((R)-1-Naphthalen-1-yl-ethylamino)-cyclobutanecarbonyl]-amino}-propionic acid ethyl ester (Compound 1026)

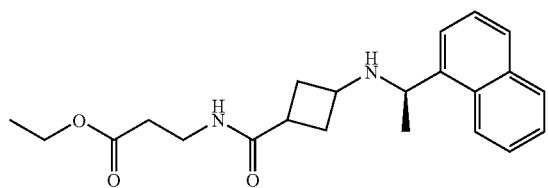 [SMILES: CCOC(=O)CCNC(=O)C1CC(N[C@H](C)c2cccc3ccccc23)C1]

General procedure D was followed using 3-aminopropionic acid ethyl ester; hydrochloride. LC-MS (method B): RT=4.57, [M+H]$^+$=369.1.

Example 27

[3-((R)-1-Naphthalen-1-yl-ethylamino)-cyclobutyl]-[4-(3-trifluoromethyl-phenyl)-piperazin-1-yl]-methanone (Compound 1027)

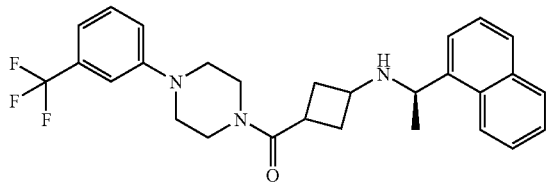 [SMILES: C[C@@H](NC1CC(C(=O)N2CCN(c3cccc(C(F)(F)F)c3)CC2)C1)c1cccc2ccccc12]

General procedure D was followed using 4-(3-trifluoromethyl-phenyl)-piperazine. LC-MS (method B): RT=5.56, [M+H]$^+$=482.1.

Example 28

{[3-((R)-1-Naphthalen-1-yl-ethylamino)-cyclobutanecarbonyl]-amino}-phenyl-acetic acid methyl ester (Compound 1028)

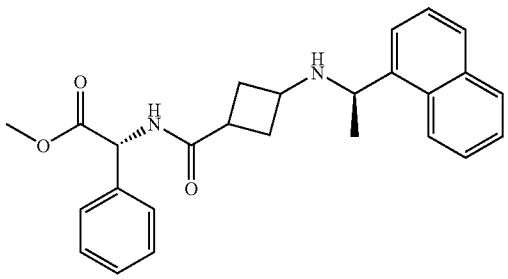 [SMILES: COC(=O)[C@H](NC(=O)C1CC(N[C@H](C)c2cccc3ccccc23)C1)c1ccccc1]

General procedure D was followed using (R)-(−)-2-phenylglycin methyl ester; hydrochloride. LC-MS (method B): RT=4.86, [M+H]$^+$=417.1.

Example 29

3-((R)-1-Naphthalen-1-yl-ethylamino)-cyclobutan-ecarboxylic acid (2-hydroxy-indan-1-yl)-amide (Compound 1029)

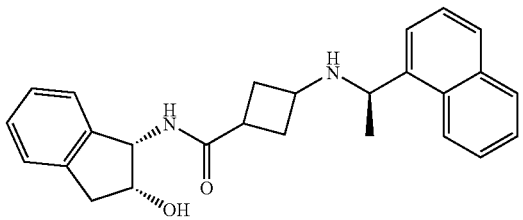 [SMILES: C[C@@H](NC1CC(C(=O)N[C@H]2c3ccccc3C[C@H]2O)C1)c1cccc2ccccc12]

General procedure D was followed using (1S,2R)-(−)cis-1-amino-2-indanol. LC-MS (method B): RT=4.67, [M+H]$^+$=401.2.

Example 30

[4-(2-Methoxy-ethyl)-piperazin-1-yl]-[3-((R)-1-Naphthalen-1-yl-ethylamino)-cyclobutyl]-methanone (Compound 1030)

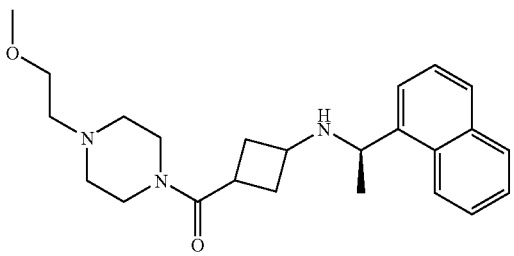 [SMILES: COCCN1CCN(C(=O)C2CC(N[C@H](C)c3cccc4ccccc34)C2)CC1]

General procedure D was followed using 4-(2-methoxy-ethyl)-piperazine. LC-MS (method B): RT=3.52, [M+H]$^+$=396.2.

Example 31

3-((R)-1-Naphthalen-1-yl-ethylamino)-cyclobutanecarboxylic acid 2,3,6-trifluoro-benzylamide (Compound 1031)

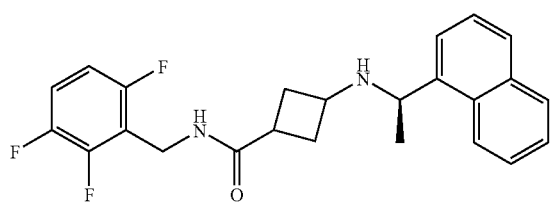 [SMILES: C[C@@H](NC1CC(C(=O)NCc2c(F)ccc(F)c2F)C1)c1cccc2ccccc12]

General procedure D was followed using 2,3,6-trifluoro benzylamine. LC-MS (method B): RT=4.99, [M+H]⁺=413.1.

Example 32

3-({[3-((R)-1-Naphthalen-1-yl-ethylamino)-cyclobutanecarbonyl]-amino}-methyl)-benzoic acid methyl ester (Compound 1032)

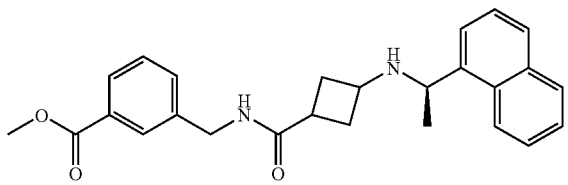 [SMILES: COC(=O)c1cccc(CNC(=O)C2CC(N[C@H](C)c3cccc4ccccc34)C2)c1]

General procedure D was followed using 3-aminomethyl benzoic acid methyl ester: hydrochloride. LC-MS (method B): RT=4.81, [M+H]⁺=417.1.

Example 33

4-({[3-((R)-1-Naphthalen-1-yl-ethylamino)-cyclobutanecarbonyl]-amino}-methyl)-benzoic acid methyl ester (Compound 1033)

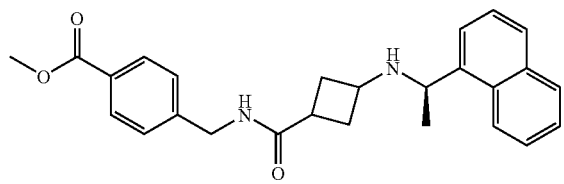 [SMILES: COC(=O)c1ccc(CNC(=O)C2CC(N[C@H](C)c3cccc4ccccc34)C2)cc1]

General procedure D was followed using 4-aminomethyl benzoic acid methyl ester. LC-MS (method B): RT=4.79, [M+H]⁺=417.1.

Example 34

{[3-((R)-1-Naphthalen-1-yl-ethylamino)-cyclobutanecarbonyl]-amino}-phenyl-acetic acid (Compound 1034)

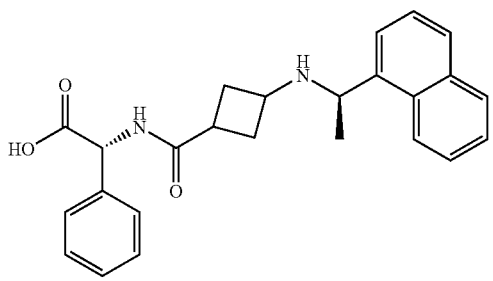 [SMILES: C[C@@H](NC1CC(C(=O)N[C@@H](C(=O)O)c2ccccc2)C1)c1cccc2ccccc12]

To a solution of {[3-((R)-1-naphthalen-1-yl-ethylamino)-cyclobutanecarbonyl]-amino}-phenyl-acetic acid methyl ester (ex. 28, 1.2 mmol) in MeOH (1 mL) were added water (0.3 mL) and LiOH (10 eq.). The mixture was shaken at r.t. overnight. Aq. HCl (4N) was added until pH=5. Solvent was decanted and the remaining oil was washed with EtOAc, dried in vacuo and purified by preparative HPLC-MS. LC-MS (method B): RT=2.47, [M+H]⁺=403.3, [M−H]⁻=401.4

Example 35

((R)-1-Naphthalen-1-yl-ethyl)-(3-phenyl-cyclobutyl)-amine (Compound 1035 and Compound 1036)

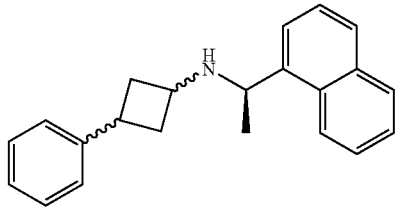

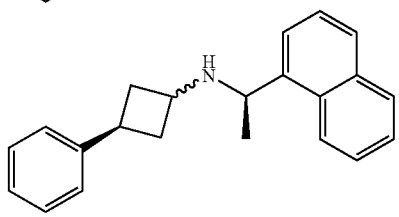

General procedure A was followed using 3-phenylcyclobutanone (1.0 g) and (+)-(R)-1-naphthalen-1-yl-ethylamine. Chromatography (PE-EtOAc-MeOH 100:0:0 to 0:100:0 to 0:80:20) afforded the title compound (compound 1035), and the title compound (compound 1036). LC-MS (method B): compound 1035: RT=2.22, [M+H]⁺=302.2; compound 1036: RT=2.28, [M+H]⁺=302.2.

Preparation 3: 3-((R)-1-Naphthalen-1-yl-ethylamino)-cyclopentanecarboxylic acid (Compound 1111)

To a solution of 3-oxo-1-cyclopentane carboxylic acid (5.3 g) in 1,2-dichlorethane (100 mL) were added (+)-(R)-

1-naphthalen-1-yl-ethylamine (7.1 g), glacial AcOH (1 eq., 2.4 mL) and NaBH(OAc)$_3$ (1.5 eq., 13.1 g). The mixture was stirred at r.t. for 4 h before removal of the solvent. The residue was treated with sat. aq. NaNCO$_3$, pH was adjusted to 7 by addition of glacial AcOH. Extraction (5 times) was performed with EtOAc. The combined extracts were dried over MgSO$_4$, filtered and concentrated in vacuo to afford an oil which upon trituration in EtOAc precipitated. Filtration afforded the title compound The pH of the aq. phase was adjusted to 6 with 4N HCl, upon standing precipitation occurred. Filtrations afforded more of the title compound.

Example 36

{3-[3-(4-Fluoro-phenyl)-[1,2,4]oxadiazol-5-yl]-cyclopentyl}-((R)-1-naphthalen-1-yl-ethyl)-amine; hydrochloride (Compound 1037)

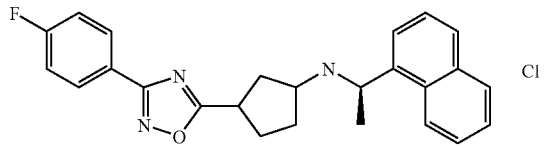 [SMILES: C[C@@H](NC1CCC(c2nc(-c3ccc(F)cc3)no2)C1)c1cccc2ccccc12 ; Cl]

General procedure C was followed using 3-((R)-1-naphthalen-1-yl-ethylamino)-cyclopentanecarboxylic acid (preparation 3, 205 mg) and N'-hydroxy-(4-fluorophenyl) imidamide (x=24 h, y=5 h). Chromatography (PE-EtOAc 100:0 to 40:60) afforded an oil which was treated with 4N HCl in dioxane. Precipitation occurred upon addition of Et$_2$O. The light-yellow precipitate was filtered and dried in vacuo to afford the title compound. $^1$N NMR (300 MHz, DMSO) $\delta_H$: 10.22 (s, 1H), 9.60 (s, 1H), 8.34 (d, 1H), 7.91-8.14 (m, 6H), 7.54-7.73 (m, 3H), 7.30-7.47 (m, 2H), 5.36 (q, 1H), 3.74-3.93 (m, 1H), 3.50-3.69 (m, 1H), 2.21-2.44 (m, 3H), 1.95-2.18 (m, 2H), 1.78-1.90 (m, 1H), 1.75 (d, 3H).

Example 37

((R)-1-Naphthalen-1-yl-ethyl)-[3-(3-phenyl-[1,2,4] oxadiazol-5-yl)-cyclopentyl]-amine; hydrochloride (Compound 1038)

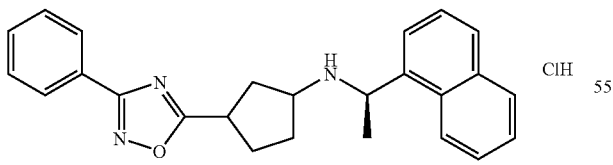

General procedure C was followed using 3-((R)-1-naphthalen-1-yl-ethylamino)-cyclopentanecarboxylic acid (preparation 3, 205 mg) and benzamidoxime (x=24 h, y=5 h). Chromatography (PE-EtOAc 100:0 to 40:60) afforded an oil which was treated with 4N HCl in dioxane. Precipitation occurred upon addition of Et$_2$O. The light-yellow precipitate was filtered and dried in vacuo to afford the title compound. LC-MS (method B): RT=2.94, [M+H]$^+$=384.2.

Example 38

[3-(3-Isopropyl-[1,2,4]oxadiazol-5-yl)-cyclopentyl]-((R)-1-naphthalen-1-yl-ethyl)-amine; hydrochloride (Compound 1039)

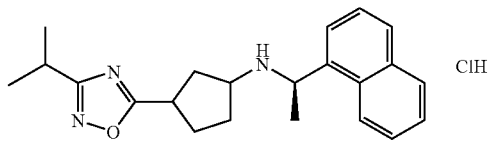 [SMILES: CC(C)c1noc(C2CCC(N[C@H](C)c3cccc4ccccc34)C2)n1 ; Cl]

General procedure C was followed using 3-((R)-1-naphthalen-1-yl-ethylamino)-cyclopentanecarboxylic acid (preparation 3, 194 mg) and N'-hydroxy-2-methylpropanimidamide (x=24 h, y=4 h). Chromatography (PE-EtOAc 100:0 to 40:60) afforded an oil which was treated with 4N HCl in dioxane. Precipitation occurred upon addition of Et$_2$O. The light-yellow precipitate was filtered and dried in vacuo to afford the title compound. $^1$H NMR (300 MHz, DMSO) as free amine $\delta_H$ 8.22-8.35 (m, 1H), 7.87-7.97 (m, 1H), 7.68-7.82 (dd, 2H), 7.44-7.59 (m, 3H), 4.64 (q, 1H), 3.45-3.66 (m, 1H), 3.04-3.19 (m, 1H), 2.88-3.03 (m, 1H), 2.34 (bs, 1H), 2.00-2.25 (m, 2H), 1.41-1.95 (m, 5H), 1.37 (d, 3H), 1.19 (d, 6H).

Example 39

((R)-1-Naphthalen-1-yl-ethyl)-{3-[3-(4-trifluoromethyl-phenyl)-[1,2,4]oxadiazol-5-yl]-cyclopentyl}-amine; hydrochloride (Compound 1040)

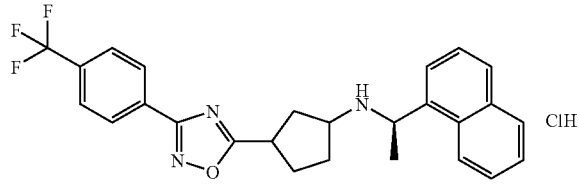 [SMILES: C[C@@H](NC1CCC(c2nc(-c3ccc(C(F)(F)F)cc3)no2)C1)c1cccc2ccccc12 ; Cl]

General procedure C was followed using 3-((R)-1-naphthalen-1-yl-ethylamino)-cyclopentanecarboxylic acid (preparation 3, 195 mg) and N'-hydroxy-(4-trifluoromethyl-phenyl)imidamide (x=24 h, y=4 h). Chromatography (PE-EtOAc 100:0 to 40:60) afforded an oil which was treated with 4N HCl in dioxane. Precipitation occurred upon addition of Et$_2$O. The colourless precipitate was filtered and dried in vacuo to afford the title compound. LC-MS (method B): RT=3.21, [M+H]$^+$=452.1.

Example 40

[3-(3-Methyl-[1,2,4]oxadiazol-5-yl)-cyclopentyl]-((R)-1-naphthalen-1-yl-ethyl)-amine; hydrochloride (Compound 1041)

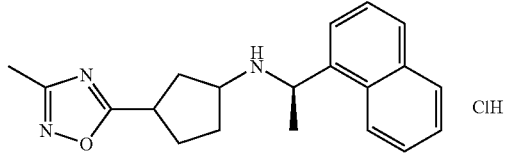 [SMILES: Cc1noc(C2CCC(N[C@H](C)c3cccc4ccccc34)C2)n1 ; Cl]

General procedure C was followed using 3-((R)-1-naphthalen-1-yl-ethylamino)-cyclopentanecarboxylic acid (preparation 3, 190 mg) and N'-hydroxy-acetamidine (x=1 h, y=20 h). Chromatography (PE-EtOAc 100:0 to 40:60) afforded an oil which was treated with 4N HCl in dioxane. Precipitation occurred upon addition of Et$_2$O. The precipitate was filtered and dried in vacuo to afford the title compound. $^1$H NMR (300 MHz, DMSO) $\delta_H$ 10.26 (s, 1H), 9.45 (s, 1H), 8.31 (d, 1H), 7.90-8.12 (m, 3H), 7.50-7.70 (m, 3H), 5.35 (q, 1H), 3.63-3.81 (m, 1H), 3.44-3.62 (m, 1H), 2.00-2.33 (m, 4H), 2.24 (s, 3H), 1.90 (s, 1H), 1.73 (d, 3H), 1.65-1.79 (m, 1H).

Example 41

{3-[3-(5-Methyl-thiazol-2-ylmethyl)-[1,2,4]oxadiazol-5-yl]-cyclo pentyl}-((R)-1-naphthalen-1-yl-ethyl)-amine (Compound 1042)

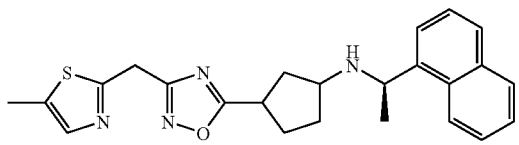 [SMILES: Cc1cnc(Cc2noc(C3CCC(N[C@H](C)c4cccc5ccccc45)C3)n2)s1]

General procedure C was followed using 3-((R)-1-naphthalen-1-yl-ethylamino)-cyclopentanecarboxylic acid (preparation 3, 190 mg) and N-hydroxy-2-(5-methyl-thiazol-2-yl)-acetamidine (x=4 h, y=20 h). Chromatography (PE-EtOAc 100:0 to 30:70 then CH$_2$Cl$_2$-MeOH 98:2 to 80:20) afforded the title compound. LC-MS (method B): RT=2.68, [M+H]$^+$=419.

Example 42

((R)-1-naphthalen-1-yl-ethyl)-[3-(3-propyl-[1,2,4]oxadiazol-5-yl)-cyclopentyl]-amine; hydrochloride (Compound 1043a and 1043b)

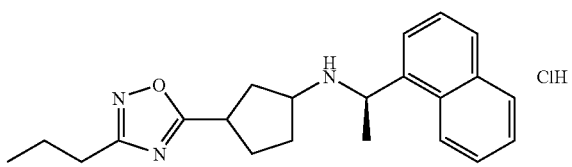 [SMILES: CCCc1noc(C2CCC(N[C@H](C)c3cccc4ccccc34)C2)n1 ; Cl]

General procedure C was followed using 3-((R)-1-naphthalen-1-yl-ethylamino)-cyclopentanecarboxylic acid (preparation 3, 190 mg) and N'-hydroxy-butyramidine (x=4 h, y=20 h). Chromatography (PE-EtOAc 100:0 to 30:70) afforded an oil which was treated with 4N HCl in dioxane. Precipitation occurred upon addition of Et$_2$O. The precipitate was filtered and dried in vacuo to afford the title compound as 2 isomers. $^{13}$C NMR (75.5 MHz, DMSO) major isomer δ: 183.03, 170.02, 142.44, 133.85, 131.34, 129.01, 126.95, 126.09, 125.98, 125.62, 123.35, 56.50, 51.48, 37.54, 34.81, 33.20, 29.43, 27.43, 24.64, 20.10, 13.74.

Example 43

1-{5-[3-((R)-1-Naphthalen-1-yl-ethylamino)-cyclopentyl]-[1,2,4]oxadiazol-3-ylmethyl}-1H-pyridin-2-one; hydrochloride (Compound 1044)

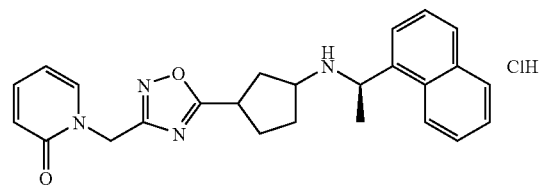 [SMILES: C[C@@H](NC1CCC(c2nc(Cn3ccccc3=O)no2)C1)c1cccc2ccccc12 ; Cl]

General procedure C was followed using 3-((R)-1-naphthalen-1-yl-ethylamino)-cyclopentanecarboxylic acid (preparation 3, 190 mg) and N-hydroxy-2-(2-oxo-2H-pyridin-1-yl)-acetamidine (x=5 h, y=19 h). Chromatography (PE-EtOAc 60:40 to 0:100 then CHCl$_3$-MeOH 100:0 to 90:10) afforded an oil which was treated with 4N HCl in dioxane. Precipitation occurred upon addition of Et$_2$O. The precipitate was filtered and dried in vacuo to afford the title compound.
LC-MS (method B): RT=2.23, [M+H]$^+$=415.3.

Example 44

{3-[3-(4-Methoxy-phenyl)-[1,2,4]oxadiazol-5-yl]-cyclopentyl}-((R)-1-naphthalen-1-yl-ethyl)-amine; hydrochloride (Compound 1045)

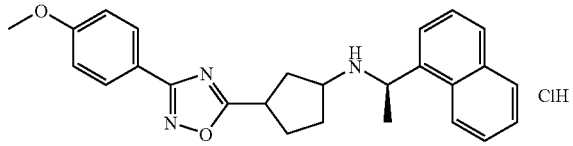 [SMILES: COc1ccc(-c2noc(C3CCC(N[C@H](C)c4cccc5ccccc45)C3)n2)cc1 ; Cl]

General procedure C was followed using 3-((R)-1-naphthalen-1-yl-ethylamino)-cyclopentanecarboxylic acid (preparation 3, 190 mg) and N'-hydroxy-(4-methoxyphenyl)imidamide (x=4 h, y=20 h). Chromatography (PE-EtOAc 100:0 to 30:70 then CH$_2$Cl$_2$-MeOH 90:10 to 70:30) afforded an oil which was treated with 4N HCl in dioxane. Precipitation occurred upon addition of Et$_2$O. The precipitate was filtered and dried in vacuo to afford the title compound.
LC-MS (method B): RT=3.11, [M+H]$^+$=414.1.

Example 45

3-((R)-1-Naphthalen-1-yl-ethylamino)-cyclopentanecarboxylic acid amide (Compound 1046)

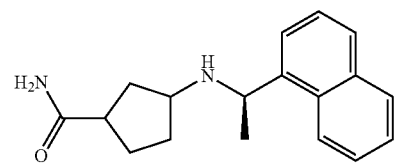 [SMILES: C[C@@H](NC1CCC(C(N)=O)C1)c1cccc2ccccc12]

General procedure B was followed using 3-((R)-1-naphthalen-1-yl-ethylamino)-cyclopentanecarboxylic acid (preparation 3, 155 mg) and aq. NH$_3$ (2.5 mL). Chromatography (CH$_2$Cl$_2$-MeOH 90:10 to 70:30) afforded the title compound.

LC-MS (method B): RT=1.93, [M+H]$^+$=283.2.

Example 46

4-Methyl-N-[3-((R)-1-naphthalen-1-yl-ethylamino)-cyclopentane carbonyl]-benzenesulfonamide (Compound 1047a, Compound 1047b, Compound 1047c and Compound 1047d)

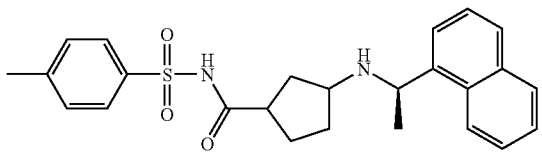 [SMILES: Cc1ccc(S(=O)(=O)NC(=O)C2CCC(N[C@H](C)c3cccc4ccccc34)C2)cc1]

To a stirred mixture of 3-oxocyclopentanecarboxylic acid (1.2 g) and NEt$_3$ (1.56 mL) in THF (50 mL) under argon was added dropwise 4-methyl-benzenesulfonyl isocyanate (1.71 mL). Stirring was continued at r.t. for 1 h before addition of N,N'-dimethyl-1,3-propane diamine. Stirring was continued at r.t. for 10 min. The mixture was diluted with EtOAc, washed with aq. HCl (1M) and brine, dried over Na$_2$SO$_4$, filtered and concentrated in vacuo to afford 4-methyl-N-(3-oxo-cyclopentanecarbonyl)-benzenesulfonamide (compound 1113) used without further purification.

General procedure A was followed using 4-methyl-N-(3-oxo-cyclopentanecarbonyl)-benzenesulfonamide (1.9 g) and (+)-(R)-1-naphthalen-1-yl-ethylamine with a reaction time of 4 h. The mixture was diluted with CH$_2$Cl$_2$, washed with sat. aq. NaHCO$_3$, and brine, dried over Na$_2$SO$_4$, filtered and concentrated in vacuo to afford a yellow foam. The foam was treated with hot EtOH. The precipitate formed upon cooling was filtered, washed with EtOH to afford the title compound as a white powder. LC-MS (method B): RT (4 isomers)=3.02, 3.10, 3.37, 4.10, [M+H]$^+$=437.4, [M−H]$^−$=435.4.

Example 47

4-[3-((R)-1-Naphthalen-1-yl-ethylamino)-cyclohexyl]-benzonitrile (Compounds 1048/1049/1050)

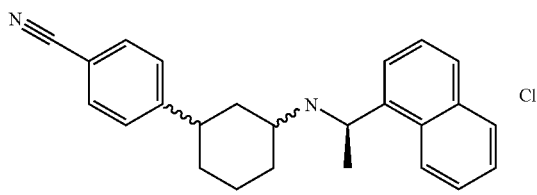 [SMILES: C[C@@H](NC1CCCC(c2ccc(C#N)cc2)C1)c1cccc2ccccc12 ; Cl]

General procedure A was followed using 3-(4-cyanophenyl)cyclohexanone (5 g) and (+)-(R)-1-naphthalen-1-yl-ethylamine (3.7 mL). Chromatography (Heptane-EtOAc 100:0 to 0:100) afforded the title compound as a solid (fraction A), the title compound as an oil (fraction B) and the title compound as an oil (fraction C). Fractions A and B contained single diastereomers: compound 1048 and compound 1049 respectively. Fraction C contained a mixture of 2 diastereomers: compound 1050. Compound 1048 $^{13}$C NMR (75.5 MHz, DMSO) δ: 153.24, 142.40, 133.48, 132.00, 130.84, 128.62, 127.76, 126.46, 125.64, 125.55, 125.17, 123.07, 122.97, 118.92, 108.37, 51.09, 50.03, 38.25, 37.30, 32.69, 28.86, 24.59, 20.15. Compound 1049 $^{13}$C NMR (75.5 MHz, DMSO) δ: 153.25, 142.12, 133.43, 132.09, 130.87, 128.60, 127.96, 126.46, 125.67, 125.54, 125.17, 122.97, 122.85, 118.97, 108.42, 50.17, 49.28, 37.07, 36.17, 32.84, 30.61, 24.38, 20.39. Compound 1050 (2 isomers ca. 2:1) $^{13}$C NMR (75 MHz, DMSO) δ: 152.65, 152.58, 142.13, 141.99, 133.46, 133.44, 132.20, 130.79, 130.76, 128.61, 128.59, 127.80, 126.50, 125.71, 125.67, 125.60, 125.19, 122.94, 122.87, 122.83, 122.72, 118.92, 108.65, 108.63, 53.79, 53.62, 49.30, 49.16, 42.67, 42.41, 40.71, 39.96, 33.25, 33.07, 32.15, 24.74, 24.49, 24.33.

General Procedure E

To a solution of nitrile (1 eq.) in EtOH (0.12 M) were added K$_2$CO$_3$ (12 eq.) and hydroxylamine; hydrochloride (7 eq.). The mixture was stirred at reflux overnight. After filtration the filter-cake was extracted with hot EtOH. The combined extracts were concentrated in vacuo. If necessary, purification was performed by continuous gradient flash chromatography.

Example 48

N-Hydroxy-4-[3-((R)-1-naphthalen-1-yl-ethyl-amino)-cyclohexyl]-benzamidine (Compound 1051)

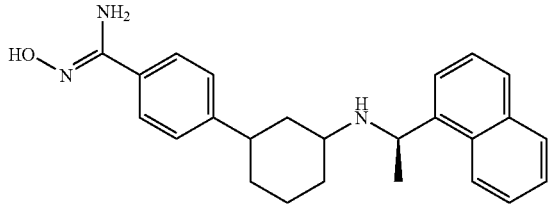 [SMILES: C[C@@H](NC1CCCC(c2ccc(/C(N)=N/O)cc2)C1)c1cccc2ccccc12]

General procedure E was followed using 4-[3-((R)-1-naphthalen-1-yl-ethylamino)-cyclohexyl]-benzonitrile (ex. 47, fraction A, 500 mg) and hydroxylamine; hydrochloride. Chromatography (PE-EtOAc-MeOH 100:0:0 to 0:100:0 to 0:80:20) afforded the title compound as a colourless solid. $^{13}$C NMR (75.5 MHz, DMSO) δ: 150.76, 148.10, 142.43, 133.47, 130.84, 130.69, 128.60, 126.42, 126.25, 125.61, 125.55, 125.16, 123.09, 122.96, 51.01, 50.14, 38.72, 36.78, 33.14, 29.04, 24.59, 20.30.

Example 49

N-Hydroxy-4-[3-((R)-1-naphthalen-1-yl-ethyl-amino)-cyclohexyl]-benzamidine (Compound 1052)

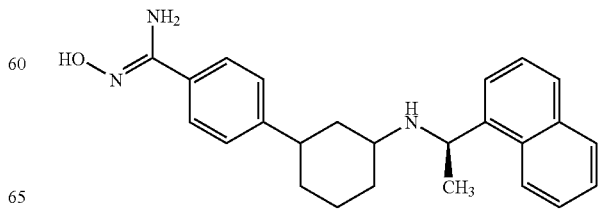

General procedure E was followed using 4-[3-((R)-1-naphthalen-1-yl-ethylamino)-cyclohexyl]-benzonitrile (ex. 47, fraction B, 500 mg) and hydroxylamine; hydrochloride. Chromatography (PE-EtOAc-MeOH 100:0:0 to 0:100:0 to 0:50:50) afforded the title compound as a yellow oil. $^{13}$C NMR (75.5 MHz, DMSO) δ: 167.78, 150.81, 148.11, 142.13, 133.43, 130.86, 130.81, 128.60, 127.44, 126.44, 125.66, 125.54, 125.29, 125.15, 122.99, 122.83, 50.19, 49.38, 36.58, 33.38, 30.78, 24.42, 20.55.

Example 50

N-Hydroxy-4-[3-((R)-1-naphthalen-1-yl-ethyl-amino)-cyclohexyl]-benzamidine (Compound 1053a and Compound 1053b)

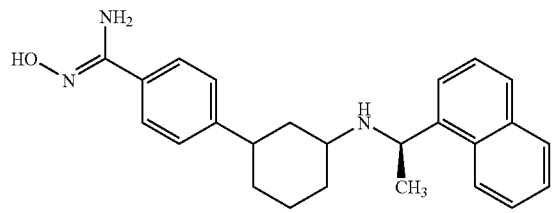 [SMILES: C[C@@H](NC1CCCC(c2ccc(/C(N)=N/O)cc2)C1)c1cccc2ccccc12]

General procedure E was followed using 4-[3-((R)-1-naphthalen-1-yl-ethylamino)-cyclohexyl]-benzonitrile (ex. 47, fraction C, 100 mg) and hydroxylamine; hydrochloride. Chromatography (PE-EtOAc-MeOH 100:0:0 to 0:100:0 to 0:90:10) afforded the title compound. $^{13}$C NMR (75.5 MHz, DMSO) δ: 168.18, 151.20, 151.20, 148.10, 148.04, 142.76, 142.66, 133.88, 131.42, 131.23, 129.04, 127.94, 126.87, 126.71, 126.04, 125.77, 125.60, 123.32, 123.24, 123.17, 54.37, 54.23, 49.65, 42.88, 42.61, 41.83, 40.98, 34.04, 32.83, 25.33, 25.09, 24.88 (2 isomers in almost equal amount).

Example 51

{3-[4-(Imino-pyrrolidin-1-yl-methyl)-phenyl]-cyclohexyl}-((R)-1-naphthalen-1-yl-ethyl)-amine (Compound 1054)

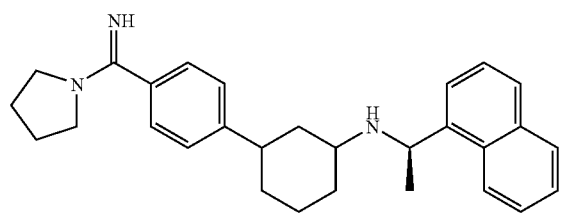 [SMILES: C[C@@H](NC1CCCC(c2ccc(C(=N)N3CCCC3)cc2)C1)c1cccc2ccccc12]

To a solution of 4-[3-(R)-1-naphthalen-1-yl-ethylamino)-cyclohexyl]-benzonitrile (ex. 47, fraction A, 150 mg) in MeOH (1.5 mL) under argon were added N-acetylcysteine (7 eq.) and pyrrolidine (7.4 eq.). The mixture was stirred at 70° C. for 4 days. MeoH was removed in vacuo. The residue was taken in water and extracted with CH$_2$Cl$_2$ (4 times). The combined extracts were concentrated in vacuo and purified by continuous gradient flash chromatography (CH$_2$Cl$_2$-MeOH 100:0 to 50:50) to afford the title corn pound.
LC-MS (method B): RT=2.01, [M+H]$^+$=426.3.

Example 52

4-[3-((R)-1-naphthalen-1-yl-ethylamino)-cyclohexyl]-benzamidine (Compound 1055)

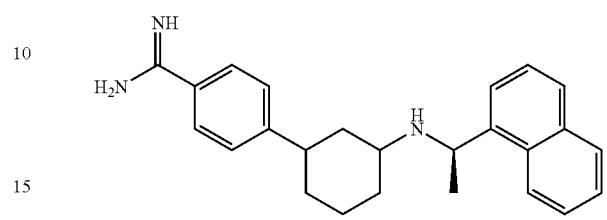

To a solution of N-hydroxy-4-[3-((R)-1-naphthalen-1-yl-ethylamino)-cyclohexyl]-benzamidine (ex 48, 200 mg) in EtOAc (10 mL) was added SnCl$_2$.2H$_2$O (3 eq.). The mixture was stirred at reflux overnight. After cooling to r.t. the mixture was diluted with EtOAc and washed with aq. sat. NaHCO$_3$. The org. phase was chromatographed (PE-EtOAc 100:0 to 0:100 to EtOAc-MeOH 90:10) to afford the title compound. LC-MS (method B): RT=1.92, [M+H]$^+$=372.3.

General Procedure F

To a solution of benzonitrile in MeOH (0.09 M, y mL) was added 28% aq NaOH (y/2 mL). The mixture was heated to reflux overnight. MeOH was removed under reduced pressure. The residue was taken in water and 4N aq. HCl was added until pH=5. The precipitate was collected, washed with water and dried in vacuo.

Example 53

4-[3-((R)-1-naphthalen-1-yl-ethylamino)-cyclohexyl]-benzoic acid (Compound 1056)

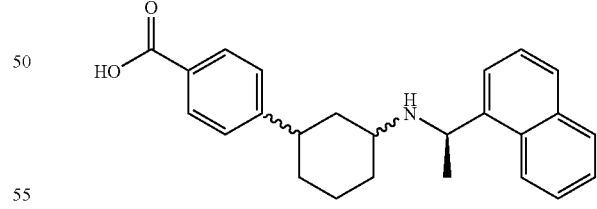

General procedure F was followed using 4-[3-((R)-1-naphthalen-1-yl-ethylamino)-cyclohexyl]-benzonitrile (ex. 47, fraction A, 3.5 g) afforded the corresponding acid. $^{13}$C NMR (75.5 MHz, DMSO) δ: 167.33, 152.18, 142.11, 133.49, 130.83, 129.16, 128.72, 128.62, 126.66, 126.54, 125.68, 125.57, 125.20, 123.19, 122.96, 51.12, 50.24, 38.38, 37.04, 32.81, 28.90, 24.45, 20.22.

Example 54

4-[3-((R)-1-naphthalen-1-yl-ethylamino)-cyclohexyl]-benzoic acid (Compound 1057)

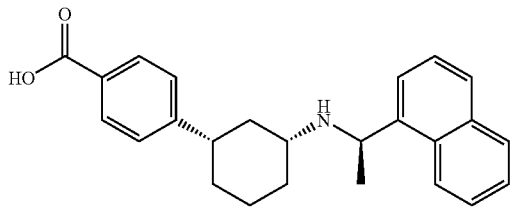

General procedure F was followed using 4-[3-((R)-1-naphthalen-1-yl-ethylamino)-cyclohexyl]-benzonitrile (ex. 47, fraction B, 0.8 g) afforded the corresponding acid. $^{13}$C NMR (75.5 MHz, DMSO) δ: 167.27, 151.71, 140.47, 133.43, 130.73, 129.26, 128.68, 128.54, 126.93, 126.85, 125.96, 125.55, 125.36, 123.33, 122.71, 50.10, 49.71, 36.63, 35.45, 32.55, 30.15, 23.72, 20.29.

Example 55

4-[3-((R)-1-naphthalen-1-yl-ethylamino)-cyclohexyl]-benzoic acid (Compound 1058)

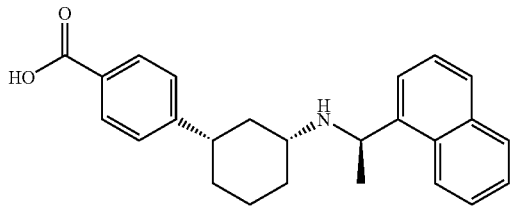 [SMILES: C[C@@H](NC1CCCC(c2ccc(C(=O)O)cc2)C1)c1cccc2ccccc12]

General procedure F was followed using 4-[3-((R)-1-naphthalen-1-yl-ethylamino)-cyclohexyl]-benzonitrile (ex. 47, fraction C, 1.0 g) afforded the corresponding acids. $^{13}$C NMR (75 MHz, DMSO) δ: 167.37, 150.91, 150.88, 133.37, 130.44, 130.38, 129.39, 129.36, 129.34, 128.73, 128.70, 127.42, 127.38, 126.63, 126.58, 126.24, 126.14, 125.55, 125.51, 123.58, 123.48, 122.65, 122.57, 53.96, 53.79, 49.04, 48.95, 42.04, 41.89, 38.71, 38.19, 32.87, 31.30, 30.20, 24.32, 24.11, 22.72.

Example 55a

4-[3-((R)-1-naphthalen-1-yl-ethylamino)-cyclohexyl]-benzoic acid (Compound 1058a)

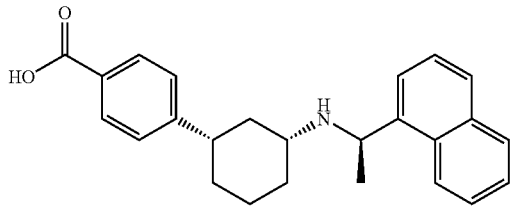

$^1$H NMR (300 MHz, DMSO) δ 8.38-8.21 (m, 1H), 7.95-7.87 (m, 1H), 7.82 (d, 2H), 7.75 (dd, 2H), 7.57-7.39 (m, 3H), 7.30 (d, 2H), 4.72 (dd, 1H), 3.17-3.06 (m, 1H), 2.82 (m, 1H), 1.91-1.68 (m, 3H), 1.66-1.27 (m, 8H).

Example 56

3-[3-((R)-1-naphthalen-1-yl-ethylamino)-cyclohexyl]-benzoic acid ethyl ester (Compound 1059)

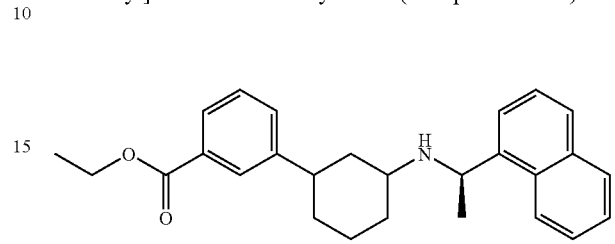

General procedure A was followed using 3-(3-oxo-cyclohexyl)-benzoic acid ethyl ester (10 g) and (+)-(R)-1-naphthalen-1-yl-ethylamine (6 mL). Chromatography (Heptane-EtOAc 100:0 to 0:100) afforded the title compound as a mixture of isomers. LC-MS (method B): RT=2.81, [M+H]$^+$=402.2.

Example 57

N-(2-Hydroxy-ethyl)-3-[3-((R)-1-naphthalen-1-yl-ethylamino)-cyclohexyl]-benzamide (Compound 1060)

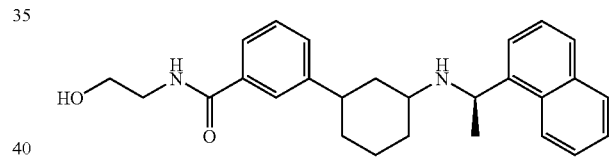

To a solution of 3-[3-((R)-1-naphthalen-1-yl-ethylamino)-cyclohexyl]-benzoic acid ethyl ester (ex. 56, 2.15 g) in anhydrous MeCN (25 mL) under argon were added ethanolamine (15 eq.) and K$_2$CO$_3$. The mixture was stirred at reflux for 2 days. MeCN was removed in vacuo. The residue was taken in EtOAc, washed with water, dried over MgSO$_4$, filtered and concentrated in vacuo. Chromatography (PE-EtOAc-MeOH 10:90:0 to 0:100:0 to 0:80:20) afforded the title compound. LC-MS (method B): RT=2.13, [M+H]$^+$=417.2, [M−H]$^-$=415.4.

Example 58

3-[3-((R)-1-naphthalen-1-yl-ethylamino)-cyclohexyl]-benzoic acid (Compounds 1061/1062)

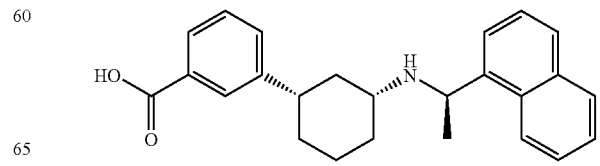

To a solution of 3-[3-((R)-1-naphthalen-1-yl-ethylamino)-cyclohexyl]-benzoic acid ethyl ester (10.4 g) in MeOH (200 mL) was added 2N aq. NaOH (100 mL). The solution was stirred at r.t. overnight and concentrated in vacuo. The residue was taken in water (150 mL) and 4N aq. HCl (ca 50 mL) was added dropwise until pH=7 and the precipitate persisted. The acid was filtered washed with water and dried in vacuo to afford the title compound as a mixture of isomers. 100 mg were purified by preparative chiral HPLC to afford the title compound (fraction A, compound 1061) and the title compound (fraction B, compound 1062), each as single isomer. Preparative chiral HPLC was performed on a Chiralpak AD-H column 250×10 mm, 5 μm at 25° C., UV detection at 280 nm. Isocratic separation with n-heptan:2-propanol:NEt$_3$:CH$_3$COOH (85:15:0.1:0.1); flow rate=3.0 mL/min.

Compound 1061: RT=13.4 min; $^{13}$C NMR (75.5 MHz, DMSO) δ: 168.11, 147.83, 141.93, 133.86, 131.89, 131.45, 131.24, 129.06, 128.72, 128.00, 127.11, 127.08, 126.20, 125.97, 125.66, 123.55, 123.22, 50.71, 50.07, 37.01, 36.83, 33.62, 30.81, 24.56, 20.89. Compound 1062: RT=15.3 min; $^{13}$C NMR (75.5 MHz, DMSO) δ: 168.58, 147.67, 142.50, 133.89, 133.22, 131.30, 130.75, 129.05, 128.39, 127.86, 127.01, 126.94, 126.11, 125.99, 125.60, 123.47, 123.31, 51.04, 50.29, 39.23, 37.31, 33.60, 29.15, 24.80, 20.68.

Example 59

((R)-1-Naphthalen-1-yl-ethyl)-(3 (S)-phenyl-cyclohexyl)-amine (Compound 1063)

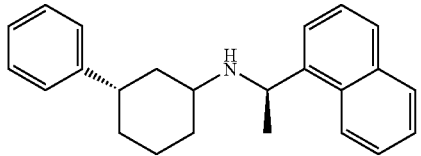 [SMILES: C[C@@H](NC1CCC[C@H](c2ccccc2)C1)c1cccc2ccccc12]

General procedure A was followed using (S)-3-phenylcyclohexanone (100 mg) and (R)-(+)-1-naphthalen-1-yl-ethylamine. Chromatography (Heptane-EtOAc 85:15 to 0:100) afforded the title compound. LC-MS (method B): RT=2.42, [M+H]$^+$=330.3.

Example 60

((R)-1-Naphthalen-1-yl-ethyl)-(3 (R)-phenyl-cyclohexyl)-amine (Compound 1064)

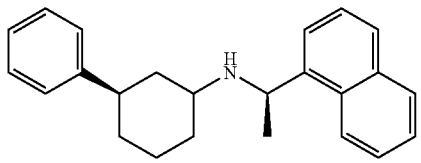 [SMILES: C[C@@H](NC1CCC[C@@H](c2ccccc2)C1)c1cccc2ccccc12]

General procedure A was followed using (R)-3-phenyl-cyclohexanone (100 mg) and (R)-(+)-1-naphthalen-1-yl-ethylamine. Chromatography (Heptane-EtOAc 90:10 to 0:100) afforded the title compound.
LC-MS (method B): RT=2.31, [M+H]$^+$=330.3.

General Procedure G

To a mixture of an amine (1 eq.), a cycloalk-2-en-1-one (1.2 eq.) and PEG2000 (4 g for 10 mmol amine) at 60° C. was added RuCl$_3$ (3%). The mixture was stirred at 60° C. overnight. After cooling to r.t. Et$_2$O (20 mL for 10 mmol) was added. The mixture was kept in the refrigerator for 30 min before filtration of the precipitate. The solid was extracted with Et$_2$O (3 times). The combined extracts were washed with water, dried over Na$_2$SO$_4$, filtered and concentrated in vacuo. If necessary, purification was performed by continuous gradient flash chromatography.

Example 61

N—((R)-1-Naphthalen-1-yl-ethyl)-N'-phenyl-cyclohexane-1,3-diamine (Compound 1065)

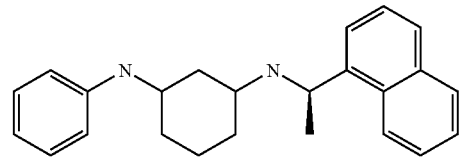 [SMILES: C[C@@H](NC1CCCC(Nc2ccccc2)C1)c1cccc2ccccc12]

General procedure G was followed using aniline (0.91 mL) and cyclohex-2-en-1-one. Chromatography (CH$_2$Cl$_2$-MeOH 100:0 to 85:15) afforded 3-phenylamino-cyclohexanone.

Procedure A was followed using 3-phenylamino-cyclohexanone (41 mg) and (+)-(R)-1-naphthalen-1-yl-ethylamine. Chromatography (PE-EtOAc-MeOH 100:0:0 to 0:100:0 to 0:90:10) afforded the title compound as a mixture of 2 isomers in the ratio 1:3. $^{13}$C NMR (75.5 MHz, DMSO) δ: 147.94, 142.31, 133.44, 130.77, 128.76, 128.65, 128.58, 126.37, 125.62, 125.59, 125.52, 125.12, 122.93, 122.83, 115.01, 114.88, 112.20, 50.22, 49.80, 49.59, 49.38, 46.15, 46.01, 37.77, 36.15, 31.78, 31.71, 29.97, 24.51, 24.34, 19.60, 19.26.

Example 62

N—((R)-1-Naphthalen-1-yl-ethyl)-N'-(3-trifluoromethyl-phenyl)-cyclohexane-1,3-diamine (Compound 1066)

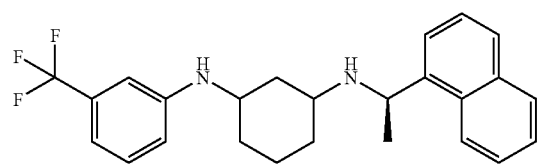 [SMILES: C[C@@H](NC1CCCC(Nc2cccc(C(F)(F)F)c2)C1)c1cccc2ccccc12]

General procedure G was followed using 3-trifluoromethylaniline (1.61 g) and cyclohex-2-en-1-one. Chromatography (PE-EtOAc 100:0 to 0:100) afforded 3-(3-trifluoromethylphenyl)amino-cyclohexanone (compound 1114).
Procedure A was followed using 3-(3-trifluoromethylphenyl)amino-cyclohexanone (125 mg) and (+)-(R)-1-naphthalen-1-yl-ethylamine. Chromatography (PE-EtOAc-MeOH 100:0:0 to 0:100:0 to 0:90:10) afforded the title compound. LC-MS (method B): RT=2.94, [M+H]$^+$=413.2.

Example 63

4-[3-((R)-1-Naphthalen-1-yl-ethylamino)-cyclohexylamino]-benzonitrile (Compound 1067)

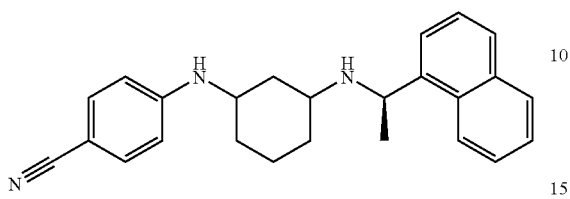

General procedure G was followed using 4-amino-benzonitrile (1.18 g) and cyclohex-2-en-1-one. Chromatography (PE-EtOAc 100:0 to 0:100) afforded 4-(3-oxo-cyclohexylamino)-benzonitrile.

Procedure A was followed using 4-(3-oxo-cyclohexylamino)-benzonitrile (145 mg) and (+)-(R)-1-naphthalen-1-yl-ethylamine. Chromatography (PE-EtOAc-MeOH 100:0:0 to 0:100:0 to 0:90:10) afforded the title compound. LC-MS (method B): RT=2.56, [M+H]$^+$=370.2.

Example 64

(3-Morpholin-4-yl-cyclohexyl)-((R)-1-naphthalen-1-yl-ethyl)-amine (Compound 1068)

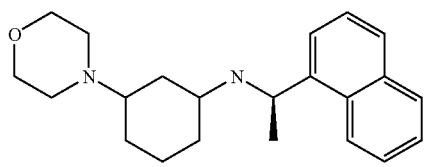 [SMILES: C[C@@H](NC1CCCC(N2CCOCC2)C1)c1cccc2ccccc12]

To a stirred mixture of morpholine (3.7 mL) and cyclohex-2-en-1-one (3.4 mL) in water (50 mL) was added Cu(OAc)$_2$.H$_2$O (350 mg). The mixture was stirred at r.t. for 15 h and filtered. The filtrate was extracted with EtOAc. The combined extracts were washed with water and brine, dried over Na$_2$SO$_4$, filtered and concentrated in vacuo to afford a 1:1 mixture of cyclohex-2-en-1-one and 3-morpholin-4-yl-cyclohexanone used without further purification.

General procedure A was followed using 3-morpholin-4-yl-cyclohexanone (1 g, 50% pure, 5.4 mmol) and (+)-(R)-1-naphthalen-1-yl-ethylamine. Chromatography (EtOAc) afforded the title compound as dark yellow oil (mixture of 2 isomers ca 1:1). $^{13}$C NMR (75.5 MHz, DMSO) δ: 142.28, 142.05, 133.47, 133.39, 130.92, 130.86, 128.58, 126.42, 126.38, 125.61, 125.57, 125.51, 125.45, 125.12, 123.21, 123.07, 122.97, 122.72, 66.41, 66.30, 57.86, 57.78, 50.54, 49.54, 49.45, 49.35, 49.19, 48.46, 34.44, 32.62, 30.84, 27.75, 27.64, 24.43, 19.68, 19.48.

Example 65

((R)-1-Naphthalen-1-yl-ethyl)-(3-pyridin-2-yl-cyclohexyl)-amine (Compounds 1069/1070)

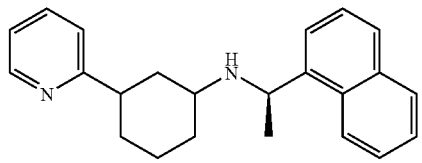 [SMILES: C[C@@H](NC1CCCC(c2ccccn2)C1)c1cccc2ccccc12]

General procedure A was followed using 3-(2-pyridinyl)cyclohexanone (1 g) and (+)-(R)-1-naphthalen-1-yl-ethylamine. Chromatography (PE-EtOAc-MeOH 100:0:0 to 0:100:0 to 0:85:15) afforded the title compound as a mixture of 2 isomers (fraction A, compound 1069) and the title compound as a mixture of 2 isomers (fraction B, compound 1070) in the ratio 1:1. Compound 1069, major isomer $^{13}$C NMR (75.5 MHz, DMSO) δ: 165.48, 148.61, 142.04, 136.19, 133.47, 130.90, 128.62, 126.49, 125.69, 125.56, 125.18, 123.02, 122.93, 121.17, 120.95, 50.37, 49.48, 39.02, 37.25, 31.80, 28.94, 24.35, 20.03. Compound 1070 $^{13}$C NMR (75.5 MHz, DMSO) δ: 165.47, 165.39, 149.12, 142.64, 142.57, 136.83, 133.90, 133.88, 131.23, 129.02, 126.89, 126.08, 126.04, 125.60, 123.38, 123.33, 123.24, 123.18, 121.61, 121.46, 121.40, 54.20, 54.06, 49.80, 49.62, 45.16, 44.86, 34.01, 32.86, 32.52, 32.45, 25.16, 24.86, 24.81.

Example 66

5-[3-((R)-1-Naphthalen-1-ylethylamino)-cyclohexyl]-thiophene-2-carboxylic acid ethyl ester (Compound 1071)

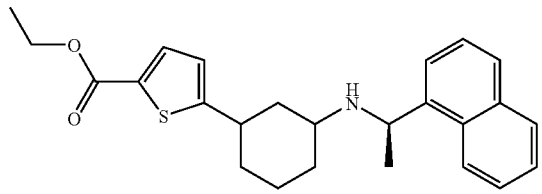

General procedure A was followed using 5-(3-oxo-cyclohexyl)-thiophene-2-carboxylic acid ethyl ester (1 g) and (+)-(R)-1-naphthalen-1-yl-ethylamine. Chromatography (PE-EtOAc-MeOH 100:0:0 to 0:100:0 to 0:90:10) afforded the title compound as a mixture of 3 isomers (fraction A) and 0.9 g of the title compound as a mixture of 3 isomers (fraction B). LC-MS (method B): RT=2.98, [M+H]$^+$=408.2.

Example 67

5-[3-((R)-1-Naphthalen-1-yl-ethylamino)-cyclohexyl]-thiophene-2-carboxylic acid (Compound 1072)

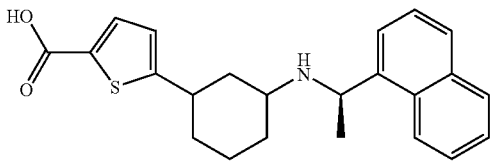

To a solution of 5-[3-((R)-1-naphthalen-1-yl-ethylamino)-cyclohexyl]-thiophene-2-carboxylic acid ethyl ester (fraction A 0.6 g) in MeOH (30 mL) and water (10 mL) was added LiOH (5 eq.). The solution was stirred at reflux for 2 h. MeOH was removed in vacuo and 4N aq. HCl was added until the precipitate persisted. The solid was filtered, washed with water and dried in vacuo to afford the title compound. $^{13}$C NMR (150.9 MHz, DMSO) δ: Major isomer: 163.41, 157.15, 140.77, 140.77, 133.43, 131.63, 130.71, 128.67, 126.84, 125.88, 125.54, 125.32, 123.38, 123.21, 122.76, 50.23, 49.74, 38.46, 33.49, 33.43, 28.64, 23.83, 19.87.

Example 68

5-[3-((R)-1-Naphthalen-1-yl-ethylamino)-cyclohexyl]-furan-2-carboxylic acid ethyl ester (Compound 1073)

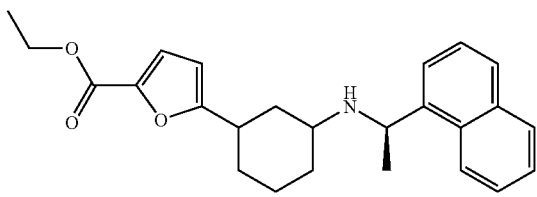 [SMILES: CCOC(=O)c1ccc(C2CCCC(N[C@H](C)c3cccc4ccccc34)C2)o1]

General procedure A was followed using 5-(3-oxo-cyclohexyl)-furan-2-carboxylic acid ethyl ester (1 g) and (+)-(R)-1-naphthalen-1-yl-ethylamine. Chromatography (PE-EtOAc-MeOH 100:0:0 to 0:100:0 to 0:90:10) afforded the title compound. LC-MS (method B): RT=2.85, [M+H]$^+$= 392.3.

Example 69

5-[3-((R)-1-Naphthalen-1-yl-ethylamino)-cyclohexyl]-furan-2-carboxylic acid (Compound 1074a, Compound 1074b and Compound 1074c)

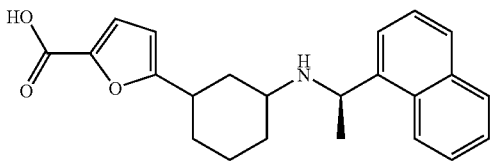 [SMILES: C[C@@H](NC1CCCC(c2ccc(C(=O)O)o2)C1)c1cccc2ccccc12]

To a solution of 5-[3-((R)-1-naphthalen-1-yl-ethylamino)-cyclohexyl]-furan-2-carboxylic acid ethyl ester (1.4 g) in MeOH (75 mL) and water (25 mL) was added LiOH (5 eq.). The solution was stirred at reflux for 2 h. MeOH was removed in vacuo and 4N aq. HCl was added until acidic pH. The compound was extracted with EtOAc. The combined extracts were dried over MgSO$_4$, filtered and concentrated in vacuo to afford the title compound as an off-white solid. 3 isomers $^{13}$C NMR (150.9 MHz, DMSO) δ: 162.64, 162.55, 162.15, 160.16, 160.10, 159.94, 145.27, 144.84, 144.79, 133.40, 130.69, 130.63, 130.49, 130.46, 128.74, 128.70, 128.67, 127.34, 127.29, 126.99, 126.89, 126.20, 126.14, 126.02, 125.95, 125.63, 125.58, 125.51, 125.38, 125.34, 123.40, 123.29, 123.14, 122.74, 122.71, 122.62, 117.11, 116.96, 116.82, 106.11, 106.07, 105.59, 105.56, 53.25, 52.95, 49.83, 49.66, 49.32, 49.16, 36.00, 35.56, 35.43, 34.98, 33.02, 31.64, 31.49, 31.40, 30.51, 30.35, 30.15, 29.60, 28.73, 23.70, 23.57, 23.47, 22.93, 22.87, 20.00, 19.68.

General Procedure H

To a solution or a suspension of acid (1 eq.) in DMF (1M) under argon was added HOBt (1.2 eq.), EDAC (1.3 eq.), 4-methyl morpholine (2 eq.) and N-hydroxyamidine (1.2 eq.). The mixture was stirred at r.t. overnight. CDI (1.1 eq.) was added and the mixture was subjected to microwave irradiation (10 min., 150° C.). The mixture was cooled to r.t., added EtOAc, washed with water and brine, dried over Na$_2$SO$_4$, filtered and concentrated in vacuo. If necessary, purification was performed by continuous gradient flash chromatography.

Preparation 4: 3-((R)-1-Naphthalen-1-yl-ethylamino)-cyclohexanecarboxylic acid

To a solution of 3-oxo-1-cyclohexane carboxylic acid (1.8 g) in 1,2-dichlorethane (60 mL) were added (+)-(R)-1-naphthalen-1-yl-ethylamine (2.2 g), glacial AcOH (1 eq., 0.75 mL) and NaBH(OAc)$_3$ (1.5 eq., 4.1 g). The mixture was stirred at r.t. for 48 h before removal of the solvent. The residue was treated with 1N NaOH (ca 100 mL) and pH was adjusted to 7 by addition of 4N HCl. The mixture was brought to reflux. The solid formed upon cooling was filtered and washed with boiling EtOH to afford the title compound as a fine powder. The filtrate was concentrated in vacuo. The residue was dissolved in hot MeCN and little MeOH. The solid formed upon cooling was filtered and washed with MeCN to afford the title compound.

Example 70

{3-[3-(4-Fluoro-phenyl)-[1,2,4]oxadiazol-5-yl]-cyclohexyl}-((R)-1-naphthalen-1-yl-ethyl)-amine (Compound 1075)

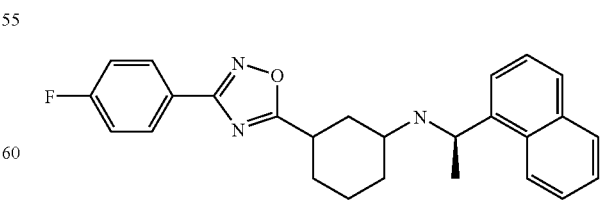

General procedure H was followed using 3-((R)-1-naphthalen-1-yl-ethylamino)-cyclohexanecarboxylic acid (preparation 4, 110 mg) and 4-fluoro-N-hydroxy-benzamidine. Chromatography (PE-EtOAc 100:0 to 0:100) afforded the title compound. $^{13}$C NMR (75.5 MHz, DMSO) δ: 183.55, 166.86, 164.24 ($^{1}J_{CF}$=249.1 Hz), 142.45, 133.92, 131.30, 129.87, 129.75, 129.06, 126.91, 126.05 ($^{3}J_{CF}$=9.8 Hz), 125.60, 123.31, 123.28, 116.68 ($^{2}J_{CF}$=21.9 Hz), 50.33, 49.29, 35.45, 31.69, 30.00, 29.29, 24.78, 20.24.

Example 71

((R)-1-Naphthalen-1-yl-ethyl)-{3-[3-(4-trifluoromethyl-phenyl)-[1,2,4]oxadiazol-5-yl]-cyclohexyl}-amine (Compound 1076)

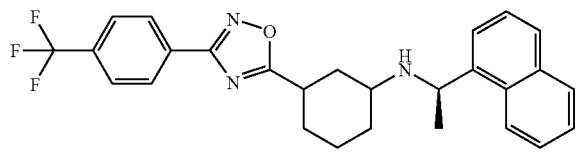 [SMILES: C[C@@H](NC1CCCC(c2nc(-c3ccc(C(F)(F)F)cc3)no2)C1)c1cccc2ccccc12]

General procedure H was followed using 3-((R)-1-naphthalen-1-yl-ethylamino)-cyclohexanecarboxylic acid (preparation 4, 110 mg) and 4-trifluoromethyl-N-hydroxy-benzamidine. Chromatography (PE-EtOAc 100:0 to 40:60) afforded the title compound. LC-MS (method B): RT=3.23, [M+H]$^{+}$=466.2.

Example 72

((R)-1-Naphthalen-1-yl-ethyl)-[3-(3-phenyl-[1,2,4]oxadiazol-5-yl)-cyclohexyl]-amine (Compound 1077)

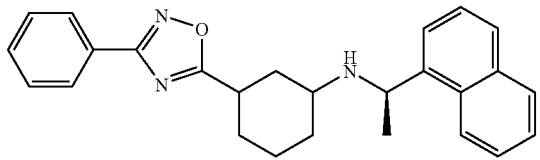 [SMILES: C[C@@H](NC1CCCC(c2nc(-c3ccccc3)no2)C1)c1cccc2ccccc12]

General procedure H was followed using 3-((R)-1-naphthalen-1-yl-ethylamino)-cyclohexanecarboxylic acid (preparation 4, 110 mg) and N-hydroxy-benzamidine. Chromatography (PE-EtOAc 100:0 to 40:60) afforded the title compound. LC-MS (method B): RT=2.93, [M+H]$^{+}$=398.2.

Example 73

4-[3-((R)-1-Naphthalen-1-yl-ethylamino)-cyclohexyl]-benzamide (Compound 1078)

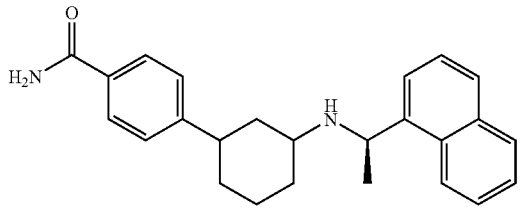 [SMILES: C[C@@H](NC1CCCC(c2ccc(C(N)=O)cc2)C1)c1cccc2ccccc12]

To a solution of 4-[3-((R)-1-naphthalen-1-yl-ethylamino)-cyclohexyl]-benzoic acid (ex. 53, 1.1 g) in DMF (40 mL) was added CDI (0.6 g). The mixture was stirred at r.t. for 2 h before addition of aq. NH$_3$ (8 mL). The mixture was stirred at r.t. overnight. Et$_2$O and water were added. After extraction the organic phase was washed with water and brine, dried over MgSO$_4$, filtered and concentrated in vacuo to afford the title compound as foam. LC-MS (method B): RT=2.46, [M+H]$^{+}$=373.3.

Example 74

N-Benzyloxy-4-[3-((R)-1-naphthalen-1-yl-ethylamino)-cyclohexyl]-benzamide (Compound 1079)

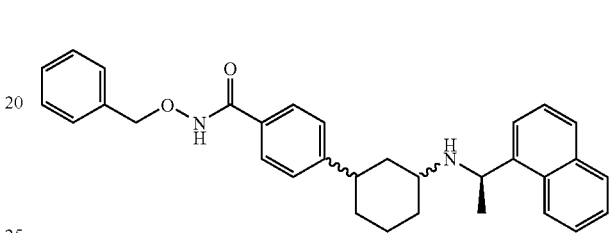

General procedure B was followed using 4-[3-((R)-1-naphthalen-1-yl-ethylamino)-cyclohexyl]-benzoic acid (ex. 53, 0.27 mmol) and O-benzylhydroxylamine; hydrochloride. Chromatography (PE-EtOAc 50:50 to 33:67) afforded the title compound. LC-MS (method B): RT=3.03, [M+H]$^{+}$=479.4.

Example 75

4-[3-((R)-1-Naphthalen-1-yl-ethylamino)-cyclohexyl]-benzoic acid 4-iodo-phenyl ester (Compound 1080)

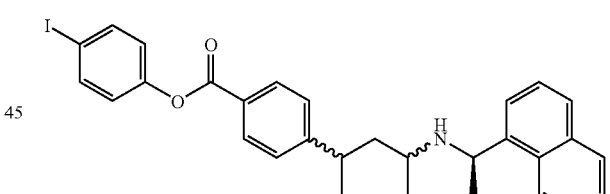

To a solution of 4-[3-((R)-1-naphthalen-1-yl-ethylamino)-cyclohexyl]-benzoic acid (ex. 53, 0.4 g) in DMF (10 mL) was added CDI (0.21 g, 1.2 eq.). The solution was stirred at r.t. for 1 h before addition of 4-iodophenol (0.33 g, 1.4 eq.) and K$_2$CO$_3$ (1.5 eq.). Stirring was continued at r.t. for 2 h. Water was added and the compound was extracted with EtOAc. The org. phase was washed with water (3 times) and brine, concentrated in vacuo and purified by chromatography (Heptane-EtOAc 100:0 to 60:40) to afford the title compound as an oil. LC-MS (method B): RT=4.15, [M+H]$^{+}$=576.3.

General Procedure I

To a solution of 4-[3-((R)-1-naphthalen-1-yl-ethylamino)-cyclohexyl]-benzoic acid (ex. 53, 1.6 g) in DMF (16 mL) was added CDI (0.83 g). The solution was stirred at r.t. for 4.5 h, 0.3 mL of this solution was added to an amine (2 eq.). If the amine was furnished as hydrochloride DIPEA (1 eq.) was added. The mixture was shaken at r.t. for 3 days, filtered and purified by preparative HPLC-MS (re-analysed by LC/MS method A).

Example 76

2-{4-[3-((R)-1-Naphthalen-1-yl-ethylamino)-cyclohexyl]-benzoyl amino}-ethanesulfonic acid (Compound 1081)

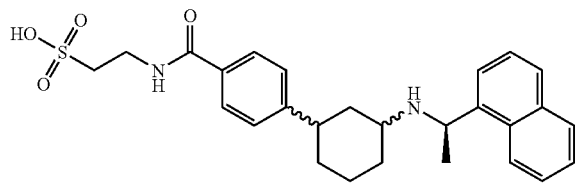 [SMILES: C[C@@H](NC1CCCC(c2ccc(C(=O)NCCS(=O)(=O)O)cc2)C1)c1cccc2ccccc12]

General procedure I was followed using 2-amino-ethanesulfonic acid. $^1$H NMR (600 MHz, DMSO) $\delta_H$ 8.86 (bs, 2H), 8.44 (t, 1H), 8.34 (d, 1H), 7.92-8.07 (m, 2H), 7.80-7.90 (m, 1H), 7.68 (d, 2H), 7.54-7.66 (m, 3H), 7.22 (d, 2H), 5.47 (bs, 1H), 3.52 (m, 2H), 3.13-3.23 (m, 1H), 3.02-3.11 (m, 1H), 2.68 (t, 2H), 1.73-2.02 (m, 5H), 1.42-1.71 (m, 6H). LC-MS (method A): RT=4.14, [M+H]$^+$=480.8, [M–H]$^-$=478.7.

Example 77

N—((R)-1-Hydroxymethyl-propyl)-4-[3-((R)-1-naphthalen-1-yl-ethyl amino)-cyclohexyl]-benzamide (Compound 1082)

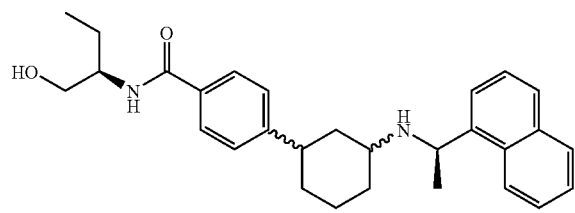 [SMILES: CC[C@H](CO)NC(=O)c1ccc(C2CCCC(N[C@H](C)c3cccc4ccccc34)C2)cc1]

General procedure I was followed using (R)-2-amino-1-butanol. LC-MS (method A): RT=3.99, [M+H]$^+$=444.8.

Example 78

N—((S)-1-Hydroxymethyl-propyl)-4-[3-((R)-1-naphthalen-1-yl-ethyl amino)-cyclohexyl]-benzamide (Compound 1083)

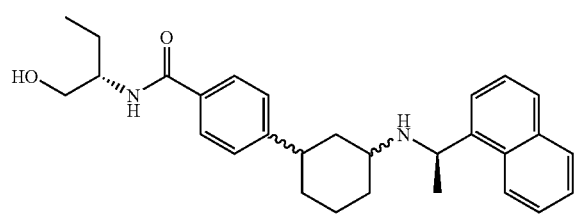 [SMILES: CC[C@@H](CO)NC(=O)c1ccc(C2CCCC(N[C@H](C)c3cccc4ccccc34)C2)cc1]

General procedure I was followed using (S)-2-amino-1-butanol. LC-MS (method A): RT=3.99, [M+H]$^+$=444.8.

Example 79

N-(2-Cyano-ethyl)-4-[3-((R)-1-naphthalen-1-yl-ethylamino)-cyclohexyl]-benzamide (Compound 1084)

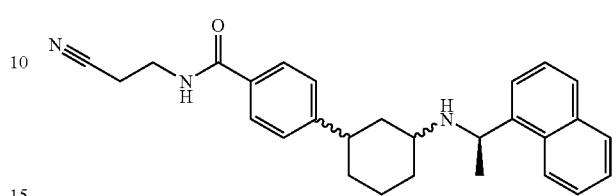

General procedure I was followed using 2-cyano-ethylamine. LC-MS (method A): RT=4.01, [M+H]$^+$=426.4.

Example 80

N-(2-Morpholin-4-yl-ethyl)-4-[3-((R)-1-naphthalen-1-yl-ethylamino)-cyclohexyl]-benzamide (Compound 1085)

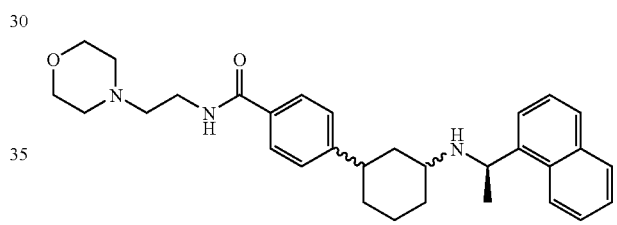

General procedure I was followed using 2-morpholin-4-yl-ethylamine. LC-MS (method A): RT=3.49, [M+H]$^+$=486.1.

Example 81

N-(2-Fluoro-ethyl)-4-[3-((R)-1-naphthalen-1-yl-ethylamino)-cyclohexyl]-benzamide (Compound 1086)

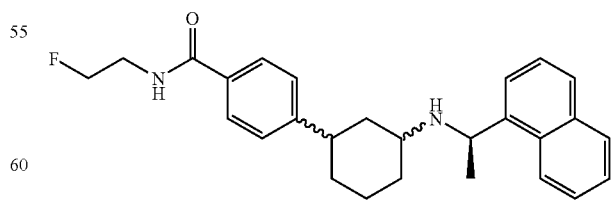 [SMILES: C[C@@H](NC1CCCC(c2ccc(C(=O)NCCC#N)cc2)C1)c1cccc2ccccc12]

General procedure I was followed using 2-fluoroethylamine; hydrochloride. LC-MS (method A): RT=4.04, [M+H]$^+$=418.8.

Example 82

N-(2,2-Difluoro-ethyl)-4-[3-((R)-1-naphthalen-1-yl-ethylamino)-cyclohexyl]-benzamide (Compound 1087)

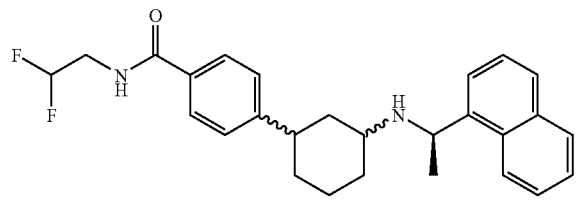 [SMILES: C[C@@H](NC1CCCC(c2ccc(C(=O)NCC(F)F)cc2)C1)c1cccc2ccccc12]

General procedure I was followed using 2,2-difluoroethylamine. LC-MS (method A): RT=4.16, [M+H]+=437.1.

Example 83

3-{4-[3-((R)-1-Naphthalen-1-yl-ethylamino)-cyclohexyl]-benzoyl amino}-propionic acid methyl ester (Compound 1088)

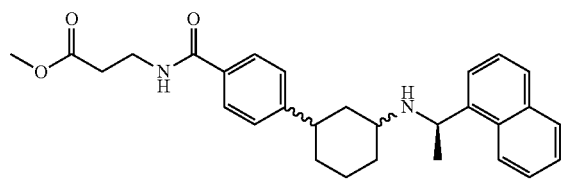 [SMILES: COC(=O)CCNC(=O)c1ccc(C2CCCC(N[C@H](C)c3cccc4ccccc34)C2)cc1]

General procedure I was followed using 3-amino-propionic acid methyl ester; hydrochloride. $^{13}$C NMR (151 MHz, DMSO) δ 171.72, 166.11, 163.16, 150.02, 133.46, 131.78, 130.69, 128.73, 127.08, 126.45, 126.03, 125.57, 125.46, 123.49, 122.81, 51.32, 50.90, 50.69, 37.20, 36.63, 35.36, 33.53, 32.48, 28.18, 23.59, 20.01. LC-MS (method A): RT=4.07, [M+H]+=459.0.

Example 84

N-Methyl-4-[3-((R)-1-naphthalen-1-yl-ethylamino)-cyclohexyl]-N-pyridin-4-ylmethyl-benzamide (Compound 1089)

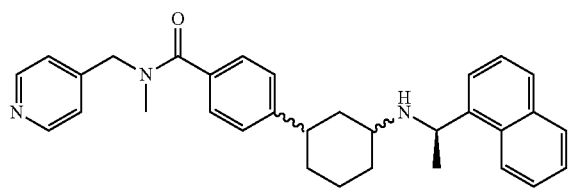 [SMILES: C[C@@H](NC1CCCC(c2ccc(C(=O)N(C)Cc3ccncc3)cc2)C1)c1cccc2ccccc12]

General procedure I was followed using methyl-pyridin-4-ylmethyl-amine. LC-MS (method A): RT=3.64, [M+H]+=477.9.

Example 85

N-(2-Dimethylamino-ethyl)-N-methyl-4-[3-((R)-1-naphthalen-1-yl-ethylamino)-cyclohexyl]-benzamide (Compound 1090)

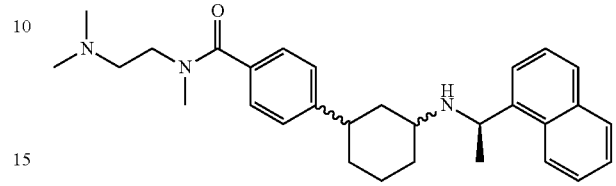

General procedure I was followed using N,N,N'-trimethyl ethylenediamine. LC-MS (method A): RT=3.49, [M+H]+=458.2, [M−H]−=456.0.

Example 86

(2-Hydroxymethyl-pyrrolidin-1-yl)-{4-[3-(1-naphthalen-1-yl-ethyl amino)-cyclohexyl]-phenyl}-methanone (Compound 1091)

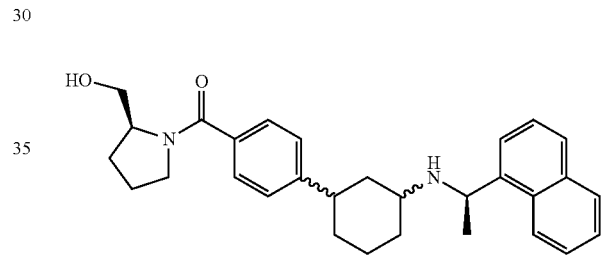

General procedure I was followed using (S)-pyrrolidin-2-yl-methanol. LC-MS (method A): RT=3.99, [M+H]+=456.8.

Example 87

N-(2-Acetylamino-ethyl)-4-[3-((R)-1-naphthalen-1-yl-ethylamino)-cyclohexyl]-benzamide (Compound 1092)

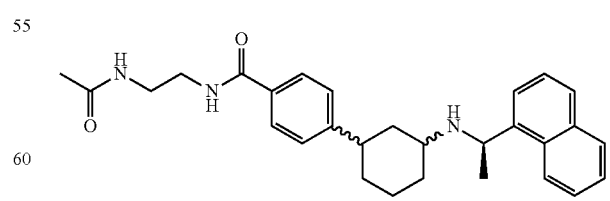

General procedure I was followed using N-(2-amino-ethyl)-acetamide. LC-MS (method A): RT=3.86, [M+H]+=458.2.

Example 88

N-Ethyl-4-[3-((R)-1-naphthalen-1-yl-ethylamino)-cyclohexyl]-benzamide (Compound 1093)

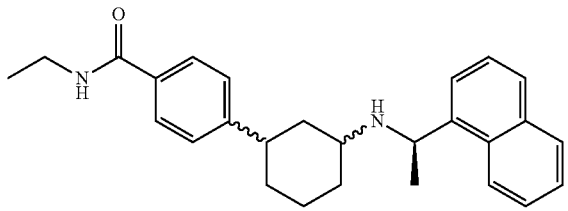 [SMILES: CCNC(=O)c1ccc(C2CCCC(N[C@H](C)c3cccc4ccccc34)C2)cc1]

General procedure I was followed using ethylamine; hydrochloride. LC-MS (method A): RT=3.97, [M+H]$^+$= 400.8.

Example 89

N-(2-Hydroxy-ethyl)-4-[3-((R)-1-naphthalen-1-yl-ethylamino)-cyclohexyl]-benzamide (Compound 1094)

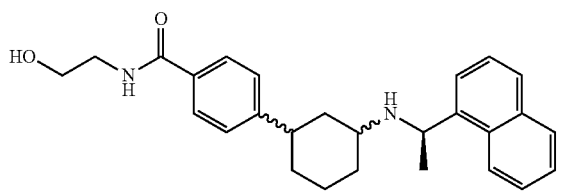

General procedure I was followed using 2-hydroxy-ethylamine. LC-MS (method A): RT=3.82, [M+H]$^+$=417.4.

Example 90

N-(2-Hydroxy-1-hydroxymethyl-1-methyl-ethyl)-4-[3-((R)-1-naphthalen-1-yl-ethylamino)-cyclohexyl]-benzamide (Compound 1095)

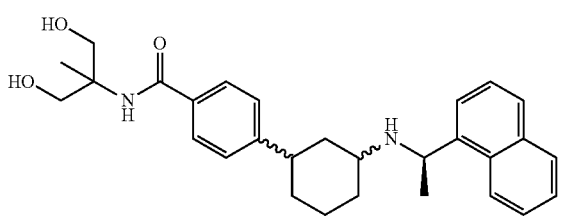 [SMILES: C[C@@H](NC1CCCC(c2ccc(C(=O)NC(C)(CO)CO)cc2)C1)c1cccc2ccccc12]

General procedure I was followed using 2-amino-2-methyl-propane-1,3-diol. LC-MS (method A): RT=3.86, [M+H]$^+$=460.9.

Example 91

N-(2-Methoxy-ethyl)-4-[3-((R)-1-naphthalen-1-yl-ethylamino)-cyclohexyl]-benzamide (Compound 1096)

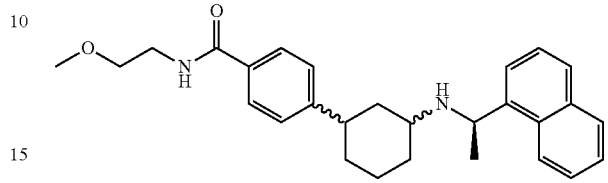

General procedure I was followed using 2-methoxy-ethylamine. LC-MS (method A): RT=3.99, [M+H]$^+$=430.8.

Example 92

N-(2-Mercapto-ethyl)-4-[3-((R)-1-naphthalen-1-yl-ethylamino)-cyclohexyl]-benzamide (Compound 1097)

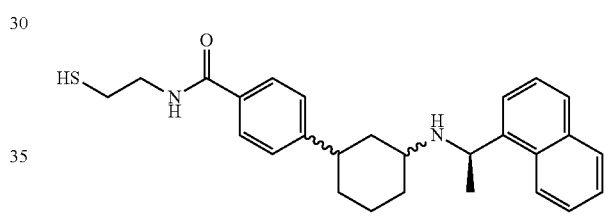

General procedure I was followed using 2-mercapto-ethylamine. LC-MS (method A): RT=4.11, [M+H]$^-$=432.0.

Example 93

{4-[3-((R)-1-Naphthalen-1-yl-ethylamino)-cyclohexyl]-benzoyl amino}-acetic acid ethyl ester (Compound 1098)

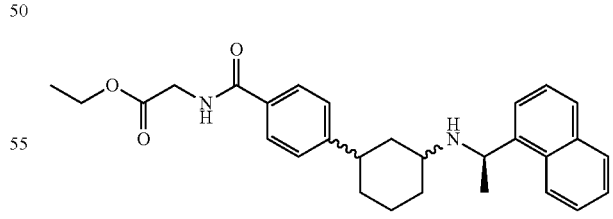

General procedure I was followed using amino-acetic acid ethyl ester; hydrochloride. $^1$H NMR (600 MHz, DMSO) δ 8.80 (t, 1H), 8.35 (d, 1H), 7.93 (d, 1H), 7.77 (dd, 2H), 7.70 (d, 2H), 7.55-7.47 (m, 3H), 7.11 (d, 2H), 4.73-4.65 (m, 1H), 4.11 (q, 2H), 3.96 (d, 2H), 3.02 (t, 1H), 2.88 (s, 1H), 1.92-1.82 (m, 1H), 1.80-1.70 (m, 2H), 1.67-1.60 (m, 1H), 1.54-1.37 (m, 6H), 1.34-1.26 (m, 1H), 1.20 (t, 3H). LC-MS (method A): RT=4.12, [M+H]$^+$=458.9.

Example 94

N,N-Dimethyl-4-[3-((R)-1-naphthalen-1-yl-ethyl-amino)-cyclohexyl]-benzamide (Compound 1099)

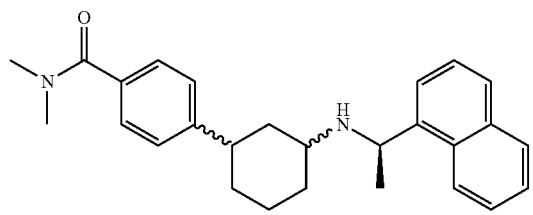 [SMILES: C[C@@H](NC1CCCC(c2ccc(C(=O)N(C)C)cc2)C1)c1cccc2ccccc12]

General procedure I was followed using dimethylamine. LC-MS (method A): RT=4.02, [M+H]$^+$=400.8, [M−H]$^-$=399.3.

Example 95

N-(2-Hydroxy-ethyl)-N-methyl-4-[3-((R)-1-naphthalen-1-yl-ethylamino)-cyclohexyl]-benzamide (Compound 1100)

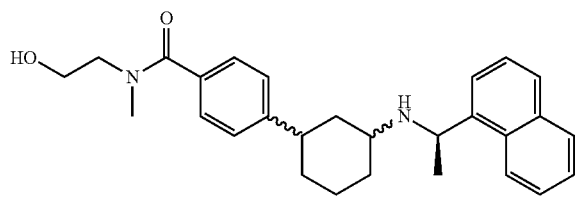 [SMILES: C[C@@H](NC1CCCC(c2ccc(C(=O)N(C)CCO)cc2)C1)c1cccc2ccccc12]

General procedure I was followed using 2-methylamino-ethanol. LC-MS (method A): RT=3.87, [M+H]$^+$=431.4.

Example 96

N-Ethyl-N-(2-hydroxy-ethyl)-4-[3-((R)-1-naphthalen-1-yl-ethyl amino)-cyclohexyl]-benzamide (Compound 1101)

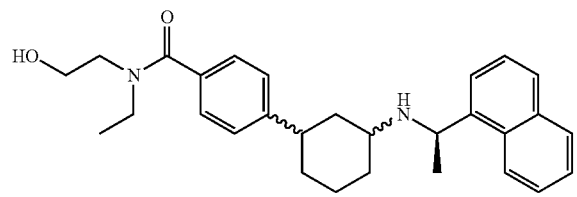 [SMILES: CCN(CCO)C(=O)c1ccc(C2CCCC(N[C@H](C)c3cccc4ccccc34)C2)cc1]

General procedure I was followed using 2-ethylamino-ethanol. LC-MS (method A): RT=3.96, [M+H]$^+$=444.9.

Example 97

N,N-Bis-(2-hydroxy-ethyl)-4-[3-((R)-1-naphthalen-1-yl-ethyl amino)-cyclohexyl]-benzamide (Compound 1102)

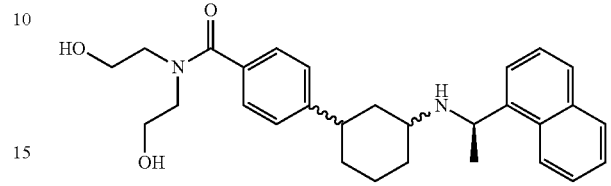

General procedure I was followed using diethanol amine. LC-MS (method A): RT=3.79, [M+H]$^+$=460.9.

Example 98

N-(2-Dimethylamino-ethyl)-4-[3-((R)-1-naphthalen-1-yl-ethyl amino)-cyclohexyl]-benzamide (Compound 1103)

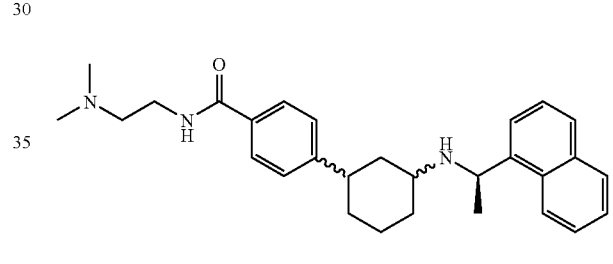

General procedure I was followed using N,N-(2-dimethylamino-ethyl)amine. LC-MS (method A): RT=3.47, [M+H]$^+$=444.2.

Example 99

N-(3-Dimethylamino-propyl)-4-[3-((R)-1-naphthalen-1-yl-ethyl amino)-cyclohexyl]-benzamide (Compound 1104)

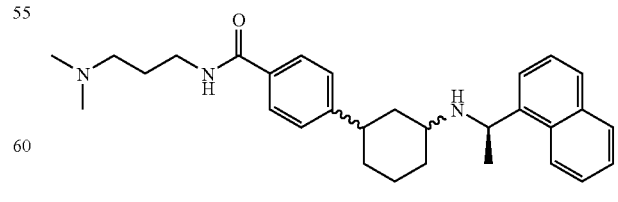

General procedure I was followed using N,N-(3-dimethylamino-propyl)amine. LC-MS (method A): RT=3.49, [M+H]$^+$=358.0.

Example 100

{4-[3-((R)-1-Naphthalen-1-yl-ethylamino)-cyclohexyl]-Phenyl}-piperidin-1-yl-methanone (Compound 1105)

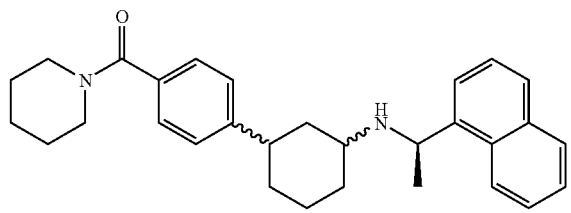 [SMILES: C[C@@H](NC1CCCC(c2ccc(C(=O)N3CCCCC3)cc2)C1)c1cccc2ccccc12]

General procedure I was followed using piperidine. LC-MS (method A): RT=4.27, [M+H]$^+$=441.1.

Example 101

(4-Methyl-piperazin-1-yl)-{4-[3-((R)-1-naphthalen-1-yl-ethyl amino)-cyclohexyl]-phenyl}-methanone (Compound 1106)

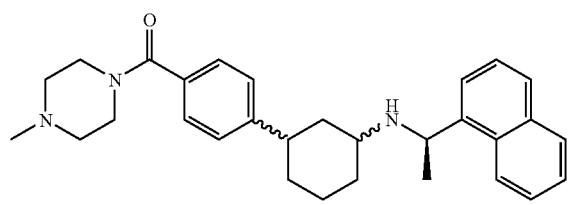 [SMILES: C[C@@H](NC1CCCC(c2ccc(C(=O)N3CCN(C)CC3)cc2)C1)c1cccc2ccccc12]

General procedure I was followed using 4-methyl-piperazine. LC-MS (method A): RT=3.46, [M+H]$^+$=456.2, [M−H]$^-$=454.0.

Example 102

[4-(2-Hydroxy-ethyl)-piperazin-1-yl]-{4-[3-((R)-1-naphthalen-1-yl-ethylamino)-cyclohexyl]-phenyl}-methanone (Compound 1107)

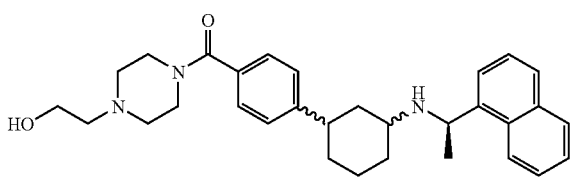 [SMILES: C[C@@H](NC1CCCC(c2ccc(C(=O)N3CCN(CCO)CC3)cc2)C1)c1cccc2ccccc12]

General procedure I was followed using 2-hydroxyethyl)-piperazine. LC-MS (method A): RT=3.44, [M+H]$^+$=486.1.

Example 103

Morpholin-4-yl-{4-[3-((R)-1-naphthalen-1-yl-ethylamino)-cyclo hexyl]-phenyl}-methanone (Compound 1108)

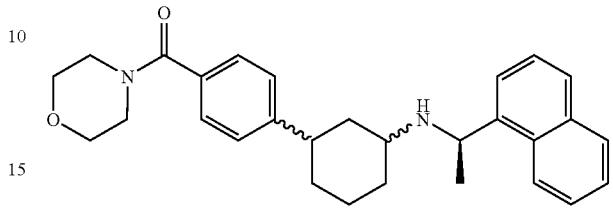

General procedure I was followed using morpholine. LC-MS (method A): RT=4.02, [M+H]$^-$=443.3.

Example 104

(4-Hydroxy-piperidin-1-yl)-{4-[3-((R)-1-naphthalen-1-yl-ethyl amino)-cyclohexyl]-phenyl}-methanone (Compound 1109)

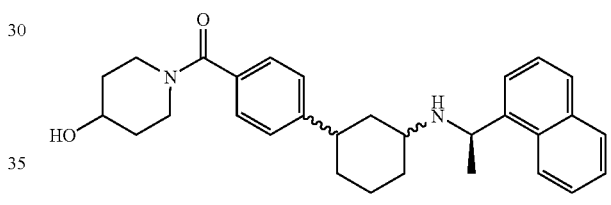

General procedure I was followed using piperidin-4-ol. LC-MS (method A): RT=3.87, [M+H]$^+$=456.9.

Example 105

N-(3-Imidazol-1-yl-propyl)-4-[3-((R)-1-naphthalen-1-yl-ethyl amino)-cyclohexyl]-benzamide (Compound 1110)

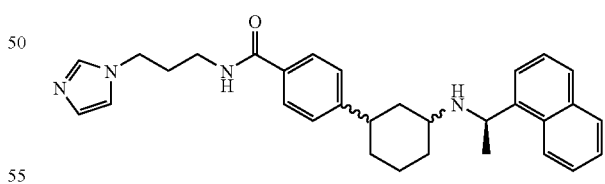

General procedure I was followed using 3-imidazol-1-yl-propylamine. LC-MS (method A): RT=3.51, [M+H]$^+$=481.3.

General Procedure J.

To a solution/suspension of ester (6.5 mmol) in MeOH (30 mL) and water (10 mL) was added LiOH (5-8 eq.). After shaking/stirring for 4 h, the reaction mixture was concentrated slightly in vacuo, and additional water was added. The product was precipitated by adding 4N aq. HCl with stirring until pH 5 (to form the neutral compound) or pH 1-2 (to form the hydrochloride salt). Precipitates were collected by filtration. If no precipitation occurred, the mixture was extracted with DCM, the organic extracts were concentrated in vacuo, the residue was dissolved in DMSO and/or DMF, and the product was purified by preparative HPLC-MS, re-analyzed by LC/MS (method B).

Example 106

{4-[(1S,3S)-3-((R)-1-Naphthalen-1-yl-ethylamino)-cyclohexyl]-benzoylamino}-acetic acid (Compound 1115)

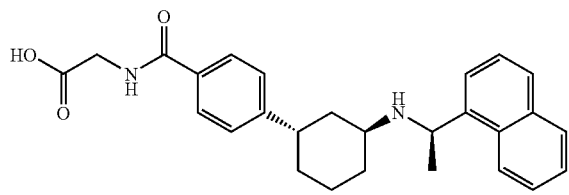 [SMILES: C[C@@H](N[C@H]1CCC[C@H](c2ccc(C(=O)NCC(=O)O)cc2)C1)c1cccc2ccccc12]

General procedure J was followed using {4-[3-((R)-1-naphthalen-1-yl-ethylamino)-cyclohexyl]-benzoyl amino}-acetic acid ethyl ester (compound 1098). $^{13}$C NMR (151 MHz, DMSO) δ 171.29, 166.16, 149.98, 133.41, 131.32, 130.61, 128.71, 127.29, 127.14, 126.48, 126.10, 125.53, 125.49, 123.58, 122.72, 50.78, 41.12, 36.76, 36.50, 32.26, 27.88, 23.25, 19.91.

Example 107

(S)-2-{4-[(1S,3S)-3-((R)-1-Naphthalen-1-yl-ethyl-amino)-cyclohexyl]-benzoylamino}-succinic acid 4-tert-butyl ester 1-methyl ester (Compound 1116)

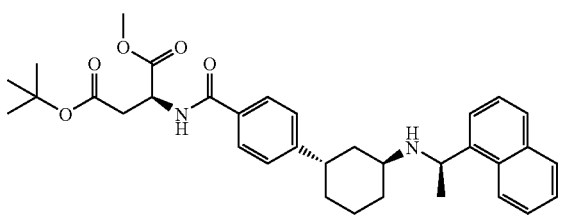 [SMILES: COC(=O)[C@H](CC(=O)OC(C)(C)C)NC(=O)c1ccc([C@H]2CCC[C@H](N[C@H](C)c3cccc4ccccc34)C2)cc1]

General procedure I was followed using L-aspartic acid 4-tert-butyl 1-methyl ester hydrochloride. $^{13}$C NMR (151 MHz, DMSO) δ 171.28, 169.04, 165.91, 151.20, 142.43, 133.45, 130.89, 130.80, 128.58, 127.17, 126.49, 126.39, 125.60, 125.53, 125.14, 123.08, 122.95, 80.25, 52.04, 51.12, 50.16, 49.15, 38.54, 36.92, 36.81, 32.98, 28.95, 27.53, 24.62, 20.21.

Example 108

(S)-2-{4-[(1S,3S)-3-((R)-1-Naphthalen-1-yl-ethyl-amino)-cyclohexyl]-benzoylamino}-succinic acid 4-tert-butyl ester (Compound 1117)

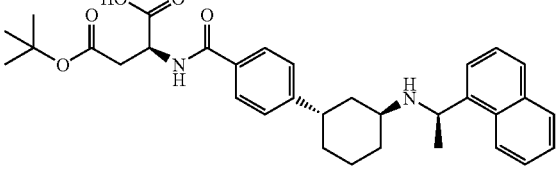

General procedure was followed using 2-{4-[3-(1-naphthalen-1-yl-ethylamino)-cyclohexyl]-benzoylamino}-succinic acid 4-tert-butyl ester 1-methyl ester (compound 1116). $^{13}$C NMR (151 MHz, DMSO) δ 172.79, 169.88, 165.42, 150.58, 141.95, 133.45, 131.72, 130.79, 128.61, 126.97, 126.54, 126.44, 125.68, 125.55, 125.20, 123.16, 122.91, 79.56, 51.01, 50.21, 50.18, 38.29, 37.80, 36.83, 32.89, 28.79, 27.59, 24.38, 20.18.

Example 109

(R)-2-{4-[(1S,3S)-3-((R)-1-Naphthalen-1-yl-ethyl-amino)-cyclohexyl]-benzoylamino}-3-phenyl-propionic acid methyl ester (Compound 1118)

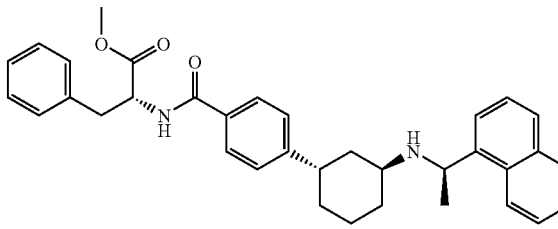

General procedure I was followed using D-phenylalanine methyl ester hydrochloride. $^{13}$C NMR (151 MHz, DMSO) δ 172.14, 166.19, 151.07, 142.42, 137.65, 133.44, 130.94, 130.80, 128.93, 128.58, 128.11, 127.20, 126.41 (two overlaying signals), 126.34, 125.61, 125.53, 125.14, 123.07, 122.94, 54.07, 51.80, 51.06, 50.11, 38.56, 36.91, 36.07, 32.94, 28.93, 24.61, 20.20.

Example 110

(R)-2-{4-[(1S,3S)-3-((R)-1-Naphthalen-1-yl-ethyl-amino)-cyclohexyl]-benzoylamino}-3-phenyl-propionic acid (Compound 1119)

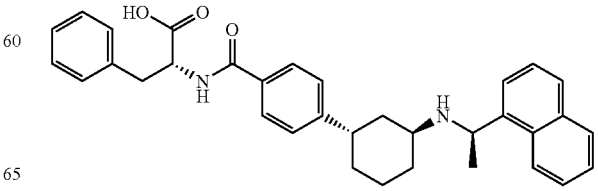

General procedure J was followed using 2-{4-[3-(1-naphthalen-1-yl-ethylamino)-cyclohexyl]-benzoylamino}-3-phenyl-propionic acid methyl ester (compound 1118) and LiOH. $^{13}$C NMR (151 MHz, DMSO) δ 172.53, 164.74, 150.30, 142.39, 139.34, 133.44, 132.53, 130.81, 129.40, 128.57, 127.47, 126.50, 126.46, 126.40, 125.60, 125.54, 125.43, 125.14, 123.06, 122.94, 55.49, 50.98, 50.05, 38.64, 37.00, 36.84, 32.94, 28.90, 24.57, 20.21.

Example 111

(S)-2-{4-[(1S,3S)-3-((R)-1-Naphthalen-1-yl-ethylamino)-cyclohexyl]-benzoylamino}-3-phenyl-propionic acid methyl ester (Compound 1120)

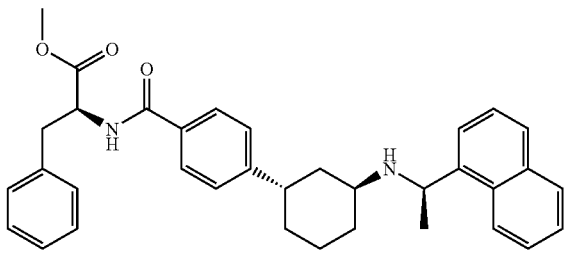 [SMILES: COC(=O)[C@H](Cc1ccccc1)NC(=O)c1ccc([C@H]2CCC[C@H](N[C@H](C)c3cccc4ccccc34)C2)cc1]

General procedure I was followed using L-phenylalanine methyl ester hydrochloride. $^{13}$C NMR (75 MHz, DMSO) δ 172.12, 166.17, 151.06, 142.33, 137.64, 133.45, 130.95, 130.80, 128.92, 128.58, 128.11, 127.20, 126.42, 126.34, 125.60, 125.52, 125.15, 123.09, 122.94, 54.06, 51.79, 51.07, 50.17, 38.43, 36.91, 36.09, 32.99, 28.94, 24.54, 20.20.

Example 112

(S)-2-{4-[(1S,3S)-3-((R)-1-Naphthalen-1-yl-ethylamino)-cyclohexyl]-benzoylamino}-3-phenyl-propionic acid; hydrochloride (Compound 1121)

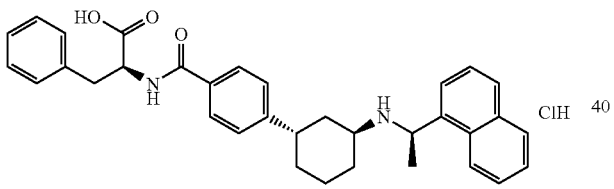

General procedure J was followed using 2-{4-[3-(1-naphthalen-1-yl-ethylamino)-cyclohexyl]-benzoylamino}-3-phenyl-propionic acid methyl ester (compound 1120). $^{13}$C NMR (151 MHz, DMSO) δ 173.05, 165.96, 148.84, 138.22, 133.31, 131.49, 130.29, 129.35, 128.96, 128.84, 128.18, 128.01, 127.29, 126.71, 126.42, 126.16, 125.85, 125.48, 124.57, 122.39, 54.14, 51.40, 50.43, 36.28, 36.11, 35.86, 31.35, 26.28, 21.73, 19.47.

Example 113

(S)-3-(1H-Indol-3-yl)-2-{4-[(1S,3S)-3-((R)-1-naphthalen-1-yl-ethylamino)-cyclohexyl]-benzoylamino}-propionic acid methyl ester (Compound 1122)

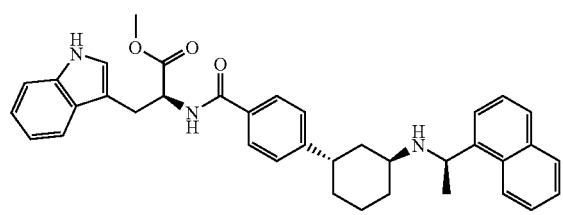 [SMILES: COC(=O)[C@H](Cc1c[nH]c2ccccc12)NC(=O)c1ccc([C@H]2CCC[C@H](N[C@H](C)c3cccc4ccccc34)C2)cc1]

General procedure I was followed using L-tryptophan methyl ester hydrochloride. $^{13}$C NMR (151 MHz, DMSO) δ 172.49, 166.18, 151.06, 142.42, 135.97, 133.44, 130.98, 130.80, 128.58, 127.24, 126.94, 126.39, 125.60, 125.53, 125.14, 123.50, 123.07, 122.94, 120.86, 118.30, 117.88, 111.35, 109.88, 53.60, 51.76, 51.08, 50.14, 38.50, 36.92, 33.02, 28.93, 26.48, 24.60, 20.20.

Example 114

(S)-3-(1H-Indol-3-yl)-2-{4-[(1S,3S)-3-((R)-1-naphthalen-1-yl-ethylamino)-cyclohexyl]-benzoylamino}-propionic acid (Compound 1123)

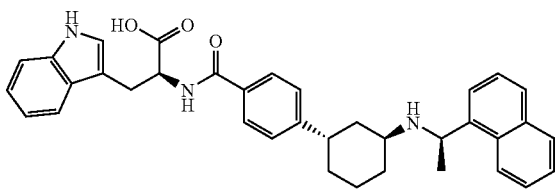 [SMILES: C[C@@H](N[C@H]1CCC[C@H](c2ccc(C(=O)N[C@@H](Cc3c[nH]c4ccccc34)C(=O)O)cc2)C1)c1cccc2ccccc12]

General procedure J was followed using 3-(1H-indol-3-yl)-2-{4-[3-(1-naphthalen-1-yl-ethylamino)-cyclohexyl]-benzoylamino}-propionic acid methyl ester (compound 1122). $^{13}$C NMR (151 MHz, DMSO) δ 172.45, 164.74, 150.15, 142.39, 135.66, 133.44, 132.79, 130.80, 128.58, 128.18, 127.24, 126.50, 126.38, 125.59, 125.54, 125.13, 123.15, 123.07, 122.94, 120.16, 118.67, 117.60, 111.57, 110.77, 55.29, 51.02, 50.09, 38.58, 36.83, 33.00, 28.92, 27.07, 24.57, 20.21.

Example 115

(R)-3-(1H-Indol-3-yl)-2-{4-[(1S,3S)-3-((R)-1-naphthalen-1-yl-ethylamino)-cyclohexyl]-benzoylamino}-propionic acid methyl ester (Compound 1124)

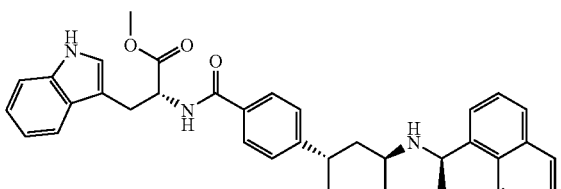

General procedure I was followed using D-tryptophan methyl ester hydrochloride. $^{13}$C NMR (151 MHz, DMSO) δ 172.48, 166.21, 151.04, 142.41, 135.98, 133.44, 130.99, 130.80, 128.58, 127.24, 126.95, 126.38, 125.60, 125.53, 125.14, 123.50, 123.07, 122.94, 120.86, 118.30, 117.89, 111.35, 109.90, 53.63, 51.76, 51.07, 50.12, 38.55, 36.91, 32.97, 28.93, 26.48, 24.60, 20.21.

Example 116

(R)-3-(1H-Indol-3-yl)-2-{4-[(1S,3S)-3-((R)-1-naphthalen-1-yl-ethylamino)-cyclohexyl]-benzoylamino}-propionic acid (Compound 1125)

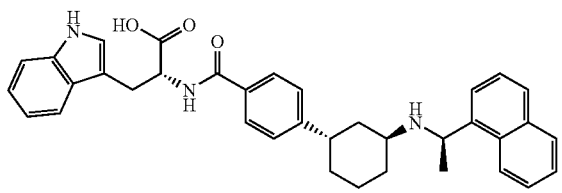 [SMILES: C[C@@H](N[C@H]1CCC[C@H](c2ccc(C(=O)N[C@H](Cc3c[nH]c4ccccc34)C(=O)O)cc2)C1)c1cccc2ccccc12]

General procedure J was followed using 3-(1H-indol-3-yl)-2-{4-[3-(1-naphthalen-1-yl-ethylamino)-cyclohexyl]-benzoylamino}-propionic acid methyl ester (compound 1124).

$^{13}$C NMR (151 MHz, DMSO) δ 172.04, 165.45, 150.47, 142.31, 135.83, 133.44, 132.05, 130.80, 128.58, 127.60, 126.86, 126.42, 126.35, 125.61, 125.53, 125.14, 123.24, 123.07, 122.93, 120.49, 118.33, 117.92, 111.04, 54.47, 50.95, 50.08, 38.54, 36.84, 32.96, 28.87, 26.88, 24.54, 20.20.

General Procedure I-1:

To a solution of 4-[(1S,3S)-3-((R)-1-naphthalen-1-yl-ethylamino)-cyclohexyl]-benzoic acid (compound 1056, 35 mg) in DMF (1 mL) was added HATU (1.2 eq.) and DIPEA (2 eq). The solution was stirred at r.t. for 2 h, then added to an amine (2 eq.). If the amine was furnished as hydrochloride DIPEA (2 eq.) was added. The mixture was shaken at r.t. overnight, filtered and purified by preparative HPLC-MS (re-analysed by LC/MS method A).

General Procedure I-2:

Similar to procedure I, except that compound 1057 (Example 54) was used instead of compound 1056

General Procedure I-3

To a solution or a suspension of 4-[(1S,3S)-3-((R)-1-naphthalen-1-yl-ethylamino)-cyclohexyl]-benzoic acid (compound 1056) in DMF (1M) under argon was added HOBt (1.1 eq.), EDAC (1 eq.), 4-methyl morpholine (1 eq.) and an amine (1 eq.). The mixture was stirred at r.t. overnight. DMF was removed in vacuo, and purification was performed by continuous gradient flash chromatography.

Example 117

(Cyclohexyl-{4-[3-(1-naphthalen-1-yl-ethylamino)-cyclohexyl]-benzoyl}-amino)-acetic acid ethyl ester (Compound 1126)

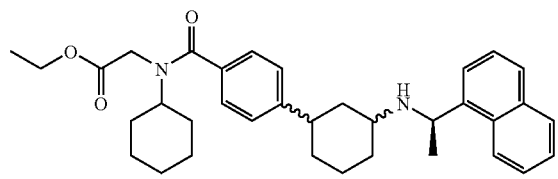 [SMILES: CCOC(=O)CN(C(=O)c1ccc(C2CCCC(N[C@H](C)c3cccc4ccccc34)C2)cc1)C1CCCCC1]

General procedure I-2 was followed using N-cyclohexyl-glycine ethyl ester. $^{1}$H NMR (500 MHz, DMSO, T=400 K) δ 8.31 (d, 1H), 7.87 (d, 1H), 7.74 (d, 1H), 7.69 (d, 1H), 7.50-7.42 (m, 3H), 7.20 (dd, 4H), 4.81-4.67 (m, 1H), 4.09 (q, 2H), 3.99 (s, 2H), 3.76-3.63 (m, 1H), 3.08 (t, 1H), 2.97-2.87 (m, 1H), 1.90-1.83 (m, 1H), 1.81-1.67 (m, 6H), 1.65-1.37 (m, 11H), 1.18 (t, 3H), 1.14-1.02 (m, 3H). LC-MS (method A): RT=5.47, [M+H]$^+$=541.3.

Example 118

2-{4-[3-((R)-1-Naphthalen-1-yl-ethylamino)-cyclohexyl]-benzoylamino}-malonic acid diethyl ester (Compound 1127)

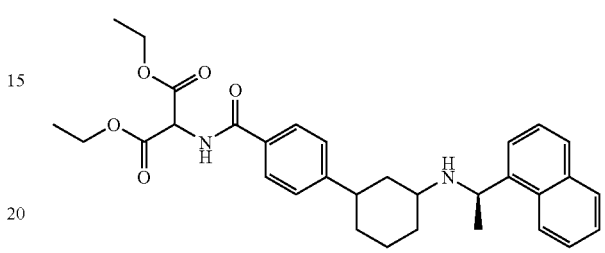

General procedure I-2 was followed using diethyl aminomalonate hydrochloride. $^{1}$H NMR (500 MHz, DMSO) δ 8.45 (s, 1H), 8.28 (d, 1H), 7.90 (d, 1H), 7.79 (d, 1H), 7.76-7.69 (m, 3H), 7.55-7.44 (m, 3H), 7.25 (d, 2H), 5.25 (d, 1H), 4.98-4.78 (m, 1H), 4.27-4.14 (m, 4H), 3.18-3.08 (m, 1H), 3.05-2.97 (m, 1H), 1.88 (m, 1H), 1.61 (m, 10H), 1.23 (t, 6H).

Example 119

(S)-3-Hydroxy-2-{4-[(1S,3S)-3-((R)-1-naphthalen-1-yl-ethylamino)-cyclohexyl]-benzoylamino}-propionic acid tert-butyl ester (Compound 1128)

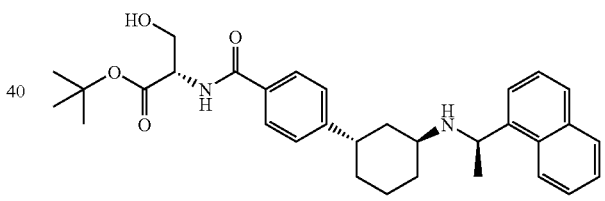

General procedure I-3 was followed using L-serine tert-butyl ester hydrochloride. $^{13}$C NMR (151 MHz, DMSO) δ 169.55, 166.25, 150.81, 133.45, 131.32, 130.78, 128.61, 127.22, 126.55, 126.42, 125.68, 125.54, 125.20, 123.15, 122.92, 80.43, 61.20, 56.10, 51.06, 50.28, 38.33, 36.86, 32.88, 28.80, 27.61, 24.40, 20.17.

Example 120

5-{4-[(1S,3S)-3-((R)-1-Naphthalen-1-yl-ethylamino)-cyclohexyl]-benzoylamino}-nicotinic acid (Compound 1129)

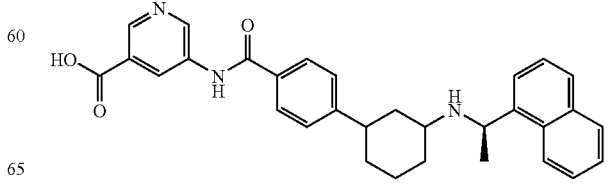

General procedure I-1 was followed using 5-amino-nicotinic acid ethyl ester. $^1$H NMR (600 MHz, DMSO) δ 9.12 (d, 1H), 8.79 (d, 1H), 8.74-8.70 (m, 1H), 8.36 (d, 1H), 7.94 (d, 1H), 7.85 (d, 2H), 7.80 (dd, 2H), 7.57-7.48 (m, 3H), 7.22 (d, 2H), 4.86-4.76 (m, 1H), 3.12-3.04 (m, 1H), 2.97-2.90 (m, 1H), 1.95-1.30 (m, 11H).

Example 121

4-{4-[(1S,3S)-3-((R)-1-Naphthalen-1-yl-ethyl-amino)-cyclohexyl]-benzoylamino}-benzoic acid (Compound 1130)

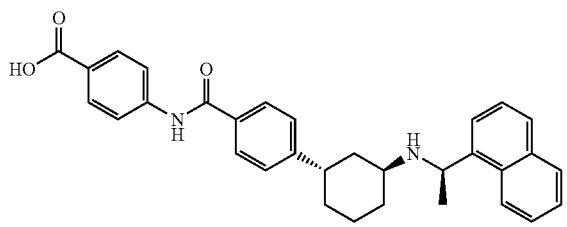 [SMILES: C[C@@H](N[C@H]1CCC[C@H](c2ccc(C(=O)Nc3ccc(C(=O)O)cc3)cc2)C1)c1cccc2ccccc12]

General procedure I-1 was followed using 4-amino-benzoic acid ethyl ester. The intermediate ethyl ester was hydrolyzed following general procedure J to afford the title compound. $^1$H NMR (600 MHz, DMSO) δ 10.41 (s, 1H), 8.35 (d, 1H), 7.97-7.88 (m, 5H), 7.86-7.77 (m, 4H), 7.59-7.50 (m, 3H), 7.22 (d, 2H), 4.84 (br s, 1H), 3.11-3.04 (m, 1H), 3.02-2.92 (m, 1H), 1.92-1.32 (m, 11H).

Example 122

4-Methoxy-3-{4-[(1S,3S)-3-((R)-1-naphthalen-1-yl-ethylamino)-cyclohexyl]-benzoylamino}-benzoic acid methyl ester hydrochloride (Compound 1131)

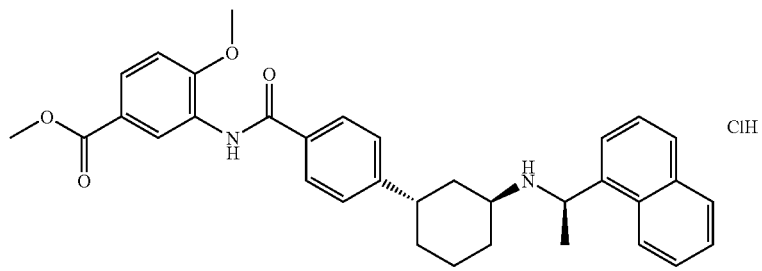 [SMILES: COC(=O)c1ccc(OC)c(NC(=O)c2ccc([C@H]3CCC[C@H](N[C@H](C)c4cccc5ccccc45)C3)cc2)c1 ; Cl]

General procedure I-1 was followed using methyl 3-amino-4-methoxybenzoate. The product was dissolved in ethyl acetate and treated with HCl in dioxane (4 M) and diethyl ether. The precipitate was filtered to afford the title compound. $^1$H NMR (600 MHz, DMSO) δ 9.48 (s, 1H), 8.85 (m, 2H), 8.42 (d, 1H), 8.35 (d, 1H), 8.03 (t, 2H), 7.89 (d, 3H), 7.83 (dd, 1H), 7.69-7.59 (m, 3H), 7.31 (d, 2H), 7.23 (d, 1H), 5.55 (s, 1H), 3.93 (s, 3H), 3.84 (s, 3H), 3.30-3.22 (m, 1H), 3.16-3.07 (m, 1H), 2.04-1.77 (m, 5H), 1.72 (d, 3H), 1.70-1.60 (m, 2H), 1.56-1.49 (m, 1H).

Example 123

2-{4-[(1S,3S)-3-((R)-1-Naphthalen-1-yl-ethyl-amino)-cyclohexyl]-benzoylamino}-benzoic acid hydrochloride (Compound 1132)

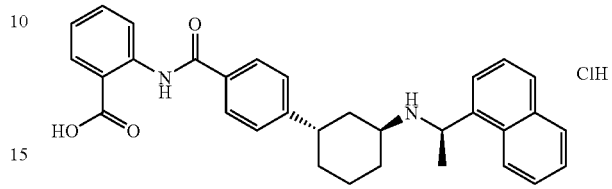

General procedure I-1 was followed using methyl 2-aminobenzoate. The intermediate methyl ester was hydrolyzed following general procedure J to afford the title compound. $^1$H NMR (600 MHz, DMSO) δ 8.69 (d, 1H), 8.35 (d, 1H), 8.06 (dd, 1H), 8.00 (dd, 2H), 7.90 (d, 3H), 7.67-7.62 (m, 2H), 7.59 (t, 1H), 7.56-7.49 (m, 1H), 7.34 (d, 2H), 7.12 (t, 1H), 5.53-5.34 (m, 1H), 3.24-3.18 (m, 1H), 3.18-3.11 (m, 1H), 2.00-1.76 (m, 5H), 1.73-1.48 (m, 6H).

Example 124

(Carboxymethyl-{4-[(1S,3S)-3-((R)-1-naphthalen-1-yl-ethylamino)-cyclohexyl]-benzoyl}-amino)-acetic acid hydrochloride (Compound 1133)

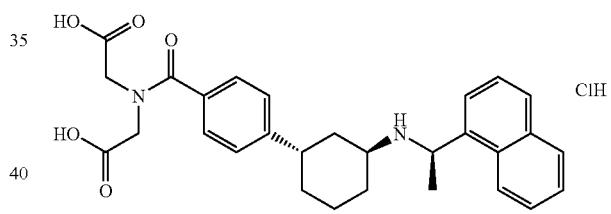

General procedure I-1 was followed using diethyl iminodiacetate. The intermediate diethyl ester was hydrolyzed following general procedure J to afford the title compound. $^1$H NMR (600 MHz, DMSO) δ 8.34 (d, 1H), 8.00 (d, 1H), 7.96 (d, 1H), 7.84 (d, 1H), 7.62 (t, 2H), 7.58 (t, 1H), 7.24 (d, 2H), 7.17 (d, 2H), 5.36 (s, 1H), 4.00 (s, 2H), 3.79 (s, 2H), 3.18-3.13 (m, 1H), 3.06-2.99 (m, 1H), 1.92-1.74 (m, 5H), 1.65 (d, 3H), 1.60-1.46 (m, 3H).

Example 125

1-({4-[(1S,3S)-3-((R)-1-Naphthalen-1-yl-ethyl-amino)-cyclohexyl]-benzoylamino}-methyl)-cyclopentanecarboxylic acid (Compound 1134)

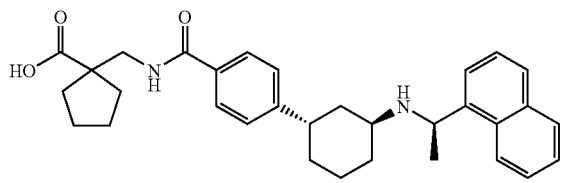 [SMILES: C[C@@H](N[C@H]1CCC[C@H](c2ccc(C(=O)NCC3(C(=O)O)CCCC3)cc2)C1)c1cccc2ccccc12]

General procedure I-1 was followed using ethyl 1-(aminomethyl)-cyclopentanecarboxylate. The intermediate ethyl ester was hydrolyzed following general procedure J to afford the title compound. $^1$H NMR (600 MHz, DMSO) δ 8.34 (d, 1H), 8.15 (d, 1H), 7.93 (d, 1H), 7.77 (dd, 2H), 7.64 (d, 2H), 7.55-7.48 (m, 3H), 7.10 (d, 2H), 4.70 (q, 1H), 3.48 (d, 2H), 3.06-2.98 (m, 1H), 2.89-2.85 (m, 1H), 1.95-1.82 (m, 3H), 1.81-1.70 (m, 2H), 1.68-1.46 (m, 10H), 1.46-1.36 (m, 1H), 1.44 (d, 3H), 1.35-1.26 (m, 1H).

Example 126

1-{4-[(1S,3S)-3-((R)-1-Naphthalen-1-yl-ethyl-amino)-cyclohexyl]-benzoylamino}-cyclopentanecarboxylic acid hydrochloride (Compound 1135)

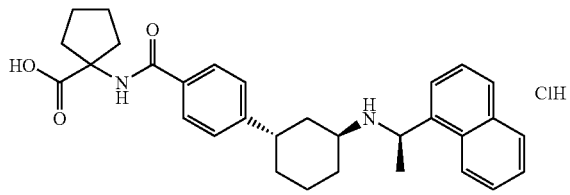 [SMILES: C[C@@H](N[C@H]1CCC[C@H](c2ccc(C(=O)NC3(C(=O)O)CCCC3)cc2)C1)c1cccc2ccccc12 ; Cl]

General procedure I-1 was followed using methyl 1-amino-1-cyclopentane-carboxylate hydrochloride. The intermediate methyl ester was hydrolyzed following general procedure J to afford the title compound. $^1$H NMR (600 MHz, DMSO) δ 11.93 (br s, 1H), 8.88 (s, 2H), 8.42 (s, 1H), 8.34 (d, 1H), 8.01 (dd, 2H), 7.89 (d, 1H), 7.77 (d, 2H), 7.69-7.63 (m, 2H), 7.61 (t, 1H), 7.23 (d, 2H), 5.54 (br s, 1H), 3.27-3.20 (m, 1H), 3.12-3.05 (m, 1H), 2.18-2.09 (m, 2H), 2.06-1.57 (m, 16H), 1.54-1.46 (m, 1H).

Example 127

3-{4-[(1S,3S)-3-((R)-1-Naphthalen-1-yl-ethyl-amino)-cyclohexyl]-benzoylamino}-propionic acid hydrochloride (Compound 1136)

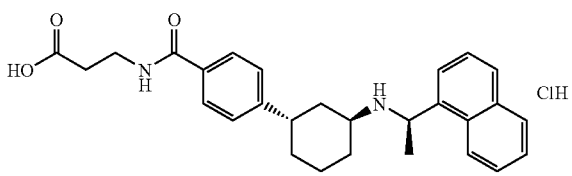 [SMILES: C[C@@H](N[C@H]1CCC[C@H](c2ccc(C(=O)NCCC(=O)O)cc2)C1)c1cccc2ccccc12 ; Cl]

General procedure J was followed using 3-{4-[3-((R)-1-naphthalen-1-yl-ethylamino)-cyclohexyl]-benzoyl amino}-propionic acid methyl ester (compound 1088). $^1$H NMR (600 MHz, DMSO) δ 9.47 (br s, 1H), 8.46 (t, 1H), 8.35 (d, 1H), 7.97 (d, 1H), 7.89 (d, 1H), 7.72 (d, 2H), 7.60-7.52 (m, 3H), 7.18 (d, 2H), 5.15 (br s, 1H), 3.45 (dd, 2H), 3.20-3.11 (m, 1H), 3.06-2.98 (m, 1H), 2.54-2.48 (m, 2H) (overlaying DMSO signal), 2.00-1.81 (m, 3H), 1.79-1.58 (m, 5H), 1.57-1.36 (m, 3H).

Example 128

(1-{4-[(1S,3S)-3-((R)-1-Naphthalen-1-yl-ethyl-amino)-cyclohexyl]-benzoylamino}-cyclohexyl)-acetic acid hydrochloride (Compound 1137)

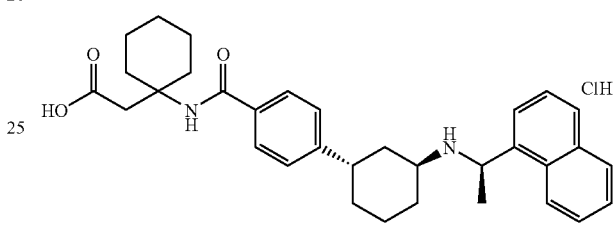

General procedure I-1 was followed using (1-amino-cyclohexyl)-acetic acid methyl ester. The intermediate methyl ester was hydrolyzed following general procedure J to afford the title compound. $^1$H NMR (600 MHz, DMSO) δ 12.94-10.67 (br s, 1H), 8.83 (s, 2H), 8.34 (d, 1H), 8.02 (dd, 2H), 7.89 (d, 1H), 7.70 (d, 2H), 7.68-7.64 (m, 2H), 7.61 (t, 1H), 7.47 (s, 1H), 7.20 (d, 2H), 5.59-5.50 (m, 1H), 3.30-3.20 (m, 1H), 3.11-3.03 (m, 1H), 2.75 (s, 2H), 2.32 (m, 2H), 2.02-1.86 (m, 3H), 1.85-1.74 (m, 2H), 1.72 (d, 3H), 1.68-1.57 (m, 2H), 1.57-1.41 (m, 8H), 1.30-1.20 (m, 1H).

Example 129

1-{4-[(1S,3S)-3-((R)-1-Naphthalen-1-yl-ethyl-amino)-cyclohexyl]-benzoylamino}-cyclopropanecarboxylic acid ethyl ester (Compound 1138)

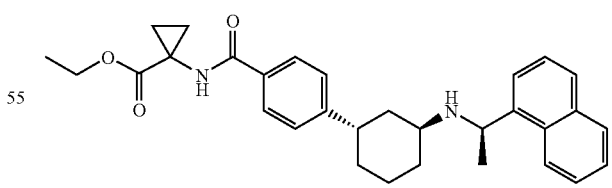

General procedure I was followed using 1-aminocyclopropane-1-carboxylic acid ethyl ester hydrochloride. $^{13}$C NMR (151 MHz, DMSO) δ 172.07, 167.00, 151.01, 142.43, 133.45, 131.26, 130.81, 128.59, 127.16, 126.40, 125.60, 125.54, 125.15, 123.08, 122.95, 60.43, 60.13, 51.10, 50.17, 38.57, 36.92, 33.25, 33.00, 28.96, 24.62, 20.22, 17.49, 16.62, 13.98.

Example 130

1-{4-[(1S,3S)-3-((R)-1-Naphthalen-1-yl-ethyl-amino)-cyclohexyl]-benzoylamino}-cyclopronan-ecarboxylic acid (Compound 1139)

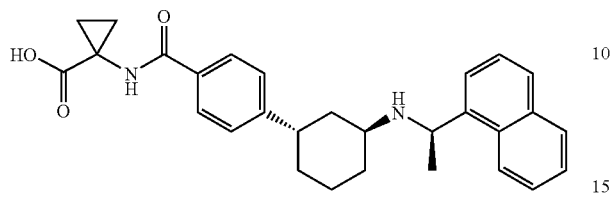

General procedure J was followed using 1-{4-[3-(1-naphthalen-1-yl-ethylamino)-cyclohexyl]-benzoylamino}-cyclopropanecarboxylic acid ethyl ester (compound 1138). $^{13}$C NMR (151 MHz, DMSO) δ 174.06, 167.01, 150.30, 133.58, 131.68, 130.79, 128.88, 127.45, 127.41, 126.59, 126.53, 126.24, 125.71, 125.63, 123.77, 122.91, 51.00, 50.89, 36.68, 33.34, 33.15, 32.56, 28.15, 23.60, 20.10, 17.01, 16.57.

Example 131

1-({4-[(1S,3S)-3-((R)-1-Naphthalen-1-yl-ethyl-amino)-cyclohexyl]-benzoylamino}-methyl)-cyclopropanecarboxylic acid (Compound 1140)

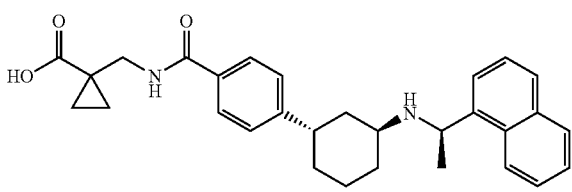 [SMILES: C[C@@H](N[C@H]1CCC[C@H](c2ccc(C(=O)NCC3(C(=O)O)CC3)cc2)C1)c1cccc2ccccc12]

General procedure I-1 was followed using 1-(aminomethyl)-cyclopropane-carboxylic acid ethyl ester. The intermediate ethyl ester was hydrolyzed following general procedure J to afford the title compound. $^1$H NMR (600 MHz, DMSO) δ 8.35 (d, 1H), 8.21 (t, 1H), 7.93 (d, 1H), 7.80 (d, 1H), 7.77 (d, 1H), 7.67 (d, 2H), 7.52 (dq, 3H), 7.10 (d, 2H), 4.76 (br s, 1H), 3.52 (d, 2H), 3.06-2.97 (m, 1H), 2.93-2.87 (m, 1H), 1.91-1.81 (m, 1H), 1.80-1.70 (m, 2H), 1.69-1.62 (m, 1H), 1.58-1.38 (m, 6H), 1.37-1.28 (m, 1H), 1.02 (q, 2H), 0.89 (dd, 2H).

Example 132

2-Methyl-2-{4-[(1S,3S)-3-((R)-1-naphthalen-1-yl-ethylamino)-cyclohexyl]-benzoylamino}-propionic acid (Compound 1141)

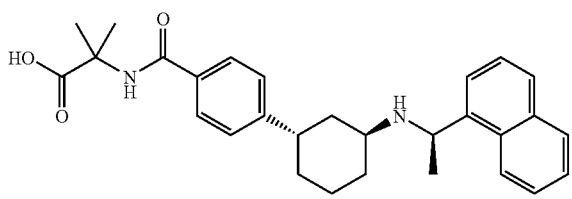 [SMILES: C[C@@H](N[C@H]1CCC[C@H](c2ccc(C(=O)NC(C)(C)C(=O)O)cc2)C1)c1cccc2ccccc12]

General procedure I-1 was followed using 2-methylalanine methyl ester hydrochloride. The intermediate methyl ester was hydrolyzed following general procedure J to afford the title compound. $^1$H NMR (300 MHz, DMSO) δ 8.35 (d, 1H), 8.31 (s, 1H), 7.98-7.89 (m, 1H), 7.82 (dd, 2H), 7.69 (d, 2H), 7.59-7.46 (m, 3H), 7.11 (d, 2H), 4.83 (q, 1H), 3.13-2.99 (m, 1H), 2.97-2.88 (m, 1H), 1.97-1.21 (m, 8H), 1.50 (d, 3H), 1.44 (s, 6H).

Example 133

1-{4-[(1S,3S)-3-((R)-1-Naphthalen-1-yl-ethyl-amino)-cyclohexyl]-benzoyl}-azetidine-3-carboxylic acid (Compound 1142)

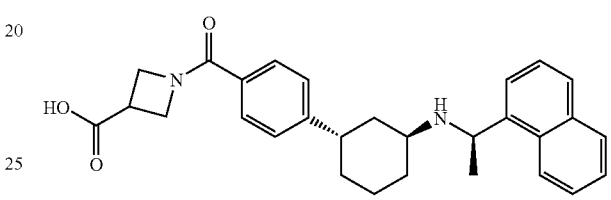

General procedure I-1 was followed using 3-azetidinecarboxylic acid methyl ester hydrochloride. The intermediate methyl ester was hydrolyzed following general procedure J to afford the title compound. $^1$H NMR (600 MHz, DMSO) δ 8.34 (d, 1H), 7.97-7.91 (m, 1H), 7.81 (d, 1H), 7.77 (d, 1H), 7.53 (m, 3H), 7.48 (d, 2H), 7.13 (d, 2H), 4.82 (br s, 1H), 4.43 (m, 1H), 4.31 (m, 1H), 4.19 (m, 1H), 4.04 (m, 1H), 3.43 (m, 1H), 3.02 (m, 1H), 2.90 (m, 1H), 1.90-1.65 (m, 4H), 1.61-1.30 (m, 7H).

Example 134

(Methyl-{4-[(1S,3S)-3-((R)-1-naphthalen-1-yl-ethyl-amino)-cyclohexyl]-benzoyl}-amino)-acetic acid (Compound 1143)

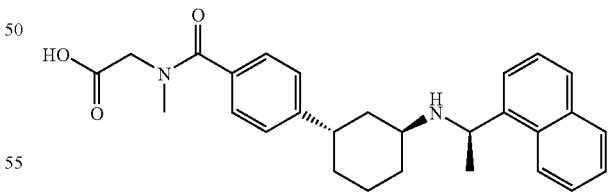

General procedure I-1 was followed using n-methylglycine ethyl ester hydrochloride. The intermediate ethyl ester was hydrolyzed following general procedure J to afford the title compound. $^1$H NMR (600 MHz, DMSO) δ 8.34 (d, 1H), 7.94 (d, 1H), 7.82 (d, 1H), 7.79-7.74 (m, 1H), 7.57-7.48 (m, 3H), 7.27 (d, 1H), 7.12 (dt, 3H), 4.91-4.76 (br s, 1H), 4.11 (s, 1H), 3.89 (s, 1H), 3.06-2.98 (m, 1H), 2.97-2.90 (m, 4H), 1.91-1.67 (m, 4H), 1.63-1.53 (m, 1H), 1.53-1.40 (m, 5H), 1.40-1.30 (m, 1H).

Example 135

4-{4-[(1S,3S)-3-((R)-1-Naphthalen-1-yl-ethyl-amino)-cyclohexyl]-benzoylamino}-butyric acid (Compound 1144)

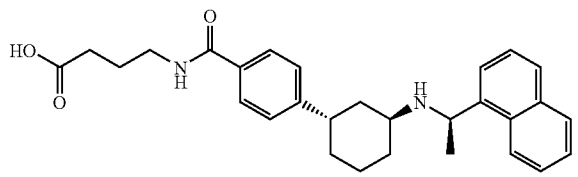 [SMILES: C[C@@H](N[C@H]1CCC[C@H](c2ccc(C(=O)NCCCC(=O)O)cc2)C1)c1cccc2ccccc12]

General procedure I-1 was followed using ethyl 4-aminobutyrate hydrochloride. The intermediate ethyl ester was hydrolyzed following general procedure J to afford the title compound. $^1$H NMR (600 MHz, DMSO) δ 8.35 (t, 2H), 7.97-7.91 (m, 1H), 7.81 (d, 1H), 7.77 (d, 1H), 7.68 (d, 2H), 7.53 (m, 3H), 7.10 (d, 2H), 4.79 (s, 1H), 3.24 (dd, 2H), 3.02 (t, 1H), 2.92 (s, 1H), 2.25 (t, 2H), 1.73 (t, 2H), 1.92-1.63 (m, 4H), 1.60-1.29 (m, 7H).

Example 136

1-{4-[(1S,3S)-3-((R)-1-Naphthalen-1-yl-ethyl-amino)-cyclohexyl]-benzoyl}-piperidine-4-carboxylic acid ethyl ester (Compound 1145)

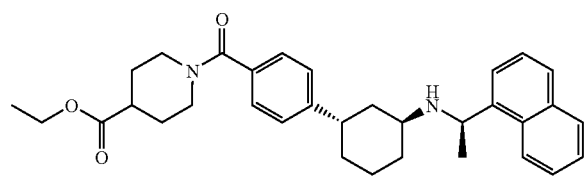 [SMILES: CCOC(=O)C1CCN(C(=O)c2ccc([C@H]3CCC[C@H](N[C@H](C)c4cccc5ccccc45)C3)cc2)CC1]

General procedure I-1 was followed using 4-piperidinecarboxylic acid ethyl ester. $^{13}$C NMR (126 MHz, DMSO) δ 173.69, 169.04, 148.70, 142.38, 133.45, 133.30, 130.83, 128.57, 126.60, 126.51, 126.40, 125.60, 125.52, 125.13, 123.04, 122.93, 59.87, 50.93, 50.00, 46.26, 39.92, 38.67, 36.85, 32.98, 28.93, 27.84, 24.50, 20.24, 13.96.

Example 137

1-{4-[(1S,3S)-3-((R)-1-Naphthalen-1-yl-ethyl-amino)-cyclohexyl]-benzoyl}-piperidine-4-carboxylic acid (Compound 1146)

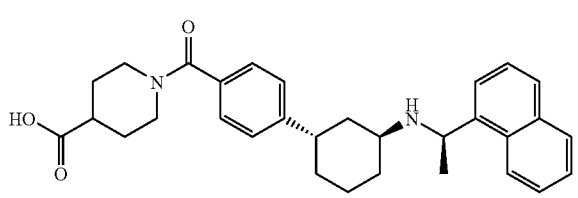 [SMILES: C[C@@H](N[C@H]1CCC[C@H](c2ccc(C(=O)N3CCC(C(=O)O)CC3)cc2)C1)c1cccc2ccccc12]

General procedure J was followed using 1-{4-[3-((R)-1-naphthalen-1-ylethylamino)-cyclohexyl]-benzoyl}-piperidine-4-carboxylic acid ethyl ester (compound 1145). $^1$H NMR (600 MHz, DMSO) δ 12.21 (br s, 1H), 9.37 (d, 2H), 8.35 (d, 1H), 8.13 (d, 1H), 7.99 (dd, 2H), 7.69-7.54 (m, 3H), 7.25 (dd, 4H), 5.50 (s, 1H), 4.43-4.18 (m, 1H), 160-3.41 (m, 1H), 3.24-3.12 (m, 2H), 3.11-2.79 (m, 2H), 2.57-2.47 (m, 1H), 2.11-1.69 (m, 10H), 1.68-1.38 (m, 5H).

Example 138

(Cyclohexyl-{4-[3-((R)-1-naphthalen-1-yl-ethyl-amino)-cyclohexyl]-benzoyl}-amino)-acetic acid ethyl ester (Compound 1147)

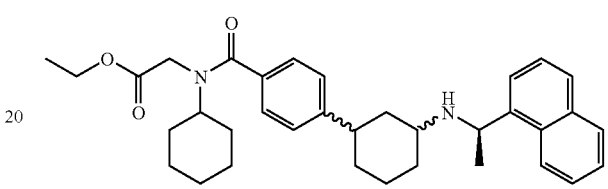

To a solution of 4-[3-((R)-1-naphthalen-1-yl-ethylamino)-cyclohexyl]-benzoic acid (ex. 54, 20 mg) in 400 μL DMF were added diisopropyl ethyl amine (3 eq.) and bromo-tris-pyrrolidino-phosphonium hexafluorophosphate (PyBroP, 1 eq.). The solution was cooled in an ice bath, and N-cyclohexylglycine ethyl ester (3 eq.) was added followed by 1-hydroxy-7-azabenzotriazole (HOAt, 3 eq.). After shaking overnight at r.t., the reaction mixture was diluted with aqueous NaHCO$_3$ and extracted with dichloromethane. The organic extracts were concentrated in vacuo and purified by HPLC-MS. $^1$H NMR (500 MHz, DMSO) δ 825 (d, 1H), 7.98 (s, 2H), 7.82 (s, 1H), 7.59 (s, 3H), 7.12 (t, 4H), 5.51-5.31 (m, 1H), 4.10 (q, 2H), 3.99 (s, 2H), 3.69-3.57 (m, 1H), 3.36-3.22 (m, 1H), 3.20-3.10 (m, 1H), 2.10-1.95 (m, 2H), 1.86-1.64 (m, 12H), 1.56-1.38 (m, 4H), 1.19 (t, 3H), 1.13-0.98 (m, 3H).

Example 139

(Cyclohexyl-{4-[3-((R)-1-naphthalen-1-yl-ethyl-amino)-cyclohexyl]-benzoyl}-amino)-acetic acid (Compound 1148)

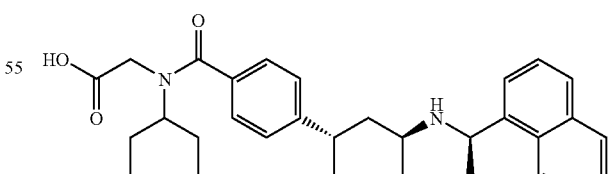

General procedure J was followed using (cyclohexyl-{4-[3-((R)-1-naphthalen-1-yl-ethylamino)-cyclohexyl]-benzoyl}-amino)-acetic acid ethyl ester (compound 1147).

LC-MS (method B): RT=3.23, [M+H]$^+$=513.5

Example 140

4-[(1S,3S)-3-((R)-1-Naphthalen-1-yl-ethylamino)-cyclohexyl]-N—((R)-2-oxo-tetrahydro-furan-3-yl)-benzamide (Compound 1149)

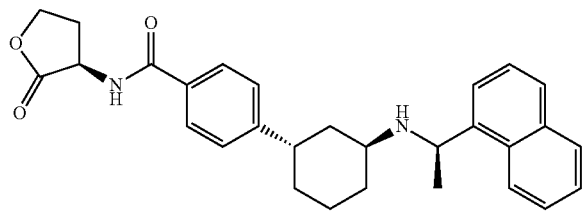 [SMILES: C[C@@H](N[C@H]1CCC[C@H](c2ccc(C(=O)N[C@@H]3CCOC3=O)cc2)C1)c1cccc2ccccc12]

General procedure I was followed using (R)-(+)-2-amino-4-butyrolactone hydrochloride. $^{13}$C NMR (75 MHz, DMSO) δ 175.25, 165.82, 151.24, 142.45, 133.46, 130.82, 130.77, 128.58, 127.08, 126.54, 126.41, 125.59, 125.53, 125.14, 123.10, 122.97, 65.21, 51.16, 50.20, 48.23, 38.56, 36.92, 32.93, 29.01, 27.90, 24.60, 20.23.

Example 141

N-Cyanomethyl-4-[(1S,3S)-3-((R)-1-naphthalen-1-yl-ethylamino)-cyclohexyl]-benzamide (Compound 1150)

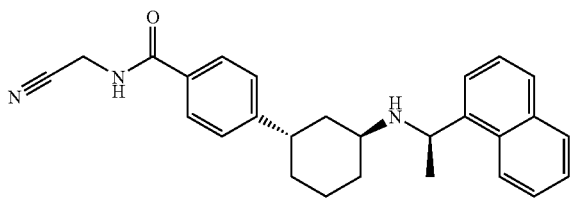 [SMILES: C[C@@H](N[C@H]1CCC[C@H](c2ccc(C(=O)NCC#N)cc2)C1)c1cccc2ccccc12]

General procedure I was followed using amino acetonitrile hydrochloride. $^1$H NMR (300 MHz, DMSO) δ 9.08 (t, 1H), 8.35 (d, 1H), 7.97-7.87 (m, 1H), 7.84-7.66 (m, 4H), 7.58-7.43 (m, 3H), 7.13 (d, 2H), 4.66 (s, 1H), 4.29 (d, 2H), 3.12-2.96 (m, 1H), 2.94-2.82 (m, 1H), 1.95-1.21 (m, 12H).

Example 142

N-(4-Cyano-1H-pyrazol-3-yl)-4-[(1S,3S)-3-((R)-1-naphthalen-1-yl-ethylamino)-cyclohexyl]-benzamide (Compound 1151)

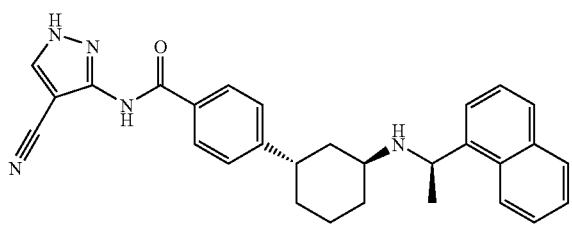 [SMILES: C[C@@H](N[C@H]1CCC[C@H](c2ccc(C(=O)Nc3n[nH]cc3C#N)cc2)C1)c1cccc2ccccc12]

General procedure I was followed using 4-cyano-5-aminopyrazole. $^1$H NMR (300 MHz, DMSO) δ 8.35 (d, 1H), 8.02 (s, 1H), 7.96-7.70 (m, 6H), 7.56-7.43 (m, 3H), 7.22-7.10 (m, 2H), 4.65 (q, 1H), 3.14-2.98 (m, 1H), 2.90-2.81 (m, 1H), 2.23 (br s, 1H), 1.97-1.20 (m, 11H).

Example 143

(R)-3-Hydroxy-2-{4-[(1S,3S)-3-((R)-1-naphthalen-1-yl-ethylamino)-cyclohexyl]-benzoylamino}-propionic acid benzyl ester (Compound 1152)

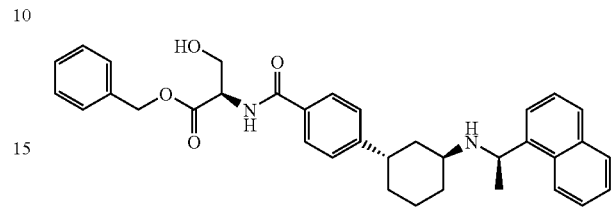

General procedure I-3 was followed using D-serine benzyl ester hydrochloride. $^1$H NMR (600 MHz, DMSO) δ 8.47 (d, 1H), 8.35 (d, 1H), 7.92 (d, 1H), 7.76 (dd, 2H), 7.73 (d, 2H), 7.55-7.46 (m, 3H), 7.40-7.29 (m, 5H), 7.11 (d, 2H), 5.15 (dd, 2H), 5.07 (t, 1H), 4.70-4.62 (m, 1H), 4.57 (dd, 1H), 3.86-3.78 (m, 2H), 3.03 (t, 1H), 2.87 (s, 1H), 2.22 (br s, 1H), 1.93-1.82 (m, 1H), 1.82-1.70 (m, 2H), 1.63 (d, 1H), 1.54-1.35 (m, 6H), 1.29 (t, 1H).

Example 144

(S)-3-Hydroxy-2-{4-[(1S,3S)-3-((R)-1-naphthalen-1-yl-ethylamino)-cyclohexyl]-benzoylamino}-propionic acid benzyl ester (Compound 1153)

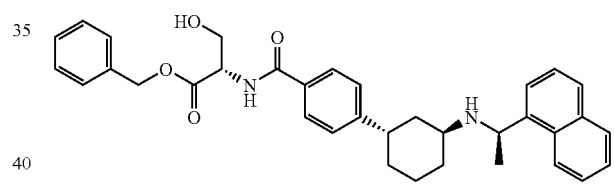

General procedure I-3 was followed using L-serine benzyl ester hydrochloride. $^1$H NMR (600 MHz, DMSO) δ 8.47 (d, 1H), 8.35 (d, 1H), 7.92 (d, 1H), 7.77 (dd, 2H), 7.73 (d, 2H), 7.55-7.46 (m, 3H), 7.39-7.29 (m, 5H), 7.12 (d, 2H), 5.15 (dd, 2H), 5.07 (t, 1H), 4.66 (br s, 1H), 4.57 (dt, 1H), 3.86-3.78 (m, 2H), 3.03 (t, 1H), 2.91-2.83 (m, 1H), 2.22 (br s, 1H), 1.94-1.83 (m, 1H), 1.81-1.70 (m, 2H), 1.67-1.59 (m, 1H), 1.53-1.24 (m, 7H).

Example 145

(S)-3-Hydroxy-2-{4-[(1S,3S)-3-((R)-1-naphthalen-1-yl-ethylamino)-cyclohexyl]-benzoylamino}-propionic acid methyl ester (Compound 1154)

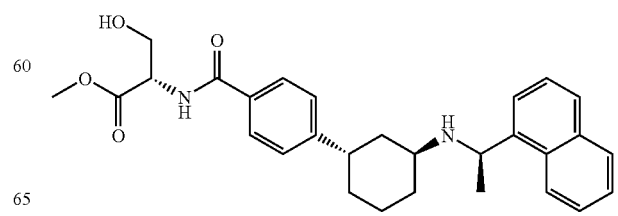

General procedure I-3 was followed using L-serine methyl ester hydrochloride. $^{13}$C NMR (126 MHz, DMSO) δ 171.12, 166.38, 151.16, 142.39, 133.58, 131.16, 130.92, 128.71, 127.39, 126.58, 126.55, 125.75, 125.65, 125.29, 123.24, 123.06, 61.09, 55.58, 51.84, 51.24, 50.36, 38.55, 37.03, 33.07, 29.06, 24.62, 20.32.

Example 146

(R)-3-Hydroxy-2-{4-[(1S,3S)-3-((R)-1-naphthalen-1-yl-ethylamino)-cyclohexyl]-benzoylamino}-propionic acid methyl ester (Compound 1155)

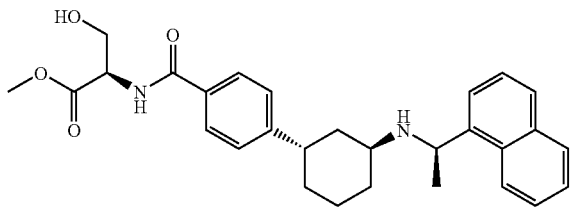 [SMILES: COC(=O)[C@@H](CO)NC(=O)c1ccc([C@H]2CCC[C@H](N[C@H](C)c3cccc4ccccc34)C2)cc1]

General procedure I-3 was followed using D-serine methyl ester hydrochloride. $^1$H NMR (600 MHz, DMSO) δ 8.43 (d, 1H), 8.35 (d, 1H), 7.93 (d, 1H), 7.77 (dd, 2H), 7.74 (d, 2H), 7.56-7.46 (m, 3H), 7.12 (d, 2H), 5.05 (t, 1H), 4.69 (s, 1H), 4.51 (dd, 1H), 3.78 (t, 2H), 3.64 (s, 3H), 3.03 (m, 1H), 2.88 (s, 1H), 1.93-1.83 (m, 1H), 1.82-1.70 (m, 2H), 1.68-1.60 (m, 1H), 1.54-1.46 (m, 2H), 1.46-1.35 (m, 1H), 1.44 (d, 3H), 1.35-1.25 (m, 1H).

Example 147

(S)-3-Hydroxy-2-{4-[(1S,3S)-3-((R)-1-naphthalen-1-yl-ethylamino)-cyclohexyl]-benzoylamino}-propionic acid ethyl ester hydrochloride (Compound 1156)

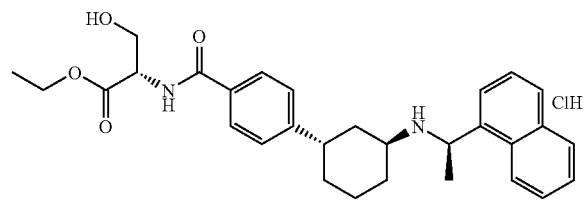 [SMILES: CCOC(=O)[C@H](CO)NC(=O)c1ccc([C@H]2CCC[C@H](N[C@H](C)c3cccc4ccccc34)C2)cc1 ; Cl]

General procedure I-3 was followed using L-serine ethyl ester hydrochloride. The product was dissolved in ethyl acetate and treated with HCl in dioxane (4 M) and diethyl ether. The precipitate was filtered to afford the title compound. $^1$H NMR (300 MHz, DMSO) δ 9.42 (s, 2H), 8.51 (d, 1H), 8.35 (d, 1H), 8.15 (d, 1H), 7.99 (t, 2H), 7.84 (d, 2H), 7.61 (dt, 13.5, 3H), 7.28 (d, 2H), 5.57-5.43 (m, 1H), 5.24-4.99 (br s, 1H), 4.48 (dd, 1H), 4.11 (q, 2H), 3.80 (d, 2H), 3.31-3.08 (m, 2H), 2.10-1.36 (m, 12H), 1.19 (t, 3H).

Example 148

3-Hydroxy-2-{4-[3-((R)-1-naphthalen-1-yl-ethylamino)-cyclohexyl]-benzoylamino}-propionic acid hydrochloride (Compound 1157)

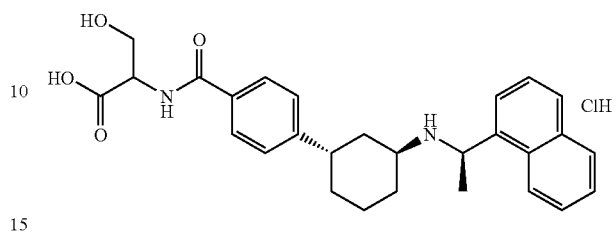

(S)-3-Hydroxy-2-{4-[(1S,3S)-3-(1-naphthalen-1-yl-ethylamino)-cyclohexyl]-benzoylamino}-propionic acid tert-butyl ester (compound 1128, 150 mg) was suspended in 5 mL HCl (4M in dioxane) and stirred overnight at room temperature. Diethylether was added to the reaction mixture, and the precipitate thus formed was filtered off, washed with additional ether and dried. $^{13}$C NMR (151 MHz, DMSO) δ 171.84, 166.00, 148.26, 133.82, 133.34, 131.63, 130.23, 129.77, 128.94, 127.50, 127.02, 126.43, 126.14, 125.52, 124.61, 122.30, 61.04, 55.58, 51.97, 48.48, 35.74, 33.44, 30.97, 25.84, 20.79, 19.32.

Example 149

(R)-4-Hydroxy-2-{4-[(1S,3S)-3-((R)-1-naphthalen-1-yl-ethylamino)-cyclohexyl]-benzoylamino}-butyric acid (Compound 1158)

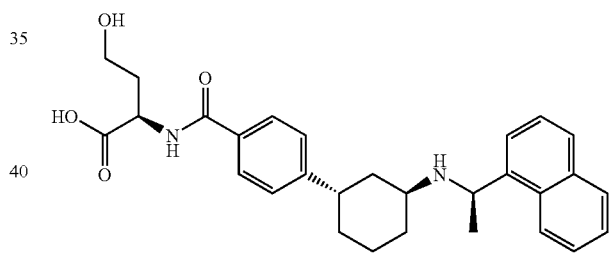

General procedure J was followed using 4-[3-(1-naphthalen-1-yl-ethylamino)-cyclohexyl]-N-(2-oxo-tetrahydrofuran-3-yl)-benzamide (compound 1149). $^{13}$C NMR (75 MHz, DMSO) δ 173.97, 166.15, 150.61, 141.77, 133.45, 131.49, 130.77, 128.61, 127.16, 126.60, 126.39, 125.70, 125.53, 125.21, 123.18, 122.90, 57.67, 51.01, 50.27, 50.12, 38.18, 36.83, 33.79, 32.87, 28.76, 24.28, 20.16.

Example 150

N-tert-Butoxy-4-[(1S,3S)-3-((R)-1-naphthalen-1-yl-ethylamino)-cyclohexyl]-benzamide formiate (Compound 1159)

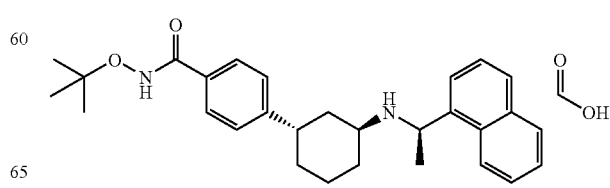

General procedure I was followed using O-(tert.-butyl)-hydroxylamine hydrochloride. $^{13}$C NMR (151 MHz, DMSO) δ 165.88, 163.70, 150.90, 142.24, 133.44, 130.78, 130.22, 128.59, 127.10, 126.50, 126.45, 125.63, 125.53, 125.16, 123.09, 122.92, 80.68, 51.00, 50.13, 38.43, 36.93, 32.99, 28.86, 26.39, 24.52, 20.18.

Example 151

N-tert-Butoxy-4-[3-((R)-1-naphthalen-1-yl-ethyl-amino)-cyclohexyl]-benzamide formiate (Compound 1160)

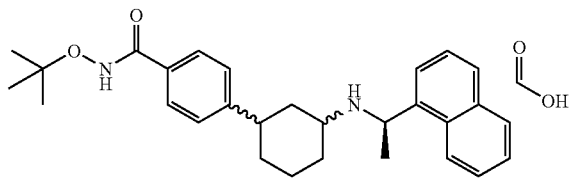

General procedure I-2 was followed using O-(tert.-butyl)-hydroxylamine hydrochloride. $^{13}$C NMR (151 MHz, DMSO) δ 165.89, 163.24, 150.59, 141.24, 133.38, 130.75, 130.31, 128.62, 127.20, 126.66, 125.80, 125.52, 125.24, 123.09, 122.71, 80.70, 50.03, 49.49, 36.60, 35.95, 32.93, 30.31, 26.40, 24.01, 20.33.

Example 152

N-Methoxy-4-[(1S,3S)-3-((R)-1-naphthalen-1-yl-ethylamino)-cyclohexyl]-benzamide formiate (Compound 1161)

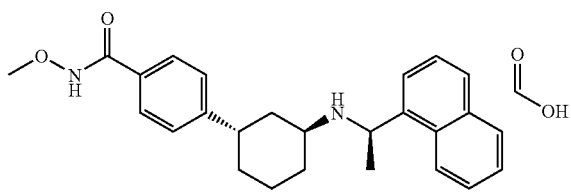

General procedure I was followed using O-methyl-hydroxylamine hydrochloride. $^{13}$C NMR (75 MHz, DMSO) δ 163.56, 150.81, 141.06, 133.57, 130.84, 129.75, 128.77, 126.99, 126.72, 125.97, 125.65, 125.44, 123.44, 122.96, 63.18, 51.10, 50.60, 37.77, 36.87, 32.69, 28.59, 24.02, 20.18.

Example 153

N-Methoxy-4-[3-((R)-1-naphthalen-1-yl-ethyl-amino)-cyclohexyl]-benzamide formiate (Compound 1162)

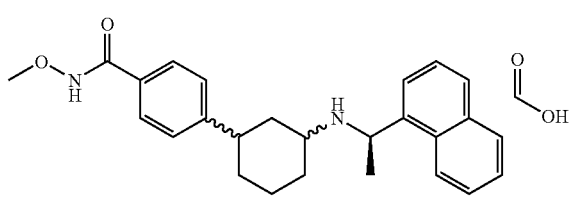

General procedure I-2 was followed using O-methyl-hydroxylamine hydrochloride. $^{13}$C NMR (151 MHz, DMSO) δ 163.43, 150.64, 140.70, 133.38, 130.71, 129.65, 128.65, 126.94, 126.83, 126.76, 125.89, 125.52, 125.31, 123.21, 122.69, 63.08, 50.05, 49.62, 36.52, 35.63, 32.71, 30.11, 23.77, 20.27.

Example 154

4-[(1S,3S)-3-((R)-1-Naphthalen-1-yl-ethylamino)-cyclohexyl]-N-(tetrahydro-furan-3-ylmethoxy)-benzamide (Compound 1163)

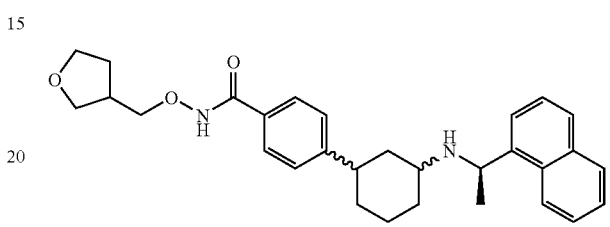

General procedure I was followed using O-(tetrahydro-furan-3-ylmethyl)-hydroxylamine (WO 2005054179). $^{13}$C NMR (75 MHz, DMSO) δ 163.30, 150.95, 141.75, 133.47, 130.78, 129.63, 128.63, 126.89, 126.61, 125.73, 125.54, 125.24, 123.19, 122.91, 77.10, 69.88, 66.72, 51.05, 50.33, 38.13, 37.28, 36.88, 32.78, 28.78, 28.37, 24.27, 20.15.

Example 155

4-[3-((R)-1-Naphthalen-1-yl-ethylamino)-cyclohexyl]-N-(tetrahydro-furan-3-ylmethoxy)-benzamide (Compound 1164)

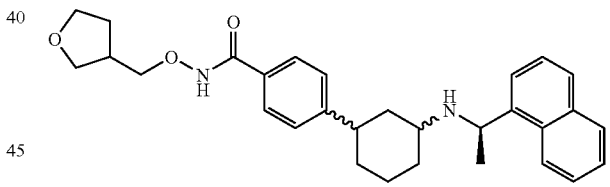

General procedure I-2 was followed using O-(tetrahydro-furan-3-ylmethyl)-hydroxylamine (WO 2005054179). LC-MS (method B): RT=2.49, [M+H]$^+$=473.3.

Example 156

N-Methoxy-N-methyl-4-[(1S,3S)-3-((R)-1-naphthalen-1-yl-ethylamino)-cyclohexyl]-benzamide; bis formate (Compound 1165)

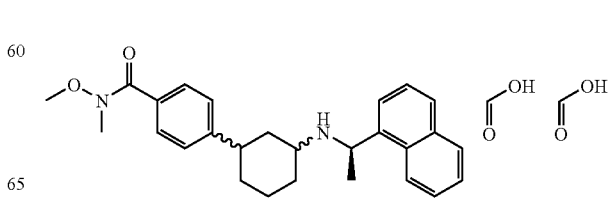

General procedure I was followed using N,O-dimethylhydroxylamine hydrochloride. ¹H NMR (300 MHz, DMSO) δ 8.34 (d, 1H), 8.20 (s, 2H), 7.97-7.88 (m, 1H), 7.76 (t, 2H), 7.57-7.39 (m, 5H), 7.09 (d, 8.2, 2H), 4.69 (q, 1H), 3.53 (s, 3H), 3.22 (s, 3H), 3.09-2.95 (m, 1H), 2.91-2.82 (m, 1H), 1.95-1.60 (m, 4H), 1.57-1.21 (m, 7H).

Example 157

N-Methoxy-N-methyl-4-[3-((R)-1-naphthalen-1-yl-ethylamino)-cyclohexyl]-benzamide (Compound 1166)

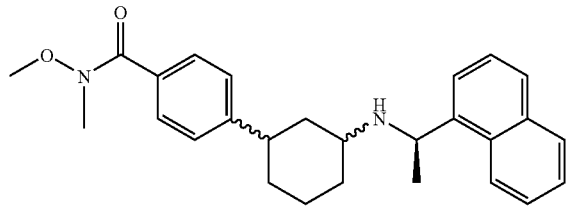 [SMILES: CON(C)C(=O)c1ccc(C2CCCC(N[C@H](C)c3cccc4ccccc34)C2)cc1]

General procedure I-2 was followed using N,O-dimethylhydroxylamine hydrochloride. ¹H NMR (300 MHz, DMSO) δ 8.34-8.27 (m, 1H), 7.96-7.88 (m, 1H), 7.76 (dd, 2H), 7.56-7.43 (m, 5H), 7.24 (d, 2H), 4.77 (q, 1H), 3.54 (s, 3H), 3.23 (s, 3H), 3.17-3.06 (m, 1H), 2.87-2.80 (m, 1H), 1.90-1.34 (m, 11H).

Example 158

N-Benzyloxy-4-[(1S,3S)-3-((R)-1-naphthalen-1-yl-ethylamino)-cyclohexyl]-benzamide (Compound 1167)

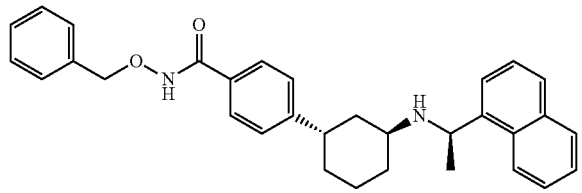 [SMILES: C[C@@H](N[C@H]1CCC[C@H](c2ccc(C(=O)NOCc3ccccc3)cc2)C1)c1cccc2ccccc12]

General procedure I was followed using O-benzyl-hydroxylamine hydrochloride. ¹³C NMR (75 MHz, DMSO) δ 163.90, 151.07, 141.88, 136.04, 133.57, 130.89, 129.74, 128.86, 128.73, 128.30, 128.25, 127.03, 126.71, 125.82, 125.65, 125.33, 123.31, 123.01, 76.92, 51.15, 50.40, 38.26, 36.98, 32.89, 28.87, 24.39, 20.26.

Example 159

N-Benzyloxy-4-[3-((R)-1-naphthalen-1-yl-ethylamino)-cyclohexyl]-benzamide (Compound 1168)

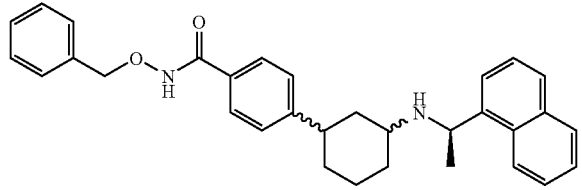 [SMILES: C[C@@H](NC1CCCC(c2ccc(C(=O)NOCc3ccccc3)cc2)C1)c1cccc2ccccc12]

General procedure I-2 was followed using O-benzyl-hydroxylamine hydrochloride. ¹³C NMR (75 MHz, DMSO) δ 163.71, 150.20, 139.74, 135.94, 133.41, 130.66, 129.73, 128.78, 128.71, 128.21, 128.17, 127.14, 127.01, 126.72, 126.07, 125.53, 125.43, 123.46, 122.63, 76.83, 50.05, 49.89, 36.39, 35.08, 32.39, 29.79, 23.35, 20.18.

Example 160

N-Hydroxy-4-[3-((R)-1-naphthalen-1-yl-ethylamino)-cyclohexyl]-benzamide (Compound 1169)

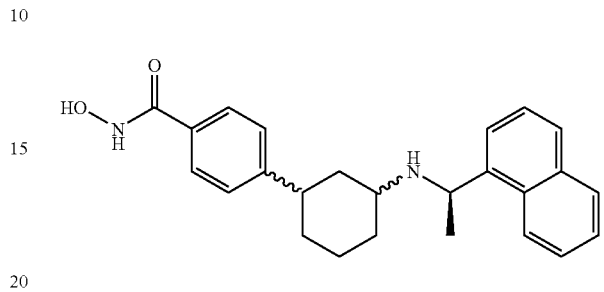

To a solution of N-benzyloxy-4-[3-(1-naphthalen-1-yl-ethylamino)-cyclohexyl]-benzamide (compound 1168, 17 mg) in 700 μL were added 2 mg palladium on carbon (10%), and the mixture was hydrogenated with vigorous stirring overnight at r.t. The catalyst was filtered off through Celite and the filtrate was concentrated in vacuo. The product was purified by HPLC. ¹H NMR (600 MHz, DMSO) δ 8.32 (d, 1H), 8.19 (s, 1H), 7.92 (dd, 1H), 7.78 (d, 1H), 7.74 (d, 1H), 7.56 (d, 2H), 7.53-7.46 (m, 3H), 7.20 (d, 2H), 4.75 (q, 1H), 3.11-3.05 (m, 1H), 2.83 (br s, 1H), 1.86-1.73 (m, 3H), 1.62-1.55 (m, 1H), 1.51-1.35 (m, 7H).

Example 161

N-Hydroxy-4-[(1S,3S)-3-((R)-1-naphthalen-1-yl-ethylamino)-cyclohexyl]-benzamide (Compound 1170)

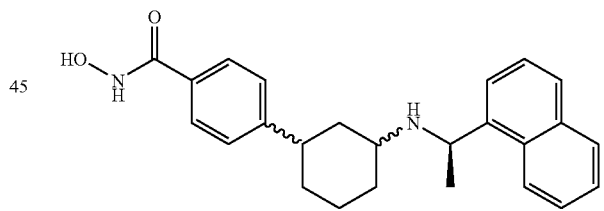

4-[(1S,3S)-3-((R)-1-naphthalen-1-yl-ethylamino)-cyclohexyl]-benzoic acid (compound 1056, 50 mg) was suspended in a 1:1 mixture of DMF and THF (each 150 μL) and cooled to −20° C. N-methyl morpholine (16 μL) and isobutyl chloroformate (18 μL) were added. The reaction mixture was kept at −20° C. for two days, after which O-(trimethylsilyl)hydroxylamine (26 μL) was added. The mixture was slowly warmed to r.t. while stirring for 3 hours and then quenched with ethyl acetate and KH₂PO₄. The aqueous phase was extracted 6 times with ethyl acetate. The combined organic extracts were concentrated in vacuo and purified by chromatography. ¹³C NMR (75 MHz, DMSO) δ 164.14, 150.60, 142.39, 133.46, 130.81, 130.09, 128.58, 126.67, 126.50, 126.42, 125.60, 125.53, 125.14, 123.08, 122.94, 51.06, 50.13, 38.58, 36.90, 32.94, 28.97, 24.55, 20.22.

Example 162

N-(2-Morpholin-4-yl-2-oxo-ethoxy)-4-[(1S,3S)-3-((R)-1-naphthalen-1-yl-ethylamino)-cyclohexyl]-benzamide (Compound 1171)

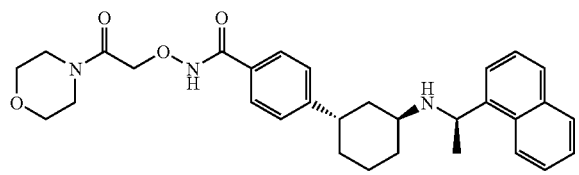 [SMILES: C[C@@H](N[C@H]1CCC[C@H](c2ccc(C(=O)NOCC(=O)N3CCOCC3)cc2)C1)c1cccc2ccccc12]

General procedure I was followed using 4-[2-(ammoniooxy)acetyl]morpholine chloride. $^{13}$C NMR (151 MHz, DMSO) δ 165.43, 163.31, 151.10, 141.54, 133.44, 130.74, 129.15, 128.63, 126.99, 126.67, 126.61, 125.75, 125.53, 125.26, 123.19, 122.88, 73.30, 66.00, 65.86, 50.98, 50.32, 45.03, 41.42, 37.99, 36.84, 32.71, 28.64, 24.19, 20.10.

Example 163

N-(2-Morpholin-4-yl-2-oxo-ethoxy)-4-[3-((R)-1-naphthalen-1-yl-ethylamino)-cyclohexyl]-benzamide (Compound 1172)

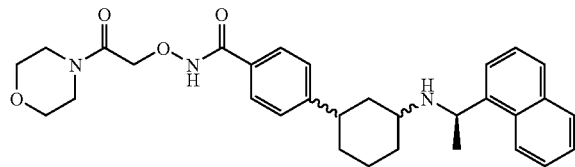 [SMILES: C[C@@H](NC1CCCC(c2ccc(C(=O)NOCC(=O)N3CCOCC3)cc2)C1)c1cccc2ccccc12]

General procedure I-2 was followed using 4-[2-(ammoniooxy)acetyl]morpholine chloride. $^{13}$C NMR (75 MHz, DMSO) δ 165.46, 163.35, 150.94, 141.00, 133.40, 130.74, 129.24, 128.64, 127.08, 126.77, 125.84, 125.52, 125.28, 123.14, 122.72, 73.32, 66.02, 65.89, 50.09, 49.57, 45.07, 41.45, 36.60, 35.85, 32.79, 30.23, 23.87, 20.30.

Example 164

N-{4-[(1S,3S)-3-((R)-1-Naphthalen-1-yl-ethylamino)-cyclohexyl]-benzoyl}-methanesulfonamide (Compound 1173)

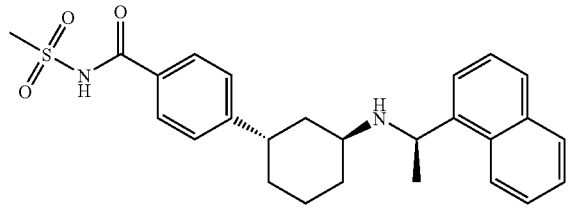 [SMILES: C[C@@H](N[C@H]1CCC[C@H](c2ccc(C(=O)NS(C)(=O)=O)cc2)C1)c1cccc2ccccc12]

General procedure I was followed using methane sulfonamide. $^{1}$H NMR (300 MHz, DMSO) δ 8.34 (d, 1H), 8.03-7.76 (m, 5H), 7.65-7.50 (m, 3H), 7.08 (d, 2H), 5.30-5.17 (m, 1H), 3.16-2.96 (m, 2H), 2.90 (s, 3H), 1.92-1.68 (m, 5H), 1.67-1.40 (m, 6H).

Example 165

4R-Hydroxy-1-{4-[(1S,3S)-3-((R)-1-naphthalen-1-yl-ethylamino)-cyclohexyl]-benzoyl}-pyrrolidine-2S-carboxylic acid methyl ester (Compound 1174)

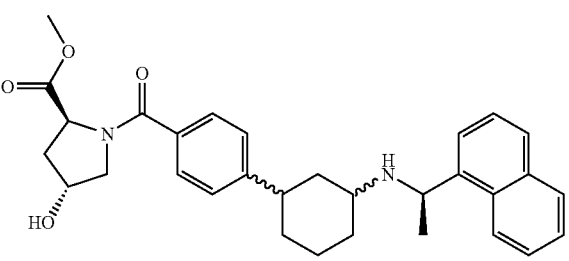 [SMILES: COC(=O)[C@@H]1C[C@@H](O)CN1C(=O)c1ccc(C2CCCC(N[C@H](C)c3cccc4ccccc34)C2)cc1]

General procedure I was followed using L-hydroxyproline methyl ester hydrochloride. $^{1}$H NMR (600 MHz, DMSO) δ 8.35 (d, 1H), 7.93 (d, 1H), 7.78 (dd, 2H), 7.56-7.47 (m, 3H), 7.39 (d, 2H), 7.11 (d, 2H), 5.07 (s, 1H), 4.74 (s, 1H), 4.58-4.52 (m, 1H), 3.73 (dd, 1H), 3.66 (s, 3H), 3.29 (s, 1H), 3.02 (t, 1H), 2.89 (s, 1H), 2.18 (dd, 1H), 1.98-1.91 (m, 1H), 1.90-1.82 (m, 1H), 1.80-1.71 (m, 2H), 1.69-1.63 (m, 1H), 1.58-1.38 (m, 6H), 1.37-1.27 (m, 1H). LC/MS (method B): RT=2.42, [M+H]$^{+}$=501.5.

Example 166

4R-Hydroxy-1-{4-[(1S,3S)-3-((R)-1-naphthalen-1-yl-ethylamino)-cyclohexyl]-benzoyl}-pyrrolidine-2S-carboxylic acid (Compound 1175)

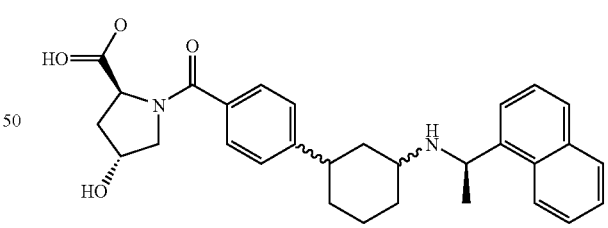

General procedure J was followed using 4-hydroxy-1-{4-[3-(1-naphthalen-1-yl-ethylamino)-cyclohexyl]-benzoyl}-pyrrolidine-2-carboxylic acid methyl ester (compound 1174). $^{1}$H NMR (600 MHz, DMSO) δ 8.35 (d, 1H), 7.92 (d, 1H), 7.77 (dd, 2H), 7.55-7.46 (m, 3H), 7.38 (d, 2H), 7.10 (d, 2H), 5.02 (br s, 1H), 4.70 (q, 1H), 4.50-4.43 (m, 1H), 4.27-4.23 (m, 1H), 3.70 (dd, 1H), 3.28 (d, 1H), 3.06-2.97 (m, 1H), 2.89-2.83 (m, 1H), 2.21-2.15 (m, 1H), 1.97-1.82 (m, 2H), 1.80-1.71 (m, 2H), 1.68-1.62 (m, 1H), 1.54-1.35 (m, 6H), 1.34-1.25 (m, 1H).

Example 167

N-{4-[3-((R)-1-Naphthalen-1-yl-ethylamino)-cyclohexyl]-benzoyl}-methanesulfonamide hydrochloride (Compound 1176)

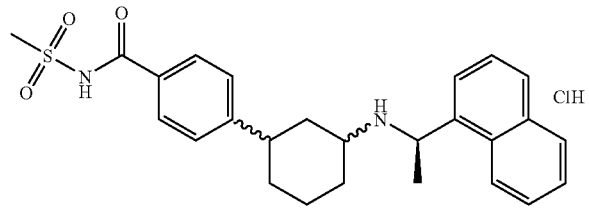 [SMILES: C[C@@H](NC1CCCC(c2ccc(C(=O)NS(C)(=O)=O)cc2)C1)c1cccc2ccccc12 ; Cl]

General procedure I-2 was followed using methanesulfonamide. The product was dissolved in ethyl acetate and treated with HCl in dioxane (4 M) and diethyl ether. The precipitate was filtered to afford the title compound. $^1$H NMR (600 MHz, DMSO) δ 9.70-8.62 (m, 1H), 8.33 (d, 1H), 8.04-7.70 (m, 5H), 7.64-7.50 (m, 3H), 7.04 (s, 2H), 5.49-4.87 (m, 1H), 3.14-2.98 (m, 2H), 2.86 (s, 3H), 1.94-1.85 (m, 1H), 1.82-1.47 (m, 9H), 1.46-1.34 (m, 1H).

General Procedure K

To a solution of arylboronic acid (4.6 mmol) and [(1,4-hydroquinone)-rhodium(COD)]BF$_4$ (Son et al., *J. Am. Chem. Soc.* 2005, 127, 12238) (2 mol %) in water/dimethoxyethane (1:1, 20 mL, degassed) was added cyclopentenone (4.6 mmol) and LiOH (8 mol %). The mixture was warmed to 50° C. and stirred overnight. Additional water was added, and the mixture was extracted with dichloromethane. The organic phase was separated, dried and concentrated in vacuo to a brown oil. This crude intermediate was redissolved in 40 mL dichloroethane. After the addition of (+)-(R)-1-naphthalen-1-yl-ethylamine (4.6 mmol) and NaBH(OAc)$_3$ (1.7 eq.), the reaction mixture was stirred overnight at r.t. The mixture was diluted with dichloromethane, washed with aqueous NaHCO$_3$, water and brine. The organic phase was dried, concentrated in vacuo, and purified on silica gel to a colorless oil. Diastereoisomers were separated by chiral HPLC.

Example 168

{4-[3-((R)-1-Naphthalen-1-yl-ethylamino)-cyclopentyl]-phenoxy}-acetic acid ethyl ester (Compound 1177/1178/1179/1180)

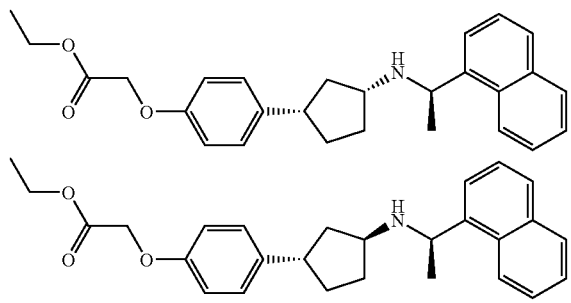

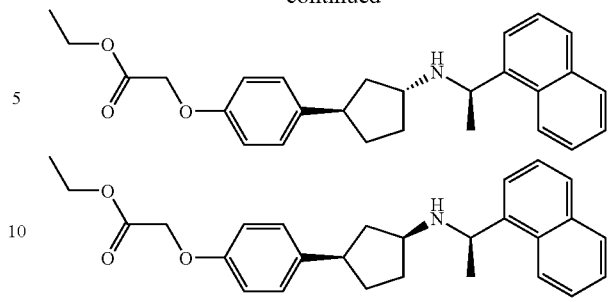

General procedure K was followed using 4-(2-ethoxy-2-oxoethoxy)-phenylboronic acid. The four resulting diastereoisomers were separated using preparative chiral HPLC on a Chiralpak AD-H column 250×20 mm, 5 μm at 25° C., UV detection at 280 nm. Isocratic separation with n-heptan: ethanol:NEt$_3$:CH$_3$COOH (75:25:0.1:0.1); flow rate=7.0 mL/min. Compound 1177: RT=11.05. $^{13}$C NMR (151 MHz, DMSO) δ 168.78, 155.62, 141.94, 138.53, 133.42, 130.87, 128.59, 127.74, 126.50, 125.67, 125.56, 125.18, 123.01, 122.91, 114.14, 64.60, 60.47, 56.58, 51.18, 42.82, 42.06, 32.52, 32.14, 24.24, 13.96. Compound 1178: RT=12.77. $^{13}$C NMR (151 MHz, DMSO) δ 168.77, 155.55, 142.09, 138.62, 133.39, 130.95, 128.58, 127.70, 126.49, 125.65, 125.57, 125.17, 122.95, 122.93, 114.14, 64.59, 60.46, 55.97, 51.02, 42.08, 40.44, 33.65, 33.23, 24.15, 13.95. Compound 1179: RT=18.35. $^{13}$C NMR (151 MHz, DMSO) δ 168.75, 155.54, 142.03, 138.60, 133.39, 130.83, 128.59, 127.63, 126.54, 125.67, 125.54, 125.19, 123.01, 122.89, 114.14, 64.57, 60.45, 56.16, 50.81, 42.00, 41.33, 33.30, 32.93, 24.05, 13.93. Compound 1180: RT=23.96. $^{13}$C NMR (151 MHz, DMSO) δ 168.91, 155.77, 141.97, 138.42, 133.53, 130.96, 128.75, 127.82, 126.80, 125.87, 125.69, 125.37, 123.20, 123.01, 114.28, 64.72, 60.60, 56.62, 51.37, 42.66, 42.05, 32.30, 31.84, 24.09, 14.09.

Example 169

3-{4-[(3S)-3-((R)-1-Naphthalen-1-yl-ethylamino)-cyclopentyl]-phenyl}-propionic acid methyl ester (Compounds 1181/1182/1183/1184)

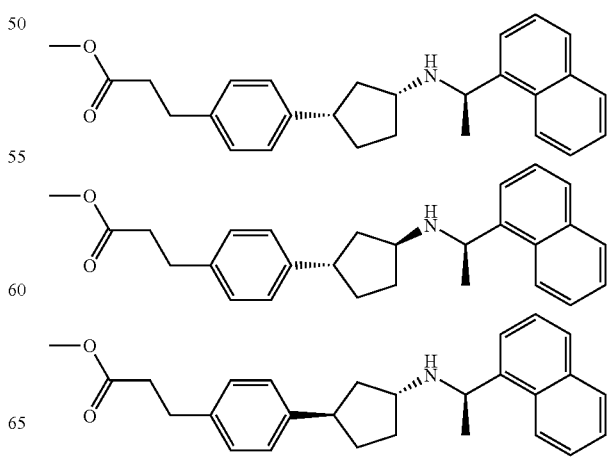

-continued

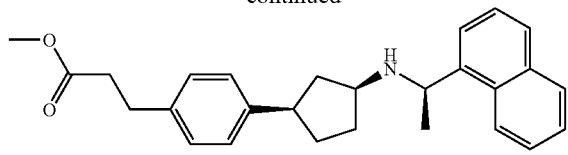

General procedure K was followed using 4-(2-methoxycarbonylethyl)-phenylboronic acid. The four resulting diastereomers were separated by preparative chiral HPLC on a Chiralpak AD-H column 250×20 mm, 5 μm at 25° C., UV detection at 280 nm. Isocratic separation with n-heptane:2-propanol:NEt$_3$:CH$_3$COOH (75:25:0.1:0.1); flow rate=7.0 mL/min. Compound 1181: RT=7.74. $^{13}$C NMR (126 MHz, DMSO) δ 172.59, 143.57, 142.01, 137.65, 133.41, 130.87, 128.57, 127.92, 126.80, 126.47, 125.63, 125.54, 125.15, 122.99, 122.90, 56.66, 51.21, 51.15, 43.23, 41.97, 34.84, 32.59, 31.99, 29.73, 24.23. Compound 1182: RT=8.75. $^{13}$C NMR (126 MHz, DMSO) δ 172.59, 143.70, 142.08, 137.57, 133.40, 130.95, 128.56, 127.92, 126.77, 126.47, 125.62, 125.55, 125.15, 122.95, 122.93, 56.07, 51.14, 51.07, 42.50, 40.37, 34.82, 33.68, 33.06, 29.71, 24.13. Compound 1183: RT=11.47. $^{13}$C NMR (126 MHz, DMSO) δ 172.58, 143.74, 142.15, 137.56, 133.40, 130.86, 128.58, 127.92, 126.71, 126.47, 125.62, 125.53, 125.15, 122.99, 122.92, 56.30, 51.14, 50.92, 42.42, 41.31, 34.79, 33.14, 33.06, 29.69, 24.14. Compound 1184: RT=15.95. $^{13}$C NMR (126 MHz, DMSO) δ 172.60, 143.44, 141.96, 137.66, 133.40, 130.88, 128.58, 127.92, 126.76, 126.50, 125.63, 125.54, 125.15, 122.99, 122.91, 56.63, 51.34, 51.15, 42.96, 42.24, 34.81, 32.06, 31.86, 29.72, 24.12.

Example 170

{4-[3-((R)-1-Naphthalen-1-yl-ethylamino)-cyclopentyl]-phenoxy}-acetic acid (Compound 1185)

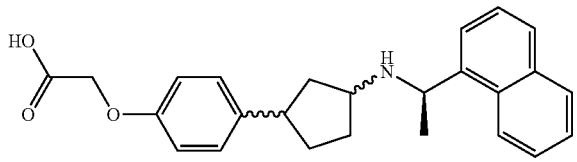

General procedure J was followed using {4-[3-((R)-1-naphthalen-1-yl-ethylamino)-cyclopentyl]-phenoxy}-acetic acid ethyl ester (compound 1178). $^{13}$C NMR (75 MHz, DMSO) δ 171.24, 156.64, 137.18, 136.14, 133.30, 130.49, 128.74, 127.83, 127.45, 126.43, 125.68, 125.53, 123.96, 122.44, 113.96, 66.07, 55.36, 50.31, 42.31, 37.78, 33.41, 31.62, 21.55.

Example 171

{4-[(1R,3S)-3-((R)-1-Naphthalen-1-yl-ethylamino)-cyclopentyl]-phenoxy}-acetic acid (Compound 1186)

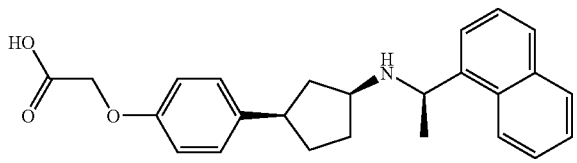 [SMILES: C[C@@H](N[C@H]1CC[C@@H](c2ccc(OCC(=O)O)cc2)C1)c1cccc2ccccc12]

General procedure J was followed using {4-[3-((R)-1-naphthalen-1-yl-ethylamino)-cyclopentyl]-phenoxy}-acetic acid ethyl ester (compound 1180). $^{13}$C NMR (151 MHz, DMSO) δ 170.60, 156.80, 141.57, 136.68, 133.37, 130.84, 128.59, 127.26, 126.57, 125.70, 125.55, 125.19, 123.06, 122.85, 114.01, 67.44, 56.46, 51.22, 42.56, 42.24, 32.23, 31.56, 23.97.

Example 172

{4-[3-((R)-1-Naphthalen-1-yl-ethylamino)-cyclopentyl]-phenoxy}-acetic acid (Compound 1187)

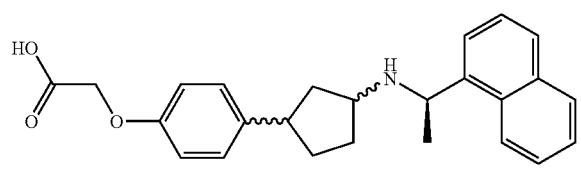

General procedure J was followed using {4-[3-((R)-1-naphthalen-1-yl-ethylamino)-cyclopentyl]-phenoxy}-acetic acid ethyl ester (compound 1177). $^{13}$C NMR (75 MHz, DMSO) δ 171.08, 156.66, 136.78, 136.00, 133.35, 130.36, 128.78, 127.89, 127.48, 126.50, 125.73, 125.53, 123.89, 122.37, 114.06, 65.94, 55.64, 50.45, 42.84, 32.02, 29.87, 21.92 (one aliphatic signal not visible).

Example 173

{4-[3-((R)-1-Naphthalen-1-yl-ethylamino)-cyclopentyl]-phenoxy}-acetic acid (Compound 1188)

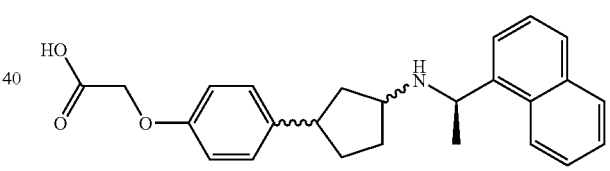

General procedure J was followed using {4-[3-((R)-1-naphthalen-1-yl-ethylamino)-cyclopentyl]-phenoxy}-acetic acid ethyl ester (compound 1179). $^{13}$C NMR (151 MHz, DMSO) δ 170.47, 156.25, 136.56, 133.51, 130.39, 129.03, 128.77, 127.82, 126.95, 126.18, 125.69, 124.37, 122.57, 114.29, 64.79, 55.73, 50.52, 42.20, 37.68, 33.44, 30.61, 21.02 (one aromatic signal not visible).

Example 174

3-{4-[3-((R)-1-Naphthalen-1-yl-ethylamino)-cyclopentyl]-phenyl}-propionic acid (Compound 1189)

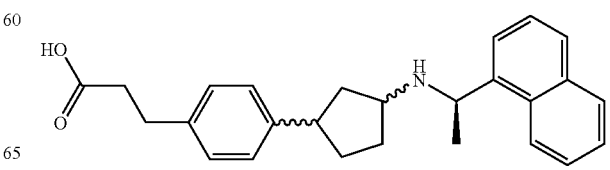

General procedure J was followed using 3-{4-[(3S)-3-((R)-1-naphthalen-1-yl-ethylamino)-cyclopentyl]-phenyl}-propionic acid methyl ester (compound 1181). $^{13}$C NMR (151 MHz, DMSO) δ 173.70, 142.32, 138.38, 133.37, 130.49, 128.73, 128.01, 127.68, 126.75, 126.32, 125.64, 125.54, 123.72, 122.60, 56.03, 50.85, 43.18, 35.25, 31.87, 30.49, 29.85, 22.43 (two signals not visible).

Example 175

3-{4-[(1S,3S)-3-((R)-1-Naphthalen-1-yl-ethylamino)-cyclopentyl]-phenyl}-propionic acid hydrochloride (Compound 1190)

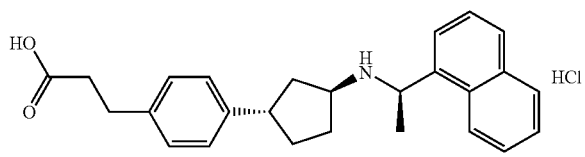 [SMILES: C[C@@H](N[C@H]1CC[C@H](c2ccc(CCC(=O)O)cc2)C1)c1cccc2ccccc12 ; Cl]

General procedure J was followed using 3-{4-[(1S,3S)-3-((R)-1-naphthalen-1-yl-ethylamino)-cyclopentyl]-phenyl}-propionic acid methyl ester (compound 1183). $^{13}$C NMR (151 MHz, DMSO) δ 173.64, 141.55, 138.53, 133.88, 133.34, 130.17, 128.91, 128.88, 128.10, 126.96, 126.73, 126.11, 125.53, 124.62, 122.36, 55.50, 50.35, 42.42, 36.83, 35.13, 33.11, 30.01, 29.78, 20.48.

Example 176

3-{4-[3-((R)-1-Naphthalen-1-yl-ethylamino)-cyclopentyl]-phenyl}-propionic acid (Compound 1191)

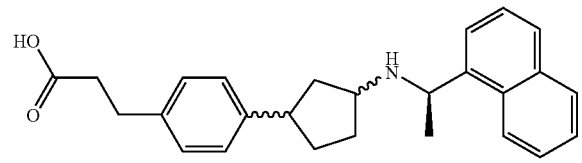 [SMILES: C[C@@H](NC1CCC(c2ccc(CCC(=O)O)cc2)C1)c1cccc2ccccc12]

General procedure J was followed using 3-{4[(3S)-3-((R)-1-naphthalen-1-yl-ethylamino)-cyclopentyl]-phenyl}-propionic acid methyl ester (compound 1182). $^{13}$C NMR (75 MHz, DMSO) δ 173.69, 143.29, 141.05, 138.04, 133.38, 130.84, 128.60, 127.94, 126.78, 126.71, 125.78, 125.54, 125.27, 123.14, 122.85, 56.00, 50.99, 42.49, 39.89, 35.25, 33.25, 33.06, 29.84, 23.58.

Example 177

3-{4-[3-((R)-1-Naphthalen-1-yl-ethylamino)-cyclopentyl]-phenyl}-propionic acid (Compound 1192)

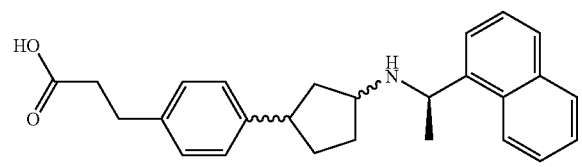 [SMILES: C[C@@H](NC1CCC(c2ccc(CCC(=O)O)cc2)C1)c1cccc2ccccc12]

General procedure J was followed using 3-{4-[(3S)-3-((R)-1-naphthalen-1-yl-ethylamino)-cyclopentyl]-phenyl}-propionic acid methyl ester (compound 1184). $^{13}$C NMR (151 MHz, DMSO) δ 173.72, 142.67, 139.63, 138.24, 133.36, 130.64, 128.67, 127.99, 127.19, 126.69, 126.03, 125.53, 125.45, 123.40, 122.74, 56.27, 51.09, 42.92, 40.90, 35.24, 31.90, 30.70, 29.85, 22.88.

Example 178

{3-[3-((R)-1-Naphthalen-1-yl-ethylamino)-cyclopentyl]-phenoxy}-acetic acid ethyl ester (Compounds 1193/1194/1195/1196)

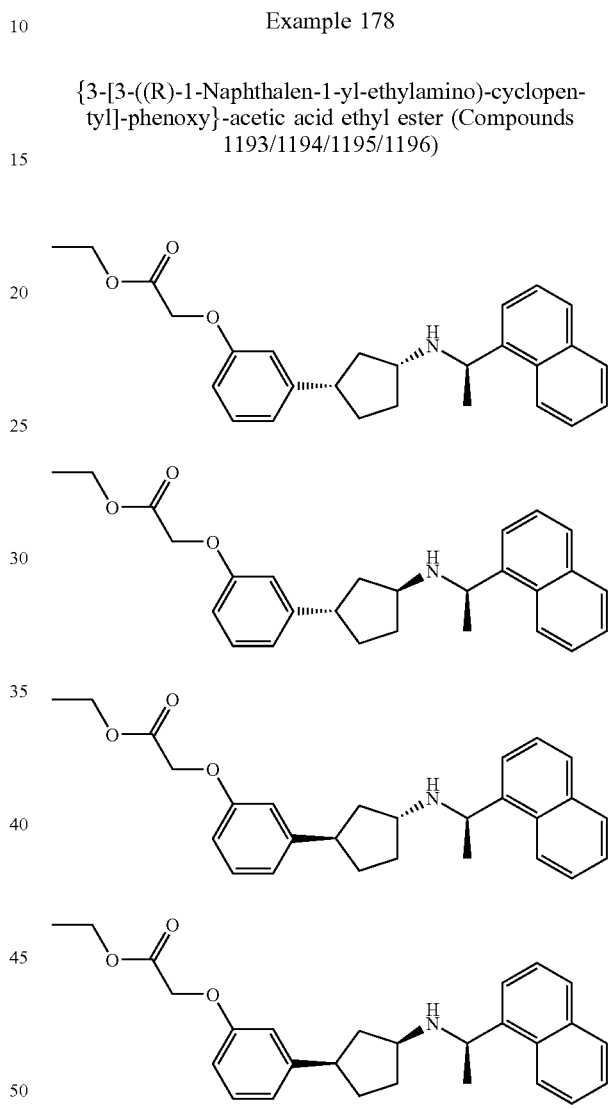

General procedure K was followed using 3-(2-ethoxy-2-oxoethoxy)-phenylboronic acid. Mixture of four diastereomers: $^1$+1 NMR (300 MHz, DMSO) δ 8.29 (d, 1H), 7.91 (dd, 1H), 7.75 (dd, 2H), 7.58-7.42 (m, 3H), 7.21-7.08 (m, 1H), 6.88-6.62 (m, 3H), 4.74-4.68 (m, 2H), 4.70-4.58 (m, 1H), 4.21-4.08 (m, 2H), 3.40-2.74 (m, 2H), 2.34-1.30 (m, 9H), 1.26-1.13 (m, 3H). The four diastereoisomers were separated using preparative chiral HPLC on a Chiralpak AD-H column 250×20 mm, 5 μm at 25° C., UV detection at 280 nm. Isocratic separation with 2-propanol:heptan:NEt$_3$:CH$_3$COOH (90:10:0.1:0.1); flow rate=17.0 mL/min. Diastereomer 1 (compound 1193): RT=21.65. Diastereomer 2 (compound 1194): RT=24.65. Diastereomer 3 (compound 1195): RT=45.89. Diastereomer 4 (compound 1196): RT=52.85.

Example 179

3-{3-[3-((R)-1-Naphthalen-1-yl-ethylamino)-cyclopentyl]-phenyl}-propionic acid ethyl ester (Compounds 1197/1198/1198/1200)

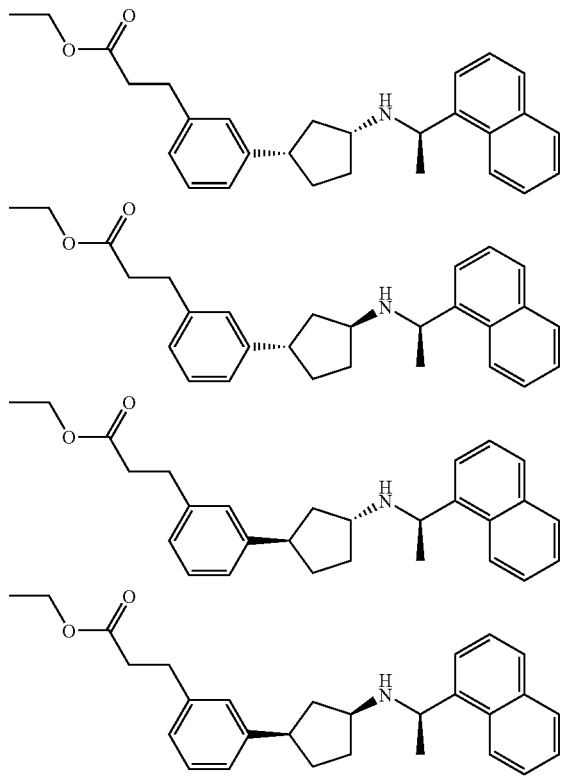

General procedure K was followed using 3-(2-ethoxycarbonylethyl)-phenyl-boronic acid. Mixture of 4 diastereomers: ¹H NMR (300 MHz, DMSO) δ 8.34-8.24 (m, 1H), 7.96-7.86 (m, 1H), 7.75 (dd, 2H), 7.58-7.43 (m, 3H), 7.20-6.92 (m, 4H), 4.71-4.59 (m, 1H), 4.08-3.95 (m, 2H), 3.36-2.93 (m, 2H), 2.87-2.71 (m, 2H), 2.63-2.51 (m, 2H), 2.32-1.32 (m, 9H), 1.20-1.07 (m, 3H). The four diastereomers were separated by preparative chiral HPLC on a Chiralpak AD-H column 250×20 mm, 5 μm at 25° C., UV detection at 280 nm. Isocratic separation with n-heptane:ethanol:NEt₃:CH₃COOH (80:20:0.1:0.1); flow rate=17.0 mL/min. Diastereomer 1 (compound 1197): RT=7.38. Diastereomer 2 (compound 1198): RT=9.09. Diastereomer 3 (compound 1199): RT=10.01. Diastereomer 4 (compound 1200): RT=14.56.

Example 180

{3-[3-((R)-1-Naphthalen-1-yl-ethylamino)-cyclopentyl]-phenoxy}-acetic acid hydrochloride (Compound 1201)

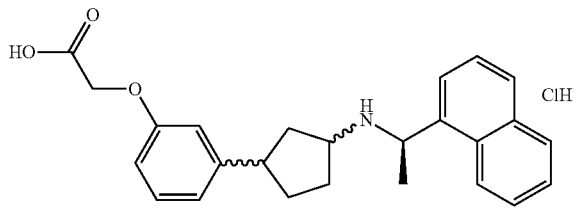 [SMILES: C[C@@H](NC1CCC(c2cccc(OCC(=O)O)c2)C1)c1cccc2ccccc12 ; Cl]

General procedure J was followed using {3-[3-(1-naphthalen-1-yl-ethylamino)-cyclopentyl]-phenoxy}-acetic acid ethyl ester (compound 1196). ¹+1 NMR (300 MHz, DMSO) δ 10.25-9.81 (m, 1H), 9.55-9.21 (m, 1H), 8.30 (d, 1H), 8.10-7.95 (m, 3H), 7.68-7.54 (m, 3H), 7.15 (t, 1H), 6.78-6.65 (m, 3H), 5.39-5.27 (m, 1H), 4.60 (s, 2H), 3.74-3.63 (m, 1H), 3.59-3.42 (m, 1H), 2.52-2.34 (m, 1H), 2.23-2.12 (m, 1H), 2.10-1.98 (m, 1H), 1.90-1.68 (m, 5H), 1.59-1.42 (m, 1H).

Example 181

{3-[3-((R)-1-Naphthalen-1-yl-ethylamino)-cyclopentyl]-phenoxy}-acetic acid (Compound 1202)

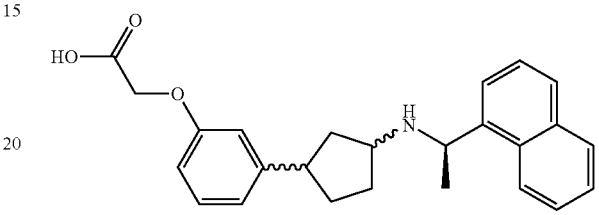

General procedure J was followed using {3-[3-(1-naphthalen-1-yl-ethylamino)-cyclopentyl]-phenoxy}-acetic acid ethyl ester (compound 1193). ¹H NMR (300 MHz, DMSO) δ 8.27 (d, 1H), 7.95 (d, 1H), 7.84 (t, 2H), 7.61-7.47 (m, 3H), 7.09 (t, 1H), 6.70-6.59 (m, 3H), 4.93 (q, 1H), 4.42 (s, 2H), 3.32-3.08 (m, 2H), 2.05-1.61 (m, 5H), 1.56-1.30 (m, 4H).

Example 182

{3-[3-((R)-1-Naphthalen-1-yl-ethylamino)-cyclopentyl]-phenoxy}-acetic acid (Compound 1203)

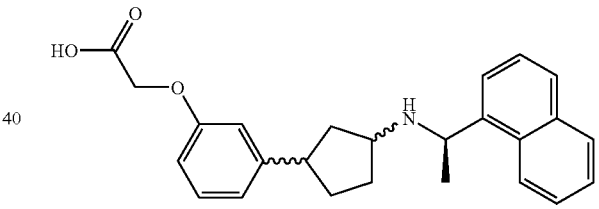

General procedure J was followed using {3-[3-(1-naphthalen-1-yl-ethylamino)-cyclopentyl]-phenoxy}-acetic acid ethyl ester (compound 1194). ¹H NMR (300 MHz, DMSO) δ 8.26 (d, 1H), 7.98-7.91 (m, 1H), 7.83 (t, 2H), 7.60-7.47 (m, 3H), 7.10 (t, 1H), 6.79-6.70 (m, 2H), 6.69-6.61 (m, 1H), 4.92 (q, 1H), 4.42 (s, 2H), 3.20-3.06 (m, 1H), 2.86-2.71 (m, 1H), 2.23-2.09 (m, 1H), 1.90-1.43 (m, 8H).

Example 184

3-{3-[3-((R)-1-Naphthalen-1-yl-ethylamino)-cyclopentyl]-phenyl}-propionic acid hydrochloride (Compound 1204)

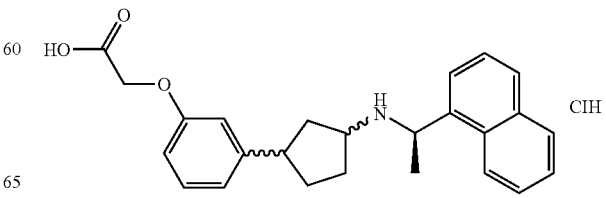

General procedure J was followed using {3-[3-(1-naphthalen-1-yl-ethylamino)-cyclopentyl]-phenoxy}-acetic acid ethyl ester (compound 1195). $^1$H NMR (300 MHz, DMSO) δ 10.14 (br s, 1H), 9.51 (br s, 1H), 8.30 (d, 1H), 8.09-7.95 (m, 3H), 7.70-7.53 (m, 3H), 7.20 (t, 1H), 6.91-6.80 (m, 2H), 6.77-6.68 (m, 1H), 5.40-5.23 (m, 1H), 4.64 (s, 2H), 3.61-3.39 (m, 1H), 2.96-2.76 (m, 1H), 2.23-1.78 (m, 6H), 1.72 (d, 3H).

Example 183

3-{3-[3-((R)-1-Naphthalen-1-yl-ethylamino)-cyclopentyl]-phenyl}-propionic acid (Compound 1205)

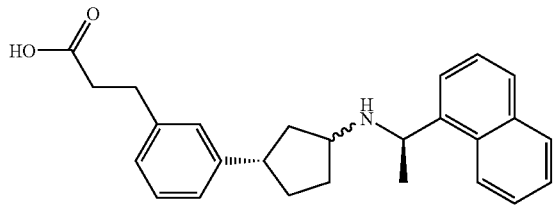 [SMILES: C[C@@H](NC1CC[C@H](c2cccc(CCC(=O)O)c2)C1)c1cccc2ccccc12]

General procedure J was followed using 3-{3-[3-(1-naphthalen-1-yl-ethylamino)-cyclopentyl]-phenyl}-propionic acid ethyl ester (compound 1199). $^1$H NMR (300 MHz, DMSO) δ 8.40-8.23 (m, 1H), 7.99-7.86 (m, 1H), 7.85-7.67 (m, 2H), 7.61-7.41 (m, 3H), 7.21-6.85 (m, 4H), 4.76-4.57 (m, 1H), 3.28-3.06 (m, 2H), 2.85-2.65 (m, 2H), 2.13-1.29 (m, 9H).

Example 185

3-{3-[3-((R)-1-Naphthalen-1-yl-ethylamino)-cyclopentyl]-phenyl}-propionic acid (Compound 1206)

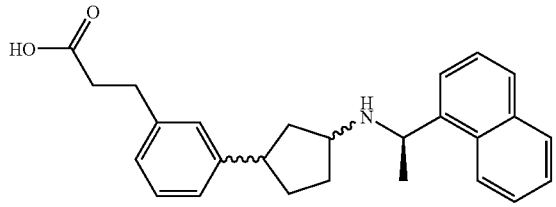 [SMILES: C[C@@H](NC1CCC(c2cccc(CCC(=O)O)c2)C1)c1cccc2ccccc12]

General procedure J was followed using 3-{3-[3-(1-naphthalen-1-yl-ethylamino)-cyclopentyl]-phenyl}-propionic acid ethyl ester (compound 1197). $^1$H NMR (300 MHz, DMSO) δ 8.29 (d, 1H), 7.96-7.87 (m, 1H), 7.76 (dd, 2H), 7.56-7.43 (m, 3H), 7.20-6.95 (m, 4H), 4.67 (q, 1H), 3.08-2.94 (m, 1H), 2.78 (t, 3H), 2.54-2.45 (m, 2H), 2.22-2.08 (m, 1H), 1.92-1.31 (m, 8H).

Example 186

3-{3-[3-((R)-1-Naphthalen-1-yl-ethylamino)-cyclopentyl]-phenyl}-propionic acid (Compound 1207)

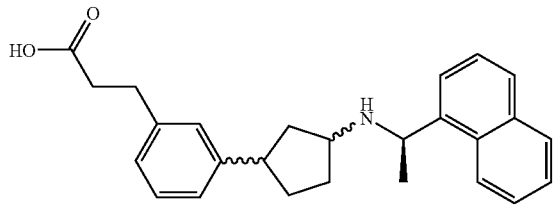 [SMILES: C[C@@H](NC1CCC(c2cccc(CCC(=O)O)c2)C1)c1cccc2ccccc12]

General procedure J was followed using 3-{3-[3-(1-naphthalen-1-yl-ethylamino)-cyclopentyl]-phenyl}-propionic acid ethyl ester (compound 1198). $^1$H NMR (300 MHz, DMSO) δ 8.29 (d, 1H), 7.92 (dd, 1H), 7.79 (d, 1H), 7.73 (d, 1H), 7.57-7.43 (m, 3H), 7.17-7.07 (m, 1H), 7.04-6.92 (m, 3H), 4.69 (q, 1H), 3.27-3.07 (m, 2H), 2.74 (t, 2H), 2.50-2.41 (m, 2H), 2.08-1.84 (m, 3H), 1.64-1.28 (m, 6H).

Example 187

3-{3-[3-((R)-1-Naphthalen-1-yl-ethylamino)-cyclopentyl]-phenyl}-propionic acid hydrochloride (Compound 1208)

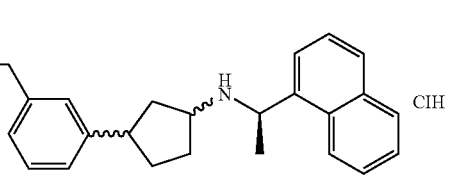

General procedure J was followed using 3-{3-[3-(1-naphthalen-1-yl-ethylamino)-cyclopentyl]-phenyl}-propionic acid ethyl ester (compound 1200). The product was dissolved in ethyl acetate and treated with HCl in dioxane (4 M) and diethyl ether. The precipitate was filtered to afford the title compound. $^1$H NMR (300 MHz, DMSO) δ 12.11 (br s, 1H), 10.15 (br s, 1H), 9.46 (br s, 1H), 8.30 (d, 1H), 8.10-7.96 (m, 3H), 7.69-7.56 (m, 3H), 7.20 (t, 1H), 7.10-7.01 (m, 3H), 5.32 (s, 1H), 3.69 (dd, 1H), 3.55-3.41 (m, 2H), 3.00-2.85 (m, 1H), 2.78 (t, 2H), 2.50 (dd, 1H), 2.23-1.68 (m, 8H).

Preparation 5: 3-(4-Iodophenyl)-cyclohexan-1-one

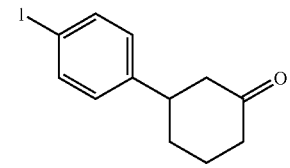

To a solution of 1,4-diiodobenzene (1.0 g, 3.0 mmol) in 6 mL dry THF was added isopropyl magnesium chloride (2 M in THF) at −30° C. The reaction mixture was stirred for 1 hour at −20° C. Meanwhile, LiCl (26 mg, 0.61 mmol), CuI (58 mg, 0.30 mmol) and TMSCl (329 mg, 3.0 mmol) were added to a solution of 2-cyclohexen-1-one (291 mg, 3.0 mmol) in dry THF (3 mL), and the resulting solution was added to the Grignard solution. The reaction mixture was stirred another hour at −20° C., then slowly warmed to r.t. over the course of an hour and finally quenched with saturated NH$_4$Cl (aq) and extracted with diethyl ether. The organic phase was dried (Na$_2$SO$_4$), filtered and concentrated under reduced pressure. The residue was purified by chromatography on silica gel (PE-EtOAc 100:0 to 80:20) to afford the title compound.

Example 188

[3-(4-Iodo-phenyl)-cyclohexyl]-(1-naphthalen-1-yl-ethyl)-amine (Compound 1209)

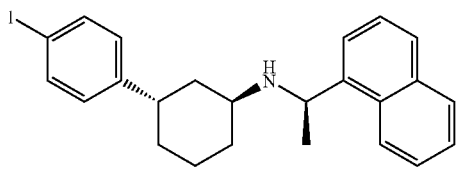

To a solution of 3-(4-iodophenyl)-cyclohexan-1-one (preparation 5) (5.0 g, 16.7 mmol) in 15 mL dry DCE were added AcOH (1.20 g, 20 mmol), NaBH(OAc)$_3$ (4.96 g, 23.4 mmol), and (+)-(R)-1-naphthalen-1-yl-ethylamine (2.85 g, 16.7 mmol), and the mixture was stirred overnight at r.t. After the addition of NaHCO$_3$, the mixture was extracted with ethyl acetate. The organic phase was dried over Na$_2$SO$_4$, filtered and concentrated under reduced pressure. The residue was purified by chromatography on silica gel (PE-EtOAc 100:0 to 75:25) to afford two fractions, each consisting of predominantly one diastereomer. The less polar fraction was the title compound. $^{13}$C NMR (75 MHz, DMSO) δ 147.07, 142.36, 136.65, 133.43, 130.79, 129.09, 128.56, 126.39, 125.56, 125.49, 125.10, 123.03, 122.91, 90.81, 51.00, 50.04, 38.58, 36.51, 32.97, 28.90, 24.52, 20.18.

Example 189

1-{4-[3-((R)-1-Naphthalen-1-yl-ethylamino)-cyclohexyl]-phenyl}-pyrrolidin-2-one (Compound 1210)

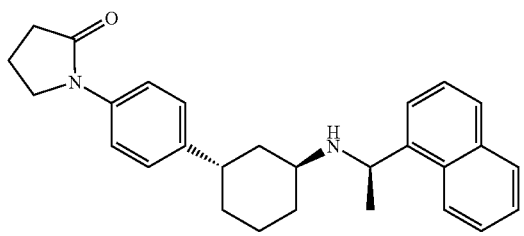 [SMILES: C[C@@H](N[C@H]1CCC[C@H](c2ccc(N3CCCC3=O)cc2)C1)c1cccc2ccccc12]

3-(4-Iodophenyl)-cyclohexan-1-one (compound 1209) (150 mg, 0.33 mmol), 2-pyrrolidone (0.40 mmol), glycine (5 mg, 0.07 mmol), K$_3$PO$_4$ (176 mg, 0.83 mmol) and CuI (3 mg, 0.017 mmol) were suspended in 3 mL dry dioxane and heated in a microwave oven at 130° C. for 8 hours. The mixture was extracted with ethyl acetate, and the organic phase was dried over MgSO$_4$, filtered and concentrated under reduced pressure. The residual oil was purified by chromatography to afford the title compound as a solid. $^{13}$C NMR (75 MHz, DMSO) δ 173.34, 142.88, 142.38, 137.15, 133.45, 130.83, 128.58, 126.59, 126.39, 125.59, 125.53, 125.12, 123.05, 122.92, 119.25, 50.87, 50.04, 47.97, 38.82, 36.38, 33.38, 32.12, 28.95, 24.53, 20.28, 17.33.

Example 190

3-{4-[3-((R)-1-Naphthalen-1-yl-ethylamino)-cyclohexyl]-phenyl}-oxazolidin-2-one (Compound 1211)

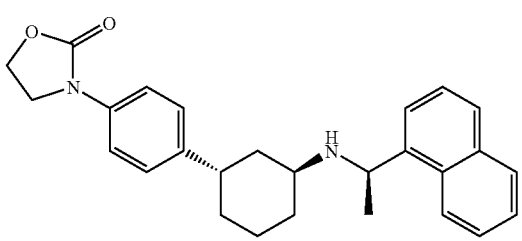 [SMILES: C[C@@H](N[C@H]1CCC[C@H](c2ccc(N3CCOC3=O)cc2)C1)c1cccc2ccccc12]

3-(4-Iodophenyl)-cyclohexan-1-one (compound 1209) (150 mg, 0.33 mmol), 2-oxazolidinone (0.40 mmol, 1.2 eq.), glycine (5 mg, 0.07 mmol), K$_3$PO$_4$ (176 mg, 0.83 mmol) and CuI (3 mg, 0.017 mmol) were suspended in 3 mL dry dioxane under argon and heated at 120° C. for 35 hours. The mixture was extracted with ethyl acetate, and the organic phase was dried over MgSO$_4$, filtered and concentrated under reduced pressure. The residual oil was purified by chromatography to afford the title compound as an oil. $^{13}$C NMR (75 MHz, DMSO) δ 154.80, 142.50, 142.34, 136.04, 133.44, 130.82, 128.56, 126.83, 126.38, 125.56, 125.50, 125.09, 123.02, 122.90, 117.87, 61.26, 50.88, 50.03, 44.67, 38.80, 36.28, 33.37, 28.93, 24.49, 20.26.

Example 191

N-{4-[3-((R)-1-Naphthalen-1-yl-ethylamino)-cyclohexyl]-phenyl}-acetamide (Compound 1212)

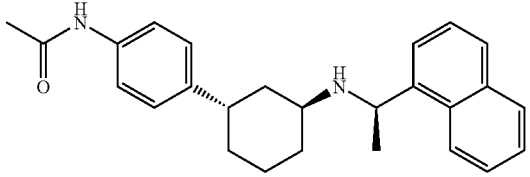 [SMILES: CC(=O)Nc1ccc([C@H]2CCC[C@H](N[C@H](C)c3cccc4ccccc34)C2)cc1]

3-(4-Iodophenyl)-cyclohexan-1-one (compound 1209) (150 mg, 0.33 mmol), acetamide (0.40 mmol, 1.2 eq.), glycine (5 mg, 0.07 mmol), K$_3$PO$_4$ (176 mg, 0.83 mmol) and CuI (3 mg, 0.017 mmol) were suspended in 3 mL dry dioxane under argon and heated at 120° C. for 35 hours. The mixture was extracted with ethyl acetate, and the organic phase was dried over MgSO$_4$, filtered and concentrated under reduced pressure. The residual oil was purified by chromatography to afford the title compound as an oil. $^{13}$C NMR (75 MHz, DMSO) δ 167.85, 142.41, 141.95, 136.86, 133.49, 130.87, 128.60, 126.61, 126.42, 125.60, 125.55, 125.13, 123.08, 122.95, 118.87, 50.95, 50.11, 38.92, 36.40, 33.44, 29.02, 24.55, 23.82, 20.35.

Example 192

4-{4-[3-((R)-1-Naphthalen-1-yl-ethylamino)-cyclohexyl]-phenyl}-tetrahydro-pyran-4-ol (Compound 1213)

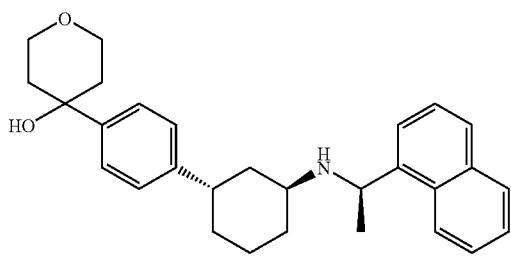 [SMILES: C[C@@H](N[C@H]1CCC[C@H](c2ccc(C3(O)CCOCC3)cc2)C1)c1cccc2ccccc12]

To a solution of 3-(4-iodophenyl)-cyclohexan-1-one (compound 1209) (455 mg, 1 mmol) in dry THF (5 mL) was added isopropyl magnesium chloride (1 mL of a 2M solution in THF) at 40° C., and the resulting mixture was stirred at −10-0° C. for 4 hours. A solution of tetrahydro-4H-pyran-4-one (150 mg, 1.5 mmol) in 0.5 mL dry THF was added, and the reaction was stirred for another hour at 0° C. and at r.t. overnight. After quenching with NH$_4$Cl, the mixture was extracted with ethyl acetate, which was dried (Na$_2$SO$_4$), filtered and concentrated under reduced pressure. Chromatography (EtOAc) afforded the title compound as an oil. $^{13}$C NMR (75 MHz, DMSO) δ 146.84, 145.25, 142.40, 133.46, 130.83, 128.58, 126.40, 126.07, 125.59, 125.54, 125.13, 124.42, 123.04, 122.93, 68.67, 63.07, 50.87, 50.06, 38.89, 38.31, 36.53, 33.30, 29.02, 24.50, 20.31.

Example 193

[3-(4-Imidazol-1-yl-phenyl)-cyclohexyl]-((R)-1-naphthalen-1-yl-ethyl)-amine (Compound 1214)

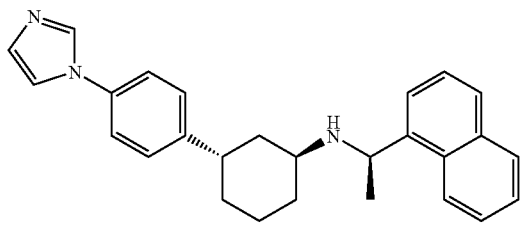 [SMILES: C[C@@H](N[C@H]1CCC[C@H](c2ccc(-n3ccnc3)cc2)C1)c1cccc2ccccc12]

3-(4-Iodophenyl)-cyclohexan-1-one (compound 1209) (150 mg, 0.33 mmol), imidazole (0.40 mmol, 1.2 eq.), glycine (5 mg, 0.07 mmol), K$_3$PO$_4$ (176 mg, 0.83 mmol) and CuI (3 mg, 0.017 mmol) were suspended in 3 mL dry dioxane under argon and heated at 120° C. for 35 hours. The mixture was extracted with ethyl acetate, and the organic phase was dried over MgSO$_4$, filtered and concentrated under reduced pressure. The residual oil was purified by chromatography to afford the title compound as an oil. $^{13}$C NMR (75 MHz, DMSO) δ 146.12, 142.37, 135.32, 134.58, 133.44, 130.82, 129.55, 128.58, 127.83, 126.41, 125.59, 125.52, 125.12, 123.02, 122.91, 120.17, 117.92, 50.91, 50.03, 38.68, 36.49, 33.23, 28.89, 24.52, 20.23.

Example 194

1-{4-[3-((R)-1-Naphthalen-1-yl-ethylamino)-cyclohexyl]-phenyl}-cyclopentanol (Compound 1215)

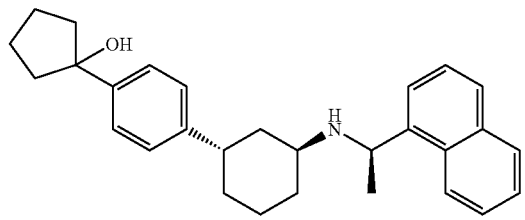 [SMILES: C[C@@H](N[C@H]1CCC[C@H](c2ccc(C3(O)CCCC3)cc2)C1)c1cccc2ccccc12]

To a solution of 3-(4-iodophenyl)-cyclohexan-1-one (compound 1209) (125 mg, 0.27 mmol) in dry THF (4 mL) was added isopropyl magnesium chloride (0.27 mL of a 2M solution in THF) at −20° C., and the mixture was stirred at −20° C. for 2 hours, after which cyclopentanone (34 mg, 0.41 mmol) in 0.2 mL THF was added. The mixture was stirred at the same temperature for another 30 min, then slowly warmed to r.t. overnight. After quenching with aqueous NH$_4$Cl, the mixture was extracted with ethyl acetate, and the organic phases were dried, filtered and concentrated under reduced pressure. Chromatography (EtOAc-PE) afforded the title compound as an oil. $^{13}$C NMR (75 MHz, DMSO) δ 145.51, 144.83, 142.35, 133.44, 130.82, 128.57, 126.39, 125.81, 125.57, 125.51, 125.10, 124.86, 123.02, 122.90, 81.17, 50.85, 50.05, 41.48, 41.45, 38.88, 36.53, 33.36, 29.01, 24.48, 23.51, 20.30.

Example 194

1-{4-[3-((R)-1-Naphthalen-1-yl-ethylamino)-cyclohexyl]-phenyl}-ethanone (Compound 1216)

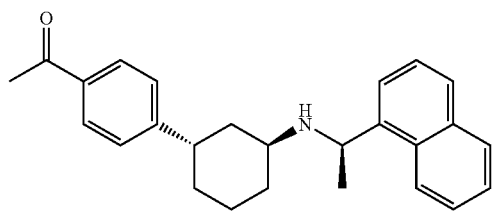 [SMILES: CC(=O)c1ccc([C@H]2CCC[C@H](N[C@H](C)c3cccc4ccccc34)C2)cc1]

To a solution of 3-(4-iodophenyl)-cyclohexan-1-one (compound 1209) (200 mg, 0.44 mmol) in dry THF (5 mL) was added isopropylmagnesium chloride (2 M in THF) at −30° C. After stirring for 45 min at −30→−15° C., a solution of N-methoxy-N-methylacetamide (49 mg, 0.48 mmol) in THF (2 mL) was added. The reaction mixture was stirred another 30 min at −20→−15° C. and then warmed to 0° C. over the course of 15 min. The reaction was quenched with NH$_4$Cl (aq.) and extracted with ethyl acetate. The organic phase was dried over Na$_2$SO$_4$, filtered and concentrated under reduced pressure. Chromatography (PE-EtOAc 100:0 to 50:50) afforded the title compound. $^{13}$C NMR (75 MHz, DMSO) δ 197.29, 152.96, 142.37, 134.49, 133.45, 130.80, 128.58, 128.09, 126.82, 126.43, 125.60, 125.52, 125.14, 123.08, 122.93, 51.06, 50.11, 38.38, 37.09, 32.81, 28.92, 26.46, 24.52, 20.16.

Example 195

4-{4-[3-((R)-1-Naphthalen-1-yl-ethylamino)-cyclohexyl]-phenyl}-tetrahydro-pyran-4-ol hydrochloride (Compound 1217)

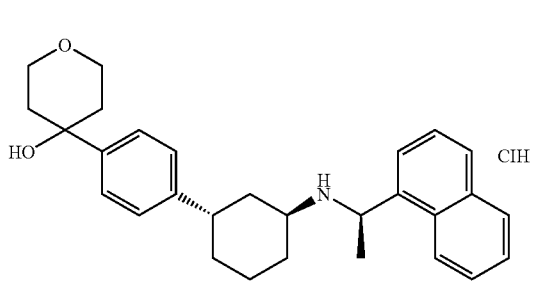

4-{4-[3-(1-Naphthalen-1-yl-ethylamino)-cyclohexyl]-phenyl}-tetrahydro-pyran-4-ol (compound 1213) was dissolved in ethyl acetate and treated with HCl in dioxane (4 M) and diethyl ether. The precipitate was filtered to afford the title compound. $^{13}$C NMR (75 MHz, DMSO) δ 147.31, 142.53, 133.86, 133.35, 130.24, 128.93, 128.87, 127.00, 126.09, 125.50, 124.67, 122.31, 68.72, 63.05, 51.97, 50.25, 38.29, 35.33, 33.63, 31.08, 26.00, 20.73, 19.34.

Example 196

{4-[3-((R)-1-Naphthalen-1-yl-ethylamino)-cyclohexyl]-phenyl}-methanol (Compound 1218)

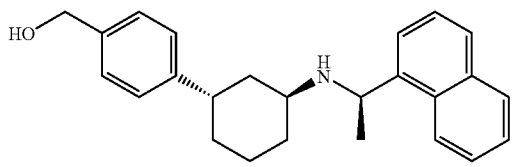 [SMILES: C[C@@H](N[C@H]1CCC[C@H](c2ccc(CO)cc2)C1)c1cccc2ccccc12]

To a solution of 4-[3-((R)-1-naphthalen-1-yl-ethylamino)-cyclohexyl]-benzoic acid (compound 1056) (0.50 g, 1.34 mmol) in dry THF (5 mL) was added borane-THF complex (1M in THF, 5.35 mmol) at −78° C. The reaction mixture was slowly heated to 0° C. in the course of 1.5 hours and then stands at r.t. overnight. After cooling in an icebath, the mixture was quenched with water, diluted with aqueous NaHCO$_3$ and extracted with diethyl ether. Combined organic extracts were dried over MgSO$_4$ and concentrated under reduced pressure. Chromatography (EtOAc-PE 1:1) afforded the title compound as an oil. $^{13}$C NMR (75 MHz, MeOH) δ 147.33, 142.64, 139.93, 135.58, 132.69, 130.06, 128.25, 128.10, 127.88, 126.94, 126.66, 126.42, 124.36, 123.81, 65.12, 52.01, 51.93, 39.65, 38.69, 34.52, 30.84, 24.26, 21.78.

Example 197

1-{4-[3-((R)-1-Naphthalen-1-yl-ethylamino)-cyclohexyl]-phenyl}-cyclobutanol (Compound 1219)

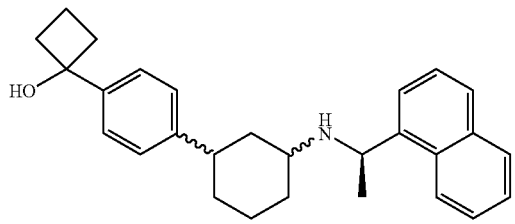 [SMILES: C[C@@H](NC1CCCC(c2ccc(C3(O)CCC3)cc2)C1)c1cccc2ccccc12]

To a solution of 3-(4-iodophenyl)-cyclohexan-1-one (compound 1209) (250 mg, 0.55 mmol) in dry THF (1 mL) under argon at −78° C. was added n-BuLi (0.37 mL, 1.6 M in THF). The resulting red solution was stirred for 2 min at the same temperature, and then cyclobutanone (45 µL, 0.60 mmol) was added dropwise. The now light yellow solution was stirred at −78° C. for 10 min before quenching with 1.2 M KH$_2$PO$_4$ (aq.). The mixture was extracted with ethyl acetate, and the organic phases were dried and concentrated in vacuo. Chromatography (EtOAc-PE 1:1) afforded the title compound. $^{13}$C NMR (75 MHz, DMSO) δ 145.25, 144.81, 142.39, 133.44, 130.82, 128.57, 126.39, 126.03, 125.59, 125.53, 125.12, 124.60, 123.04, 122.92, 74.88, 50.86, 50.05, 38.88, 37.05, 36.58, 33.33, 29.01, 24.51, 20.30, 12.59.

Example 198

2-{4-[3-((R)-1-Naphthalen-1-yl-ethylamino)-cyclohexyl]-phenyl}-malonic acid diethyl ester (Compound 1220)

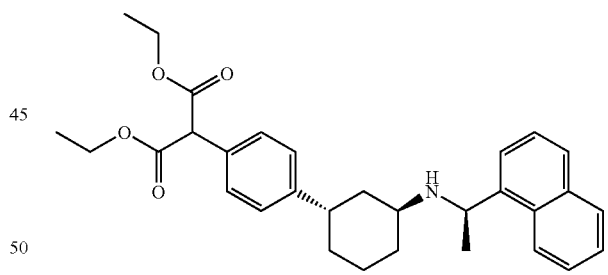

3-(4-Iodophenyl)-cyclohexan-1-one (compound 1209) (0.80 g, 1.76 mmol), malonic acid diethyl ester (0.56 g, 3.52 mmol), CsCO$_3$ (0.86 g, 2.64 mmol), CuI (33 mg, 0.18 mmol) and 2-hydroxybiphenyl (60 mg, 0.35 mmol) were mixed in dry THF (5 mL) under argon and heated at 100° C. for 8 days. The mixture was diluted with water and extracted with ethyl acetate. The organic phase was washed with brine, dried over Na$_2$SO$_4$, filtered and concentrated under reduced pressure. Chromatography (PE-EtOAc 100:0 to 50:50) afforded the title compound as a solid, which was recrystallized in ethanol. $^{13}$C NMR (75 MHz, DMSO) δ 167.91, 147.02, 142.35, 133.44, 130.82, 130.05, 128.88, 128.55, 126.56, 126.39, 125.58, 125.51, 125.11, 123.02, 122.92, 61.10, 56.27, 50.92, 50.02, 38.78, 36.63, 33.11, 28.91, 24.48, 20.25, 13.74.

Example 199

{4-[3-((R)-1-Naphthalen-1-yl-ethylamino)-cyclohexyl]-phenyl}-acetic acid ethyl ester (Compound 1221)

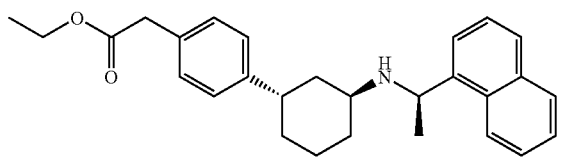 [SMILES: CCOC(=O)Cc1ccc([C@H]2CCC[C@H](N[C@H](C)c3cccc4ccccc34)C2)cc1]

To a solution of 2-{4-[3-(1-naphthalen-1-yl-ethylamino)-cyclohexyl]-phenyl}-malonic acid diethyl ester (compound 1220) (100 mg, 0.20 mmol) in DMSO (5 mL) was added water (3.6 mg, 0.20 mmol) and LiCl (17 mg, 0.41 mmol). The resulting mixture was heated at 150° C. overnight, diluted with water and extracted with EtOAc. The organic phase was washed with brine, dried over $Na_2SO_4$ and concentrated under reduced pressure. Chromatography (PE-EtOAc 50:50) afforded the title compound as an oil. $^{13}C$ NMR (75 MHz, DMSO) δ 171.14, 145.78, 142.40, 133.45, 131.40, 130.83, 128.89, 128.57, 126.53, 126.39, 125.59, 125.53, 125.12, 123.05, 122.93, 60.06, 50.91, 50.05, 39.81, 38.89, 36.59, 33.27, 28.96, 24.52, 20.29, 13.98.

Example 200

{4-[3-((R)-1-Naphthalen-1-yl-ethylamino)-cyclohexyl]-phenyl}-acetic acid (Compound 1222)

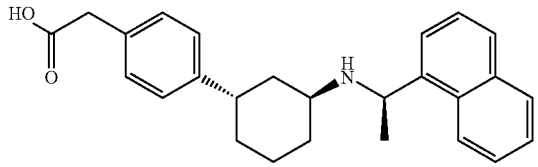 [SMILES: C[C@@H](N[C@H]1CCC[C@H](c2ccc(CC(=O)O)cc2)C1)c1cccc2ccccc12]

A solution of {4-[3-(1-naphthalen-1-yl-ethylamino)-cyclohexyl]-phenyl}-acetic acid ethyl ester (compound 1221) (400 mg) in methanol (5 mL) was treated with 2M NaOH in methanol and stirred for 1 day at r.t. Methanol was removed under reduced pressure. The remaining aqueous phase was acidified with 4M aqueous HCl and extracted with ethyl acetate. The organic phase was dried over $Na_2SO_4$, filtered, and concentrated under reduced pressure. Chromatography (MeOH $CH_2Cl_2$ 20:80) afforded the title compound as a solid. $^{13}C$ NMR (75 MHz, DMSO) δ 172.72, 144.65, 133.42, 132.24, 130.63, 129.05, 128.70, 127.24, 126.41, 126.07, 125.52, 125.45, 123.63, 122.71, 50.69, 40.27, 37.09, 36.18, 32.57, 27.93, 23.24, 19.97.

Example 201

3-{4-[3-((R)-1-Naphthalen-1-yl-ethylamino)-cyclohexyl]-phenyl}-oxetan-3-ol (Compound 1223)

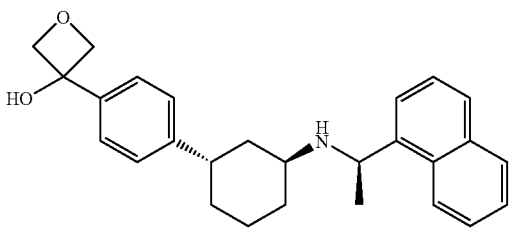 [SMILES: C[C@@H](N[C@H]1CCC[C@H](c2ccc(C3(O)COC3)cc2)C1)c1cccc2ccccc12]

To a solution of 3-(4-iodophenyl)-cyclohexan-1-one (compound 1209) (3.7 g, 8.1 mmol) in dry THF (25 mL) under argon was added isopropyl magnesium chloride (8.1 mL of a 2M solution in THF) at −30-−40° C. The reaction mixture was heated to −10-0° C. and stirred at this temperature for 5 hours, upon which a solution of 3-oxetanone (0.50 g, 6.9 mmol) in THF (3 mL) was added. Stirring was continued for another 2 hours at the same temperature. The reaction mixture was finally heated slowly to r.t. overnight, quenched with $NH_4Cl$ and extracted with ethyl acetate. The organic phase was washed with brine, dried over $Na_2SO_4$, filtered and concentrated under reduced pressure. Chromatography ($CHCl_3$-MeOH 100:0 to 95:5) afforded the title compound as an oil. $^{13}C$ NMR (75 MHz, DMSO) δ 146.09, 142.40, 141.30, 133.47, 130.83, 128.59, 126.41, 126.34, 125.59, 125.54, 125.13, 124.31, 123.07, 122.94, 85.13, 73.78, 50.96, 50.13, 38.89, 36.62, 33.27, 29.03, 24.53, 20.31.

Example 202

{3-[4-(3-Fluoro-oxetan-3-yl)-phenyl]-cyclohexyl}-((R)-1-naphthalen-1-yl-ethyl)-amine (Compound 1224)

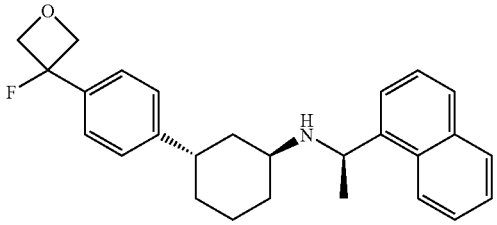 [SMILES: C[C@@H](N[C@H]1CCC[C@H](c2ccc(C3(F)COC3)cc2)C1)c1cccc2ccccc12]

To a solution of 3-{4-[3-(1-naphthalen-1-yl-ethylamino)-cyclohexyl]-phenyl}-oxetan-3-ol in $CH_2Cl_2$ (compound 1223) (5 mL) was added diethylaminosulfur trifluoride (0.21 mL). The mixture was stirred for ½ hour, quenched with $NaHCO_3$ and extracted with $CH_2Cl_2$. The organic phase was dried over $Na_2SO_4$, filtered and concentrated under reduced pressure. Chromatography (MeOH—$CH_2Cl_2$ 1:99) afforded the title compound as an oil. $^{13}C$ NMR (75 MHz, DMSO) δ 148.01, 142.39, 134.93, 134.62, 133.47, 130.83, 128.59, 126.88, 126.42, 125.61, 125.54, 125.14, 124.45, 124.35, 123.07, 122.94, 97.01, 94.31, 81.42, 81.08, 50.98, 50.09, 38.71, 36.73, 33.11, 28.97, 24.53, 20.25.

Example 203

{3-[4-(3-Amino-3-methyl-but-1-ynyl)-phenyl]-cyclohexyl}-((R)-1-naphthalen-1-yl-ethyl)-amine (Compound 1225)

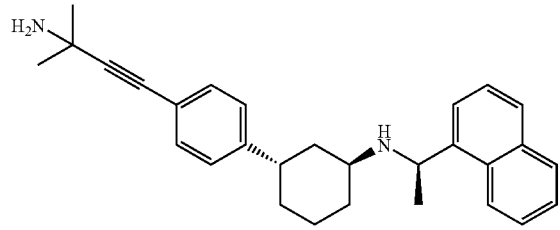 [SMILES: C[C@@H](N[C@H]1CCC[C@H](c2ccc(C#CC(C)(C)N)cc2)C1)c1cccc2ccccc12]

To a solution of 3-(4-iodophenyl)-cyclohexan-1-one (compound 1209) (150 mg, 0.33 mmol) in diethylamine (3 mL, degassed by bubbling argon through the solution for 5 min) were added $PdCl_2(Ph_3P)_2$ (15 mg) and CuI (8 mg). The mixture was argon degassed for another 5 min., cooled to 0° C., and 2-methyl-3-butin-2-yl-amin (137 mg, 1.65 mmol) was added. The reaction mixture was stirred at 0° C. for 30 min and at r.t. for 1 hour and extracted with EtOAc. The organic phase was dried ($Na_2SO_4$), filtered and concentrated under reduced pressure. Chromatography (EtOAc) afforded the title compound as an oil. $^{13}$C NMR (126 MHz, CDCl3) δ 146.47, 141.93, 133.09, 130.37, 130.17, 127.84, 125.90, 125.82, 124.69, 124.31, 122.61, 122.41, 119.69, 78.93, 51.09, 49.97, 44.76, 39.10, 37.90, 36.30, 32.16, 31.32, 29.36, 23.45, 19.73.

General Procedure L

Acid chloride (41 μmol), N-hydroxy-4-[3-(1-naphthalen-1-yl-ethylamino)-cyclohexyl]-benzamidine (compound 1051, 49 μmol) and CDI (45 μmol) in 150 μl. DMF were shaken at r.t. overnight. Additional CDI (45 μmol) in 50 μL DMF were added, and the reaction mixture was heated at 115° C. overnight. The product was purified by preparative HPLC.

Example 204

{3-[4-(5-Cyclopropyl-[1,2,4]oxadiazol-3-yl)-phenyl]-cyclohexyl}-((R)-1-naphthalen-1-yl-ethyl)-amine (Compound 1226)

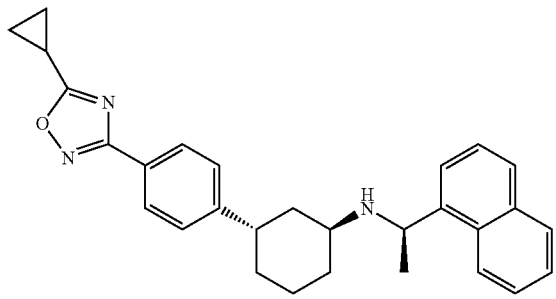 [SMILES: C[C@@H](N[C@H]1CCC[C@H](c2ccc(-c3noc(C4CC4)n3)cc2)C1)c1cccc2ccccc12]

General procedure L was followed using cyclopropanecarbonyl chloride. $^1$H NMR (600 MHz, DMSO) δ 8.35 (d, 1H), 7.93 (d, 1H), 7.83-7.74 (m, 4H), 7.56-7.47 (m, 3H), 7.18 (d, 2H), 4.74 (s, 1H), 3.08-3.00 (m, 1H), 2.93-2.86 (m, 1H), 2.41-2.35 (m, 1H), 1.93-1.82 (m, 1H), 1.81-1.72 (m, 2H), 1.70-1.63 (m, 1H), 1.56-1.39 (m, 6H), 1.36-1.24 (m, 3H), 1.20-1.14 (m, 2H).

Example 205

{3-[4-(5-Cyclopentyl-[1,2,4]oxadiazol-3-yl)-phenyl]-cyclohexyl}-((R)-1-naphthalen-1-yl-ethyl)-amine (Compound 1227)

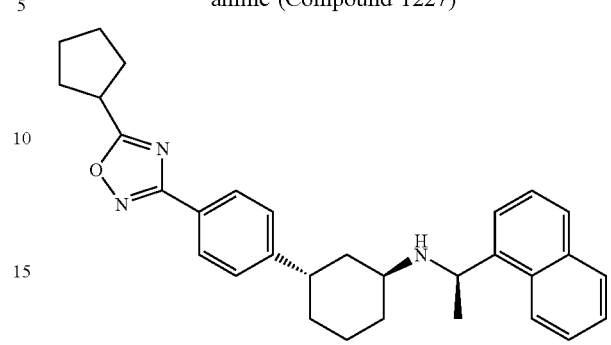

General procedure L was followed using cyclopentanecarbonyl chloride. $^1$H NMR (600 MHz, DMSO) δ 8.36 (d, 1H), 7.93 (d, 1H), 7.82 (d, 2H), 7.80 (d, 1H), 7.76 (d, 1H), 7.55-7.48 (m, 3H), 7.20 (d, 2H), 4.74 (s, 1H), 3.47 (dt, 1H), 3.08-3.01 (m, 1H), 2.92-2.87 (m, 1H), 2.16-2.09 (m, 2H), 1.92-1.83 (m, 3H), 1.81-1.72 (m, 4H), 1.72-1.63 (m, 3H), 1.56-1.40 (m, 6H), 1.37-1.28 (m, 1H).

Example 206

{3-[4-(5-Methyl-[1,2,4]oxadiazol-3-yl)-phenyl]-cyclohexyl}-((R)-1-naphthalen-1-yl-ethyl)-amine (Compound 1228)

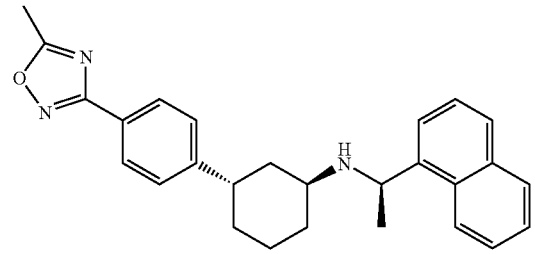 [SMILES: Cc1nc(-c2ccc([C@H]3CCC[C@H](N[C@H](C)c4cccc5ccccc45)C3)cc2)no1]

General procedure L was followed using acetyl chloride. $^1$H NMR (600 MHz, DMSO) δ 8.36 (d, 1H), 7.93 (d, 1H), 7.82 (d, 2H), 7.79 (d, 1H), 7.76 (d, 1H), 7.56-7.47 (m, 3H), 7.19 (d, 2H), 4.71 (s, 1H), 3.08-3.00 (m, 1H), 2.91-2.84 (m, 1H), 2.64 (s, 3H), 1.93-1.83 (m, 1H), 1.81-1.61 (m, 3H), 1.56-1.37 (m, 6H), 1.35-1.27 (m, 1H).

Example 207

{3-[4-(5-Isopropyl-[1,2,4]oxadiazol-3-yl)-phenyl]-cyclohexyl}-((R)-1-naphthalen-1-yl-ethyl)-amine (Compound 1229)

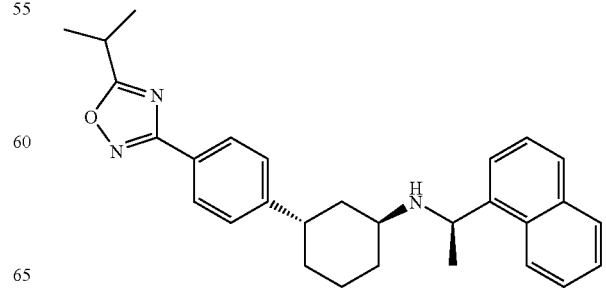

General procedure L was followed using isobuturyl chloride. ¹H NMR (600 MHz, DMSO) δ 8.36 (d, 1H), 7.93 (d, 1H), 7.83 (d, 2H), 7.77 (d, 1H), 7.76 (d, 1H), 7.56-7.47 (m, 3H), 7.19 (d, 2H), 4.74-4.66 (m, 1H), 3.34 (m, 1H overlaying water signal), 3.08-3.01 (m, 1H), 2.91-2.86 (m, 1H), 1.93-1.83 (m, 1H), 1.82-1.73 (m, 2H), 1.70-1.64 (m, 1H), 1.44 (d, 3H), 1.55-1.26 (m, 4H), 1.37 (d, 6H).

Example 208

{3-[4-(5-tert-Butyl-[1,2,4]oxadiazol-3-yl)-phenyl]-cyclohexyl}-(R)-1-naphthalen-1-yl-ethyl)-amine (Compound 1230)

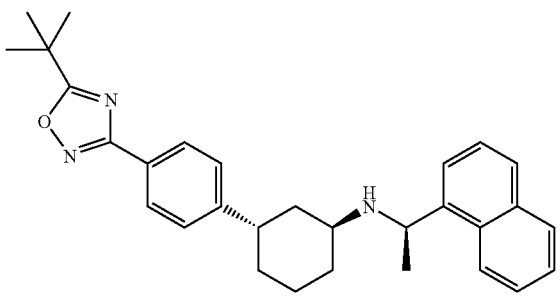 [SMILES: C[C@@H](N[C@H]1CCC[C@H](c2ccc(-c3noc(C(C)(C)C)n3)cc2)C1)c1cccc2ccccc12]

General procedure L was followed using 2,2-dimethyl-propionyl chloride. ¹H NMR (600 MHz, DMSO) δ 8.36 (d, 1H), 7.93 (d, 1H), 7.83 (d, 2H), 7.79 (d, 1H), 7.76 (d, 1H), 7.56-7.47 (m, 3H), 7.20 (d, 2H), 4.70 (s, 1H), 3.08-3.01 (m, 1H), 2.91-2.85 (m, 1H), 1.94-1.83 (m, 1H), 1.81-1.73 (m, 2H), 1.70-1.63 (m, 1H), 1.57-1.38 (m, 6H), 1.44 (s, 9H), 1.36-1.26 (m, 1H).

Example 209

{3-[4-(5-Cyclohexyl-[1,2,4]oxadiazol-3-yl)-phenyl]-cyclohexyl}-((R)-1-naphthalen-1-yl-ethyl)-amine (Compound 1231)

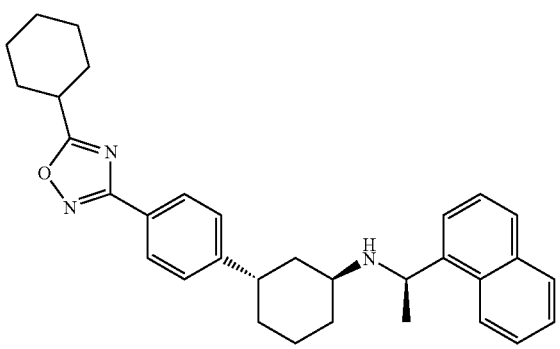 [SMILES: C[C@@H](N[C@H]1CCC[C@H](c2ccc(-c3noc(C4CCCCC4)n3)cc2)C1)c1cccc2ccccc12]

General procedure L was followed using cyclohexanecarbonyl chloride. ¹H NMR (600 MHz, DMSO) δ 8.36 (d, 1H), 7.93 (d, 1H), 7.82 (d, 2H), 7.79 (d, 1H), 7.76 (d, 1H), 7.56-7.47 (m, 3H), 7.19 (d, 2H), 4.72 (q, 1H), 3.13-3.01 (m, 2H), 2.91-2.86 (m, 1H), 2.10-2.02 (m, 2H), 1.93-1.83 (m, 1H), 1.81-1.72 (m, 4H), 1.70-1.56 (m, 4H), 1.55-1.36 (m, 8H), 1.35-1.23 (m, 2H).

Example 210

(3-{4-[5-(3-Methyl-butyl)-[1,2,4]oxadiazol-3-yl]-phenyl}-cyclohexyl)-((R)-1-naphthalen-1-yl-ethyl)-amine (Compound 1232)

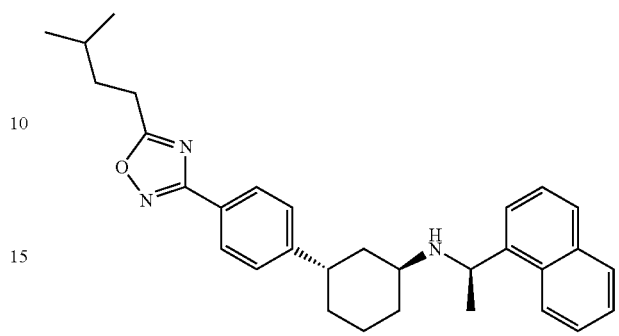

General procedure L was followed using 4-methyl-pentanoyl chloride. ¹H NMR (600 MHz, DMSO) δ 8.36 (d, 1H), 7.93 (d, 1H), 7.83 (d, 2H), 7.80 (d, 1H), 7.77 (d, 1H), 7.56-7.48 (m, 3H), 7.20 (d, 2H), 4.77-4.71 (m, 1H), 3.08-3.01 (m, 1H), 3.00-2.96 (m, 2H), 2.92-2.88 (m, 1H), 1.92-1.83 (m, 1H), 1.82-1.73 (m, 2H), 1.71-1.58 (m, 4H), 1.57-1.40 (m, 6H), 1.37-1.29 (m, 1H), 0.92 (d, 6H).

Example 211

5-(3-{4-[3-((R)-1-Naphthalen-1-yl-ethylamino)-cyclohexyl]-phenyl}-[1,2,4]oxadiazol-5-ylmethyl)-imidazolidine-2,4-dione (Compound 1233)

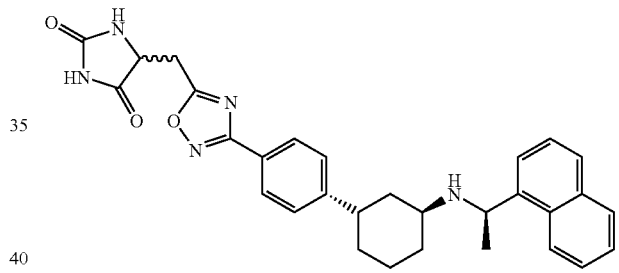

General procedure L was followed using (2,5-dioxo-imidazolidin-4-yl)-acetyl chloride. ¹H NMR (600 MHz, DMSO) δ 10.83 (br s, 1H), 8.36 (d, 1H), 8.05 (d, 1H), 7.94 (dd, 1H), 7.83 (d, 2H), 7.80 (d, 1H), 7.77 (d, 1H), 7.56-7.48 (m, 3H), 7.21 (d, 2H), 4.74 (q, 1H), 4.59-4.56 (m, 1H), 3.43 (dd, 1H), 3.38 (dd, 1H), 3.08-3.02 (m, 1H), 2.92-2.88 (m, 1H), 1.93-1.83 (m, 1H), 1.82-1.73 (m, 2H), 1.71-1.65 (m, 1H), 1.58-1.40 (m, 6H), 1.36-1.29 (m, 1H).

Example 212

(3-{4-[5-(4-Methyl-oxazol-5-yl]-[1,2,4]oxadiazol-3-yl-phenyl}-cyclohexyl)-((R)-1-naphthalen-1-yl-ethyl)-amine (Compound 1234)

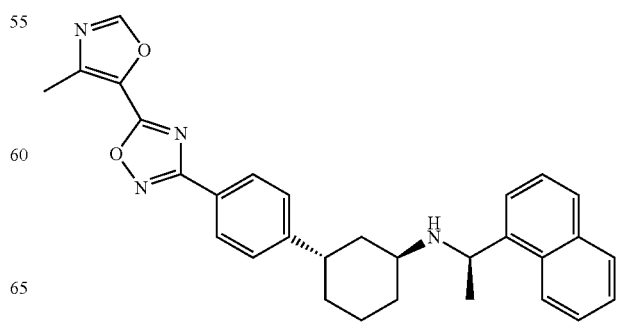

General procedure L was followed using 4-methyl-oxazole-5-carbonyl chloride. $^1$H NMR (600 MHz, DMSO) δ 8.75 (s, 1H), 8.36 (d, 1H), 7.97-7.89 (m, 3H), 7.79 (d, 1H), 7.77 (d, 1H), 7.56-7.48 (m, 3H), 7.25 (d, 2H), 4.75-4.69 (m, 1H), 3.11-3.04 (m, 1H), 2.92-2.87 (m, 1H), 2.58 (s, 3H), 1.89 (dd, 1H), 1.78 (s, 2H), 1.68 (d, 1H), 1.57-1.40 (m, 6H), 1.32 (t, 1H).

Example 213

(3-{4-[5-(2,5-Dimethyl-oxazol-4-yl)-[1,2,4]oxadiazol-3-yl]-phenyl}-cyclohexyl)-((R)-1-naphthalen-1-yl-ethyl)-amine (Compound 1235)

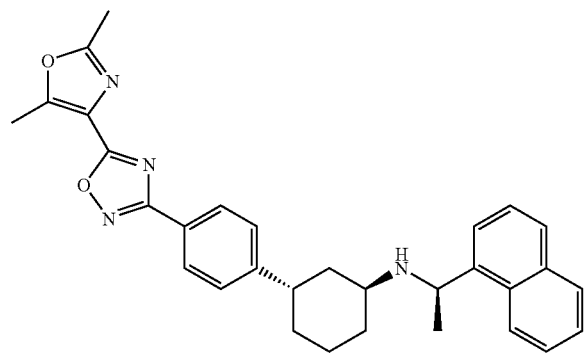 [SMILES: Cc1nc(-c2nc(-c3ccc([C@H]4CCC[C@H](N[C@H](C)c5cccc6ccccc56)C4)cc3)no2)c(C)o1]

General procedure L was followed using 2,5-dimethyl-oxazole-4-carbonyl chloride. $^1$H NMR (600 MHz, DMSO) δ 8.36 (d, 1H), 7.94 (dd, 1H), 7.90 (d, 2H), 7.79 (d, 1H), 7.77 (d, 1H), 7.56-7.48 (m, 3H), 7.23 (d, 2H), 4.71 (q, 1H), 3.11-3.02 (m, 1H), 2.91-2.86 (m, 1H), 2.73 (s, 3H), 2.49 (s, 3H), 1.94-1.84 (m, 1H), 1.82-1.74 (m, 2H), 1.71-1.65 (m, 1H), 1.57-1.40 (m, 6H), 1.36-1.27 (m, 1H).
General Procedure M.

To a solution of cycloalkenone (400 μmol) in 400 μL DME were added boronic acid (480 μmol, 1.2 eq.), (COD) Rh(1,4-dihydroquinone)BF$_4$ (1 mol %) in 100 pt DME, and LiOH (4 mol %) in 600 μL water. After shaking the mixture overnight at 50° C., the solvent was removed in vacuo. The crude intermediate ketone was dissolved in DCE containing acetic acid (1.2 eq.). (+)-(R)-1-naphthalen-1-yl-ethylamine (1 eq.) in DCE was added followed by NaBH(OAc)$_3$ (1.2 eq.) The mixture was shaken overnight at r. t., filtered and the solvents were removed in vacuo. The residue was redissolved in 750 μL DMSO and purified by HPLC.

Example 214

2-Methyl-2-{4-[3-((R)-1-naphthalen-1-yl-ethyl-amino)-cyclohexyl]-phenyl}-propionitrile (Compound 1236/1237)

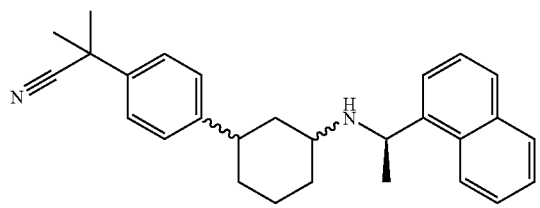 [SMILES: C[C@@H](NC1CCCC(c2ccc(C(C)(C)C#N)cc2)C1)c1cccc2ccccc12]

General procedure M was followed using 4-(2-cyanopropan-2-yl)phenylboronic acid and 2-cyclohexen-1-one. The title compounds were purified by chromatography on 20 g silica gel in a gradient from 0 to 60% EtOAc in n-heptane, flow rate 30 mL/min. Compound 1236 (1 isomer, less polar, RT~11 min): $^{13}$C NMR (75 MHz, DMSO) δ 146.84, 142.38, 138.59, 133.47, 130.84, 128.60, 127.05, 126.42, 125.62, 125.54, 125.15, 124.80, 124.69, 123.04, 122.94, 50.88, 49.99, 38.75, 36.56, 36.17, 33.17, 28.94, 28.26, 24.52, 20.25. Compound 1237 (1 isomer, more polar, RT~13 min): $^{13}$C NMR (75 MHz, DMSO) δ 146.76, 142.14, 138.61, 133.39, 130.84, 128.55, 127.18, 126.39, 125.62, 125.50, 125.10, 124.85, 124.76, 122.92, 122.80, 50.11, 49.30, 36.44, 36.28, 36.15, 33.36, 30.74, 28.24, 24.40, 20.50.

Example 215

2-Methyl-2-{4-[3-((R)-1-naphthalen-1-yl-ethyl-amino)-cyclohexyl]-phenyl}-propionic acid (Compound 1238)

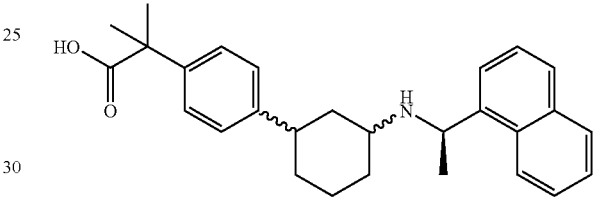

To a solution of 2-methyl-2-{4-[3-(1-naphthalen-1-yl-ethylamino)-cyclohexyl]-phenyl}-propionitrile (compound 1236) in MeOH (0.09 M, y mL) was added 28% aq NaOH (y/2 mL). The mixture was heated to reflux over a period of 3 days. MeOH was removed under reduced pressure. The residue was taken in water and 4N aq. HCl was added until pH=5. The precipitate was collected, washed with water and dried in vacuo to afford the title compound. $^{13}$C NMR (126 MHz, DMSO) δ 177.53, 145.26, 142.13, 133.45, 130.83, 128.58, 126.44, 126.38, 125.63, 125.53, 125.22, 125.15, 123.03, 122.92, 50.77, 49.95, 45.22, 38.78, 36.48, 33.22, 28.88, 26.29, 24.40, 20.25.

Example 216

2-Methyl-2-{4-[3-((R)-1-naphthalen-1-yl-ethyl-amino)-cyclohexyl]-phenyl}-propionic acid (Compound 1239)

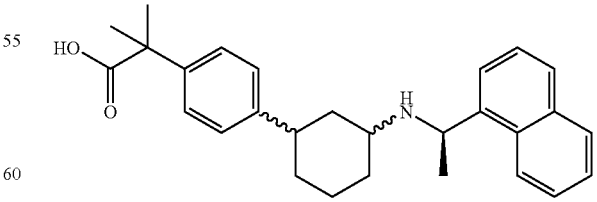

To a solution of 2-methyl-2-{4-[3-(1-naphthalen-1-yl-ethylamino)-cyclohexyl]-phenyl}-propionitrile (compound 1237) in MeOH (0.09 M, y mL) was added 28% aq NaOH (y/2 mL). The mixture was heated to reflux over a period of 3 days. MeOH was removed under reduced pressure. The residue was taken in water and 4N aq. HCl was added until pH=5. The precipitate was collected, washed with water and dried in vacuo to afford the title compound. $^1$H NMR (600 MHz, DMSO) δ 8.31 (d, 1H), 7.94 (d, 1H), 7.85-7.73 (m, 2H), 7.52 (t, 3H), 7.22-6.99 (m, 4H), 5.10-4.53 (m, 1H), 3.05 (br t, 1H), 2.84 (br s, 1H), 1.90-1.26 (m, 17H).

Example 217

[3-(4-Methanesulfonyl-phenyl)-cyclohexyl]-((R)-1-naphthalen-1-yl-ethyl)-amine (Compounds 1240)

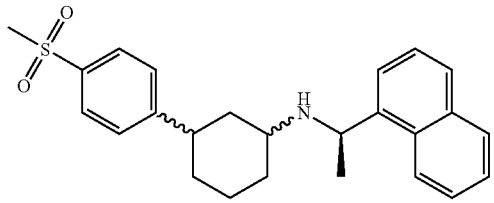 [SMILES: C[C@@H](NC1CCCC(c2ccc(S(C)(=O)=O)cc2)C1)c1cccc2ccccc12]

General procedure M was followed using 4-(methanesulfonyl)-benzeneboronic acid and 2-cyclohexen-1-one. Compound 1240 (1 isomer): LC-MS (method B): RT=4.14, [M+H]$^+$=408.1. $^1$H NMR (600 MHz, DMSO) δ 8.30 (d, 1H), 7.96-7.88 (m, 1H), 7.80 (d, 2H), 7.77 (d, 1H), 7.72 (d, 1H), 7.55-7.44 (m, 5H), 4.71 (q, 1H), 3.18 (s, 3H), 3.23-3.15 (m, 1H), 2.82 (s, 1H), 1.86-1.73 (m, 3H), 1.64-1.56 (m, 1H), 1.51-1.34 (m, 7H).

Example 218

2-Fluoro-4-[3-((R)-1-naphthalen-1-yl-ethylamino)-cyclohexyl]-benzoic acid methyl ester (Compound 1241)

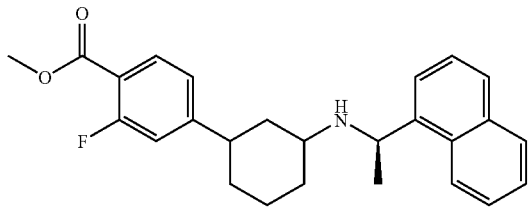 [SMILES: COC(=O)c1ccc(C2CCCC(N[C@H](C)c3cccc4ccccc34)C2)cc1F]

General procedure M was followed using 3-fluoro-4-(methoxycarbonyl)-benzeneboronic acid and 2-cyclohexen-1-one. Compound 1241: (1 isomer): LC-MS (method B): RT=4.44, [M+H]$^+$=406.1. $^1$H NMR (600 MHz, DMSO) δ 8.30 (d, 1H), 7.93-7.89 (m, 1H), 7.77 (dt, 2H), 7.72 (d, 1H), 7.52-7.45 (m, 3H), 7.18 (dd, 2H), 4.71 (q, 1H), 3.83 (s, 3H), 3.17 (t, 2H), 2.81 (s, 1H), 1.85-1.72 (m, 3H), 1.58 (d, 1H), 1.50-1.32 (m, 7H).

Example 219

{4-[3-((R)-1-Naphthalen-1-yl-ethylamino)-cyclohexyl]-phenyl}-methanol (Compound 1242)

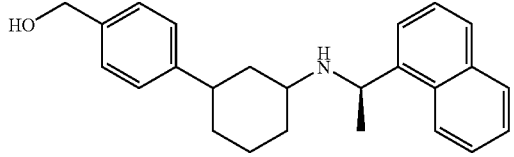 [SMILES: C[C@@H](NC1CCCC(c2ccc(CO)cc2)C1)c1cccc2ccccc12]

General procedure M was followed using 4-(hydroxymethyl)phenyl boronic acid and 2-cyclohexen-1-one. LC-MS (method B): RT=4.21, [M+H]$^+$=360.2 (mixture of 2 isomers).

Example 220

N-{4-[3-((R)-1-Naphthalen-1-yl-ethylamino)-cyclohexyl]-benzyl}-methanesulfonamide (Compound 1243)

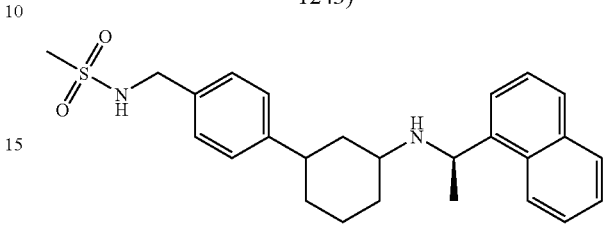

General procedure M was followed using (4-methanesulfonylamino-methylphenyl)boronic acid and 2-cyclohexen-1-one. Compound 1243 (1 isomer): LC-MS (method B): RT=4.27, [M+H]$^+$=437.1. $^1$H NMR (600 MHz, DMSO) δ 8.34 (d, 1H), 7.92 (dd, 1H), 7.77 (dd, 2H), 7.55-7.47 (m, 3H), 7.44 (t, 1H), 7.16 (d, 2H), 7.01 (d, 2H), 4.69 (q, 1H), 4.06 (d, 2H), 2.99-2.91 (m, 1H), 2.88-2.80 (m, 4H), 1.90-1.80 (m, 1H), 1.73 (dd, 2H), 1.65-1.60 (m, 1H), 1.51-1.25 (m, 7H).

Example 221

{3-[4-(Morpholine-4-sulfonyl)-phenyl]-cyclohexyl}-((R)-1-naphthalen-1-yl-ethyl)-amine (Compound 1244/1245)

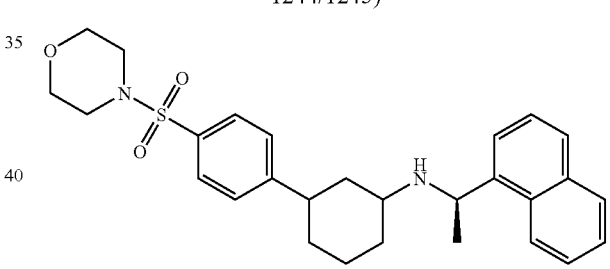

General procedure M was followed using 4-N-morpholinylsulfonyl-phenylboronic acid and 2-cyclohexen-1-one. Compound 1244 (mixture of 2 isomers): LC-MS (method B): RT=4.32, [M+H]$^+$=479.2. Compound 1245 (mixture of 2 isomers): LC-MS (method B): RT=4.36, [M+H]$^+$=479.1.

Example 222

N-{4-[3-((R)-1-Naphthalen-1-yl-ethylamino)-cyclohexyl]-benzyl}-acetamide (Compounds 1246/1247)

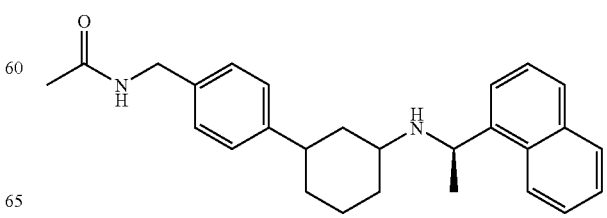

General procedure M was followed using (4-acetamidomethylphenyl)-boronic acid and 2-cyclohexen-1-one. Compound 1246 (mixture of 2 isomers): LC-MS (method B): RT=4.09, [M+H]$^+$=401.1, [M+HCOO]$^-$=445.2. Compound 1247 (mixture of 3 isomers): LC-MS (method B): RT=4.12, [M+H]$^+$=401.1, [M+HCOO]$^-$=445.0.

Example 223

3-Fluoro-4-[3-((R)-1-naphthalen-1-yl-ethylamino)-cyclohexyl]-benzoic acid methyl ester (Compound 1248)

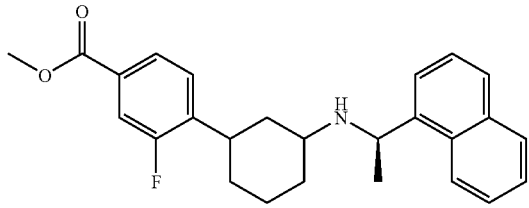 [SMILES: COC(=O)c1ccc(C2CCCC(N[C@H](C)c3cccc4ccccc34)C2)c(F)c1]

General procedure M was followed using 2-fluoro-4-methoxycarbonyl-phenylboronic acid and 2-cyclohexen-1-one. Compound 1248 (mixture of 2 isomers): LC-MS (method B): RT=4.56, [M+H]$^+$=406.0.

Example 224

N-{4-[3-((R)-1-Naphthalen-1-yl-ethylamino)-cyclohexyl]-phenyl}-methanesulfonamide (Compound 1249/1250)

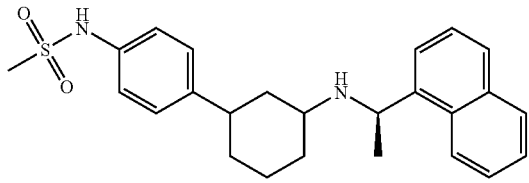 [SMILES: C[C@@H](NC1CCCC(c2ccc(NS(C)(=O)=O)cc2)C1)c1cccc2ccccc12]

General procedure M was followed using 4-(methanesulfonylamino)-phenylboronic acid and 2-cyclohexen-1-one. Compound 1249 (mixture of 2 isomers): LC-MS (method B): RT=4.24, [M+H]$^+$=423.1, [M–H]$^-$=421.1. Compound 1250 (mixture of 2 isomers): LC-MS (method B): RT=4.34, [M+H]$^+$=423.2, [M–H]$^-$=421.0.

Example 225

N-{3-[3-((R)-1-Naphthalen-1-yl-ethylamino)-cyclohexyl]-phenyl}-methanesulfonamide (Compound 1251)

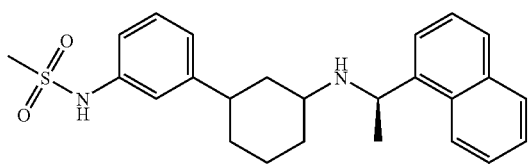 [SMILES: C[C@@H](NC1CCCC(c2cccc(NS(C)(=O)=O)c2)C1)c1cccc2ccccc12]

General procedure M was followed using 3-(methylsulfonylamino)-phenylboronic acid and 2-cyclohexen-1-one. Compound 1251 (mixture of 2 isomers): LC-MS (method B): RT=4.29, [M+H]$^+$=423.1, [M–]$^-$=421.0.

Example 226

N-(2-Hydroxy-ethyl)-4-[3-((R)-1-naphthalen-1-yl-ethylamino)-cyclohexyl]-benzenesulfonamide (Compounds 1252/1253)

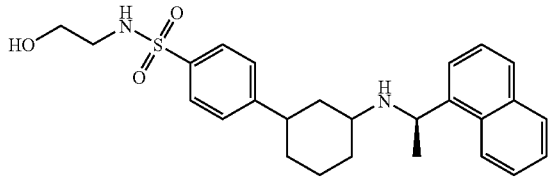 [SMILES: C[C@@H](NC1CCCC(c2ccc(S(=O)(=O)NCCO)cc2)C1)c1cccc2ccccc12]

General procedure M was followed using 4-(2-hydroxyethylsulfamoyl)-phenylboronic acid and 2-cyclohexen-1-one. Compound 1252 (mixture of 2 isomers): LC-MS (method B): RT=4.11, [M+H]$^+$=453.1, [M–H]$^-$=451.0. Compound 1253 (mixture of 4 isomers): LC-MS (method B): RT=4.22, [M+H]$^+$=453.1, [M–H]$^+$=451.0.

Example 227

3-{4-[3-((R)-1-Naphthalen-1-yl-ethylamino)-cyclohexyl]-phenyl}-propionic acid (Compound 1254)

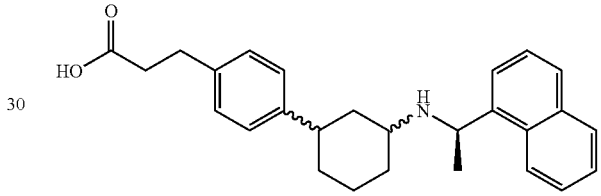

General procedure M was followed using 2-methoxycarbonylethyl phenylboronic acid and 2-cyclohexenone. The intermediate ester was hydrolyzed following general procedure J. Preparative HPLC afforded the title compound as an oil and as a single isomer. LC-MS (method B): RT=4.32, [M+H]$^-$=402.1. $^1$H NMR (600 MHz, DMSO) δ 8.28 (d, 1H), 7.91 (d, 1H), 7.77 (d, 1H), 7.71 (d, 1H), 7.53-7.45 (m, 3H), 7.15-7.00 (m, 4H), 4.75-4.66 (m, 1H), 3.05-2.96 (m, 1H), 2.87-2.72 (m, 3H), 1.84-1.67 (m, 3H), 1.62-1.54 (m, 1H), 1.47-1.31 (m, 7H). (2 hydrogens hidden under water signal at 3.2-3.6 ppm)

Example 228

{4-[3-((R)-1-Naphthalen-1-yl-ethylamino)-cyclohexyl]-phenoxy}-acetic acid (Compound 1255)

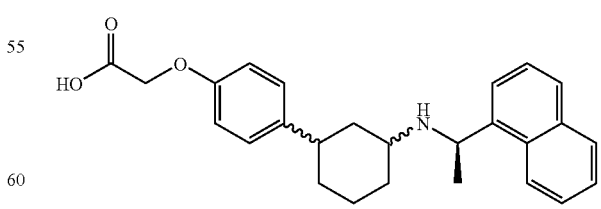

General procedure M was followed using 4-(2-ethoxy-2-oxoethoxy)-benzeneboronic acid and 2-cyclohexenone. The intermediate ester was hydrolyzed following general procedure J. Preparative HPLC afforded the title compound as an oil and as a single isomer. LC-MS (method B): RT=4.22,

[M+H]⁺=404.1. ¹H NMR (600 MHz, DMSO) δ 8.29 (d, 1H), 7.92 (d, 1H), 7.78 (d, 1H), 7.76-7.71 (m, 1H), 7.54-7.46 (m, 3H), 7.17-6.99 (m, 2H), 6.87-6.64 (m, 2H), 4.79-4.70 (m, 1H), 3.06-2.94 (m, 1H), 2.87-2.77 (m, 1H), 1.84-1.67 (m, 3H), 1.62-1.54 (m, 1H), 1.50-1.31 (m, 7H).

Example 229

[3-(4-Methanesulfonyl-phenyl)-cyclopentyl]-((R)-1-naphthalen-1-yl-ethyl)-amine (Compounds 1256/1257)

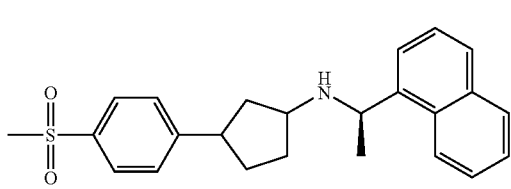 [SMILES: C[C@@H](NC1CCC(c2ccc(S(C)(=O)=O)cc2)C1)c1cccc2ccccc12]

General procedure M was followed using 4-(methanesulfonyl)-benzeneboronic acid and 2-cyclopenten-1-one. Compound 1256 (mixture of 2 isomers): LC-MS (method B): RT=4.22, [M+H]⁺=394.1. Compound 1257 (mixture of 3 isomers): LC-MS (method B): RT=4.24, [M+H]⁺=394.1.

Example 230

N-{3-[3-((R)-1-Naphthalen-1-yl-ethylamino)-cyclopentyl]-phenyl}-methanesulfonamide (Compounds 1258/1259)

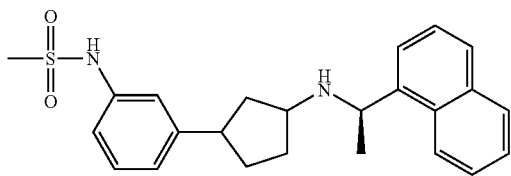 [SMILES: C[C@@H](NC1CCC(c2cccc(NS(C)(=O)=O)c2)C1)c1cccc2ccccc12]

General procedure M was followed using 3-(methylsulfonylamino)-phenylboronic acid and 2-cyclopenten-1-one. Compound 1258 (mixture of 2 isomers): LC-MS (method B): RT=4.27, [M+H]⁺=409.1, [M−H]⁺=407.0. Compound 1259 (mixture of 3 isomers): LC-MS (method B): RT=4.29, [M+H]⁺=409.1, [M−H]⁺=407.1.

Example 231

N-{4-[3-((R)-1-Naphthalen-1-yl-ethylamino)-cyclopentyl]-Phenyl}-acetamide (Compounds 1260/1261)

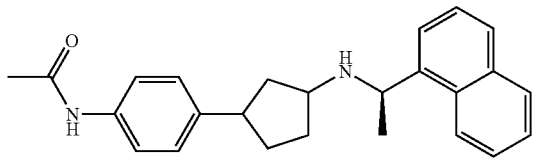 [SMILES: CC(=O)Nc1ccc(C2CCC(N[C@H](C)c3cccc4ccccc34)C2)cc1]

General procedure M was followed using 4-acetamidophenylboronic acid and 2-cyclopenten-1-one. Compound 1260 (mixture of 2 isomers): LC-MS (method B): RT=4.16, [M+H]⁺=373.2, [M+HCOO]⁻=417.1. Compound 1261 (mixture of isomers): LC-MS (method B): RT=4.19, [M+H]⁺=373.2, [M+HCOO]⁻=417.1.

Example 232

N-{4-[3-((R)-1-Naphthalen-1-yl-ethylamino)-cyclopentyl]-benzyl}-acetamide (Compound 1262/1263)

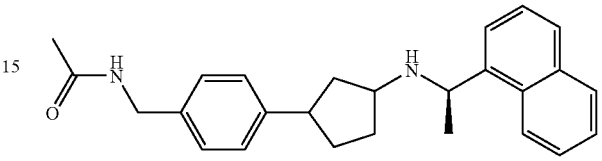

General procedure M was followed using (4-acetamidomethylphenyl) boronic acid and 2-cyclopenten-1-one. Compound 1262 (mixture of 2 isomers): LC-MS (method B): RT=4.12, [M+H]⁺=387.1, [M+HCOO]⁻=431.0. Compound 1263 (mixture of 4 isomers): LC-MS (method B): RT=4.14, [M+H]⁺=387.1, [M+HCOO]⁻=431.0.

Example 233

N-{4-[3-((R)-1-Naphthalen-1-yl-ethylamino)-cyclopentyl]-benzyl}-methanesulfonamide (Compounds 1264/1265)

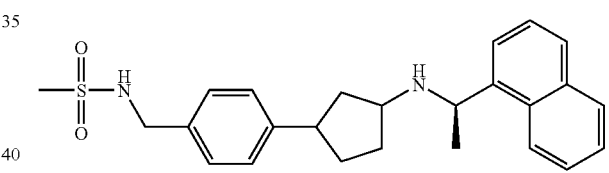

General procedure M was followed using (4-methanesulfonylamino-methylphenyl)boronic acid and 2-cyclopenten-1-one. Compound 1264 (mixture of 2 isomers): LC-MS (method B): RT=4.24, [M+H]⁺=423.1, [M+HCOO]⁻=467.0. Compound 1265 (mixture of 4 isomers): LC-MS (method B): RT=4.27, [M+H]⁺=423.1, [M+HCOO]⁻=467.0.

Example 234

N-{4-[3-((R)-1-Naphthalen-1-yl-ethylamino)-cyclopentyl]-phenyl}-methanesulfonamide (Compounds 1266/1267)

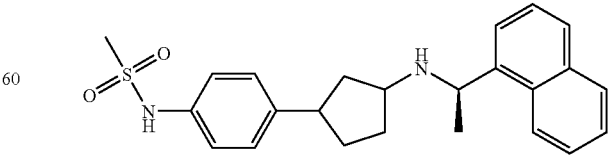

General procedure M was followed using 4-(methanesulfonylamino)-phenylboronic acid and 2-cyclopenten-1-one. Compound 1266 (mixture of 2 isomers): LC-MS (method B): RT=4.26, [M+H]⁺=409.0, [M−H]⁺=407.0. Compound 1267 (mixture of 3 isomers): LC-MS (method B): RT=4.27, [M+H]⁻=409.0, [M−H]⁺=406.9.

Example 235

[3-(4-Methanesulfonyl-phenyl)-cycloheptyl]-((R)-1-naphthalen-1-yl-ethyl)-amine (compound 1268)

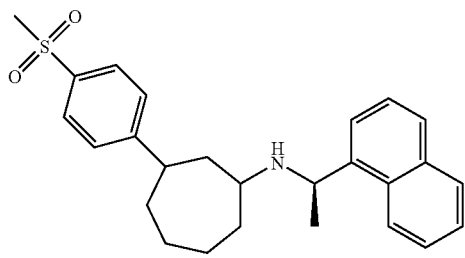 [SMILES: C[C@@H](NC1CCCCC(c2ccc(S(C)(=O)=O)cc2)C1)c1cccc2ccccc12]

General procedure M was followed using 4-(methanesulfonyl)-benzeneboronic acid and 2-cyclohepten-1-one. Compound 1268 (mixture of isomers): LC-MS (method B): RT=4.34, [M+H]⁻=422.1.

Example 236

2-Fluoro-4-[3-((R)-1-naphthalen-1-yl-ethylamino)-cycloheptyl]-benzoic acid methyl ester (Compound 1269)

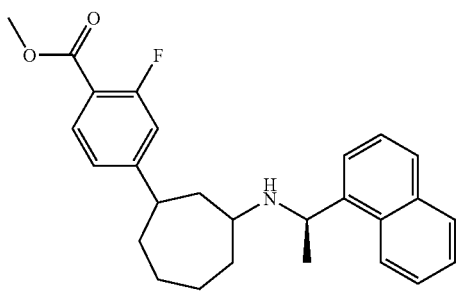 [SMILES: COC(=O)c1ccc(C2CCCCC(N[C@H](C)c3cccc4ccccc34)C2)cc1F]

General procedure M was followed using 3-fluoro-4-(methoxycarbonyl)-benzeneboronic acid and 2-cyclohepten-1-one. Compound 1269 (mixture of isomers): LC-MS (method B): RT=4.57, [M+H]⁺=420.1.

Example 237

N-{3-[3-((R)-1-Naphthalen-1-yl-ethylamino)-cycloheptyl]-phenyl}-methanesulfonamide (Compound 1270)

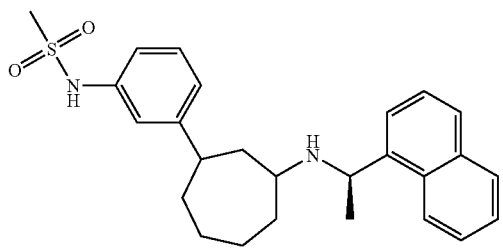 [SMILES: C[C@@H](NC1CCCCC(c2cccc(NS(C)(=O)=O)c2)C1)c1cccc2ccccc12]

General procedure M was followed using 3-(methylsulfonylamino)-phenylboronic acid and 2-cyclohepten-1-one. Compound 1270 (mixture of isomers): LC-MS (method B): RT=4.41, [M+H]⁺=437.1, [M−H]⁺=435.0.

Example 238

N-{4-[3-((R)-1-Naphthalen-1-yl-ethylamino)-cycloheptyl]-phenyl}-acetamide (Compound 1271/1272)

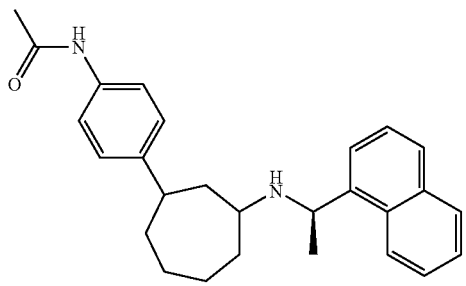 [SMILES: CC(=O)Nc1ccc(C2CCCCC(N[C@H](C)c3cccc4ccccc34)C2)cc1]

General procedure M was followed using 4-acetamidophenylboronic acid and 2-cyclohepten-1-one. Compound 1271 (mixture of isomers): LC-MS (method B): RT=4.27, [M+H]⁺=401.1, [M+HCOO]⁻=445.2. Compound 1272 (mixture of isomers): LC-MS (method B): RT=4.32, [M+H]⁺=401.2, [M+HCOO]⁻=445.2.

Example 239

N-{4-[3-((R)-1-Naphthalen-1-yl-ethylamino)-cycloheptyl]-benzyl}-acetamide (Compounds 1273/1274)

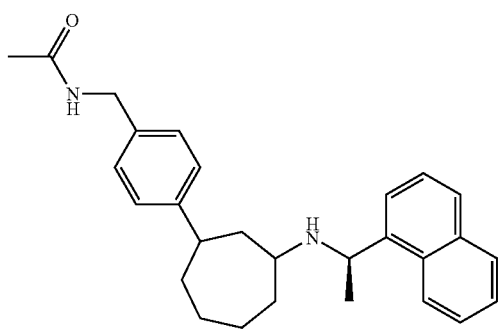 [SMILES: CC(=O)NCc1ccc(C2CCCCC(N[C@H](C)c3cccc4ccccc34)C2)cc1]

General procedure M was followed using (4-acetamidomethylphenyl)-boronic acid and 2-cyclohepten-1-one. Compound 1273 (mixture of 2 isomers): LC-MS (method B): RT=4.24, [M+H]⁺=415.2, [M+HCOO]⁻=459.1. Compound 1274 (mixture of 2 isomers): LC-MS (method B): RT=4.26, [M+H]⁺=415.2, [M+HCOO]⁻=459.2.

Example 240

N-{4-[3-((R)-1-Naphthalen-1-yl-ethylamino)-cycloheptyl]-benzyl}-methanesulfonamide (Compounds 1275/1276)

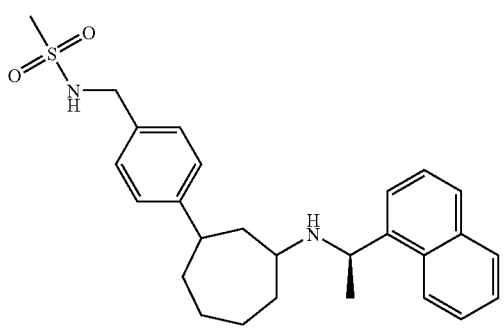 [SMILES: C[C@@H](NC1CCCCC(c2ccc(CNS(C)(=O)=O)cc2)C1)c1cccc2ccccc12]

General procedure M was followed using (4-methanesulfonylamino-methylphenyl)boronic acid and 2-cyclohepten-1-one. Compound 1275 (mixture of isomers): LC-MS (method B): RT=4.37, [M+H]⁺=451.1, [M+HCOO]⁻=495.2. Compound 1276 (mixture of isomers): LC-MS (method B): RT=4.39, [M+H]⁺=451.1, [M+HCOO]⁻=495.0.

Example 241

{4-[3-((R)-1-Naphthalen-1-yl-ethylamino)-cycloheptyl]-phenoxy}-acetic acid ethyl ester (Compound 1277)

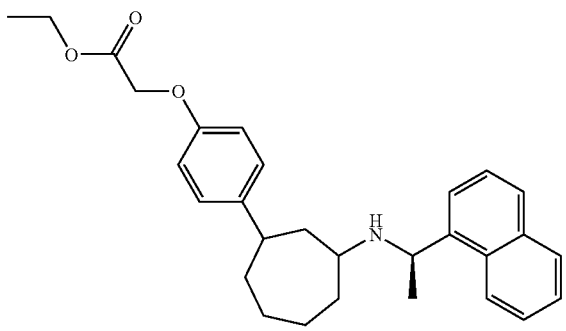 [SMILES: CCOC(=O)COc1ccc(C2CCCCC(N[C@H](C)c3cccc4ccccc34)C2)cc1]

General procedure M was followed using 4-(2-ethoxy-2-oxoethoxy)-phenylboronic acid and 2-cyclohepten-1-one. Compound 1277 (mixture of 2 isomers): LC-MS (method B): RT=4.66, [M+H]⁺=446.2.

Example 242

3-{4-[3-((R)-1-Naphthalen-1-yl-ethylamino)-cycloheptyl]-phenyl}-propionic acid methyl ester (Compounds 1278/1279)

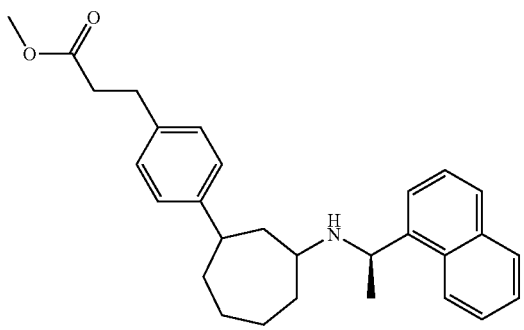 [SMILES: COC(=O)CCc1ccc(C2CCCCC(N[C@H](C)c3cccc4ccccc34)C2)cc1]

General procedure M was followed using 4-(2-methoxycarbonylethyl)-phenylboronic acid and 2-cyclohepten-1-one. Compound 1278 (mixture of 2 isomers): LC-MS (method B): RT=4.66, [M+H]⁺=430.2. Compound 1279 (mixture of 3 isomers): LC-MS (method B): RT=4.66, [M+H]⁺=430.1.

Example 243

N-{4-[3-((R)-1-Naphthalen-1-yl-ethylamino)-cycloheptyl]-phenyl}-methanesulfonamide (Compounds 1280/1281)

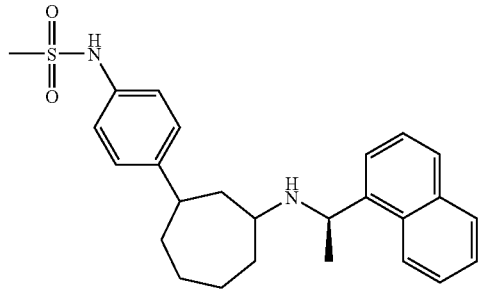 [SMILES: C[C@@H](NC1CCCCC(c2ccc(NS(C)(=O)=O)cc2)C1)c1cccc2ccccc12]

General procedure M was followed using 4-(methanesulfonylamino)-phenylboronic acid and 2-cyclohepten-1-one. Compound 1280 (mixture of isomers): LC-MS (method B): RT=4.36, [M+H]⁺=437.1, [M−H]⁻=434.9. Compound 1281 (mixture of isomers): LC-MS (method B): RT=4.37, [M+H]⁺=437.1, [M−H]⁻=434.9.

Example 244

{3-[4-(Morpholine-4-sulfonyl)-phenyl]-cycloheptyl}-((R)-1-naphthalen-1-yl-ethyl)-amine (Compound 1282)

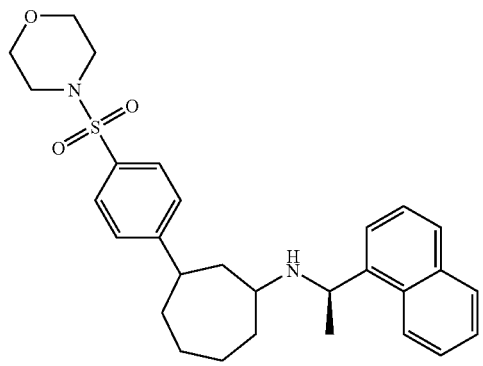 [SMILES: C[C@@H](NC1CCCCC(c2ccc(S(=O)(=O)N3CCOCC3)cc2)C1)c1cccc2ccccc12]

General procedure M was followed using 4-(4-morpholinylsulfonyl)-phenylboronic acid and 2-cyclohepten-1-one. Compound 1282 (mixture of isomers): LC-MS (method B): RT=4.47, [M+H]⁺=493.2.

Example 245

{4-[3-((R)-1-Naphthalen-1-yl-ethylamino)-cycloheptyl]-phenyl}-methanol (Compound 1283)

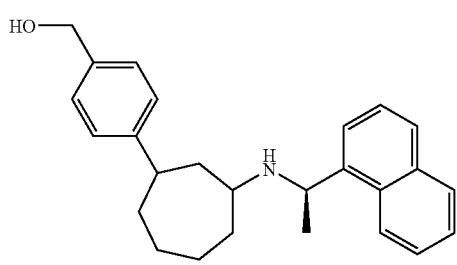 [SMILES: C[C@@H](NC1CCCCC(c2ccc(CO)cc2)C1)c1cccc2ccccc12]

General procedure M was followed using 4-(hydroxymethyl)phenylboronic acid and 2-cyclohepten-1-one. Compound 1283 (mixture of isomers): LC-MS (method B): RT=4.32, [M+H]⁻=374.2.

General Procedure N

To a solution of 4-[3-((R)-1-naphthalen-1-yl-ethylamino)-cyclohexyl]-benzoic acid (compound 1056, 1.5 mmol) in 6 mL dry DMF was added CDI (1.8 mmol). After stirring the solution for 4 hours at r.t., an alcohol (22 mmol, 15 eq.) was added, and stirring was continued overnight at r.t. The solvent was removed under reduced pressure, and the residue was purified by chromatography.

Example 246

4-[3-((R)-1-Naphthalen-1-yl-ethylamino)-cyclohexyl]-benzoic acid methyl ester (Compound 1284)

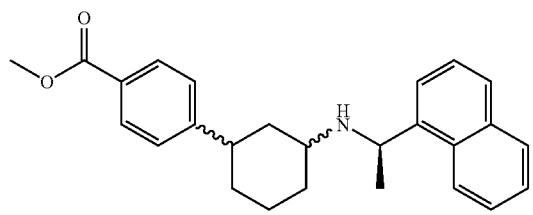

General procedure N was followed using methanol. Chromatography (CH$_2$Cl$_2$-MeOH 100:0 to 95:5) afforded the title compound. $^{13}$C NMR (75 MHz, DMSO) δ 166.13, 153.14, 147.17, 142.50, 133.54, 130.88, 129.04, 128.64, 126.99, 126.48, 125.66, 125.60, 125.20, 123.16, 123.03, 51.86, 51.24, 50.22, 38.57, 37.15, 32.82, 29.04, 24.64, 20.26.

Example 247

4-[3-((R)-1-Naphthalen-1-yl-ethylamino)-cyclohexyl]-benzoic acid ethyl ester (Compound 1285)

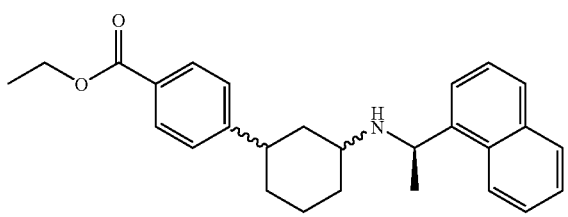 [SMILES: CCOC(=O)c1ccc(C2CCCC(N[C@H](C)c3cccc4ccccc34)C2)cc1]

General procedure N was followed using ethanol. Chromatography (CH$_2$Cl$_2$-MeOH 100:0 to 97:3) afforded the title compound as an oil. $^{13}$C NMR (75 MHz, DMSO) δ 165.58, 153.03, 142.44, 133.50, 130.85, 128.97, 128.60, 127.26, 126.90, 126.44, 125.61, 125.55, 125.16, 123.11, 122.98, 60.35, 51.16, 50.15, 38.51, 37.12, 32.85, 28.98, 24.59, 20.21, 14.10.

Example 248

4-[3-((R)-1-Naphthalen-1-yl-ethylamino)-cyclohexyl]-benzoic acid 2-morpholin-4-yl-ethyl ester dihydrochloride (Compound 1286)

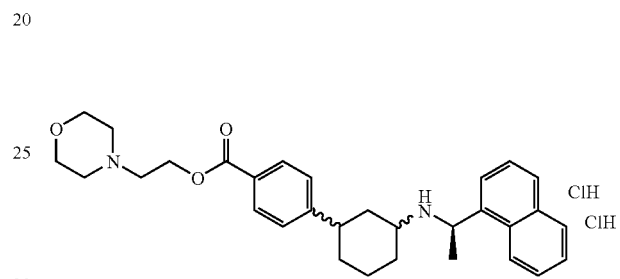

General procedure N was followed using N-(2-hydroxyethyl)-morpholine. Chromatography (CH$_2$Cl$_2$-MeOH 100:0 to 97:3) afforded an oil, which was dissolved in ethyl acetate and treated with HCl in dioxane (4 M) and diethyl ether. The precipitate was filtered to afford the title compound. $^{13}$C NMR (75 MHz, DMSO) δ 165.07, 150.89, 133.85, 133.32, 130.24, 129.60, 128.92, 128.84, 126.99, 126.89, 126.09, 125.50, 124.80, 122.29, 63.07, 58.87, 54.40, 51.88, 51.25, 50.42, 35.91, 33.45, 30.81, 25.66, 20.94, 19.28.

Example 249

4-[3-((R)-1-Naphthalen-1-yl-ethylamino)-cyclohexyl]-benzoic acid 2-(2-methoxy-ethoxy)-ethyl ester hydrochloride (Compound 1287)

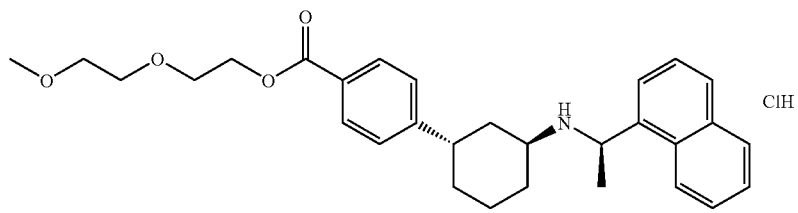 [SMILES: COCCOCCOC(=O)c1ccc([C@H]2CCC[C@H](N[C@H](C)c3cccc4ccccc34)C2)cc1 ; Cl]

General procedure N was followed using diethylene glycol monomethyl ether. Chromatography (CH$_2$Cl$_2$-MeOH 100:0 to 80:20) afforded an oil, which was dissolved in ethyl acetate and treated with HCl in dioxane (4 M) and diethyl ether. The precipitate was filtered to afford the title compound. $^1$H NMR (300 MHz, DMSO) δ 9.54 (br m, 2H), 8.35 (d, 1H), 8.20 (d, 1H), 8.03-7.94 (m, 2H), 7.85 (d, 2H), 7.60 (dt, 3H), 7.32 (d, 2H), 5.56-5.42 (m, 1H), 4.41-4.34 (m, 2H), 3.78-3.70 (m, 2H), 3.59 (dd, 2H), 3.46 (dd, 2H), 3.36-3.26 (m, 1H), 3.24 (s, 3H), 3.19-3.07 (m, 1H), 2.12-1.37 (m, 11H).

Example 250

4-[3-((R)-1-Naphthalen-1-yl-ethylamino)-cyclohexyl]-benzoic acid 2-[2-(2-methoxy-ethoxy)-ethoxy]-ethyl ester hydrochloride (Compound 1288)

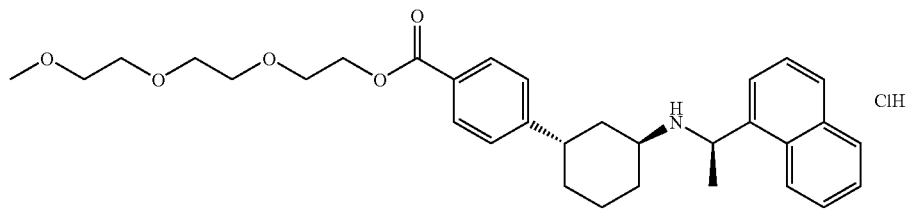 [SMILES: COCCOCCOCCOC(=O)c1ccc([C@H]2CCC[C@H](N[C@H](C)c3cccc4ccccc34)C2)cc1 ; Cl]

General procedure N was followed using triethylene glycol monomethyl ether. Chromatography (CH$_2$Cl$_2$-MeOH 100:0 to 80:20) afforded an oil, which was dissolved in ethyl acetate and treated with HCl in dioxane (4 M) and diethyl ether. The precipitate was filtered to afford the title compound. $^1$H NMR (300 MHz, DMSO) δ 9.48 (s, 2H), 8.35 (d, 1H), 8.17 (d, 1H), 7.99 (t, 2H), 7.86 (d, 2H), 7.62 (dd, 3H), 7.31 (d, 2H), 5.57-5.42 (m, 1H), 4.42-4.33 (m, 2H), 3.78-3.70 (m, 2H), 3.62-3.56 (m, 2H), 3.55-3.47 (m, 4H), 3.45-3.36 (m, 2H), 3.33-3.26 (m, 1H), 3.20 (s, 3H), 3.18-3.08 (m, 1H), 2.11-1.37 (m, 11H).

Example 251

4-[3-((R)-1-Naphthalen-1-yl-ethylamino)-cyclohexyl]-benzoic acid 2-[2-(2-ethoxy-ethoxy)-ethoxy]-ethyl ester hydrochloride (Compound 1289)

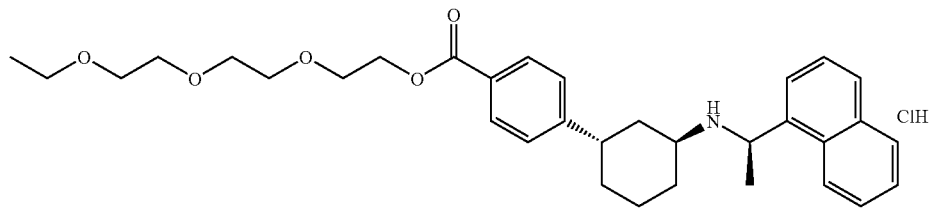 [SMILES: CCOCCOCCOCCOC(=O)c1ccc([C@H]2CCC[C@H](N[C@H](C)c3cccc4ccccc34)C2)cc1 ; Cl]

General procedure N was followed using triethylene glycol monoethyl ether. Chromatography (CH$_2$Cl$_2$-MeOH 100:0 to 80:20) afforded an oil, which was dissolved in ethyl acetate and treated with HCl in dioxane (4 M) and diethyl ether. The precipitate was filtered to afford the title compound. $^1$H NMR (300 MHz, DMSO) δ 9.47 (br s, 2H), 8.34 (d, 1H), 8.15 (d, 1H), 7.99 (t, 2H), 7.86 (d, 2H), 7.61 (dd, 3H), 7.31 (d, 2H), 5.48 (br s, 1H), 4.43-4.33 (m, 2H), 3.79-3.70 (m, 2H), 3.63-3.57 (m, 2H), 3.56-3.47 (m, 4H), 3.46-3.21 (m, 5H), 3.20-3.09 (m, 1H), 2.09-1.37 (m, 11H), 1.05 (t, 3H).

Example 252

4-[3-((R)-1-Naphthalen-1-yl-ethylamino)-cyclohexyl]-benzoic acid 2,3-dihydroxy-propyl ester hydrochloride (Compound 1290)

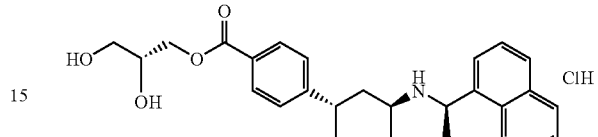

General procedure N was followed using D-α,β-isopropylidene glycerol. The intermediate acetonide was purified by chromatography (CH$_2$Cl$_2$-MeOH 100:0 to 80:20) to afford an oil, which was dissolved in EtOAc and treated with HCl in dioxane (4 M). After the addition of diethyl ether, the precipitate was filtered to afford the title compound. $^{13}$C NMR (75 MHz, DMSO) δ 165.53, 150.34, 133.82, 133.32, 130.24, 129.28, 128.91, 127.63, 127.01, 126.88, 126.09, 125.49, 124.70, 122.28, 69.28, 66.11, 62.51, 51.93, 50.42, 35.89, 33.40, 30.81, 25.80, 20.83, 19.29.

Example 253

4-[3-((R)-1-Naphthalen-1-yl-ethylamino)-cyclohexyl]-benzoic acid tetrahydro-furan-2-ylmethyl ester hydrochloride (Compound 1291)

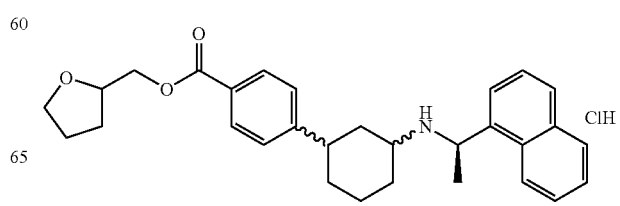

General procedure N was followed using tetrahydrofurfuryl alcohol. Chromatography (CH$_2$Cl$_2$-MeOH 100:0 to 80:20) afforded an oil, which was dissolved in ethyl acetate and treated with HCl in dioxane (4 M) and diethyl ether. The precipitate was filtered to afford the title compound. $^1$H NMR (300 MHz, DMSO) δ 9.45 (br s, 2H), 8.35 (d, 1H), 8.16 (d, 1H), 7.99 (t, 2H), 7.85 (d, 2H), 7.61 (dt, 3H), 7.32 (d, 2H), 5.56-5.42 (m, 1H), 4.31-4.10 (m, 3H), 3.79 (dt, 1H), 3.73-3.63 (m, 1H), 3.36-3.21 (m, 1H), 3.20-3.08 (m, 1H), 2.12-1.37 (m, 15H).

General Procedure O

[Rh(R-BINAP)(nbd)]BF$_4$ or [Rh(S-BINAP)(nbd)]BF$_4$ (Tani, K.; Yamagata, T.; Akutagawa, S.; Kumobayashi, H.; Taketomi, T.; Takaya, H.; Miyashita, A.; Noyori, R.; Otsuka, S. *J. Am. Chem. Soc.* 1984, 106, 5208) (0.03 mmol) and arylboronic acid (1.5 mmol) were added to a 25 mL-flask containing a magnetic stirring bar and a septum inlet. The flask was flashed with argon and charged with aqueous 1,4-dioxane (6/1, 3 mL). Triethylamine (1.5 mmol) and 2-cyclopenten-1-one (1.0 mmol) were then added. The mixture was stirred for 6 h at 25° C. Brine was added, and the mixture was extracted with ethyl acetate. If necessary the product was purified by chromatography over silica gel.

Preparation 6:
3R-(4-Hydroxy-phenyl)-cyclopentanone

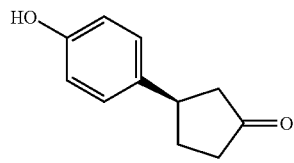 [SMILES: O=C1CC[C@@H](c2ccc(O)cc2)C1]

General procedure O was followed using 4-hydroxyphenylboronic acid and [Rh(R-BINAP)(nbd)]BF$_4$. $^1$H NMR (300 MHz, DMSO) δ 9.19 (s, 1H), 7.10 (d, 2H), 6.70 (d, 2H), 3.33-3.19 (m, 1H), 2.44 (d, 1H), 2.34-2.14 (m, 4H), 1.91-1.76 (m, 1H).

Example 254

4-[(1R,3S)-3-((R)-1-Naphthalen-1-yl-ethylamino)-cyclopentyl]-phenol (compound 1292)

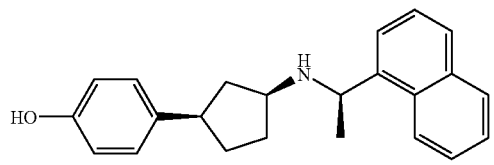 [SMILES: C[C@@H](N[C@H]1CC[C@@H](c2ccc(O)cc2)C1)c1cccc2ccccc12]

General procedure A was followed using 3-(4-hydroxyphenyl)-cyclopentanone (preparation 6). The two resulting diastereomers were separated by preparative chiral HPLC on a Chiralpak AD-H column 250×20 mm, 5 µm at 25° C., UV detection at 280 nm. Isocratic separation with n-heptane: ethanol:NEt$_3$:CH$_3$COOH (75:25:0.1:0:1); flow rate=17.0 mL/min. Compound 1292: RT=17.15. $^1$H NMR (300 MHz, DMSO) δ 8.34-8.24 (m, 1H), 7.96-7.87 (m, 1H), 7.82-7.68 (m, 2H), 7.57-7.43 (m, 3H), 7.03-6.94 (m, 2H), 6.67-6.59 (m, 2H), 4.67 (q, 1H), 3.05-2.93 (m, 1H), 2.80-2.66 (m, 1H), 2.13-1.99 (m, 1H), 1.88-1.52 (m, 4H), 1.41-1.22 (m, 4H).

General Procedure P:

4-[(1R,3S)-3-((R)-1-Naphthalen-1-yl-ethylamino)-cyclopentyl]-phenol (compound 1292) (0.1 mmol) was weighed into a vial and dissolved in 1 ml acetonitrile. To this solution was added alkylbromide or carbamoyl chloride (0.12-0.15 mmol) and K$_2$CO$_3$ (0.15-0.2 mmol). The vial was sealed and the reaction mixture was heated to 80° C. and stirred for 16 hours. Conversion was checked with LC/MS. The reaction mixture was filtered through a pad of celite and concentrated in vacuo. The crude product was purified by preparative HPLC.

Example 255

2-{4-[(1R,3S)-3-((R)-1-Naphthalen-1-yl-ethylamino)-cyclopentyl]-phenoxy}-butyric acid ethyl ester (Compound 1293)

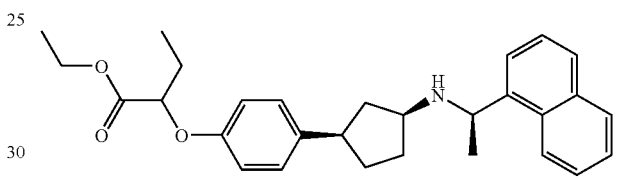

General procedure P was followed using 2-bromo-butanoic acid ethyl ester as alkylbromide. Mixture of 2 isomers. $^1$H NMR (300 MHz, DMSO) δ 8.33-8.25 (m, 1H), 7.91 (dd, 1H), 7.77 (d, 1H), 7.72 (d, 1H), 7.56-7.44 (m, 3H), 7.11 (d, 2H), 6.75 (d, 2H), 4.71-4.61 (m, 2H), 4.13 (q, 2H), 3.05-2.93 (m, 1H), 2.85-2.70 (m, 1H), 2.17-2.01 (m, 1H), 1.93-1.55 (m, 7H), 1.41-1.26 (m, 4H), 1.18 (t, 3H), 0.96 (t, 3H).

Example 256

2-{4-[(1R,3S)-3-((R)-1-Naphthalen-1-yl-ethylamino)-cyclopentyl]-phenoxy}-butyric acid (Compound 1294)

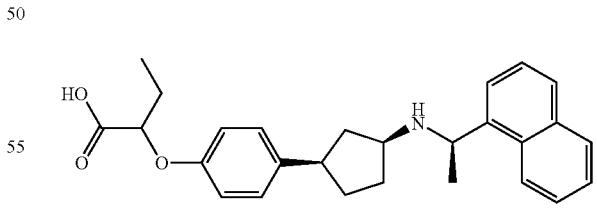

General procedure J was followed using 2-{4-[3-(1-naphthalen-1-yl-ethylamino)-cyclopentyl]-phenoxy}-butyric acid ethyl ester. Mixture of 2 isomers. $^1$H NMR (300 MHz, DMSO) δ 8.25 (d, 1H), 8.00-7.93 (m, 1H), 7.87 (t, 2H), 7.63-7.48 (m, 3H), 7.09-7.00 (m, 1H), 6.97 (d, 1H), 6.75 (dd, 2H), 5.12-4.98 (m, 1H), 4.42-4.33 (m, 1H), 3.22-3.06 (m, 1H), 2.83-2.65 (m, 1H), 2.22-2.06 (m, 1H), 2.03-1.42 (m, 10H), 0.97 (t, 3H).

Example 257

2-{4-[(1R,3S)-3-((R)-1-Naphthalen-1-yl-ethyl-amino)-cyclopentyl]-phenoxy}-propionic acid (Compound 1295)

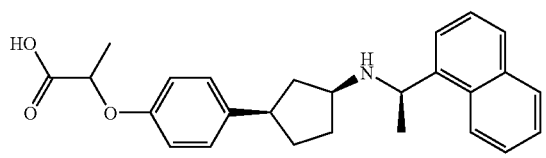 [SMILES: CC(Oc1ccc([C@@H]2CC[C@H](N[C@H](C)c3cccc4ccccc34)C2)cc1)C(=O)O]

General procedure P was followed using ethyl 2-bromopropionate as alkylbromide. The intermediate ester was hydrolyzed following general procedure J. Mixture of 2 isomers. $^1$H NMR (300 MHz, DMSO) δ 8.24 (d, 1H), 8.02-7.74 (m, 3H), 7.63-7.44 (m, 3H), 7.00 (dd, 2H), 6.82-6.64 (m, 2H), 5.05-4.88 (m, 1H), 4.60-4.44 (m, 1H), 3.15-2.96 (m, 1H), 2.82-2.63 (m, 1H), 2.20-2.02 (m, 1H), 1.96-1.28 (m, 11H).

Example 258

3-{4-[(1R,3S)-3-((R)-1-Naphthalen-1-yl-ethyl-amino)-cyclopentyl]-phenoxy}-dihydro-furan-2-one (Compound 1296)

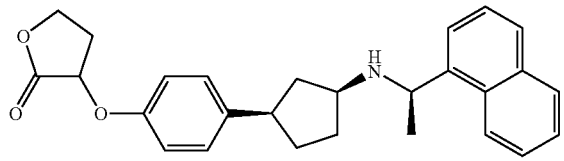 [SMILES: C[C@@H](N[C@H]1CC[C@@H](c2ccc(OC3CCOC3=O)cc2)C1)c1cccc2ccccc12]

General procedure P was followed using α-bromo-butyrolactone as alkylbromide.
Mixture of 2 isomers. $^1$H NMR (300 MHz, DMSO) δ 8.29 (d, 1H), 7.95 (dd, 1H), 7.85 (d, 1H), 7.80-7.75 (m, 1H), 7.62-7.47 (m, 3H), 7.21-7.11 (m, 2H), 6.99-6.90 (m, 2H), 5.26 (dd, 1H), 4.87 (q, 1H), 4.42 (td, 1H), 4.34-4.22 (m, 1H), 3.17 (dq, 1H), 2.92-2.67 (m, 2H), 2.21 (ddt, 2H), 1.96-1.60 (m, 4H), 1.55-1.40 (m, 4H).

Example 259

(S)-{3R-[4-(2-Ethoxy-ethoxy)-phenyl]-cyclopentyl}-((R)-1-naphthalen-1-yl-ethyl)-amine (Compound 1297)

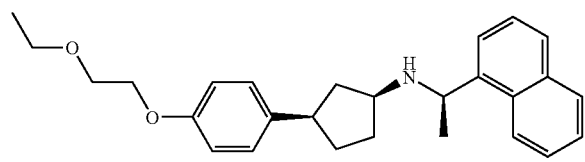 [SMILES: CCOCCOc1ccc([C@@H]2CC[C@H](N[C@H](C)c3cccc4ccccc34)C2)cc1]

General procedure P was followed using 2-ethoxy-ethylbromide as alkylbromide. $^1$H NMR (300 MHz, DMSO) δ 8.33-8.25 (m, 1H), 7.98-7.92 (m, 1H), 7.85 (d, 1H), 7.82-7.76 (m, 1H), 7.60-7.48 (m, 3H), 7.15-7.07 (m, 2H), 6.87-6.79 (m, 2H), 4.89 (q, 1H), 4.02 (dd, 2H), 3.70-3.63 (m, 2H), 3.48 (q, 2H), 3.24-3.11 (m, 1H), 2.89-2.72 (m, 1H), 2.24-2.13 (m, 1H), 1.92-1.59 (m, 4H), 1.55-1.41 (m, 4H), 1.12 (t, 3H).

Example 260

3-{4-[(1R,3S)-3-((R)-1-Naphthalen-1-yl-ethyl-amino)-cyclopentyl]-phenoxy}-propionic acid ethyl ester (Compound 1298)

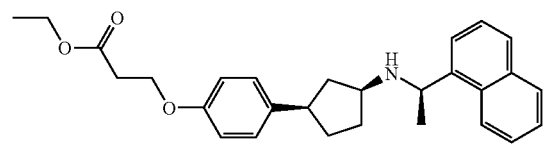 [SMILES: CCOC(=O)CCOc1ccc([C@@H]2CC[C@H](N[C@H](C)c3cccc4ccccc34)C2)cc1]

General procedure P was followed using ethyl 3-bromopropionate as alkylbromide. $^1$H NMR (300 MHz, DMSO) δ 8.29 (d, 1H), 7.94 (dd, 1H), 7.82 (d, 1H), 7.77-7.72 (m, 1H), 7.59-7.47 (m, 3H), 7.11 (d, 2H), 6.82 (d, 2H), 4.79 (q, 1H), 4.14 (t, 2H), 4.09 (q, 3H), 3.17-3.04 (m, 1H), 2.88-2.76 (m, 1H), 2.73 (t, 2H), 2.21-2.08 (m, 1H), 1.92-1.57 (m, 4H), 1.49-1.34 (m, 4H), 1.18 (t, 3H).

Example 261

4-{4-[(1R,3S)-3-((R)-1-Naphthalen-1-yl-ethyl-amino)-cyclopentyl]-phenoxymethyl}-benzonitrile (Compound 1299)

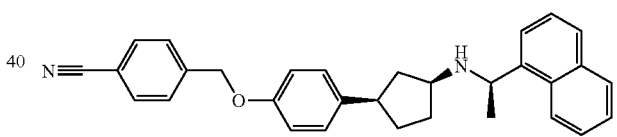

General procedure P was followed using 4-cyano-benzylbromide as alkylbromide. $^1$H NMR (300 MHz, DMSO) δ 8.29 (d, 1H), 7.93 (dd, 1H), 7.89-7.78 (m, 3H), 7.75 (d, 1H), 7.62 (d, 2H), 7.58-7.46 (m, 3H), 7.13 (d, 2H), 6.90 (d, 2H), 5.18 (s, 2H), 4.78 (q, 1H), 3.16-3.03 (m, 1H), 2.89-2.71 (m, 1H), 2.19-2.07 (m, 1H), 1.91-1.57 (m, 4H), 1.47-1.33 (m, 4H).

Example 262

(S)—((R)-1-Naphthalen-1-yl-ethyl)-{3R-[4-(pyridin-3-ylmethoxy)-phenyl]-cyclopentyl}-amine (Compound 1300)

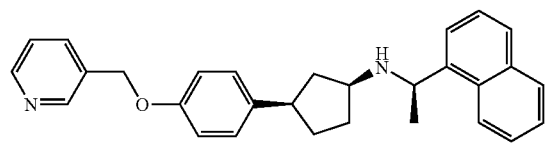 [SMILES: C[C@@H](N[C@H]1CC[C@@H](c2ccc(OCc3cccnc3)cc2)C1)c1cccc2ccccc12]

General procedure P was followed using 3-(bromomethyl)pyridine hydrobromide as alkylbromide. ¹H NMR (300 MHz, DMSO) δ 8.65 (d, 1H), 8.53 (dd, 1H), 8.29 (d, 1H), 7.97-7.90 (m, 1H), 7.88-7.79 (m, 2H), 7.75 (d, 1H), 7.59-7.47 (m, 3H), 7.44-7.38 (m, 1H), 7.14 (d, 2H), 6.93 (d, 2H), 5.10 (s, 2H), 4.79 (q, 1H), 3.16-3.04 (m, 1H), 2.89-2.71 (m, 1H), 2.21-2.08 (m, 1H), 1.91-1.56 (m, 4H), 1.48-1.34 (m, 4H).

Example 263

(S)—((R)-1-Naphthalen-1-yl-ethyl)-{3R-[4-(2-pyrazol-1-yl-ethoxy)-phenyl]-cyclopentyl}-amine (Compound 1301)

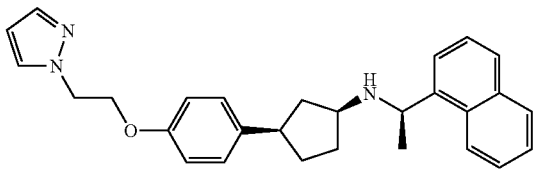 [SMILES: C[C@@H](N[C@H]1CC[C@@H](c2ccc(OCCn3cccn3)cc2)C1)c1cccc2ccccc12]

General procedure P was followed using 1-(2-bromoethyl)-1H-pyrrazole as alkylbromide. ¹H NMR (300 MHz, DMSO) δ 8.28 (d, 1H), 7.94 (dd, 1H), 7.82 (d, 1H), 7.75 (dd, 2H), 7.59-7.47 (m, 3H), 7.46-7.43 (m, 1H), 7.10 (d, 2H), 6.79 (d, 2H), 6.23 (t, 1H), 4.81 (q, 1H), 4.46 (t, 2H), 4.27 (t, 2H), 3.19-3.05 (m, 1H), 2.88-2.70 (m, 1H), 2.21-2.08 (m, 1H), 1.92-1.55 (m, 4H), 1.49-1.32 (m, 4H).

Example 264

(S)-(3R-{4-[2-(1H-Indol-3-yl)-ethoxy]-phenyl}-cyclopentyl)-((R)-1-naphthalen-1-yl-ethyl)-amine (Compound 1302)

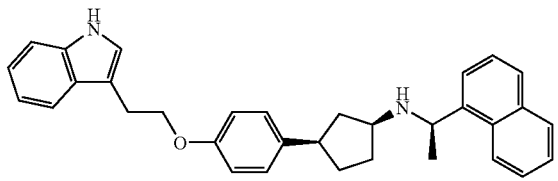 [SMILES: C[C@@H](N[C@H]1CC[C@@H](c2ccc(OCCc3c[nH]c4ccccc34)cc2)C1)c1cccc2ccccc12]

General procedure P was followed using 3-(2-bromoethyl)-indole as alkylbromide. ¹H NMR (300 MHz, DMSO) δ 10.86 (s, 1H), 8.29 (d, 1H), 7.97-7.91 (m, 1H), 7.82 (d, 1H), 7.75 (d, 1H), 7.61-7.46 (m, 4H), 7.34 (d, 1H), 7.23 (d, 1H), 7.15-6.94 (m, 4H), 6.85 (d, 2H), 4.81 (q, 1H), 4.16 (t, 2H), 3.17-3.06 (m, 3H), 2.88-2.71 (m, 1H), 2.21-2.09 (m, 1H), 1.92-1.56 (m, 4H), 1.49-1.35 (m, 4H).

Example 265

2-Methyl-2-{4-[(1R,3S)-3-((R)-1-naphthalen-1-yl-ethylamino)-cyclopentyl]-phenoxy}-propionic acid hydrochloride (Compound 1303)

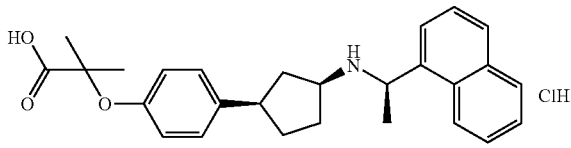 [SMILES: C[C@@H](N[C@H]1CC[C@@H](c2ccc(OC(C)(C)C(=O)O)cc2)C1)c1cccc2ccccc12 ; Cl]

General procedure P was followed using ethyl 2-bromo-2-methylpropionate as alkylbromide. The intermediate ester was hydrolyzed following general procedure J to the neutral acid. The neutral acid was dissolved in ethyl acetate and treated with HCl in dioxane (4 M) and diethyl ether. The precipitate was filtered to afford the title compound. ¹H NMR (300 MHz, DMSO) δ 12.96 (br s, 1H), 10.18-10.02 (br s, 1H), 9.49-9.33 (br s, 1H), 8.30 (d, 1H), 8.08-7.94 (m, 3H), 7.69-7.54 (m, 3H), 7.12 (d, 2H), 6.75 (d, 2H), 5.38-5.24 (m, 1H), 3.53-3.43 (m, 1H), 2.98-2.79 (m, 1H), 2.46-2.32 (m, 1H), 2.20-2.04 (m, 1H), 1.97-1.65 (m, 7H), 1.47 (s, 6H).

Example 266

4-Hydroxy-2-{4-[(1R,3S)-3-((R)-1-naphthalen-1-yl-ethylamino)-cyclopentyl]-phenoxy}-butyric acid (Compound 1304)

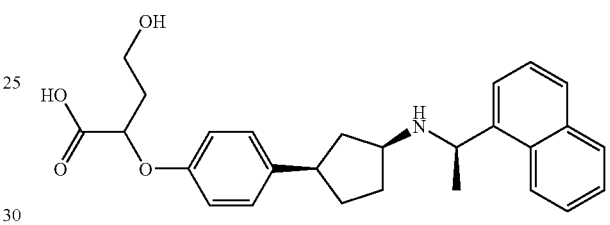

General procedure J was followed using 3-{4-[3-(1-naphthalen-1-yl-ethylamino)-cyclopentyl]-phenoxy}-dihydrofuran-2-one (compound 1296). Mixture of 2 isomers. ¹H NMR (300 MHz, DMSO) δ 8.24 (d, 1H), 8.02-7.94 (m, 1H), 7.93-7.82 (m, 2H), 7.63-7.49 (m, 3H), 7.08-6.90 (m, 2H), 6.80-6.67 (m, 2H), 5.16-5.02 (m, 1H), 4.58-4.47 (m, 1H), 3.66-3.50 (m, 2H), 3.22-3.08 (m, 2H), 2.83-2.65 (m, 1H), 2.22-1.84 (m, 4H), 1.81-1.44 (m, 7H).

Example 267

2-{4-[(1R,3S)-3-((R)-1-Naphthalen-1-yl-ethylamino)-cyclopentyl]-phenoxy}-propionic acid hydrochloride (Compound 1305)

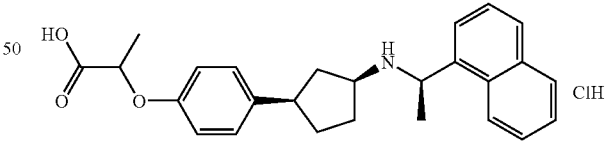

General procedure P was followed using ethyl 2-bromopropioniate as alkylbromide. The intermediate ester was hydrolyzed following general procedure J to the neutral acid. The neutral acid was dissolved in ethyl acetate and treated with HCl in dioxane (4 M) and diethyl ether. The precipitate was filtered to afford the title compound as a mixture of two isomers. ¹H NMR (300 MHz, DMSO) δ 9.65 (br s, 1H), 9.27 (br s, 1H), 8.30 (d, 1H), 8.02 (t, 2H), 7.93 (d, 1H), 7.71-7.56 (m, 3H), 7.13 (d, 2H), 6.80 (d, 2H), 5.40-5.25 (m, 1H), 4.83-4.71 (m, 1H), 3.63-3.45 (m, 1H), 2.92 (s, 1H), 2.53-2.35 (m, 1H), 2.14-1.85 (m, 3H), 1.73 (t, 5H), 1.47 (d, 3H).

Example 268

{4-[(1R,3S)-3-((R)-1-Naphthalen-1-yl-ethylamino)-cyclopentyl]-phenoxy}-phenyl-acetic acid hydrochloride (Compound 1306)

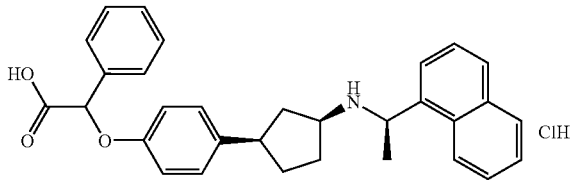 [SMILES: C[C@@H](N[C@H]1CC[C@@H](c2ccc(OC(C(=O)O)c3ccccc3)cc2)C1)c1cccc2ccccc12 ; Cl]

General procedure P was followed using ethyl bromophenylacetate as alkylbromide. The intermediate ester was hydrolyzed using general procedure J. The product was dissolved in ethyl acetate and treated with HCl in dioxane (4 M) and diethyl ether. The precipitate was filtered to afford the title compound as a mixture of 2 isomers. $^1$H NMR (300 MHz, DMSO) δ 9.65 (br s, 1H), 9.27 (br s, 1H), 8.30 (d, 1H), 8.07-7.97 (m, 2H), 7.93 (d, 1H), 7.70-7.56 (m, 3H), 7.13 (d, 2H), 6.80 (d, 2H), 5.39-5.26 (m, 1H), 4.75 (q, 1H), 3.62-3.47 (m, 1H), 2.92 (s, 1H), 2.51-2.36 (m, 1H), 2.13-1.85 (m, 3H), 1.80-1.63 (m, 5H), 1.47 (d, 3H).

Example 269

2-Methyl-1-{4-[(1R,3S)-3-((R)-1-naphthalen-1-yl-ethylamino)-cyclopentyl]-phenoxy}-propan-2-ol (Compound 1307)

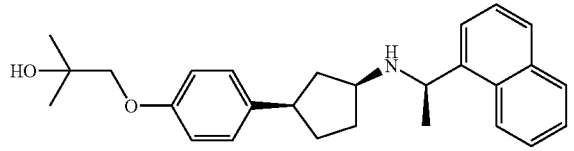 [SMILES: C[C@@H](N[C@H]1CC[C@@H](c2ccc(OCC(C)(C)O)cc2)C1)c1cccc2ccccc12]

To a solution of {4-[(1R,3S)-3-((R)-1-naphthalen-1-yl-ethylamino)-cyclopentyl]-phenoxy}-acetic acid ethyl ester (compound 1180) (150 mg, 360 μmol) in dry THF (2 mL) was added methylmagnesium bromide (3.0 M in THF, 0.6 mL) at −78° C. After stirring for 5 hours at this −78-−40° C., the reaction mixture was quenched with aqueous NaHCO$_3$ and extracted with ethyl acetate. The organic fase was concentrated in vacuo and purified by HPLC to afford the title compound. $^{13}$C NMR (75 MHz, DMSO) δ 157.00, 141.09, 137.34, 133.38, 130.78, 128.60, 127.59, 126.74, 125.76, 125.53, 125.25, 123.13, 122.83, 114.20, 76.07, 68.52, 56.45, 51.23, 42.52, 41.92, 32.12, 31.41, 26.53, 23.65.

Example 270

3-{4-[(1R,3S)-3-((R)-1-Naphthalen-1-yl-ethylamino)-cyclopentyl]-phenoxymethyl}-pentan-3-ol (Compound 1308)

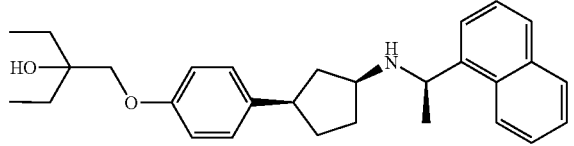 [SMILES: CCC(O)(CC)COc1ccc([C@@H]2CC[C@H](N[C@H](C)c3cccc4ccccc34)C2)cc1]

To a solution of {4-[(1R,3S)-3-((R)-1-naphthalen-1-yl-ethylamino)-cyclopentyl]-phenoxy}-acetic acid ethyl ester (compound 1180) (150 mg, 360 μmol) in dry THF (2 mL) was added ethylmagnesium bromide (1.0 M in THF, 718 μL) at −78° C. After stirring for 2.5 hours at this temperature, additional ethylmagnesium bromide was added (360 μL), and the reaction mixture was stirred for another hour before quenching with aqueous NaHCO$_3$ and extracting with ethyl acetate. The organic fase was concentrated in vacuo and purified by HPLC to afford the title compound. $^{13}$C NMR (75 MHz, DMSO) δ 156.92, 142.08, 137.61, 133.39, 130.88, 128.56, 127.60, 126.44, 125.59, 125.53, 125.12, 122.96, 122.91, 114.14, 72.12, 71.80, 56.60, 51.34, 42.54, 42.47, 32.21, 31.89, 28.68, 24.18, 7.40.

Example 271

Dimethyl-carbamic acid 4-[(1R,3S)-3-((R)-1-naphthalen-1-yl-ethylamino)-cyclopentyl]-phenyl ester (Compound 1309)

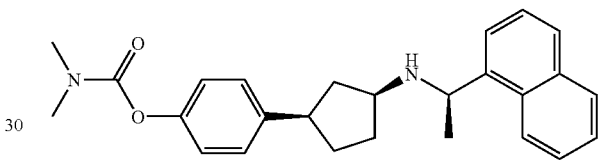

General procedure P was followed using N,N-dimethylcarbamoyl chloride. $^1$H NMR (300 MHz, DMSO) δ 8.30 (d, 1H), 7.91 (dd, 1H), 7.75 (dd, 2H), 7.57-7.43 (m, 3H), 7.21 (d, 2H), 6.97 (d, 2H), 4.67 (q, 1H), 3.02 (s, 3H), 2.89 (s, 4H), 2.18-2.06 (m, 1H), 1.93-1.58 (m, 4H), 1.47-1.30 (m, 4H). A signal (1H) is presumably hidden under the water signal at 3.32 ppm.

Example 272

3-Ethyl-1-{4-[(1S,3S)-3-((R)-1-naphthalen-1-yl-ethylamino)-cyclopentyl]-phenyl}-pentan-3-ol (Compound 1310)

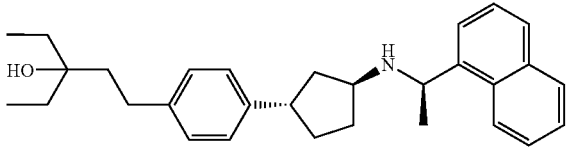 [SMILES: CCC(O)(CC)CCc1ccc([C@H]2CC[C@H](N[C@H](C)c3cccc4ccccc34)C2)cc1]

To a solution of 3-{4-[(1S,3S)-3-((R)-1-naphthalen-1-yl-ethylamino)-cyclopentyl]-phenyl}-propionic acid methyl ester (compound 1183) (150 mg) in dry THF (2 mL) was slowly added ethylmagnesium bromide (1.8 mL of a 1.0 M solution in THF) at −78° C. The reaction mixture was stirred for 5 hours while slowly warming to −40° C. Ethyl acetate was added to the mixture, and the product was purified by HPLC. $^1$H NMR (300 MHz, DMSO) δ 8.30 (d, 1H), 7.97-7.89 (m, 1H), 7.81 (d, 1H), 7.75 (d, 1H), 7.59-7.46 (m, 3H), 7.03 (s, 4H), 4.75 (q, 1H), 3.27-3.10 (m, 2H), 2.50-2.38 (m, 2H), 2.09-1.79 (m, 3H), 1.70-1.46 (m, 4H), 1.45-1.30 (m, 8H), 0.79 (t, 6H).

Example 273

2-Methyl-4-{4-[(1S,3S)-3-((R)-1-naphthalen-1-yl-ethylamino)-cyclopentyl]-phenyl}-butan-2-ol (Compound 1311)

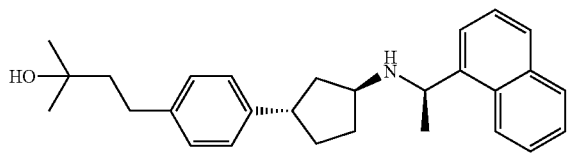 [SMILES: C[C@@H](N[C@H]1CC[C@H](c2ccc(CCC(C)(C)O)cc2)C1)c1cccc2ccccc12]

To a solution of 3-{4-[(3S)-3-((R)-1-naphthalen-1-yl-ethylamino)-cyclopentyl]-phenyl}-propionic acid methyl ester (compound 1183) (150 mg) in dry THF (2 mL) was added methyl magnesiumbromide (0.6 mL of a 3M solution in THF) at −78° C. The reaction mixture was stirred for 5 hours while slowly warming to −40° C. Ethyl acetate (0.5 mL) was added, and the mixture was purified by HPLC to afford the title compound. $^{13}$C NMR (75 MHz, DMSO) δ 142.76, 141.00, 140.11, 133.40, 130.77, 128.63, 127.90, 126.81, 126.63, 125.81, 125.54, 125.29, 123.19, 122.84, 68.54, 56.20, 50.83, 45.71, 42.42, 40.71, 33.17, 32.65, 29.68, 29.17, 23.61.

Example 274

3-{4-[(1R,3S)-3-((R)-1-Naphthalen-1-yl-ethylamino)-cyclopentyl]-phenoxy}-propane-1,2-diol (Compound 1312)

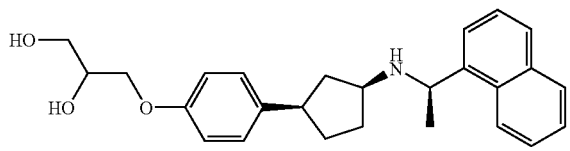 [SMILES: C[C@@H](N[C@H]1CC[C@@H](c2ccc(OCC(O)CO)cc2)C1)c1cccc2ccccc12]

General procedure P was followed using 3-bromo-propane-1,2-diol as alkylbromide. Compound 1312 (mixture of 2 isomers): LC-MS (method A): RT=2.44, [M+H]$^+$=406.5.

Example 275

(2-Fluoro-phenyl)-{4-[(1R,3S)-3-((R)-1-naphthalen-1-yl-ethylamino)-cyclopentyl]-phenoxy}-acetic acid hydrochloride (Compound 1313)

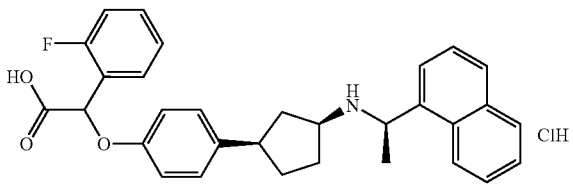 [SMILES: C[C@@H](N[C@H]1CC[C@@H](c2ccc(OC(C(=O)O)c3ccccc3F)cc2)C1)c1cccc2ccccc12 ; Cl]

General procedure P was followed using bromo-(2-fluoro-phenyl)-acetic acid methyl ester as alkylbromide. The intermediate ester was hydrolyzed following general procedure J to the neutral acid. The neutral acid was dissolved in ethyl acetate and treated with HCl in dioxane (4 M) and diethyl ether. The precipitate was filtered to afford the title compound as a mixture of 2 isomers. $^1$H NMR (300 MHz, DMSO) δ 8.29 (d, 1H), 8.12 (d, 1H), 8.04-7.94 (m, 2H), 7.67-7.50 (m, 4H), 7.48-7.36 (m, 1H), 7.30-7.19 (m, 2H), 7.14 (d, 2H), 6.88 (d, 2H), 5.89 (s, 1H), 5.35-5.22 (m, 1H), 4.53-4.42 (m, 1H), 2.94-2.79 (m, 1H), 2.41-2.09 (m, 2H), 1.91-1.67 (m, 7H).

Example 276

2-{4-[(1R,3S)-3-((R)-1-Naphthalen-1-yl-ethylamino)-cyclopentyl]-phenoxy}-ethanol formiate (Compound 1314)

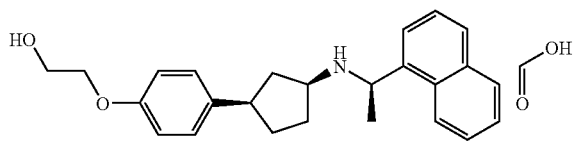

To a solution of {4-[3-((R)-1-naphthalen-1-yl-ethylamino)-cyclopentyl]-phenoxy}-acetic acid ethyl ester (compound 1180) (180 mg) in dry diethyl ether (3 mL) was added LiAlH$_4$ (0.52 mL of a 1M solution in THF) at 0° C. After 30 min, the reaction was quenched with water and purified by preparative HPLC to afford the title compound as an oil. $^1$H NMR (300 MHz, DMSO) δ 8.33-8.24 (m, 2H), 7.98-7.92 (m, 1H), 7.85 (d, 1H), 7.78 (d, 1H), 7.61-7.48 (m, 3H), 7.11 (d, 2H), 6.82 (d, 2H), 4.88 (q, 1H), 3.93 (t, 2H), 3.69 (t, 2H), 3.23-3.11 (m, 1H), 2.88-2.73 (m, 1H), 2.19 (dt, 1H), 1.92-1.59 (m, 4H), 1.55-1.40 (m, 4H).

Preparation 7: 4-(3-Oxo-cyclohexyl)-benzaldehyde

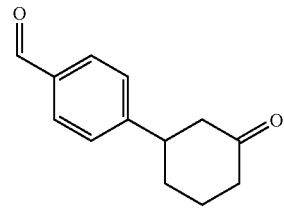 [SMILES: O=Cc1ccc(C2CCCC(=O)C2)cc1]

General procedure K was followed using 4-formylphenylboronic acid. $^{13}$C NMR (75 MHz, DMSO) δ 209.52, 192.53, 151.70, 134.67, 129.75, 127.46, 47.42, 43.72, 40.32, 31.66, 24.80.

General Procedure Q

To a solution of 4-(3-oxo-cyclohexyl)-benzaldehyde (0.082 mmol) in DCE (1 mL) were added an amine (165 μL of a 0.5 mM solution in DCE) and NaBH(OAc)$_3$ (0.24 mmol, 3 eq.). After shaking the reaction mixture overnight at r.t., (+)-(R)-1-naphthalen-1-yl-ethylamine (0.090 mmol) in 0.5 mL DCE was added, and shaking was continued overnight at r.t. Solvents were removed in vacuo. The residue was redissolved in DMSO and purified by preparative HPLC.

Example 277

(1-{4-[3-((R)-1-Naphthalen-1-yl-ethylamino)-cyclohexyl]-benzyl}-pyrrolidin-2-yl)-methanol (Compound 1315)

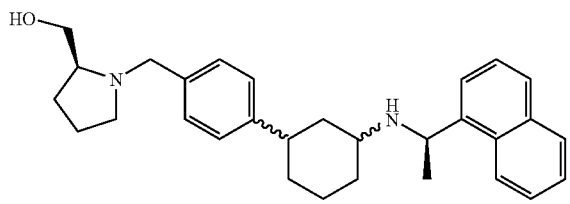 [SMILES: C[C@@H](NC1CCCC(c2ccc(CN3CCC[C@H]3CO)cc2)C1)c1cccc2ccccc12]

General procedure Q was followed using (S)-(+)-2-(hydroxymethyl)-pyrrolidine. LC-MS (method B): RT=3.67, [M+HCOO]⁻=487.3.

Example 278

1-{4-[3-((R)-1-Naphthalen-1-yl-ethylamino)-cyclohexyl]-benzyl}-pyrrolidin-3-ol (Compound 1316)

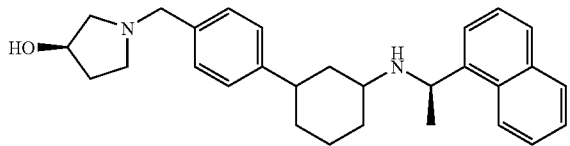 [SMILES: C[C@@H](NC1CCCC(c2ccc(CN3CC[C@@H](O)C3)cc2)C1)c1cccc2ccccc12]

General procedure Q was followed using (R)-3-hydroxypyrrolidine. LC-MS (method B): RT=3.67, [M+H]⁺=429.2.

Example 279

1-{4-[3-((R)-1-Naphthalen-1-yl-ethylamino)-cyclohexyl]-benzyl}-piperidine-3-carboxylic acid ethyl ester (Compound 1317)

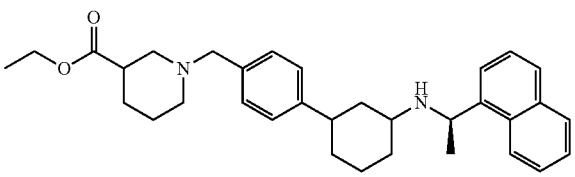 [SMILES: CCOC(=O)C1CCCN(Cc2ccc(C3CCCC(N[C@H](C)c4cccc5ccccc45)C3)cc2)C1]

General procedure Q was followed using piperidine-3-carboxylic acid ethyl ester. LC-MS (method B): RT=3.86, [M+H]⁺=499.3.

Example 280

[3-(4-{[Methyl-(tetrahydro-furan-2-ylmethyl)-amino]-methyl}-phenly)-cyclohexyl]-((R)-1-naphthalen-1-yl-ethyl)-amine (Compound 1318)

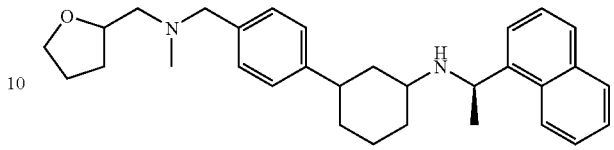

General procedure Q was followed using N-methyltetrahydrofurfurylamine. LC-MS (method B): RT=3.76, [M+H]⁺=457.3, Preparation 8: 3-[4-((1S)-3-Oxo-cyclopentyl)-phenyl]-propionic acid ethyl ester

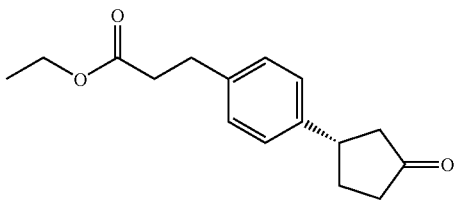 [SMILES: CCOC(=O)CCc1ccc([C@H]2CCC(=O)C2)cc1]

General procedure O was followed using [4-(2-ethoxycarbonylethyl)-phenyl]-boronic acid and [Rh(S-BINAP)(nbd)]BF₄. ¹H NMR (300 MHz, DMSO) δ 7.26-7.20 (m, 2H), 7.19-7.13 (m, 2H), 4.04 (q, 2H), 3.43-3.24 (m, 1H), 2.82 (t, 2H), 2.63-2.45 (m, 3H), 2.35-2.21 (m, 4H), 1.96-1.77 (m, 1H), 1.15 (t, 3H).

Preparation 9: 3-[4-((1S,3R)-3-Acetoxy-cyclopentyl)-phenyl]-propionic acid ethyl ester

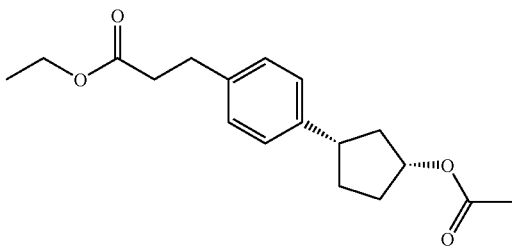 [SMILES: CCOC(=O)CCc1ccc([C@H]2CC[C@@H](OC(C)=O)C2)cc1]

To a solution of 3-[4-(3-oxo-cyclopentyl)-phenyl]-propionic acid ethyl ester (preparation 8) (26.2 g, 100 mmol) in ethanol (300 mL) was added NaBH₄ (5.7 g, 151 mmol) in portions. The mixture was stirred at r.t. for 1 hour, and then the solvent was removed in vacuo. Water was added to the residue and the mixture was extracted multiple times with dichloromethane. The combined organic extracts were dried over MgSO₄ and concentrated in vacuo. To the crude cyclopentanol (25.7 g, 98.0 mmol) in dry n-hexane (340 mL) were added vinyl acetate (340 mL, 50 eq.), molecular sieves (4 Å) and PPL (lipase from hog pancreas, EC 3.1.1.3, 30.1 U/mg, 20 g). The mixture was stirred under argon for 2 hours, filtered through Celite and concentrated under reduced pressure. Chromatography (EtOAc-PE 0:100 to 50:50) and collection of the less polar fractions afforded the title compound as an oil. ¹H NMR (300 MHz, DMSO) δ 7.20-7.09 (m, 4H), 5.16-5.06 (m, 1H), 4.04 (q, 2H), 3.09-2.94 (m, 1H), 2.80 (t, 2H), 2.58 (t, 2H), 2.52-2.39 (m, 1H), 2.04-1.51 (m, 8H), 1.15 (t, 3H).

Preparation 10: 3-[4-((1S,3R)-3-Hydroxy-cyclopentyl)-phenyl]-propionic acid ethyl ester

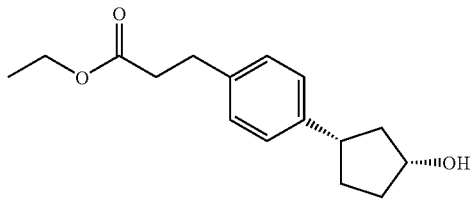 [SMILES: CCOC(=O)CCc1ccc([C@H]2CC[C@@H](O)C2)cc1]

To a solution of 3-[4-(3-acetoxy-cyclopentyl)-phenyl]-propionic acid ethyl ester (preparation 9) (23.1 g, 75.9 mmol) in dry ethanol (1.1 l) under argon was added K$_2$CO$_3$ (31.5 g, 228 mmol). The mixture was heated at 50-60° C. for 3 hours, then filtered through Celite and concentrated under reduced pressure. The residue was suspended in water and extracted with dichloromethane. The organic phase was dried over MgSO$_4$, filtered, and concentrated under reduced pressure. The crude product was used without further purification. $^1$H NMR (300 MHz, DMSO) δ 7.17 (d, 2H), 7.11 (d, 2H), 4.61-4.56 (m, 1H), 4.24-4.14 (m, 1H), 4.04 (q, 2H), 2.99-2.85 (m, 1H), 2.80 (t, 2H), 2.57 (t, 2H), 2.32-2.19 (m, 1H), 1.96-1.58 (m, 4H), 1.52-1.38 (m, 1H), 1.20-1.10 (m, 3H).

Preparation 11: 3-[4-((1S,3R)-3-Methanesulfonyloxy-cyclopentyl)-phenyl]-propionic acid ethyl ester

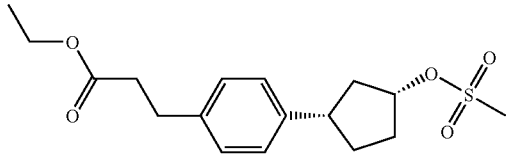

To a solution of 3-[4-(3-hydroxy-cyclopentyl)-phenyl]-propionic acid ethyl ester (preparation 10) (3.16 g, 12.1 mmol) in dry CH$_2$Cl$_2$ (30 mL) under argon were added NEt$_3$ (3.66 g, 36.1 mmol) and methanesulfonylchloride (1.38 g, 24.1 mmol) at 0° C. After stirring the resulting solution for 1 hour at 0° C., the reaction was quenched with water and extracted with CH$_2$Cl$_2$. The organic phase was dried over MgSO$_4$, filtered and concentrated under reduced pressure. The crude product was used immediately without further purification. $^1$H NMR (300 MHz, DMSO) δ 7.21-7.09 (m, 4H), 5.22-5.13 (m, 1H), 4.04 (q, 2H), 3.17 (s, 3H), 3.13-2.93 (m, 1H), 2.81 (t, 2H), 2.63-2.52 (m, 3H), 2.08-1.93 (m, 3H), 1.86-1.61 (m, 2H), 1.15 (t, 3H).

General Procedure R

To a suspension of 3-[4-(3-methanesulfonyloxy-cyclopentyl)-phenyl]-propionic acid ethyl ester (preparation 11) (1.20 mmol) in propionitrile (3 mL) were added K$_2$CO$_3$ (3.6 mmol) and amine (1.20 mmol), and the reaction mixture was heated at 80° C. overnight. The mixture was filtered, and the filtrate was concentrated under reduced pressure. The product was purified by preparative HPLC, 10→80% ethyl acetate in hexanes.

Example 281

3-(4-{(1S,3S)-3-[(R)-1-(4-Fluoro-3-methoxy-phenyl)-ethylamino]-cyclopentyl}-phenyl)-propionic acid ethyl ester (Compound 1319)

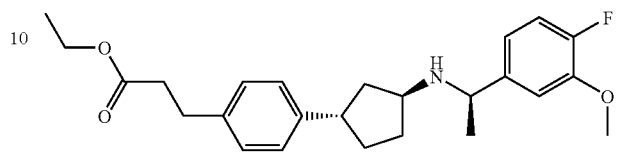

General procedure R was followed using 1-(4-fluoro-3-methoxy-phenyl)-ethylamine. $^1$H NMR (300 MHz, DMSO) δ 7.22 (dd, 1H), 7.10 (m, 5H), 6.94 (m, 1H), 4.03 (q, 2H), 3.85 (m, 4H), 3.15 (m, 2H), 2.78 (t, 2H), 2.56 (t, 2H), 1.99 (m, 2H), 1.78 (m, 1H), 1.70-1.35 (m, 3H), 1.30 (d, 3H), 1.14 (t, 3H).

Example 282

3-(4-{(1S,3S)-3-[(R)-1-(3-Cyano-phenyl)-ethylamino]-cyclopentyl}-phenyl)-propionic acid ethyl ester (Compound 1320)

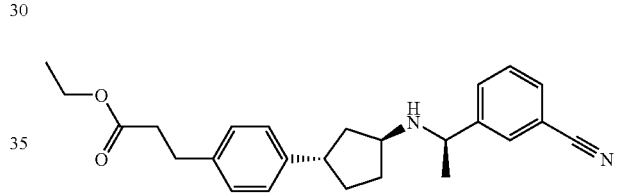

General procedure R was followed using 1-(3-cyano-phenyl)-ethylamine. $^1$H NMR (300 MHz, DMSO) δ 7.82 (s, 1H), 7.69 (m, 2H), 7.52 (t, 1H), 7.07 (m, 4H), 4.03 (q, 2H), 3.82 (q, 1H), 3.15 (m, 1H), 2.98 (m, 1H), 2.78 (t, 2H), 2.55 (t, 2H), 2.01 (m, 1H), 1.91 (m, 1H), 1.70 (ddd, 1H), 1.57 (m, 1H), 1.45 (m, 2H), 1.25 (d, 3H), 1.14 (t, 3H).

Example 283

3-{4-[(1S,3S)-3-((R)-1-Benzo[b]thiophen-3-yl-ethylamino)-cyclopentyl]-phenyl}-propionic acid ethyl ester (Compound 1321)

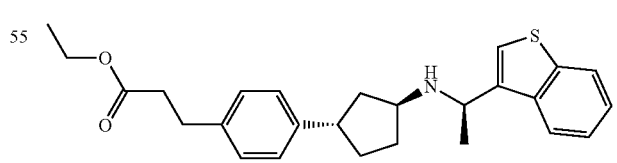

General procedure R was followed using 1-benzo[b]thiophen-3-yl-ethylamine. $^1$H NMR (300 MHz, DMSO) δ 8.03 (dd, 1H), 7.97 (dd, 1H), 7.65 (s, 1H), 7.38 (m, 2H), 7.08 (m, 4H), 4.36 (q, 1H), 4.03 (q, 2H), 3.28 (m, 1H), 3.17 (m, 1H), 2.77 (t, 2H), 2.55 (t, 2H), 2.00 (m, 2H), 1.84 (m, 1H), 1.59 (m, 2H), 1.45 (d, 3H), 1.40 (m, 1H), 1.14 (t, 3H).

Example 284

3-(4-{(1S,3S)-3-[1-((R)-2,3-Dihydro-benzo[1,4]dioxin-6-yl)-ethylamino]-cyclopentyl}-phenyl)-propionic acid ethyl ester (Compound 1322)

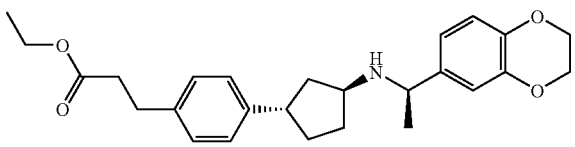 [SMILES: CCOC(=O)CCc1ccc([C@H]2CC[C@H](N[C@H](C)c3ccc4c(c3)OCCO4)C2)cc1]

General procedure R was followed using 1-(2,3-dihydro-benzo[1,4]dioxin-6-yl)-ethylamine. ¹H NMR (300 MHz, DMSO) δ 7.09 (2, 4H), 6.92 (s, 1H), 6.85 (d, 1H), 6.80 (d, 1H), 4.22 (s, 4H), 4.03 (q, 2H), 3.84 (q, 1H), 3.15 (m, 2H), 2.78 (t, 2H), 2.56 (t, 2H), 2.00 (m, 2H), 1.85 (m, 1H), 1.68 (m, 1H), 1.56 (m, 1H), 1.45 (m, 1H), 1.30 (d, 3H), 1.14 (t, 3H).

Example 285

3-{4-[(1S,3S)-3-((R)-1-Phenyl-ethylamino)-cyclopentyl]-phenyl}-propionic acid ethyl ester (Compound 1323)

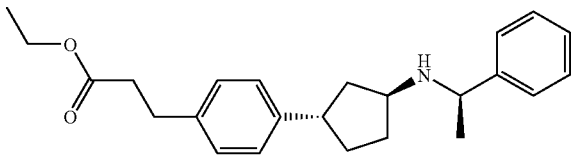 [SMILES: CCOC(=O)CCc1ccc([C@H]2CC[C@H](N[C@H](C)c3ccccc3)C2)cc1]

General procedure R was followed using 1-phenyl-ethylamine. ¹H NMR (300 MHz, DMSO) δ 7.3 (m, 4H), 7.22 (tt, 1H), 7.07 (dd, 4H), 4.03 (q, 2H), 3.82 (q, 1H), 3.15 (m, 1H), 3.05 (m, 1H), 2.77 (t, 2H), 2.55 (t, 2H), 2.01 (m, 1H), 1.93 (m, 1H), 1.76 (m, 1H), 1.65-1.35 (m, 3H), 1.29 (d, 3H), 1.14 (t, 3H).

Example 286

3-(4-{(1S,3S)-3-[(R)-1-(2,3-Dihydro-benzofuran-5-yl)-ethylamino]-cyclopentyl}-phenyl)-propionic acid ethyl ester (Compound 1324)

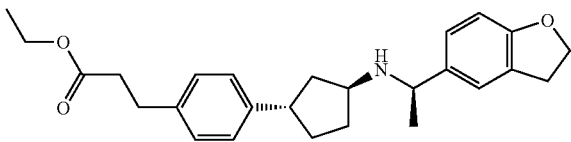 [SMILES: CCOC(=O)CCc1ccc([C@H]2CC[C@H](N[C@H](C)c3ccc4c(c3)CCO4)C2)cc1]

General procedure R was followed using 1-(2,3-dihydro-benzofuran-5-yl)-ethylamine. ¹H NMR (300 MHz, DMSO) δ 7.18 (d, 1H), 7.06 (m, 5H), 6.65 (d, 1H), 4.47 (t, 2H), 4.03 (q, 2H), 3.66 (q, 1H), 3.14 (m, 3H), 3.00 (m, 1H), 2.78 (t, 2H), 2.56 (t, 2H), 2.01 (m, 1H), 1.89 (m, 1H), 1.70 (m, 1H), 1.57 (m, 1H), 1.44 (m, 2H), 1.21 (d, 3H), 1.14 (t, 3H).

Example 287

3-(4-{(1S,3S)-3-[(R)-1-(1H-Indol-7-yl)-ethylamino]-cyclopentyl}-phenyl)-propionic acid hydroformiate (Compound 1325)

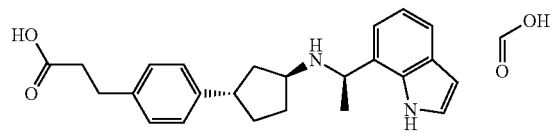

General procedure J was followed using ethyl 3-(4-{3-[1-(1H-indol-7-yl)-ethylamino]-cyclopentyl}-phenyl)-propionate. ¹H NMR (300 MHz, DMSO) δ 11.20 (s, 1H), 8.32 (s, 1H), 7.46 (d, 1H), 7.35 (m, 1H), 7.20 (d, 1H), 7.08 (d, 2H), 7.04 (d, 2H), 7.01 (t, 1H), 6.45 (dd, 1H), 4.54 (dd, 1H), 3.23 (m, 1H), 3.18 (m, 1H), 2.74 (t, 2H), 2.46 (t, 2H), 2.02 (m, 1H), 1.94 (m, 2H), 1.68 (m, 2H), 1.49 (d, 3H), 1.42 (d, 1H).

Example 288

3-(4-{(1S,3S)-3-[(R)-1-(2,3-Dihydro-benzo[1,4]dioxin-5-yl)-ethylamino]-cyclopentyl}-phenyl)-propionic acid hydroformiate (Compound 1326)

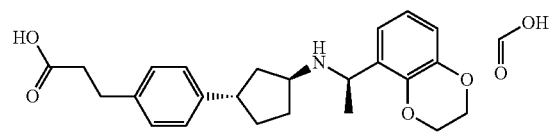

General procedure J was followed using ethyl 3-(4-{3-[1-(2,3-dihydro-benzo[1,4]dioxin-5-yl)-ethylamino]-cyclopentyl}-phenyl)-propionate. ¹H NMR (300 MHz, DMSO) δ 8.25 (s, 1H), 7.11 (d, 2H), 7.08 (d, 2H), 7.00 (dd, 1H), 6.83 (dd, 1H), 6.76 (dd, 1H), 4.28 (m, 2H), 4.23 (m, 2H), 3.20 (m, 1H), 3.16 (m, 1H), 2.75 (m, ²H), 2.47 (m, 2H), 2.02 (m, 1H), 1.96 (m, 1H), 1.88 (m, 1H), 1.71 (m, 1H), 1.59 (m, 1H), 1.46 (m, 1H), 1.33 (d, 3H).

Example 289

3-(4-{(1S,3S)-3-[(R)-1-(1H-Indol-4-yl)-ethylamino]-cyclopentyl}-phenyl)-propionic acid hydroformiate (Compound 1327)

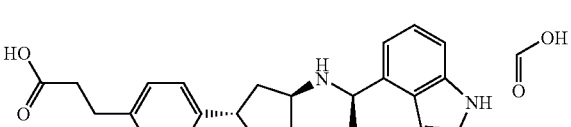

General procedure J was followed using ethyl 3-(4-{3-[1-(1H-indol-4-yl)-ethylamino]-cyclopentyl}-phenyl)-propionate. ¹H NMR (300 MHz, DMSO) δ 11.28 (s, 1H), 8.33 (s, 1H), 7.39 (m, 1H), 7.37 (d, 1H), 7.24 (d, 1H), 7.14 (m, 1H), 7.09 (d, 2H), 7.05 (d, 2H), 6.71 (m, 1H), 4.61 (q, 1H), 3.28 (m, 1H), 3.23 (m, 1H), 2.75 (t, 2H), 2.47 (t, 2H), 2.00 (m, 3H), 1.83 (m, 1H), 1.74 (m, 1H), 1.59 (d, 3H), 1.41 (m, 1H).

Example 290

3-(4-{(1S,3S)-3-[(R)-1-(3-Cyano-phenyl)-ethylamino]-cyclopentyl}-phenyl)-propionic acid, hydroformiate (Compound 1328)

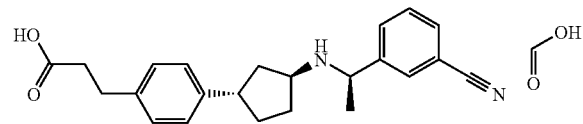

General procedure J was followed using ethyl 3-(4-{3-[1-(3-cyano-phenyl)-ethylamino]-cyclopentyl}-phenyl)-propionate. $^1$H NMR (300 MHz, DMSO) δ 8.18 (s, 1H), 7.86 (s, 1H), 7.74 (s, 1H), 7.71 (d, 1H), 7.55 (t, 1H), 7.09 (d, 2H), 7.06 (d, 2H), 3.92 (q, 1H), 3.15 (m, 1H), 3.04 (m, 1H), 2.74 (t, 2H), 2.48 (t, 2H), 2.02 (m, 1H), 1.94 (m, 1H), 1.75 (m, 1H), 1.62 (m, 1H), 1.52 (m, 1H), 1.43 (m, 1H), 1.30 (d, 3H).

Example 291

3-(4-{(1S,3S)-3-[(R)-1-(3-Pyrrolidin-1-yl-phenyl)-ethylamino]-cyclopentyl}-phenyl)-propionic acid hydroformiate (Compound 1329)

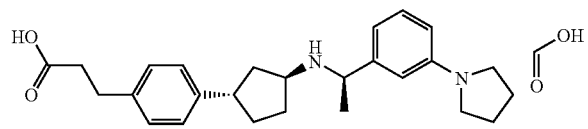

General procedure J was followed using ethyl 3-(4-{3-[1-(3-pyrrolidin-1-yl-phenyl)-ethylamino]-cyclopentyl}-phenyl)-propionate. $^1$H NMR (300 MHz, DMSO) δ8.26 (2, 1H), 7.07 (m, 4H), 6.60 (d, 1H), 6.55 (s, 1H), 6.40 (d, 1H), 3.77 (s, 1H), 3.21 (m, 4H), 3.15 (m, 1H), 3.11 (m, 1H), 2.74 (t, 2H), 2.47 (t, 2H), 2.01 (m, 1H), 1.94 (m, 5H), 1.79 (m, 1H), 1.64 (m, 1H), 1.53 (m, 1H), 1.43 (m, 1H), 1.29 (d, 3H).

Example 292

3-(4-{(1S,3S)-3-[(R)-1-(2,3-Dihydro-benzofuran-5-yl)-ethylamino]-cyclopentyl}-phenyl)-propionic acid hydroformiate (Compound 1330)

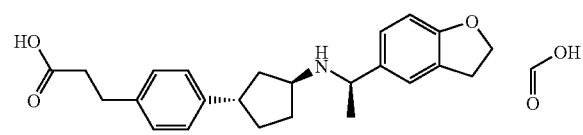

General procedure J was followed using ethyl 3-(4-{3-[1-(2,3-dihydro-benzofuran-5-yl)-ethylamino]-cyclopentyl}-phenyl)-propionate. $^1$H NMR (300 MHz, DMSO) δ8.23 (s, 1H), 7.24 (s, 1H), 7.08 (m, 5H), 6.69 (m, 1H), 4.49 (m, 2H), 3.79 (m, 1H), 3.16 (m, 3H), 3.09 (m, 1H), 2.75 (t, 2H), 2.47 (t, 2H), 2.00 (m, 1H), 1.95 (m, 1H), 1.77 (m, 1H), 1.63 (m, 1H), 1.52 (m, 1H), 1.44 (m, 1H), 1.27 (d, 3H).

Example 293

3-(4-{(1S,3S)-3-[(R)-1-(2,3-Dihydro-benzo[1,4]dioxin-6-yl)-ethylamino]-cyclopentyl}-phenyl)-propionic acid (Compound 1331)

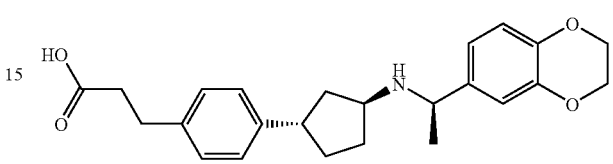

General procedure J was followed using ethyl 3-(4-{3-[1-(2,3-dihydro-benzo[1,4]dioxin-6-yl)-ethylamino]-cyclopentyl}-phenyl)-propionate. $^1$H NMR (300 MHz, DMSO) δ7.10 (m, 5H), 6.99 (d, 1H), 6.87 (d, 1H), 4.24 (m, 4H), 4.09 (m, 1H), 3.26 (m, 2H), 2.76 (t, 2H), 2.48 (t, 2H), 2.04 (m, 3H), 1.78 (m 2H), 1.47 (m, 4H).

Example 294

3-(4-{(1S,3S)-3-[(R)-1-(4-fluoro-3-methoxy-1-yl-phenyl)-ethylamino]-cyclopentyl}-phenyl)-propionic acid (Compound 1332)

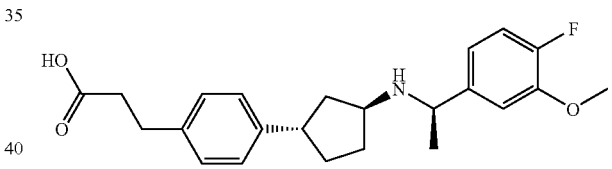

General procedure J was followed using ethyl 3-(4-{3-[1-(4-fluoro-3-methoxy-1-yl-phenyl)-ethylamino]-cyclopentyl}-phenyl)-propionate. $^1$H NMR (300 MHz, DMSO) δ 7.33 (d, 1H), 7.17 (dd, 1H), 7.08 (dd, 4H), 6.99 (m, 1H), 3.99 (m, 1H), 3.84 (s, 3H), 3.19 (m, 2H), 2.75 (t, 2H), 2.18 (t, 2H), 2.01 (m, 2H), 1.89 (m, 1H), 1.68 (m, 1H), 1.62 (m, 1H), 1.44 (m, 1H), 1.38 (d, 3H).

Example 295

3-{4-[(1S,3S)-3-((R)-1-Benzo[b]thiophen-3-yl-ethylamino)-cyclopentyl]-phenyl}-propionic acid hydrochloride (Compound 1333)

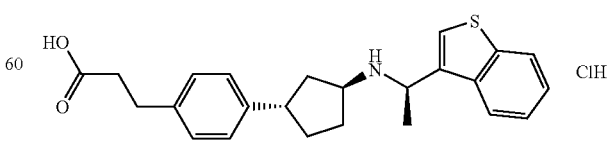

General procedure was followed using ethyl 3-{4-[3-(1-benzo[b]thiophen-3-yl-ethylamino)-cyclopentyl]-phenyl}-propionate. $^1$H NMR (300 MHz, DMSO) δ 8.29 (s, 1H), 8.12 (d, 1H), 8.07 (d, 1H), 7.47 (ddd, 2H), 7.10 (dd, 4H), 4.94 (q, 1H), 3.52 (m, 1H), 3.31 (m, 1H), 2.19 (t, 2H), 2.47 (t, 2H), 2.24 (m, 1H), 2.05 (m, 2H), 1.96 (m, 1H), 1.87 (m, 1H), 1.73 (d, 3H), 1.47 (m, 1H).

Example 296

3-{4-[(1S,3S)-3-((R)-1-Phenyl-ethylamino)-cyclopentyl]-phenyl}-propionic acid (Compound 1334)

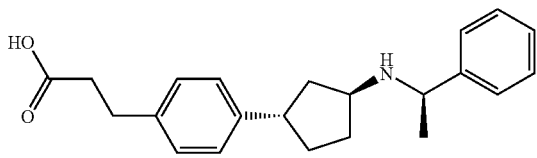 [SMILES: C[C@@H](N[C@H]1CC[C@H](c2ccc(CCC(=O)O)cc2)C1)c1ccccc1]

General procedure J was followed using ethyl 3-{4-[3-(1-phenyl-ethylamino)-cyclopentyl]-phenyl}-propionate. $^1$H NMR (300 MHz, DMSO) δ 7.94 (d, 2H), 7.37 (t, 2H), 7.29 (t, 1H), 7.09 (dd, 4H), 3.99 (m, 1H), 3.17 (m, 2H), 2.75 (t, 2H), 2.47 (t, 2H), 2.02 (m, 2H), 1.84 (m, 1H), 1.69 (m, 1H), 1.60 (m, 1H), 1.44 (m, 1H), 1.37 (bs, 3H).

Preparation 12: 4-(3S-Oxo-cyclopentyl)-benzoic acid ethyl ester

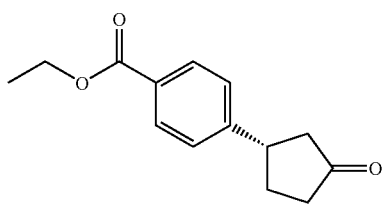 [SMILES: CCOC(=O)c1ccc([C@H]2CCC(=O)C2)cc1]

General procedure O was followed using 4-ethoxycarbonylphenylboronic acid and [Rh(S-BINAP)(nbd)]BF$_4$. $^1$H NMR (300 MHz, CDCl3) δ 8.05-7.98 (m, 2H), 7.36-7.29 (m, 2H), 4.38 (q, 2H), 3.55-3.40 (m, 1H), 2.75-2.63 (m, 1H), 2.55-2.41 (m, 2H), 2.41-2.25 (m, 2H), 2.08-1.92 (m, 1H), 1.39 (t, 3H).

Example 297

4-[3-((R)-1-Naphthalen-1-yl-ethylamino)-cyclopentyl]-benzoic acid ethyl ester (Compound 1335/1336)

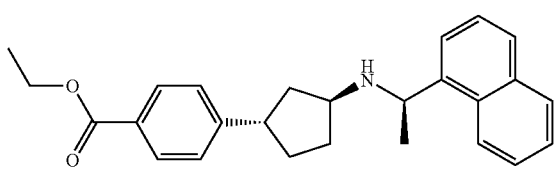

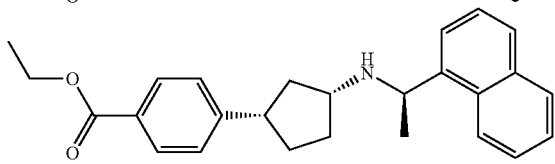

General procedure A was followed using 4-(3S-oxo-cyclopentyl)-benzoic acid ethyl ester (preparation 12) and (+)-(R)-1-naphthalen-1-yl-ethylamine. The two resulting diastereomers were separated by preparative chiral HPLC on a Chiralpak AD-H column 250×20 mm, 5 μm at 25° C., UV detection at 280 nm. Isocratic separation with n-heptane:ethanol:NEt$_3$:CH$_3$COOH (75:25:0.1:0.1); flow rate=17.0 mL/min. Compound 1335: RT=8.82. $^1$H NMR (300 MHz, DMSO) δ 8.29 (d, 1H), 7.95-7.89 (m, 1H), 7.86 (d, 2H), 7.82-7.70 (m, 2H), 7.55-7.44 (m, 3H), 7.39 (d, 2H), 4.65 (q, 1H), 4.29 (q, 2H), 3.11-2.88 (m, 2H), 2.41-2.27 (m, 1H), 2.26-2.14 (m, 1H), 1.98-1.42 (m, 5H), 1.37 (d, 3H), 1.31 (t, 3H). Compound 1336: RT=12.04. $^1$H NMR (300 MHz, DMSO) δ 8.30 (d, 1H), 7.95-7.88 (m, 1H), 7.85-7.69 (m, 4H), 7.56-7.45 (m, 3H), 7.28 (d, 2H), 4.64 (q, 1H), 4.27 (t, 2H), 3.35-3.23 (m, 1H), 3.21-3.11 (m, 1H), 2.33-2.20 (m, 1H), 2.17-2.02 (m, 1H), 1.98-1.79 (m, 2H), 1.71-1.41 (m, 3H), 1.38 (d, 3H), 1.29 (t, 3H).

Example 298

4-[3-((R)-1-Naphthalen-1-yl-ethylamino)-cyclopentyl]-benzoic acid (compound 1337)

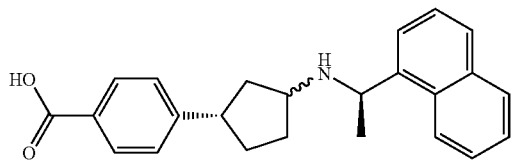 [SMILES: C[C@@H](NC1CC[C@H](c2ccc(C(=O)O)cc2)C1)c1cccc2ccccc12]

General procedure J was followed using 4-[3-(1-naphthalen-1-yl-ethylamino)-cyclopentyl]-benzoic acid ethyl ester (compound 1335). $^1$H NMR (500 MHz, DMSO) δ 8.30 (d, 1H), 8.24 (s, 1H), 7.94 (d, 1H), 7.82 (t, 3H), 7.76 (d, 1H), 7.52 (dt, 3H), 7.28 (d, 2H), 4.80 (q, 1H), 3.37-3.28 (m, 1H), 3.25-3.19 (m, 1H), 2.16-2.09 (m, 1H), 2.08-1.95 (m, 2H), 1.66-1.58 (m, 1H), 1.56-1.41 (m, 5H).

Example 299

4-[3-((R)-1-Naphthalen-1-yl-ethylamino)-cyclopentyl]-benzoic acid (compound 1338)

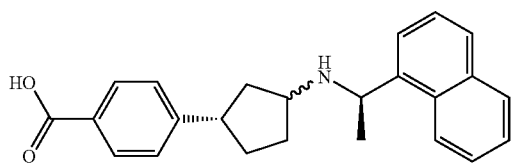 [SMILES: C[C@@H](NC1CC[C@H](c2ccc(C(=O)O)cc2)C1)c1cccc2ccccc12]

General procedure J was followed using 4-[3-(1-naphthalen-1-yl-ethylamino)-cyclopentyl]-benzoic acid ethyl ester (compound 1336). $^1$H NMR (500 MHz, DMSO) δ 8.31 (d, 1H), 8.23 (s, 1H), 7.94 (d, 1H), 7.85-7.79 (m, 3H), 7.77 (d, 1H), 7.58-7.50 (m, 3H), 7.26 (d, 2H), 4.81 (q, 1H), 3.35-3.23 (m, 2H), 2.13-2.05 (m, 1H), 1.97-1.89 (m, 2H), 1.76-1.63 (m, 2H), 1.52-1.42 (m, 4H).

Example 300

3-{4-[3-((R)-1-Naphthalen-1-yl-ethylamino)-cyclopentyl]-benzoylamino}-propionic acid methyl ester (Compound 1339)

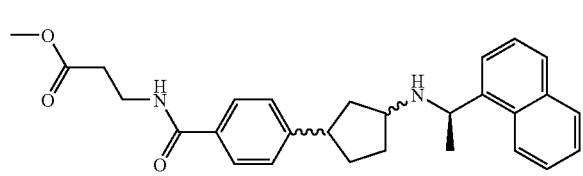 [SMILES: COC(=O)CCNC(=O)c1ccc(C2CCC(N[C@H](C)c3cccc4ccccc34)C2)cc1]

To a solution of 4-[3-(1-naphthalen-1-yl-ethylamino)-cyclopentyl]-benzoic acid (compound 1338) (100 mg) in DMF (1 mL) was added CDI (53 mg) and DIPEA (33 mg). After stirring the solution at r.t. for 4.5 h, β-alanine methyl ester hydrochloride (105 mg) was added. The mixture was stirred overnight, filtered and purified by preparative HPLC-MS (re-analysed by LC/MS method A). $^1$H NMR (300 MHz, DMSO) δ 8.41 (t, 1H), 8.30 (d, 1H), 7.95-7.87 (m, 1H), 7.81-7.64 (m, 4H), 7.57-7.45 (m, 3H), 7.21 (d, 2H), 4.65 (q, 1H), 3.59 (s, 3H), 3.46 (dd, 2H), 3.32-3.11 (m, 2H), 2.57 (t, 2H), 2.28 (br s, 1H), 2.15-2.01 (m, 1H), 1.98-1.77 (m, 2H), 1.70-1.41 (m, 3H), 1.38 (d, 3H).

Example 301

1-{4-[3-((R)-1-Naphthalen-1-yl-ethylamino)-cyclopentyl]-benzoyl}-piperidine-4-carboxylic acid hydrochloride (Compound 1340)

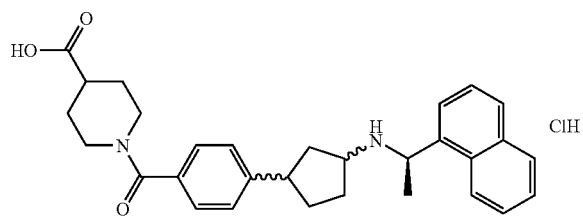 [SMILES: C[C@@H](NC1CCC(c2ccc(C(=O)N3CCC(C(=O)O)CC3)cc2)C1)c1cccc2ccccc12 ; Cl]

A solution of 4-[3-(1-naphthalen-1-yl-ethylamino)-cyclopentyl]-benzoic acid (compound 1338) (104 mg, 0.29 mmol), CDI (56 mg, 0.35 mmol) and DIPEA (50 µl, 0.29 mmol) in dry DMF (2 mL) was stirred at r.t. overnight. Piperidine-4-carboxylic acid ethyl ester (168 mg, 0.87 mmol) was added, and the resulting suspension was stirred at r.t. for 3 days. The reaction mixture was filtered, resuspended in DMSO and purified by preparative HPLC.

The intermediate ethyl ester was hydrolyzed to the title compound following general procedure J. $^{13}$C NMR (151 MHz, DMSO) δ 175.38, 168.84, 145.41, 133.95, 133.83, 133.33, 130.15, 128.90, 128.86, 126.96, 126.83, 126.78, 126.10, 125.54, 124.70, 122.35, 55.41, 50.32, 46.38, 42.61, 39.99, 36.66, 32.97, 29.96, 28.14, 20.50.

Example 302

3-{4-[3-((R)-1-Naphthalen-1-yl-ethylamino)-cyclopentyl]-benzoylamino}-propionic acid hydrochloride (Compound 1341)

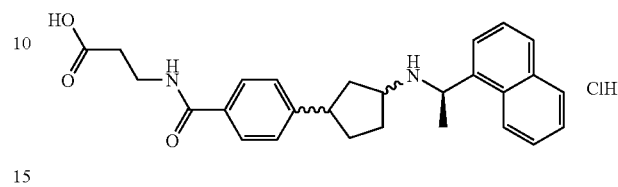

General procedure J was followed using 3-{4-[3-(1-naphthalen-1-yl-ethylamino)-cyclopentyl]-benzoylamino}-propionic acid methyl ester (compound 1339). $^1$H NMR (600 MHz, DMSO) δ 10.08 (br s, 2H), 8.48 (t, 1H), 8.33 (d, 1H), 8.05 (d, 1H), 8.01 (d, 1H), 7.96 (d, 1H), 7.74 (d, 2H), 7.60 (dt, 3H), 7.25 (d, 2H), 5.28-5.18 (m, 1H), 3.50-3.35 (m, 4H), 2.53-2.48 (m, 2H), 2.28-2.19 (m, 1H), 2.11-2.04 (m, 1H), 2.00-1.86 (m, 3H), 1.69 (d, 3H), 1.52-1.43 (m, 1H).

Preparation 13: 4-((1S,4S)-4-Acetoxy-cyclopent-2-enyloxy)-benzoic acid methyl ester

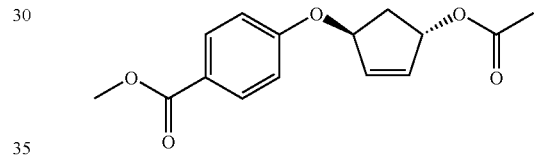

4-hydroxy-benzoic acid methyl ester (6 mmol), (1R,4S)-cis-4-acetoxy-2-cyclopenten-1-ol (4 mmol), and triphenyl phosphine (4.8 mmol) were placed in a flask under argon. Dry THF (15 ml) was added through a septum and the resulting solution cooled to 0° C. DIAD was added dropwise, neat, over a period of 20 min. The reaction mixture was left over night. THF was removed in vacuo and the residue was taken up in MTBE, 10 ml, and diluted to double volume with PE. After standing for 2 hours in the cold, a precipitate of triphenylphosphine oxide was removed on a filter. The filtrate was concentrated in vacuo and purified by chromatography in a gradient from 0 to 20% EtOAc in Heptane.

Preparation 14: 4-((1S,4S)-4-Hydroxy-cyclopent-2-enyloxy)-benzoic acid methyl ester

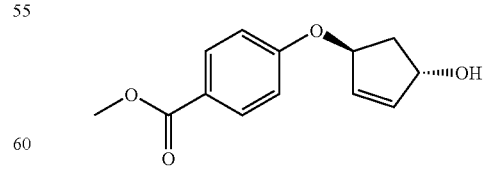

4-(4-Acetoxy-cyclopent-2-enyloxy)-benzoic acid methyl ester (preparation 13) (3 mmol) and potassium carbonate (3 mmol) were placed in a flask under argon. Dry methanol (15 ml) was added, and the resulting suspension heated at reflux for 1 hour, when TLC indicated complete conversion of substrate. The reaction mixture was concentrated in vacuo and purified by chromatography in a gradient from 0 to 90% EtOAc in Heptane. $^{13}$C NMR (75 MHz, CDCl3) δ 166.86, 161.87, 139.76, 133.01, 131.68, 122.64, 114.79, 81.73, 76.01, 51.88, 41.04.

Preparation 15: 4-((1S,4R)-4-Chloro-cyclopent-2-enyloxy)-benzoic acid methyl ester

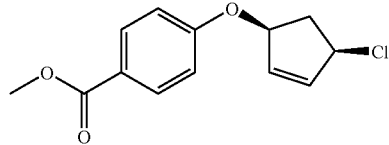 [SMILES: COC(=O)c1ccc(O[C@@H]2C=C[C@H](Cl)C2)cc1]

4-(4-Hydroxy-cyclopent-2-enyloxy)-benzoic acid methyl ester (preparation 14) (2 mmol), tosyl chloride (2.5 mmol) and DMAP (200 μmol) were placed in a vial. DCM (1 ml) was added through a septum followed by Triethyl amine (250 μmol). The reaction mixture was left at r.t. over night. The reaction mixture was concentrated in vacuo and purified by chromatography in a gradient from 0 to 60% EtOAc in Heptane. $^{13}$C NMR (75 MHz, CDCl3) δ 166.75, 161.50, 137.52, 132.48, 131.70, 122.95, 114.87, 80.52, 59.82, 51.89, 41.61.

Preparation 16: 4-[(1S,4S)-4-((R)-1-Naphthalen-1-yl-ethylamino)-cyclopent-2-enyloxy]-benzoic acid methyl ester

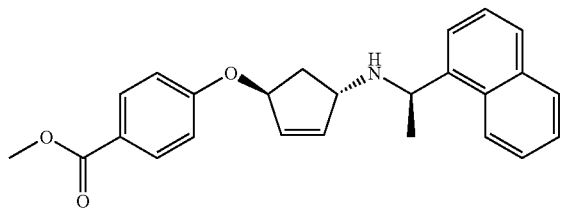 [SMILES: COC(=O)c1ccc(O[C@@H]2C=C[C@@H](N[C@H](C)c3cccc4ccccc34)C2)cc1]

4-(4-chloro-cyclopent-2-enyloxy)-benzoic acid methyl ester (preparation 15) (630 μmol), (+)-(R)-1-naphthalen-1-yl-ethylamine (630 μmol), and potassium carbonate (630 μmol) were placed in a vial. Dry DMF (1 ml) was added, and the resulting suspension heated at 50° C. for 72 hours. The reaction mixture was diluted with water (25 ml) and extracted twice with ethyl acetate. The extract was dried, concentrated in vacuo and purified by chromatography in a gradient from 0 to 40% EtOAc in heptane. $^{13}$C NMR (75 MHz, CDCl3) δ 166.82, 161.93, 140.94, 134.00, 131.64, 131.57, 131.24, 130.32, 129.03, 127.38, 125.86, 125.67, 125.37, 123.23, 122.79, 122.35, 114.76, 81.98, 61.10, 52.01, 51.79, 39.23, 24.10.

Example 303

4-[(1R,3R)-3-((R)-1-Naphthalen-1-yl-ethylamino)-cyclopentyloxy]-benzoic acid methyl ester (Compound 1342)

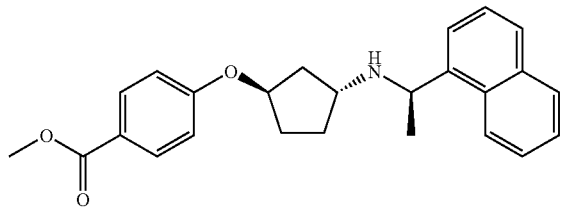 [SMILES: COC(=O)c1ccc(O[C@@H]2CC[C@@H](N[C@H](C)c3cccc4ccccc34)C2)cc1]

4-[4-(1-Naphthalen-1-yl-ethylamino)-cyclopent-2-enyloxy]-benzoic acid methyl ester (preparation 16) was diluted to 0.05 M in iso-propanol. This solution was passed through an H-Cube hydrogenation apparatus at 1 atm. hydrogen pressure and a flow rate of 1 ml/min. over 10% Pd on carbon. The product was concentrated and purified by chromatography in a gradient from 0 to 40% EtOAc in Heptane. $^{13}$C NMR (75 MHz, CDCl3) δ 166.91, 161.78, 141.58, 133.99, 131.57, 131.50, 131.23, 129.00, 127.22, 125.81, 125.63, 125.35, 122.85, 122.79, 122.15, 114.92, 78.33, 56.02, 52.09, 51.78, 40.71, 31.86, 31.06, 24.03.

Example 304

4-[(1R,3R)-3-((R)-1-Naphthalen-1-yl-ethylamino)-cyclopentyloxy]-benzoic acid formiate (Compound 1343)

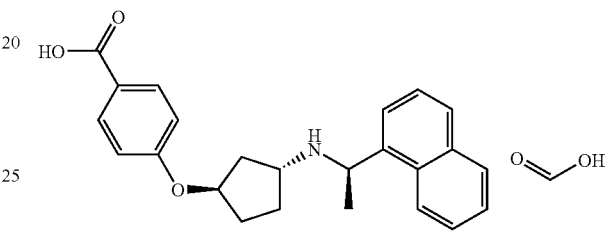

General procedure J was followed using 4-[3-(1-naphthalen-1-yl-ethylamino)-cyclopentyloxy]-benzoic acid methyl ester (compound 1342). $^{13}$C NMR (75 MHz, DMSO) δ 167.01, 163.75, 160.88, 140.56, 133.38, 131.14, 130.68, 128.63, 126.96, 125.87, 125.52, 125.34, 123.19, 122.97, 122.81, 114.79, 77.87, 55.23, 51.22, 38.71, 30.41, 30.36, 23.33.

Preparation 17: 3-((1S,4S)-4-Acetoxy-cyclopent-2-enyl)-5-methyl-3H-imidazole-4-carboxylic acid ethyl ester

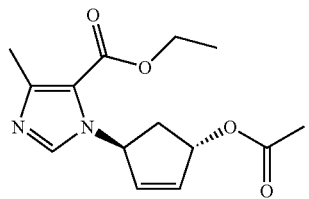 [SMILES: CCOC(=O)c1c(C)ncn1[C@@H]1C=C[C@@H](OC(C)=O)C1]

5-Methyl-1H-imidazole-4-carboxylic acid ethyl ester (6 mmol), (1R,4S)-cis-4-acetoxy-2-cyclopenten-1-ol (4 mmol), and triphenyl phosphine (4.8 mmol) were placed in a flask under argon. Dry THF (15 ml) was added through a septum and the resulting solution cooled to 0° C. DIAD was added dropwise, neat, over a period of 20 min. The reaction mixture was left over night. THF was removed in vacuo and the residue was taken up in MTBE, 10 ml, and diluted to double volume with PE. After standing for 2 hours in the cold, a precipitate of triphenylphosphine oxide was removed on a filter. The filtrate was concentrated in vacuo and purified by chromatography in a gradient from 0 to 20% EtOAc in Heptane. $^1$H NMR (300 MHz, CDCl$_3$) δ7.43 (s, 1H), 6.28 (m, 1H), 6.17 (m, 2H), 5.83 (m, 1H), 4.34 (q, 2H), 2.58 (ddd, 1H), 2.49 (s, 3H), 2.16 (ddd, 1H), 2.05 (s, 3H), 1.39 (t, 3H).

Preparation 18: 3-((1S,4S)-4-Hydroxy-cyclopent-2-enyl)-5-methyl-3H-imidazole-4-carboxylic acid ethyl ester

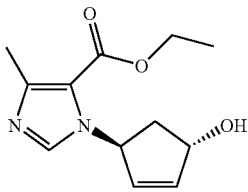 [SMILES: CCOC(=O)c1c(C)ncn1[C@@H]1C=C[C@@H](O)C1]

3-(4-Acetoxy-cyclopent-2-enyl)-5-methyl-3H-imidazole-4-carboxylic acid ethyl ester (preparation 17) (3 mmol) and potassium carbonate (3 mmol) were placed in a flask under argon. Dry methanol (15 ml) was added, and the resulting suspension heated at reflux for 1 hour, when TLC indicated complete conversion of substrate. The reaction mixture was concentrated in vacuo and purified by chromatography in a gradient from 0 to 90% EtOAc in Heptane. $^1$H NMR (300 MHz, CDCl$_3$) δ7.41 (s, 1H), 6.28 (m, 1H), 6.12 (m, 1H), 6.04 (m, 1H), 5.08 (m, 1H), 4.34 (q, 2H), 3.62 (bs, 1H), 2.47 (s, 3H), 2.42 (m, 1H) m, 2.14 (m, 1H), 1.39 (t, 3H).

Preparation 19: 3-((1S,4R)-4-Chloro-cyclopent-2-enyl)-5-methyl-3H-imidazole-4-carboxylic acid ethyl ester

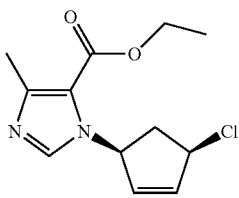 [SMILES: CCOC(=O)c1c(C)ncn1[C@@H]1C=C[C@H](Cl)C1]

3-(4-Acetoxy-cyclopent-2-enyl)-5-methyl-3H-imidazole-4-carboxylic acid ethyl ester (preparation 18) (2 mmol), tosyl chloride (2.5 mmol) and DMAP (200 µmol) were placed in a vial. DCM (1 ml) was added through a septum followed by triethyl amine (250 µmol). The reaction mixture was left at r.t. over night. The reaction mixture was concentrated in vacuo and purified by chromatography in a gradient from 0 to 60% EtOAc in heptane. $^1$H NMR (300 MHz, CDCl$_3$) δ7.61 (s, 1H), 6.29 (m, 1H), 6.09 (m, 1H), 6.01 (m, 1H), 4.95 (m, 1H), 4.34 (q, 2H), 3.20 (m, 1H), 2.48 (s, 3H), 2.15 (m, 1H), 1.38 (t, 3H).

Preparation 20: 5-Methyl-3-[(1S,4S)-4-((R)-1-naphthalen-1-yl-ethylamino)-cyclopent-2-enyl]-3H-imidazole-4-carboxylic acid ethyl ester

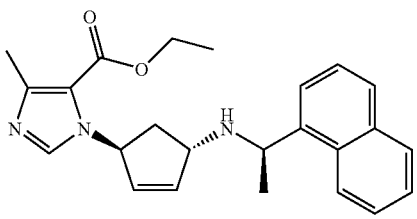 [SMILES: CCOC(=O)c1c(C)ncn1[C@@H]1C=C[C@@H](N[C@H](C)c2cccc3ccccc23)C1]

3-(4-Chloro-cyclopent-2-enyl)-5-methyl-3H-imidazole-4-carboxylic acid ethyl ester (preparation 19) (630 µmol), (+)-(R)-1-naphthalen-1-yl-ethylamine (630 µmol), and potassium carbonate (630 µmol) were placed in a vial. Dry DMF (1 ml) was added, and the resulting suspension heated at 50° C. for 72 hours. The reaction mixture was diluted with water (25 ml) and extracted twice with ethyl acetate. The extract was dried, concentrated in vacuo and purified by chromatography in a gradient from 0 to 40% EtOAc in heptane. $^1$H NMR (300 MHz, CDCl$_3$) δ8.19 (d, 1H) 7.85 (d, 1H), 7.71 (m, 2H), 7.47 (m, 3H), 7.30 (s, 1H), 6.16 (m, 1H), 6.04 (m, 1H), 5.88 (m, 1H), 4.74 (q, 1H), 4.33 (q, 2H), 3.94 (m, 1H), 2.45 (s, 3H), 2.35 (m, 1H), 2.05 (m, 1H), 1.48 (d, 3H), 1.38 (t, 3H).

Example 305

5-Methyl-3-[(1R,3R)-3-((R)-1-naphthalen-1-yl-ethylamino)-cyclopentyl]-3H-imidazole-4-carboxylic acid (Compound 1344)

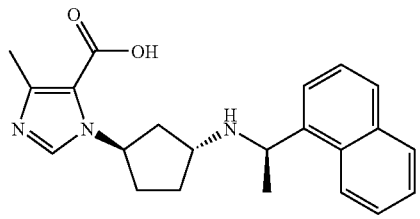 [SMILES: Cc1ncn([C@@H]2CC[C@@H](N[C@H](C)c3cccc4ccccc34)C2)c1C(=O)O]

Step 1

5-Methyl-3-[4-(1-naphthalen-1-yl-ethylamino)-cyclopent-2-enyl]-3H-imidazole-4-carboxylic acid ethyl ester (preparation 20) was diluted to 0.05 M in iso-propanol. This solution was passed through an H-Cube hydrogenation apparatus at 1 atm. hydrogen pressure and a flow rate of 1 ml/min. over 10% Pd on carbon. The product was concentrated and purified by chromatography in a gradient from 0 to 40% EtOAc in Heptane, affording 5-methyl-3-[3-(1-naphthalen-1-yl-ethylamino)-cyclopentyl]-3H-imidazole-4-carboxylic acid ethyl ester.

Step 2

General procedure J was followed using 5-methyl-3-[3-(1-naphthalen-1-yl-ethylamino)-cyclopentyl]-3H-imidazole-4-carboxylic acid ethyl ester. $^1$H NMR (300 MHz, DMSO) δ 8.27 (m, 1H), 7.95 (m, 1H), 7.86 (m, 1H), 7.78 (m, 1H), 7.71 (m, 1H), 7.54 (m, 3H), 5.43 (m, 1H), 4.87 (m, 1H), 3.37 (m, 1H), 2.31 (s, 3H), 2.20 (m, 2H), 2.05-1.55 (m, 4H), 1.49 (d, 3H).

Example 306

(3S,4S-Diphenyl-cyclopentyl)-((R)-1-naphthalen-1-yl-ethyl)-amine (compound 1345)

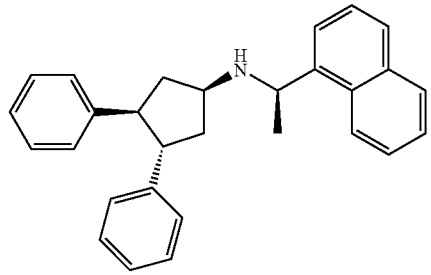

General procedure A was followed using 3S,4S-diphenyl-cyclopentanone and (+)-(R)-1-naphthalen-1-yl-ethylamine. $^1$H NMR (300 MHz, CDCl3) δ 8.19 (d, 1H), 7.91-7.84 (m, 1H), 7.76 (d, 1H), 7.72-7.64 (m, 1H), 7.55-7.42 (m, 3H), 7.23-6.97 (m, 10H), 4.84-4.73 (m, 1H), 3.48-3.28 (m, 2H), 3.05-2.92 (m, 1H), 2.52-2.38 (m, 1H), 2.17-2.00 (m, 2H), 1.89-1.70 (m, 1H), 1.54 (d, 3H).

Example 307

5-(4-ethoxy-phenyl)-2-propyl-cyclohexyl]-((R)-1-naphthalen-1-yl-ethyl)-amine (compound 1346)

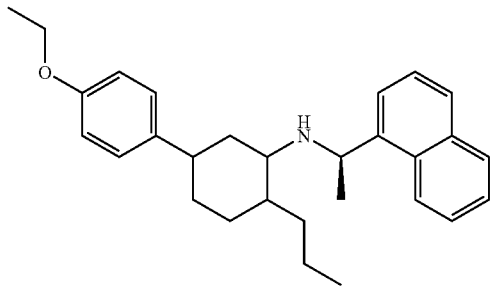 [SMILES: CCCC1CCC(c2ccc(OCC)cc2)CC1N[C@H](C)c1cccc2ccccc12]

A solution of 3-(4-ethoxy-phenyl)-6-propyl-cyclohex-2-enone (100 mg) in isopropanol (8 mL) was hydrogenated in an H-CUBE (Catalyst: Pd/C, Flow: 1 ml/min, H$_2$ pressure: 1 bar and loop size: 5 ml). The conjugated doublebond was hydrogenated in 2 runs (~80% conversion). Evaporation of the isopropanol resulted in a colourless oil, which was dissolved in acetonitrile (3 ml). (R)-1-Naphthalen-1-yl-ethylamine and NaBH(OAc)$_3$ were added and the reaction was stirred over night at room temperature. The reaction mixture was extracted with EtOAc/NaHCO$_3$ aq. The organic phase was dried (MgSO$_4$) and evaporated after filtration. The oil was dissolved in methanol and purified by preparative HPLC-MS. LC/MS (method B): RT=3.72, [M+H]$^+$=416.6.

Example 308

[2-(4-Fluoro-phenyl)-5-((R)-1-naphthalen-1-yl-ethylamino)-cyclopentyl]-acetic acid hydrochloride (Compound 1347)

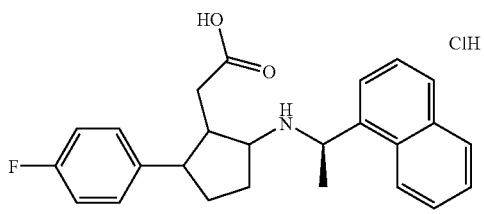 [SMILES: C[C@@H](NC1CCC(c2ccc(F)cc2)C1CC(=O)O)c1cccc2ccccc12 ; Cl]

A mixture of [2-(4-fluoro-phenyl)-5-oxo-cyclopent-1-enyl]-acetic acid and 10% Pd/C in methanol was left under an H$_2$-atmosphere for 3 days. The reaction mixture was filtered through Celite and evaporated to an oil. The oil was dissolved in acetonitrile. (R)-1-Naphthalen-1-yl-ethylamine and NaBH(OAc)$_3$ were added and the reaction was stirred over night at room temperature. The reaction mixture was extracted with EtOAc/NaHCO$_3$ aq. The organic phase was isolated, dried (MgSO$_4$) and evaporated after filtration. The oil was dissolved in methanol and purified by preparative HPLC-MS resulting in the desired product. The desired product was dissolved in acetonitrile. HCl in dioxane (1 eq) was added and the HCl salt of the product (title compound) precipitated and was collected by filtration. $^1$H NMR (300 MHz, DMSO) δ 12.37 (br s, 1H), 9.71 (br s, 2H), 8.28 (d, 1H), 8.09-7.96 (m, 3H), 7.69-7.56 (m, 3H), 7.38-7.28 (m, 2H), 7.12 (t, 2H), 5.43-5.29 (m, 1H), 3.87-3.73 (m, 1H), 2.86-2.71 (m, 1H), 2.58-2.45 (m, 1H), 2.44-2.36 (m, 2H), 2.14-1.83 (m, 4H), 1.75 (d, 3H).

Example 309

3-{4-[(1S,3S)-3-((R)-1-Naphthalen-1-yl-ethyl-amino)-cyclopentyl]-phenyl}-propan-1-ol (Compound 1348)

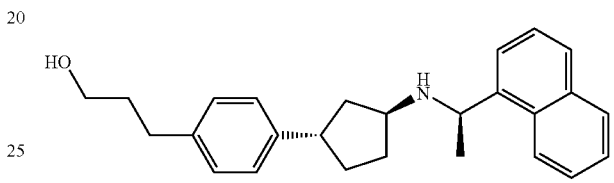

To a solution of 3-{4-[(1S,3S)-3-((R)-1-naphthalen-1-yl-ethylamino)-cyclopentyl]-phenyl}-propionic acid methyl ester (compound 1183) (215 mg, 0.54 mmol) in dry diethyl ether (3 mL) was added LiAlH$_4$ (0.62 mL of a 1M solution in THF) at 0° C. After 30 min, the reaction was quenched with water and purified by preparative HPLC to afford the title compound as an oil. $^1$H NMR (300 MHz, DMSO) δ 8.30 (d, 1H), 7.95-7.87 (m, 1H), 7.80-7.68 (m, 2H), 7.57-7.44 (m, 3H), 7.03 (s, 4H), 4.64 (q, 1H), 4.42 (t, 1H), 3.46-3.29 (m, 2H), 3.24-3.08 (m, 2H), 2.59-2.47 (m, 2H), 2.35-1.30 (m, 11H).

Example 310

Functional Whole Cell Assay

On the assay day cells were harvested and resuspended to 13*10$^6$ cells/ml in stimulation buffer (containing: Hepes 10 mM, MgCl$_2$ 0.5 mM, KCl 4.2 mM, NaCl 146 mM, glucose 5.5 mM, LiCl 50 mM at pH 7.4). Five μl cell solution were pipetted into a well (white 384-well plate, Perkin Elmer Optiplate) followed by 5 μl compound diluted in a Ca$^{2+}$-containing (to the final concentration of 2 mM) buffer. After compound stimulation for 1 hour at 37° C. 10 ul of IP-One assay reagents were added and incubated for another 1 hour at room temperature. Finally the plate was read using a Perkin Elmer EnVision, according to protocol supplied by the IP-One assay kit manufacturer. The FRET ratio was calculated by dividing the 665 nm emission signal with that of the 615 nm.

Molar concentrations of a compound that produces 50% of the maximum possible agonistic response (the IC50 value) is calculated according to equation General sigmoidal curve with Hill slope, a to d (Equation 1) This model describes a sigmoidal curve with an adjustable baseline, a. The equation can be used to fit curves where response is either increasing or decreasing with respect to the independent variable, X.

$$y=(a-d)/(1+(x/c)^b)+d \qquad \text{Equation 1}$$

Parameters:
x=concentration of tested compound
y=response (%)
a=min response as compound concentration approaches 0
d=max response as concentration of tested compound increasing
c=IC50 for the curve
b=Hill coefficient or curve slope Testing data of compounds of the present invention indicate that compounds of the present invention are potent modulators of CaSR, thus making them potentially useful in the treatment of diseases related to kidneys or bones. See table 1 below.

TABLE 1

In vitro testing of compounds in CaSR functional whole cell assay

| Compound | IC50 (nM) |
|---|---|
| Cinacalcet | 630 |
| Compound 1056 | 250 |
| Compound 1115 | 50 |
| Compound 1136 | 40 |
| Compound 1142 | 50 |
| Compound 1146 | 50 |
| Compound 1186 | 40 |
| Compound 1188 | 20 |
| Compound 1190 | 8 |
| Compound 1338 | 16 |

Example 311

Screening for P450 2D6 Inhibition

The assay rapidly screen for potential inhibitors of human P450 2D6 catalytic activity, by using recombinant human P450 2D6. The IC50 determination is performed in duplicate at eight concentrations.

Incubations were conducted in 96 well microtiter plates based on a method described by BD Biosciences. To the first well in each row, a NADPH regenerating system and test compound was added. In the second well and all remaining wells, NADPH regenerating system and acetonitrile (final concentration of 2%) was added. The final assay concentration of the NADPH regenerating system was 8.2 µM NADP$^+$, 0.41 mM glucose-6-phosphate, 0.41 mM magnesium chloride hexahydrate and 0.4 U/ml glucose-6-phosphate dehydrogenase and 0.01 mg/mL control insect cell membrane protein. The test compound solution was serially diluted 1:3 through the eighth wells.

The final concentration of the test compounds were in the range 100 µM to 45.7 nM in the eight rows. Wells 9 and 10 contained no test compound (only NADPH regenerating system and enzyme/substrate mix) and wells 11 and 12 were used as controls for background fluorescence (enzyme and substrate were added after the reaction was terminated). The plate was then pre-incubated at 37° C. for 10 min, and the reaction was initiated by the addition of pre-warmed enzyme/substrate mix. The assay concentration of the enzyme/substrate mix was 100 mM potassium phosphate, pH 7.4, 1.5 pmol recombinant human P450 CYP2D6 and 1.5 µM of the fluorescent substrate 3-[2-(N,N diethyl-N-methylamino)ethyl]-7-methoxy-4-methylcounnarin (AMMC). The assay was conducted in duplicate in a final volume of 200 µL per well. Reactions were terminated after 30 min by addition of a 4:1, acetonitrile:0.5 M Tris base solution. Quinidine was used as positive control, 0.5 µM as highest concentration. Fluorescence per well was measured using a fluorescence plate reader (excitation: 390 nm, emission: 460 nm). The IC50 values were calculated.

Testing data of compounds of the present invention indicate that compounds of the present invention show low or no inhibition towards human P450 2D6 (pIC50-value below 6). See table 2 below.

TABLE 2

In vitro testing of compounds in CYP 2D6 and CYP 3A4 inhibition assay.

| Compound | IC50 (µM) |
|---|---|
| Cinacalcet | 0.050 |
| Compound 1186 | 50 |
| Compound 1190 | 79 |
| Compound 1338 | 100 |
| Compound 1146 | 16 |
| Compound 1142 | 25 |
| Compound 1136 | 10 |
| Compound 1115 | 13 |
| Compound 1056 | 10 |

Example 312

Profiling of a Compound According to the Present Invention on Off-Target, G-Protein Coupled Receptors A compound according to the present invention along with Cinacalcet was sent to CEREP for functional testing on cell membrane receptors. All experiments were carried out on human receptors which were expressed in mammalian cells. $EC_{50}$ (agonism) and $IC_{50}$ (antagonism) were calculated on a 6 point curve with concentrations ranging from 0.01-100 mM.

The results of the functional cell-based screening showed that the compound according to the present invention was significantly less potent on the opiate (MOP) receptor, serotonin 5-HT1A receptor and norepinephrine uptake transporter compared to Cinacalcet.

Example 313

Profiling of Compounds of the Present Invention on Cardiac-Related, In Vitro Ion Channels Compounds of the present invention were in vitro tested on three cardiac ion channels that are responsible for three major components of the cardiac action potential. These channels are:
1. Cloned hERG potassium channels (encoded by the KCNH2 gene and expressed in human embryonic kidney, HEK293, cells), responsible for $I_{Kr}$.
2. Cloned hNav1.5 sodium channel (encoded by the human SCN5A gene and expressed in HEK293 cells), responsible for $I_{Na}$, fast sodium current
3. Cloned L-type calcium channels (hCav1.2, encoded by the human CACNA1C gene in CHO cells), responsible for $I_{Ca,L}$, high threshold calcium current.

The effect of a compound according to the present invention was evaluated at the ChanTest Corporation, Ion Channel Company in Cleveland, Ohio, USA. The compound was tested at room temperature using the PatchXpress 7000A (Molecular Devices) on the channels listed above and evaluated at 0.01, 0.1, 1, 10, and 100 µM with each concentration tested in 2-6 cells (n≥2) for 5 min. The effect the compound on hNav1.5 was determined using 5 Hz repetitive stimulation for 5 min.

The IC$_{50}$ values for the tested compound were >100 μM in the hERG and hCav1.2 channel assays. No use dependent inhibition was observed at concentrations up to 100 μM on the hNav1.5 channel. The results of the positive controls (E-4031 for hERG, Lidocaine for hNav1.5, and Nifedipine for hCav1.2) confirmed the sensitivity of the test system. In summary, no significant activity was detected on the three cardiac ion channels that are responsible for three major components of the cardiac action potential.

Example 314

In Vivo Test in Normal Rats

Various compounds were administered to normal male Sprague Dawley rats in order to examine the pharmacological effect on serum levels of total calcium and parathyroid hormone (PTH). The experiments were performed by orally administering a single dose of the respective compounds as compared to vehicle-treated animals or animals treated with the competitor compound Cinacalcet.

As a standard, a group of six animals were treated orally with 1 mg/kg of compound as a 1% methylcellulose suspension and two hours thereafter, blood was obtained by retro-orbital bleeding under anaesthesia and the serum calcium and PTH levels were measured. Percent PTH and calcium suppression, respectively, compared to vehicle-treated animals is shown in table 3.

In some instances, rats were treated orally with various doses of a given compound in 1% methylcellulose (six rats/dose) and blood was obtained by retro-orbital bleeding two hours thereafter. The dose-response curve for suppression of serum PTH and serum calcium levels by the indicated compounds are shown in FIG. 1-FIG. 4. Using the software GraphPad Prism® 5, ED$_{50}$ values for Cinacalcet, Compound 1056, Compound 1186, and Compound 1190 with respect to PTH suppression were calculated to be 0.9 mg/kg, 0.1 mg/kg, 0.04 mg/kg, and 0.002 mg/kg, respectively.

For some compounds, rats were bled at several timepoints after oral administration (six rats/time point), and suppression of serum PTH levels was observed over time. Results are shown in FIGS. 5-8.

TABLE 3

Percent PTH and calcium suppression, respectively, of compounds in this invention compared to vehicle-treated animals.

| Compound | Dose p.o. | PTH suppression | Suppression of Ca$^{2+}$ |
|---|---|---|---|
| Cinacalcet | 1 mg/kg | 48% | 5% |
| Compound 1056 | 1 mg/kg | 85% | 1% |
| Compound 1115 | 1 mg/kg | 50% | 3% |
| Compound 1136 | 1 mg/kg | 61% | 7% |
| Compound 1146 | 1 mg/kg | 84% | 0% |
| Compound 1186 | 1 mg/kg | 98% | 6% |
| Compound 1188 | 1 mg/kg | 97% | 12% |
| Compound 1190 | 1 mg/kg | 93% | 18.5% |
| Compound 1338 | 1 mg/kg | 85% | 29% |

Example 315

In Vivo Test Using the 5/6 Nephrectomy Model in Rats

The lowering effect of different compounds on serum PTH was examined in vivo in the rat 5/6 nephrectomy model which is a widely accepted animal model of secondary hyperparathyroidism.

Two-third of the rats' (Sprague Dawley, at least 8 weeks old) left kidney was surgically removed followed by removal of the right kidney one week later. Immediately after this procedure, the rodent diet was switched from a standard diet (Altromin, 0.9% Ca2+, 0.7% Pi) to a high-phosphorus diet (Altromin, 0.9% Ca2+, 1.2% Pi) and animals were observed for 3 weeks, in which they developed severe secondary hyperparathyroidism.

After disease initiation, blood was obtained by retro-orbital bleeding and urine was collected using metabolic cages. Serum PTH, calcium, phosphorus, albumin, creatinine, and BUN as well as urinary creatinine and albumin were measured. Rats were then stratified into different treatment groups (9-12 rats/group) based on the results obtained. One group of normal rats without surgery served as control ("control") and one group of nephrectomized rats treated with vehicle (1% Methylcellulose) was used as another control ("5/6 NEPX"). All other groups were treated orally with test compound at various doses once daily for two weeks and the above mentioned parameters were monitored weekly.

Figure 9:
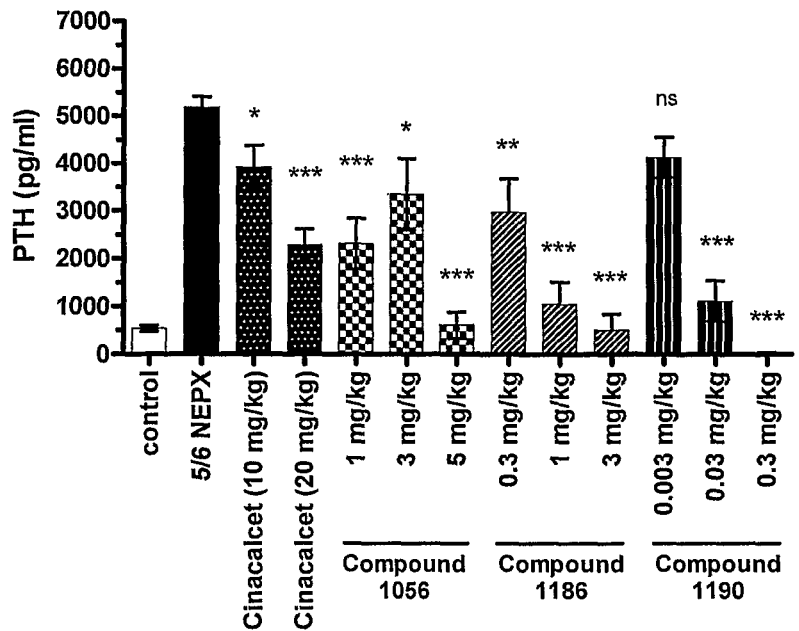
FIG. 9 shows a graph of the PTH lowering effect of the indicated compounds.

As shown in FIG. 9, the PTH lowering effect the test compounds was confirmed. The calculated ED$_{50}$ values for Cinacalcet, compound 1056, compound 1186, and compound 1190 were approx. 20 mg/kg, 2 mg/kg, 0.3 mg/kg, and 0.01 mg/kg, respectively.

The invention claimed is:
1. A compound of formula I

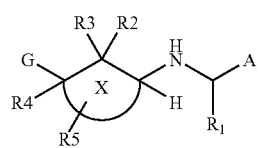

wherein

represents cycloalkyl comprising 4-7 carbon atoms optionally being substituted with one or more, same or different substituents selected from R$_2$, R$_3$, R$_4$ or R$_5$;
A represents 1-naphthyl;
R$_1$ is methyl, ethyl or n-propyl,
each of which are optionally substituted with one or more, same or different substituents selected from halogen or hydroxyl;
R$_2$ and R$_3$ represent hydrogen;
R$_4$ represents hydrogen, halogen, hydroxy, or C$_{1-6}$alkyl;
each of R$_5$ represents independently one or more same or different substituents represented by hydrogen or C$_{1-6}$alkyl;

G represents —C(O)H, —C(O)NH$_2$, C$_{3-8}$cycloalkyl, C$_{1-6}$heterocycloalkyl, C$_{1-6}$heterocycloalkenyl, C$_{3-8}$cycloalkenyl, C$_{6-14}$aryl, C$_{1-10}$heteroaryl, C$_{6-10}$arylamino, hydroxyaminocarbonyl, C$_{6-10}$arylaminocarbonyl, C$_{1-4}$aminocarbonyl, C$_{1-6}$heterocycloalkylcarbonyl, C$_{1-10}$heteroarylaminocarbonyl, C$_{6-10}$arylsulfonylaminocarbonyl, C$_{6-14}$aryloxy, C$_{1-4}$alkoxycarbonyl, wherein said —C(O)H, —C(O)NH$_2$, C$_{3-8}$cycloalkyl, C$_{1-6}$heterocycloalkyl, C$_{1-6}$heterocycloalkenyl, C$_{3-8}$cycloalkenyl, C$_{6-14}$aryl, C$_{1-10}$heteroaryl, C$_{6-10}$arylamino, hydroxyaminocarbonyl, C$_{6-10}$arylaminocarbonyl, C$_{1-4}$aminocarbonyl, C$_{1-6}$heterocycloalkylcarbonyl, C$_{1-10}$heteroarylaminocarbonyl, C$_{6-10}$arylsulfonylaminocarbonyl, C$_{6-14}$aryloxy, C$_{1-4}$alkoxycarbonyl, are optionally further substituted with one or more, same or different substituents represented by halogen, cyano, carboxy, —NH$_2$, C$_{1-6}$amino, iminomethyl, hydroxyiminomethyl, amidino, hydroxy, mercapto, —C(O)H, —C(O)NH$_2$, nitro, oxo, trifluoromethyl, C$_{1-6}$alkyl, C$_{2-4}$alkenyl, C$_{2-4}$alkynyl, C$_{1-4}$hydroxyalkyl, aminoC$_{1-3}$alkyl, C$_{1-6}$haloalkyl, C$_{1-4}$alkoxy, C$_{1-4}$alkoxycarbonyl, C$_{1-4}$alkylcarbonyl, C$_{1-4}$aminocarbonyl, hydroxyaminocarbonyl, C$_{3-6}$cycloalkylaminocarbonyl, C$_{1-6}$heterocycloalkylaminocarbonyl, C$_{3-6}$cycloalkyl, C$_{3-6}$cycloalkenyl, C$_{1-6}$cycloalkylamino, C$_{1-6}$heterocycloalkyl, C$_{1-6}$heterocycloalkenyl, C$_{1-6}$heterocycloalkylcarbonyl, C$_{6-14}$aryl, carboxyC$_{6-10}$aryl, C$_{1-6}$heteroaryl, C$_{1-6}$heteroarylaminocarbonyl, —S(O)$_2$NH$_2$, C$_{1-6}$ureido, C$_{1-6}$thioureido, C$_{1-4}$alkylcarbonyloxy, C$_{1-4}$alkoxycarbonyloxy, C$_{1-4}$alkoxysulfonyloxy, C$_{1-6}$heterocycloalkyloxy, C$_{1-4}$alkylthio, C$_{1-4}$aminosulfonyl, C$_{1-4}$aminocarbonyloxy, C$_{1-4}$alkylsulfonylamino, C$_{6-10}$arylamino, C$_{6-10}$arylaminocarbonyl, C$_{6-10}$aryloxycarbonyl, C$_{1-4}$alkoxycarbamoyl, C$_{6-10}$arylcarbonylamino, C$_{6-10}$arylsulfonylamino, C$_{1-4}$alkylcarbonylamino, C$_{1-4}$alkenylcarbonylamino, C$_{3-6}$cycloalkenylcarbonylamino, C$_{3-6}$cycloalkylcarbonylamino, C$_{1-4}$alkoxycarbonylamino, C$_{1-6}$heterocycloalkylcarbonylamino, C$_{1-4}$alkylsulfonyl, C$_{1-6}$heterocycloalkylsulfonyl or C$_{1-3}$alkylsulfonylaminocarbonyl, wherein said carboxy, C$_{1-6}$amino, iminomethyl, hydroxyiminomethyl, C(O)NH$_2$, C$_{1-6}$alkyl, C$_{2-4}$alkenyl, C$_{2-4}$alkynyl, C$_{1-4}$hydroxyalkyl, aminoC$_{1-3}$alkyl, C$_{1-6}$haloalkyl, C$_{1-4}$alkoxy, C$_{1-4}$alkoxycarbonyl, C$_{1-4}$alkylcarbonyl, C$_{1-4}$aminocarbonyl, hydroxyaminocarbonyl, C$_{3-6}$cycloalkylaminocarbonyl, C$_{1-6}$heterocycloalkylaminocarbonyl, C$_{3-6}$cycloalkyl, C$_{3-6}$cycloalkenyl, C$_{1-6}$cycloalkylamino, C$_{1-6}$heterocycloalkyl, C$_{1-6}$heterocycloalkenyl, C$_{1-6}$heterocycloalkylcarbonyl, C$_{6-14}$aryl, carboxyC$_{6-10}$aryl, C$_{1-6}$heteroaryl, C$_{1-6}$heteroarylaminocarbonyl, —S(O)$_2$NH$_2$, C$_{1-6}$ureido, C$_{1-6}$thioureido, C$_{1-4}$alkylcarbonyloxy, C$_{1-4}$alkoxycarbonyloxy, C$_{1-4}$alkoxysulfonyloxy, C$_{1-6}$heterocycloalkyloxy, C$_{1-4}$alkylthio, C$_{1-4}$aminosulfonyl, C$_{1-4}$aminocarbonyloxy, C$_{1-4}$alkylsulfonylamino, C$_{6-10}$arylamino, C$_{6-10}$arylaminocarbonyl, C$_{6-10}$aryloxycarbonyl, C$_{1-4}$alkoxycarbamoyl, C$_{6-10}$arylcarbonylamino, C$_{6-10}$arylsulfonylamino, C$_{1-4}$alkylcarbonylamino, C$_{1-4}$alkenylcarbonylamino, C$_{3-6}$cycloalkenylcarbonylamino, C$_{3-6}$cycloalkylcarbonylamino, C$_{1-4}$alkoxycarbonylamino, C$_{1-6}$heterocycloalkylcarbonylamino, C$_{1-4}$alkylsulfonyl, C$_{1-6}$heterocycloalkylsulfonyl or C$_{1-3}$alkylsulfonylaminocarbonyl, are optionally further substituted with one or more, same or different substituents selected from hydroxy, —NH$_2$, C$_{1-6}$amino, iminomethyl, hydroxyiminomethyl, carboxy, trifluoromethyl, halogen, oxo, mercapto, cyano, —C(O)NH$_2$, nitro, C$_{1-6}$alkyl, C$_{2-4}$alkenyl, C$_{2-4}$alkynyl, C$_{1-4}$hydroxyalkyl, C$_{1-6}$haloalkyl, C$_{1-3}$alkoxy, C$_{1-4}$alkoxycarbonyl, C$_{1-4}$alkylcarbonyl, C$_{3-8}$cycloalkyl, C$_{3-8}$cycloalkenyl, C$_{1-6}$heterocycloalkyl, C$_{6-12}$aryl, C$_{1-10}$heteroaryl, C$_{1-3}$alkoxyC$_{6-10}$aryl, C$_{1-10}$heterocycloalkylaryl, C$_{1-6}$heterocycloalkenyl, —S(O)$_2$NH$_2$, —S(O)$_2$OH, —S(O)$_2$CH$_3$, C$_{1-6}$ureido, C$_{1-6}$thioureido, C$_{1-4}$alkylcarbonyloxy, C$_{1-4}$alkoxycarbonyloxy, C$_{1-4}$alkoxysulfonyloxy, C$_{1-4}$alkoxycarbamoyl, C$_{1-4}$aminocarbonyl, C$_{1-6}$heterocycloalkylcarbonyl, C$_{1-4}$alkylthio, C$_{1-4}$aminosulfonyl, C$_{1-4}$aminocarbonyloxy, C$_{1-4}$alkylsulfonylamino, C$_{6-14}$arylsulfonyl, C$_{6-10}$arylsulfonylamino, hydroxyiminomethyl, C$_{1-4}$alkylcarbonylamino or C$_{1-4}$alkylsulfonyl, wherein said —C(O)NH$_2$, C$_{1-6}$amino, C$_{1-6}$alkyl, C$_{2-4}$alkenyl, C$_{2-4}$alkynyl, C$_{1-4}$hydroxyalkyl, C$_{1-6}$haloalkyl, C$_{1-3}$alkoxy, C$_{1-4}$alkoxycarbonyl, C$_{3-8}$cycloalkyl, C$_{3-8}$cycloalkenyl, C$_{1-6}$heterocycloalkyl, C$_{6-12}$aryl, C$_{1-10}$heteroaryl, C$_{1-3}$alkoxyC$_{6-10}$aryl, C$_{1-10}$heterocycloalkylaryl, C$_{1-6}$heterocycloalkenyl, —S(O)$_2$NH$_2$, —S(O)$_2$OH, C$_{1-6}$ureido, C$_{1-6}$thioureido, C$_{1-4}$alkylcarbonyloxy, C$_{1-4}$alkoxycarbonyloxy, C$_{1-4}$alkoxysulfonyloxy, C$_{1-4}$alkoxycarbamoyl, C$_{1-4}$aminocarbonyl, C$_{1-6}$heterocycloalkylcarbonyl, C$_{1-4}$alkylthio, C$_{1-4}$aminosulfonyl, C$_{1-4}$aminocarbonyloxy, C$_{1-4}$alkylsulfonylamino, C$_{6-14}$arylsulfonyl, C$_{6-10}$arylsulfonylamino, hydroxyiminomethyl, C$_{1-4}$alkylcarbonylamino or C$_{1-4}$alkylsulfonyl, are optionally further substituted with one or more, same or different substituents selected from hydroxy, oxo, cyano, halogen, C$_{1-3}$alkoxy, C$_{1-3}$alkoxyC$_{1-3}$alkoxy, C$_{1-6}$amino, mercapto, carboxy, —C(O)NH$_2$, nitro, C$_{1-6}$alkyl, C$_{1-3}$hydroxyalkyl, C$_{1-4}$alkoxycarbonyl, C$_{1-3}$alkylcarbonylamino, C$_{1-6}$heterocycloalkyl, C$_{6-12}$aryl, C$_{1-6}$heteroaryl, —S(O)$_2$NH$_2$ or —S(O)$_2$OH;

or G, together with R$_4$, forms an oxo group;

or a pharmaceutically acceptable salt, solvate or in vivo hydrolysable ester thereof.

2. The compound according to claim 1 wherein compound I represents

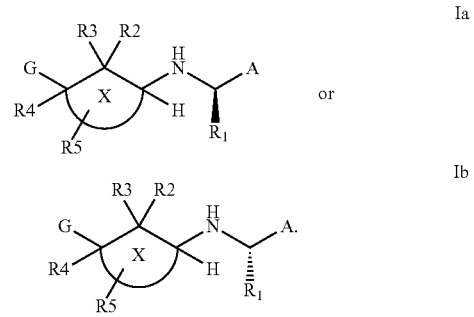

3. The compound according to claim 1 or 2, wherein

represents:

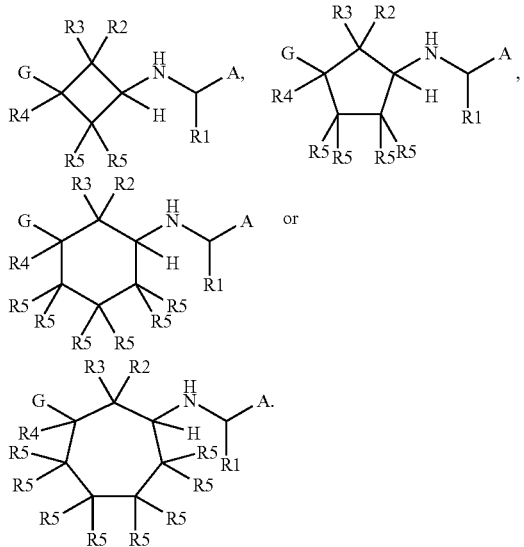

4. The compound according to claim 1, wherein G represents —C(O)—$R_6$, wherein $R_6$ represents —$NH_2$, $C_{1-6}$amino, hydroxy, mercapto, —C(O)$NH_2$, trifluoromethyl, carboxy, $C_{1-6}$alkyl, $C_{2-4}$alkenyl, $C_{2-4}$alkynyl, $C_{1-4}$hydroxyalkyl, $C_{1-6}$haloalkyl, $C_{1-4}$alkoxy, $C_{1-4}$alkoxycarbonyl, $C_{1-4}$aminocarbonyl, $C_{3-6}$cycloalkyl, $C_{3-6}$cycloalkenyl, $C_{1-6}$heterocycloalkenyl, $C_{3-6}$cycloalkylamino, $C_{1-6}$heterocycloalkyl, $C_{1-6}$heterocycloalkylcarbonyl, $C_{6-14}$aryl, $C_{1-6}$heteroaryl, $C_{6-10}$arylamino, carboxy$C_{6-10}$aryl, $C_{1-4}$alkylcarbonyloxy, $C_{1-4}$alkoxycarbonyloxy, $C_{1-4}$alkoxysulfonyloxy, $C_{1-4}$alkylthio, $C_{1-4}$aminocarbonyloxy, $C_{1-4}$alkylsulfonylamino, $C_{1-4}$alkylcarbonylamino, $C_{1-4}$alkenylcarbonylamino, $C_{3-6}$cycloalkenylcarbonylamino, $C_{3-6}$cycloalkylcarbonylamino, $C_{1-4}$alkoxycarbonylamino, $C_{6-10}$arylcarbonylamino or $C_{6-10}$arylsulfonylamino, wherein said $C_{1-6}$amino, $C_{1-6}$alkyl, $C_{2-4}$alkenyl, $C_{2-4}$alkynyl, $C_{1-4}$hydroxyalkyl, $C_{1-6}$haloalkyl, $C_{1-4}$alkoxy, $C_{1-4}$alkoxycarbonyl, $C_{1-4}$aminocarbonyl, $C_{3-6}$cycloalkyl, $C_{3-6}$cycloalkenyl, $C_{1-6}$heterocycloalkyl, $C_{3-6}$cycloalkylamino, $C_{1-6}$heterocycloalkyl, $C_{1-6}$heterocycloalkylcarbonyl, $C_{6-14}$aryl, $C_{1-6}$heteroaryl, $C_{6-10}$arylamino, carboxy$C_{6-10}$aryl, $C_{1-4}$alkylcarbonyloxy, $C_{1-4}$alkoxycarbonyloxy, $C_{1-4}$alkoxysulfonyloxy, $C_{1-4}$alkylthio, $C_{1-4}$aminocarbonyloxy, $C_{1-4}$alkylsulfonylamino, $C_{1-4}$alkylcarbonylamino, $C_{1-4}$alkenylcarbonylamino, $C_{3-6}$cycloalkenylcarbonylamino, $C_{3-6}$cycloalkylcarbonylamino, $C_{1-4}$alkoxycarbonylamino, $C_{6-10}$arylcarbonylamino or $C_{640}$arylsulfonylamino, may further be optionally substituted with one or more same or different substituents represented by hydroxy, halogen, $C_{1-4}$alkyl, $C_{1-3}$alkoxy, $C_{1-4}$alkoxycarbonyl, $C_{1-6}$heterocycloalkyl, $C_{6-12}$aryl or oxo, wherein said $C_{1-4}$alkyl, $C_{1-3}$alkoxy, $C_{1-4}$alkoxycarbonyl, $C_{1-6}$heterocycloalkyl or $C_{6-12}$aryl are optionally further substituted with halogen, $C_{1-4}$alkyl, $C_{1-3}$alkoxy or $C_{1-4}$alkoxycarbonyl.

5. The compound according to claim 1, wherein G represents —C(O)$NH_2$, $C_{1-4}$aminocarbonyl, $C_{4-5}$heterocycloalkylcarbonyl, $C_{6-10}$arylaminocarbonyl or $C_{6-10}$arylsulfonylaminocarbonyl, wherein said $C_{1-4}$aminocarbonyl, $C_{4-5}$heterocycloalkylcarbonyl, $C_{6-10}$arylaminocarbonyl or $C_{6-10}$arylsulfonylaminocarbonyl, are optionally substituted with one or more, same or different substituents selected from oxo, hydroxy, $C_{1-4}$alkyl, $C_{1-3}$alkoxy, $C_{1-3}$alkoxycarbonyl, $C_{4-5}$heterocycloalkyl, $C_{6-10}$aryl, wherein said $C_{1-4}$alkyl, $C_{1-3}$alkoxy, $C_{1-3}$alkoxycarbonyl, $C_{4-5}$heterocycloalkyl or $C_{6-10}$aryl are optionally substituted with one or more, same or different substituents represented by halogen, $C_{1-3}$alkoxy or $C_{1-3}$alkoxycarbonyl.

6. The compound according to claim 1, wherein G represents methylpiperazinylcarbonyl, cyclopropylaminocarbonyl, isopropylaminocarbonyl, propylaminocarbonyl, morpholinocarbonyl, dimethylaminocarbonyl, isobutylaminocarbonyl, ethylaminocarbonyl, N-methoxy-N-methylaminocarbonyl, methoxycarbonylmethyleneaminocarbonyl, methoxyethyleneaminocarbonyl, ethoxycarbonylphenyleneaminocarbonyl, dimethylmorpholinocarbonyl, morpholinopropylaminocarbonyl, ethoxycarbonylpiperidinocarbonyl, chlorobenzylaminocarbonyl, phenylhydroxyethylaminocarbonyl, ethoxycarbonylethyleneaminocarbonyl, trifluoromethylphenylenepiperazinylcarbonyl, hydroxyindanylaminocarbonyl, phenylmethoxycarbonylmethyleneaminocarbonyl, methoxyethylenepiperazinylcarbonyl, trifluorobenzylaminocarbonyl, methoxycarbonylbenzylaminocarbonyl, methylphenylenesulfonylaminocarbonyl or carboxyphenylmethyleneaminocarbonyl.

7. The compound according to claim 1, wherein G represents phenyl optionally substituted with one or more, same or different substituents selected from —C(O)H, —C(O)$NH_2$, hydroxy, halogen, cyano, nitro, amidino, carboxy, trifluoromethyl, $C_{1-6}$alkyl, $C_{2-4}$alkenyl, $C_{2-4}$alkynyl, $C_{1-4}$hydroxyalkyl, $C_{1-6}$amino, amino$C_{1-3}$alkyl, iminomethyl, hydroxyiminomethyl, $C_{1-6}$haloalkyl, $C_{1-4}$alkoxy, $C_{1-4}$alkoxycarbonyl, $C_{1-3}$alkoxycarbamoyl, $C_{1-4}$aminocarbonyl, $C_{1-3}$alkylsulfonylaminocarbonyl, hydroxyaminocarbonyl, $C_{1-6}$heterocycloalkyloxy, $C_{1-6}$heterocycloalkylaminocarbonyl, $C_{3-6}$cycloalkylaminocarbonyl, $C_{6-10}$arylaminocarbonyl, $C_{1-10}$heteroarylaminocarbonyl, $C_{3-6}$cycloalkyl, $C_{1-6}$heterocycloalkyl, $C_{1-6}$heterocycloalkenyl, $C_{1-6}$heterocycloalkylcarbonyl, $C_{1-4}$alkylcarbonyloxy, $C_{1-4}$alkoxycarbonyloxy, $C_{1-4}$alkoxysulfonyloxy, $C_{1-4}$alkylthio, $C_{3-6}$cycloalkenyl, $C_{1-4}$aminosulfonyl, $C_{1-4}$aminocarbonyloxy, $C_{1-4}$alkylsulfonylamino, $C_{1-6}$heteroaryl, $C_{6-10}$arylamino, $C_{6-10}$aryloxycarbonyl, $C_{6-10}$arylcarbonylamino, $C_{6-10}$arylsulfonylamino, $C_{1-4}$alkylcarbonylamino, $C_{1-4}$alkenylcarbonylamino, $C_{3-6}$cycloalkenylcarbonylamino, $C_{3-6}$cycloalkylcarbonylamino, $C_{1-4}$alkoxycarbonylamino, $C_{1-6}$heterocycloalkylcarbonylamino, $C_{1-4}$alkylsulfonyl or $C_{1-6}$heterocycloalkylsulfonyl, wherein said C(O)$NH_2$, $C_{1-6}$alkyl, $C_{2-4}$alkenyl, $C_{2-4}$alkynyl, $C_{1-4}$hydroxyalkyl, $C_{1-6}$amino, amino$C_{1-3}$alkyl, iminomethyl, hydroxyiminomethyl, $C_{1-6}$haloalkyl, $C_{1-4}$alkoxy, $C_{1-4}$alkoxycarbonyl, $C_{1-3}$alkoxycarbamoyl, $C_{1-4}$aminocarbonyl, $C_{1-3}$alkylsulfonylaminocarbonyl, hydroxyaminocarbonyl, $C_{1-6}$heterocycloalkyloxy, $C_{1-6}$heterocycloalkylaminocarbonyl, $C_{3-6}$cycloalkylaminocarbonyl, $C_{6-10}$arylaminocarbonyl, $C_{1-10}$heteroarylaminocarbonyl, $C_{3-6}$cycloalkyl, $C_{1-6}$heterocycloalkyl, $C_{1-6}$heterocycloalkenyl, $C_{1-6}$heterocycloalkylcarbonyl, $C_{1-4}$alkylcarbonyloxy, $C_{1-4}$alkoxycarbonyloxy, $C_{1-4}$alkoxysulfonyloxy, $C_{1-4}$alkylthio, $C_{3-6}$cycloalkenyl, $C_{1-4}$aminosulfonyl, $C_{1-4}$aminocarbonyloxy, $C_{1-4}$alkylsulfonylamino, $C_{1-6}$heteroaryl, $C_{6-10}$arylamino, $C_{6-10}$aryloxycarbonyl, $C_{6-10}$arylcarbonylamino, $C_{6-10}$arylsulfonylamino, $C_{1-4}$alkylcarbonylamino, $C_{1-4}$alkenylcarbonylamino, $C_{3-6}$cycloalkenylcarbonylamino, $C_{3-6}$cycloalkylcarbonylamino, $C_{1-4}$alkoxycarbonylamino, $C_{1-6}$heterocycloalkylcarbonylamino, $C_{1-4}$alkylsulfonyl, or $C_{1-6}$heterocycloalkylsulfonyl are optionally further substituted with one or more, same or different substituents selected from the group consisting of hydroxy, —NH$_2$, $C_{1-6}$amino, iminomethyl, hydroxyiminomethyl, carboxy, trifluoromethyl, halogen, oxo, mercapto, cyano, —C(O)NH$_2$, nitro, $C_{1-6}$alkyl, $C_{2-4}$alkenyl, $C_{2-4}$alkynyl, $C_{1-4}$hydroxyalkyl, $C_{1-6}$haloalkyl, $C_{1-3}$alkoxy, $C_{1-4}$alkoxycarbonyl, $C_{1-6}$heterocycloalkylcarbonyl, $C_{3-6}$cycloalkyl, $C_{3-6}$cycloalkenyl, $C_{1-6}$heterocycloalkyl, $C_{6-12}$aryl, $C_{1-10}$heteroaryl, $C_{1-3}$alkoxy $C_{6-10}$aryl, $C_{1-10}$heterocycloalkylaryl, $C_{1-6}$heterocycloalkenyl, —S(O)$_2$NH$_2$, —S(O)$_2$OH, $C_{1-6}$ureido, $C_{1-6}$thioureido, $C_{1-4}$alkylcarbonyloxy, $C_{1-4}$alkoxycarbonyloxy, $C_{1-4}$alkoxysulfonyloxy, $C_{1-4}$alkoxycarbamoyl, $C_{1-4}$aminocarbonyl, $C_{1-4}$alkylthio, $C_{1-4}$aminosulfonyl, $C_{1-4}$aminocarbonyloxy, $C_{1-4}$alkylsulfonylamino, $C_{6-12}$arylsulfonyl, $C_{6-10}$arylsulfonylamino, $C_{1-4}$alkylcarbonylamino or $C_{1-4}$alkylsulfonyl, wherein said $C_{3-6}$cycloalkyl, $C_{1-6}$alkyl, $C_{1-3}$alkoxy, $C_{1-4}$alkoxycarbonyl, $C_{1-6}$heterocycloalkyl, $C_{6-10}$aryl or $C_{1-10}$heteroaryl may be further substituted with carboxy, halogen, hydroxy, cyano, $C_{1-6}$heterocycloalkyl, one or more $C_{1-6}$alkyl, $C_{1-3}$alkoxy, $C_{1-3}$alkoxy$C_{1-3}$alkoxy $C_{1-4}$alkoxycarbonyl, $C_{1-3}$hydroxyalkyl or $C_{6-10}$aryl.

8. The compound according to claim 7, wherein G represents phenyl substituted with one or more same or different substituents selected from cyano, carboxy, —C(O)H, —C(O)NH$_2$, hydroxyl, halogen, amidino, iminomethyl, hydroxyiminomethyl, $C_{1-6}$alkyl, $C_{2-4}$alkynyl, amino$C_{1-3}$alkyl, $C_{1-3}$alkoxy, $C_{1-3}$alkoxycarbonyl, $C_{1-4}$alkoxycarbamoyl, $C_{1-3}$aminocarbonyl, $C_{3-6}$cycloalkyl, $C_{1-6}$heterocycloalkyl, $C_{1-6}$heterocycloalkylcarbonyl, $C_{1-6}$heterocycloalkyloxy, $C_{1-3}$aminocarbonyloxy, $C_{1-6}$heteroaryl, $C_{6-10}$arylamino, $C_{6-10}$aryloxycarbonyl, $C_{1-3}$alkylsulfonylaminocarbonyl, hydroxyaminocarbonyl, $C_{1-3}$alkylsulfonyl, $C_{1-6}$heterocycloalkylsulfonyl, $C_{1-6}$heterocycloalkylaminocarbonyl, $C_{3-6}$cycloalkylaminocarbonyl, $C_{6-10}$arylaminocarbonyl, $C_{1-3}$ aminosulfonyl, $C_{1-10}$heteroarylaminocarbonyl, $C_{1-3}$alkylcarbonylamino, $C_{1-3}$alkylsulfonylamino or $C_{6-10}$arylsulfonylamino, each of which is optionally substituted with one or more same or different substituents selected from hydroxy, —NH$_2$, $C_{1-3}$amino, iminomethyl, carboxy, trifluoromethyl, cyano, fluoro, chloro, iodo, oxo, mercapto, $C_{1-4}$alkyl, $C_{1-3}$hydroxyalkyl, $C_{1-2}$alkoxy, $C_{1-4}$alkoxycarbonyl, $C_{3-6}$cycloalkyl, $C_{3-5}$heterocycloalkyl, $C_{1-6}$heterocycloalkylcarbonyl, $C_{6-10}$aryl, $C_{1-10}$heteroaryl, $C_{1-2}$alkoxy$C_{6-10}$aryl, $C_{1-3}$alkylsulfonylamino, —S(O)$_2$OH or $C_{1-3}$alkylcarbonylamino, wherein said $C_{3-6}$cycloalkyl, $C_{1-4}$alkyl, $C_{1-2}$alkoxy, $C_{1-4}$alkoxycarbonyl, $C_{3-5}$heterocycloalkyl, $C_{6-10}$aryl or $C_{1-10}$heteroaryl are optionally further substituted with carboxy, halogen, hydroxy, cyano, $C_{1-6}$heterocycloalkyl, one or more $C_{1-6}$alkyl, $C_{1-3}$alkoxy, $C_{1-3}$alkoxy$C_{1-3}$alkoxy, $C_{1-4}$alkoxycarbonyl, $C_{1-3}$hydroxyalkyl or $C_{6-10}$aryl.

9. The compound according to any one of claim 7 or 8, wherein G represents phenyl substituted with iodo, fluoro, hydroxymethylpyrrolidinylcarbonyl, ethylaminocarbonyl, dimethylaminoethylaminocarbonyl, pyrrolidinyliminomethyl, amidino, aminohydroxyiminomethyl, methoxycarbonyl, ethoxycarbonyl, hydroxyethylaminocarbonyl, N-hydroxyethyl-N-methylaminocarbonyl, N-hydroxym-ethyl-N-propylaminocarbonyl, bishydroxyethylaminocarbonyl, dihydroxytert-butylaminocarbonyl, N-hydroxyethyl-N-ethylaminocarbonyl, cyanoethylaminocarbonyl, morpholinoethylaminocarbonyl, fluoroethylaminocarbonyl, difluoroethylaminocarbonyl, methoxycarbonylethylaminocarbonyl, N-pyridylmethyl-N-methylaminocarbonyl, benzyloxycarbamoyl, methylcarbonylaminoethylaminocarbonyl, iodophenyleneoxycarbonyl, methoxyethylaminocarbonyl, mercaptoethylaminocarbonyl, ethoxycarbonylmethylaminocarbonyl, sulfoethylaminocarbonyl, dimethylaminocarbonyl, dimethylaminoethylaminocarbonyl, dimethylaminopropylaminocarbonyl, piperidinocarbonyl, methylpiperazinylcarbonyl, hydroxyethylpiperazinylcarbonyl, morpholinocarbonyl, hydroxypiperidinocarbonyl, imidazolylpropylaminocarbonyl, carboxymethylaminocarbonyl, tert-butoxycabonylmethoxycarbonylethylaminocarbonyl, tert-butoxycarbonylcarboxyethylaminocarbonyl, methoxycarbonylphenylethylaminocarbonyl, carboxyphenylethylaminocarbonyl, methoxycarbonylindolylethylaminocarbonyl, carboxyindolylethylaminocarbonyl, N-ethoxycarbonylmethyl-N-cyclohexylaminocarbonyl, diethoxycarbonylmethylaminocarbonyl, tert-butoxycarbonylhydroxyethylaminocarbonyl, carboxypyridylaminocarbonyl, carboxyphenylaminocarbonyl, methoxyethoxycarbonylphenylaminocarbonyl, N,N-dicarboxymethylaminocarbonyl, carboxycyclopentylmethylaminocarbonyl, carboxyethylaminocarbonyl, carboxymethylcyclohexylaminocarbonyl, ethylcarboxycyclopropylaminocarbonyl, carboxycyclopropylaminocarbonyl, carboxyisopropylaminocarbonyl, carboxyazetidinylcarbonyl, N-methyl-N-carboxymethylaminocarbonyl, carboxypropylaminocarbonyl, ethoxycarbonylpiperidylcarbonyl, carboxypiperidylcarbonyl, N-ethoxycarbonylmethyl-N-cyclohexylaminocarbonyl, N-carboxymethyl-N-cyclohexylaminocarbonyl, oxotetrahydrofurylaminocarbonyl, cyanomethylaminocarbonyl, cyanopyrazolaminocarbonyl, phenylmethoxycarbonylhydroxyethylaminocarbonyl, methoxycarbonylhydroxyethylaminocarbonyl, ethoxycarbonylhydroxyethylaminocarbonyl, carboxyhydroxyethylaminocarbonyl, carboxyhydroxypropylaminocarbonyl, tert-butoxyaminocarbonyl, methoxyaminocarbonyl, tetrahydrofurylmethoxyaminocarbonyl, N-methoxy-N-methylaminocarbonyl, phenylmethoxyaminocarbonyl, hydroxyaminocarbonyl, morpholinocarbonylmethoxyaminocarbonyl, methylsulfonylaminocarbonyl, methoxycarbonylhydroxypyrrolidinylcarbonyl, carboxyhydroxypyrrolidinylcarbonyl, ethoxycarbonylmethoxy, methoxycarbonylethyl, carboxymethoxy, carboxyethyl, ethoxycarbonylethyl, carboxymethoxy, oxopyrrolidinyl, oxooxazolidinyl, methylcarbonylamino, hydroxytetrahydropyranyl, imidazolyl, hydroxycyclopentyl, methylcarboxy, hydroxymethyl, hydroxycyclobutyl, diethoxycarbonylmethyl, ethoxycarbonylmethyl, carboxymethyl, fluorooxetanyl, aminomethylbutynyl, cyclopropyl[1,2,4]oxadiazolyl, cyclopentyl[1,2,4]oxadiazolyl, methyl[1,2,4]oxadiazolyl, isopropyl[1,2,4]oxadiazolyl, tert-butyl[1,2,4]oxadiazolyl, cyclohexyl[1,2,4]oxadiazolyl, methylbutyl[1,2,4]oxadiazolyl, dioxoimidazolidinyl[1,2,4]oxadiazolyl, methyloxazolyl[1,2,4]oxadiazolyl, dimethyloxazolyl[1,2,4]oxadiazolyl, cyanomethylethyl, carboxymethylethyl, methylsulfonyl, methoxycarbonyl, hydroxymethyl, methylsulfonylaminomethyl, morpholinylsulfonyl, methylcarboxyaminomethyl, hydroxyethylaminosulfonyl, methylsulfonylamino, morpholinylethoxycarbonyl, methoxyethoxyethoxycarbonyl, methoxyethoxyethoxyethoxycarbonyl, ethoxyethoxyethoxyethoxycarbonyl, dihydroxypropoxycarbonyl, tetrahydrofuranylmethoxycarbonyl, hydroxy, ethoxycarbonylpropoxy, carboxypropoxy, carboxyethoxy, oxodihydrofuranyloxy, ethoxyethoxy, ethoxycarbonylethoxy, cyanophenylmethoxy, pyridylmethoxy, pyrazolylethoxy, indolylethoxy, carboxymethylethoxy carboxyhydroxypropoxy, carboxyphenylmethoxy, hydroxymethylpropoxy, hydroxydiethylethoxy, dimethylaminocarbonyloxy, hydroxydiethylpropyl, hydroxymethylbutyl, dihydroxypropoxy, carboxyfluorophenylmethoxy, hydroxyethoxy, hydroxymethylpyrrolidinylmethyl, hydroxypyrrolidinylmethyl, ethoxycarbonylpyridylmethyl, mehyltetrahydrofuranylmethylaminomethyl, carboxy, ethoxy or hydroxypropyl.

10. The compound according to claim 8, wherein when G represents phenyl being further substituted, the substituent is attached to the phenylene ring in the meta or para position from where the phenyl ring is attached to the cycloalkyl representing

11. The compound according to claim 1, wherein G represents $C_{1-10}$heteroaryl or $C_{1-6}$heterocycloalkyl and wherein said $C_{1-10}$heteroaryl or $C_{1-6}$heterocycloalkyl is optionally substituted with carboxy, $C_{1-6}$alkyl, $C_{6-10}$aryl, $C_{1-3}$alkoxycarbonyl, which may further be optionally substituted with trifluoromethyl, halogen, $C_{1-3}$alkyl, $C_{1-3}$alkoxy, $C_{1-10}$heteroaryl,
wherein $C_{1-10}$heteroaryl may further be substituted with $C_{1-3}$alkyl or oxo.

12. The compound according to claim 11, wherein G represents fluorophenylene[1,2,4]oxadiazolyl, phenyl[1,2,4]oxadiazolyl, isopropyl[1,2,4]oxadiazolyl, trifluoromethylphenylene[1,2,4]oxadiazolyl, methyl[1,2,4]oxadiazolyl, methylthiazolylmethylene[1,2,4]oxadiazolyl, propyl[1,2,4]oxadiazolyl, oxopyridinylmethylene[1,2,4]oxadiazolyl, methoxyphenylene[1,2,4]oxadiazolyl, methylcarboxyimidazolyl, ethoxycarbonylthienyl, ethoxycarbonylfuryl, pyridyl, carboxythienyl or carboxyfuryl.

13. The compound according to claim 1, wherein G represents phenylamino or phenyloxy, optionally substituted with cyano, carboxy, $C_{1-4}$alkoxycarbonyl or trifluoromethyl.

14. The compound according to claim 1 wherein $R_2$, $R_3$, $R_4$ and $R_5$ represent hydrogen.

15. The compound according to claim 1, wherein $R_1$ represents methyl.

16. The compound according to claim 1, wherein G represents $C_{6-10}$aryl, $C_{1-3}$aminocarbonyl$C_{6-10}$aryl or $C_{1-4}$alkyl$C_{6-10}$aryl optionally substituted with carboxy, $C_{1-3}$alkoxy or $C_{1-3}$alkoxycarbonyl, A represents 1-naphthyl, $R_2$, $R_3$, $R_4$ and $R_5$ represent hydrogen and $R_1$ represents methyl.

17. The compound according to claim 1 selected from the group consisting of
3-((R)-1-naphthalen-1-yl-ethylamino)-cyclobutanecarboxylic acid (compound 1000),
cyclobutyl-((R)-1-naphthalen-1-yl-ethyl)-amine, hydrochloride (compound 1001),
3-((R)-1-naphthalen-1-yl-ethylamino)-cyclobutanecarboxylic acid dimethylamide (compound 1002),
3-((R)-1-naphthalen-1-yl-ethylamino)-cyclobutanecarboxylic acid amide (compound 1003),
(4-Methyl-piperazin-1-yl)-[3-((R)-1-naphthalen-1-yl-ethylamino)-cyclobut yl]-methanone; hydrochloride (compound 1004),
3-((R)-1-naphthalen-1-yl-ethylamino)-cyclobutanecarboxylic acid cyclopropylamide (compound 1005),
3-((R)-1-naphthalen-1-yl-ethylamino)-cyclobutanecarboxylic acid isopropylamide (compound 1006),
3-((R)-1-naphthalen-1-yl-ethylamino)-cyclobutanecarboxylic acid propylamide (compound 1007),
Morpholin-4-yl-[3-((R)-1-naphthalen-1-yl-ethylamino)-cyclobutyl]-methanone (compound 1008),
3-((R)-1-naphthalen-1-yl-ethylamino)-cyclobutanecarboxylic acid tert-butylamide (compound 1009),
3-((R)-1-naphthalen-1-yl-ethylamino)-cyclobutanecarboxylic acid ethylamide (compound 1010),
3-((R)-1-naphthalen-1-yl-ethylamino)-cyclobutanecarboxylic acid methoxy-methyl-amide; hydrochloride (compound 1011),
[3-(3-Isopropyl-[1,2,4]oxadiazol-5-yl)-cyclobutyl]-((R)-1-naphthalen-1-yl-ethyl)-amine; hydrochloride (compound 1012),
((R)-1-Naphthalen-1-yl-ethyl)-{3-[3-(3-trifluoromethyl-phenyl)-[1,2,4]oxadiazol-5-yl]-cyclobutyl}-amine; hydrochloride (compound 1013),
[3-(3-Methyl-[1,2,4]oxadiazol-5-yl)-cyclobutyl]-((R)-1-naphthalen-1-yl-ethyl)-amine; hydrochloride (compound 1014),
((R)-1-Naphthalen-1-yl-ethyl)-[3-(3-phenyl-[1,2,4]oxadiazol-5-yl)-cyclobutyl]-amine; hydrochloride (compound 1015),
((R)-1-Naphthalen-1-yl-ethyl)-{3-[3-(4-trifluoromethyl-phenyl)-[1,2,4]oxadiazol-5-yl]-cyclobutyl}-amine; hydrochloride (compound 1016),
{3-(3-[3-(4-Methoxy-phenyl)-[1,2,4]oxadiazol-5-yl]-cyclobutyl}-((R)-1-naphthalen-1-yl-ethyl)-amine; hydrochloride (compound 1017),
3-((R)-1-Naphthalen-1-yl-ethylamino)-cyclobutanecarboxylic acid 4-chloro-benzylamide (compound 1018),
{[3-((R)-1-Naphthalen-1-yl-ethylamino)-cyclobutanecarbonyl]-amino}-acetic acid methyl ester (compound 1019),
3-((R)-1-Naphthalen-1-yl-ethylamino)-cyclobutanecarboxylic acid (2-methoxy-ethyl)-amide (compound 1020), 4-{[3-((R)-1-Naphthalen-1-yl-ethylamino)-cyclobutanecarbonyl]-amino}-benzoic acid ethyl ester (compound 1021),
(2,6-Dimethyl-morpholin-4-yl)-[3-((R)-1-naphthalen-1-yl-ethylamino)-cyclobutyl]-methanone (compound 1022),
3-((R)-1-Naphthalen-1-yl-ethylamino)-cyclobutanecarboxylic acid (3-morpholin-4-yl-propyl)-amide (compound 1023),
1-[3-((R)-1-Naphthalen-1-yl-ethylamino)-cyclobutanecarbonyl]-piperidine-4-carboxylic acid ethyl ester (compound 1024),
3-((R)-1-Naphthalen-1-yl-ethylamino)-cyclobutanecarboxylic acid (2-hydroxy-2-phenyl-ethyl)-amide (compound 1025),
3-{[3-((R)-1-Naphthalen-1-yl-ethylamino)-cyclobutanecarbonyl]-amino}-propionic acid ethyl ester (compound 1026),
{[3-((R)-1-Naphthalen-1-yl-ethylamino)-cyclobutanecarbonyl]-amino}-phenyl-acetic acid methyl ester (compound 1028),
3-((R)-1-Naphthalen-1-yl-ethylamino)-cyclobutanecarboxylic acid (2-hydroxy-indan-1-yl)-amide (compound 1029),

[4-(2-Methoxy-ethyl)-piperazin-1-yl]-[3-((R)-1-Naphthalen-1-yl-ethylamino)-cyclobutyl]-methanone (compound 1030),
3-((R)-1-Naphthalen-1-yl-ethylamino)-cyclobutanecarboxylic acid 2,3,6-trifluoro-benzylamide (compound 1031),
3-({[3-((R)-1-Naphthalen-1-yl-ethylamino)-cyclobutanecarbonyl]-amino}-methyl)-benzoic acid methyl ester (compound 1032),
4-({[3-((R)-1-Naphthalen-1-yl-ethylamino)-cyclobutanecarbonyl]-amino}-methyl)-benzoic acid methyl ester (compound 1033),
{[3-((R)-1-Naphthalen-1-yl-ethylamino)-cyclobutanecarbonyl]-amino}-phenyl-acetic acid (compound 1034),
((R)-1-Naphthalen-1-yl-ethyl)-(3-phenyl-cyclobutyl)-amine (compound 1035 and compound 1036),
{3-[3-(4-Fluoro-phenyl)-[1,2,4]oxadiazol-5-yl]-cyclopentyl}-((R)-1-naphthalen-1-yl-ethyl)-amine; hydrochloride (compound 1037),
((R)-1-Naphthalen-1-yl-ethyl)-[3-(3-phenyl-[1,2,4]oxadiazol-5-yl)-cyclopentyl]-amine; hydrochloride (compound 1038),
[3-(3-Isopropyl-[1,2,4]oxadiazol-5-yl)-cyclopentyl]-(R)-1-naphthalen-1-yl-ethyl)-amine; hydrochloride (compound 1039),
((R)-1-Naphthalen-1-yl-ethyl)-{3-[3-(4-trifluoromethyl-phenyl)-[1,2,4]oxadiazol-5-yl]-cyclopentyl}-amine; hydrochloride (compound 1040),
[3-(3-Methyl-[1,2,4]oxadiazol-5-yl)-cyclopentyl]-((R)-1-naphthalen-1-yl-ethyl)-amine; hydrochloride (compound 1041),
{3-[3-(5-Methyl-thiazol-2-ylmethyl)-[1,2,4]oxadiazol-5-yl]-cyclopentyl}-((R)-1-naphthalen-1-yl-ethyl)-amine (compound 1042),
((R)-1-naphthalen-1-yl-ethyl)-[3-(3-propyl-[1,2,4]oxadiazol-5-yl)-cyclopentyl]-amine; hydrochloride (compound 1043a and 1043b),
1-{5-[3-((R)-1-Naphthalen-1-yl-ethylamino)-cyclopentyl]-[1,2,4]oxadiazol-3-ylmethyl}-1H-pyridin-2-one; hydrochloride (compound 1044),
{3-[3-(4-Methoxy-phenyl)-[1,2,4]oxadiazol-5-yl]-cyclopentyl}-((R)-1-naphthalen-1-yl-ethyl)-amine; hydrochloride (compound 1045),
3-((R)-1-Naphthalen-1-yl-ethylamino)-cyclopentanecarboxylic acid amide (compound 1046),
4-Methyl-N-[3-((R)-1-naphthalen-1-yl-ethylamino)-cyclopentane carbonyl]-benzenesulfonamide (compound 1047a, compound 1047b, compound 1047c and compound 1047d),
4-[3-((R)-Naphthalen-1-yl-ethylamino)-cyclohexyl]-benzonitrile (compounds 1048/1049/1050),
N-Hydroxy-4-[3-((R)-1-naphthalen-1-yl-ethylamino)-cyclohexyl]-benzamidine (compound 1051),
N-Hydroxy-4-[3-((R)-1-naphthalen-1-yl-ethylamino)-cyclohexyl]-benzamidine (compound 1052),
N-Hydroxy-4-[3-((R)-1-naphthalen-1-yl-ethylamino)-cyclohexyl]-benzamidine (compound 1053a and compound 1053b),
{3-[4-(Imino-pyrrolidin-1-yl-methyl)-phenyl]-cyclohexyl}-((R)-1-naphthalen-1-yl-ethyl)-amine (compound 1054),
4-[3-((R)-1-naphthalen-1-yl-ethylamino)-cyclohexyl]-benzamidine (compound 1055),
4-[3-((R)-1-naphthalen-1-yl-ethylamino)-cyclohexyl]-benzoic acid (compound 1056),
4-[3-((R)-1-naphthalen-1-yl-ethylamino)-cyclohexyl]-benzoic acid (compound 1057),
4-[3-((R)-1-naphthalen-1-yl-ethylamino)-cyclohexyl]-benzoic acid (compound 1058, 1058a),
3-[3-((R)-1-naphthalen-1-yl-ethylamino)-cyclohexyl]-benzoic acid ethyl ester (compound 1059),
N-(2-Hydroxy-ethyl)-3-[3-((R)-1-naphthalen-1-yl-ethylamino)-cyclohexyl]-benzamide (compound 1060),
3-[3-((R)-1-naphthalen-1-yl-ethylamino)-cyclohexyl]-benzoic acid (compounds 1061/1062),
((R)-1-Naphthalen-1-yl-ethyl)-(3 (S)-phenyl-cyclohexyl)-amine (compound 1063),
((R)-1-Naphthalen-1-yl-ethyl)-(3 (R)-phenyl-cyclohexyl)-amine (compound 1064),
N—((R)-1-Naphthalen-1-yl-ethyl)-N'-phenyl-cyclohexane-1,3-diamine (compound 1065),
N—((R)-1-Naphthalen-1-yl-ethyl)-N'-(3-trifluoromethyl-phenyl)-cyclohexane-1,3-diamine (compound 1066),
4-[3-((R)-1-Naphthalen-1-yl-ethylamino)-cyclohexylamino]-benzonitrile (compound 1067),
(3-Morpholin-4-yl-cyclohexyl)-((R)-1-naphthalen-1-yl-ethyl)-amine (compound 1068),
((R)-1-Naphthalen-1-yl-ethyl)-(3-pyridin-2-yl-cyclohexyl)-amine (compounds 1069/1070),
5-[3-((R)-1-Naphthalen-1-yl-ethylamino)-cyclohexyl]-thiophene-2-carboxylic acid ethyl ester (compound 1071),
5-[3-((R)-1-naphthalen-1-yl-ethylamino)-cyclohexyl]-thiophene-2-carboxylic acid (compound 1072),
5-[3-((R)-1-naphthalen-1-yl-ethylamino)-cyclohexyl]-furan-2-carboxylic acid ethyl ester (compound 1073),
5-[3-((R)-1-naphthalen-1-yl-ethylamino)-cyclohexyl]-furan-2-carboxylic acid (compound 1074a, compound 1074b and compound 1074c),
{3-[3-(4-Fluoro-phenyl)-[1,2,4]oxadiazol-5-yl]-cyclohexyl}-((R)-1-naphthalen-1-yl-ethyl)-amine (compound 1075),
((R)-1-Naphthalen-1-yl-ethyl)-{3-[3-(4-trifluoromethyl-phenyl)-[1,2,4]oxadiazol-5-yl]-cyclohexyl}-amine (compound 1076),
((R)-1-Naphthalen-1-yl-ethyl)-[3-(3-phenyl-[1,2,4]oxadiazol-5-yl)-cyclohexyl]-amine (compound 1077),
4-[3-((R)-1-Naphthalen-1-yl-ethylamino)-cyclohexyl]-benzamide (compound 1078),
N-Benzyloxy-4-[3-((R)-1-naphthalen-1-yl-ethylamino)-cyclohexyl]-benzamide (compound 1079),
4-[3-((R)-1-Naphthalen-1-yl-ethylamino)-cyclohexyl]-benzoic acid 4-iodo-phenyl ester (compound 1080),
2-{4-[3-((R)-1-Naphthalen-1-yl-ethylamino)-cyclohexyl]-benzoylamino}-ethanesulfonic acid (compound 1081),
N—((R)-1-Hydroxymethyl-propyl)-4-[3-((R)-1-naphthalen-1-yl-ethylamino)-cyclohexyl]-benzamide (compound 1082),
N—((S)-1-Hydroxymethyl-propyl)-4-[3-((R)-1-naphthalen-1-yl-ethylamino)-cyclohexyl]-benzamide (compound 1083),
N-(2-Cyano-ethyl)-4-[3-((R)-1-naphthalen-1-yl-ethylamino)-cyclohexyl]-benzamide (compound 1084),
N-(2-Morpholin-4-yl-ethyl)-4-[3-((R)-1-naphthalen-1-yl-ethylamino)-cyclohexyl]-benzamide (compound 1085),
N-(2-Fluoro-ethyl)-4-[3-((R)-1-naphthalen-1-yl-ethylamino)-cyclohexyl]-benzamide (compound 1086),
N-(2,2-Difluoro-ethyl)-4-[3-((R)-1-naphthalen-1-yl-ethylamino)-cyclohexyl]-benzamide (compound 1087),
3-{4-[3-((R)-1-Naphthalen-1-yl-ethylamino)-cyclohexyl]-benzoylamino}-propionic acid methyl ester (compound 1088), N-Methyl-4-[3-((R)-1-naphthalen-1-yl-ethylamino)-cyclohexyl]-N-pyridin-4-ylmethyl-benzamide (compound 1089),
N-(2-Dimethylamino-ethyl)-N-methyl-4-[3-((R)-1-naphthalen-1-yl-ethylamino)-cyclohexyl]-benzamide (compound 1090),
(2-Hydroxymethyl-pyrrolidin-1-yl)-{4-[3-(1-naphthalen-1-yl-ethylamino)-cyclohexyl]-phenyl}-methanone (compound 1091),
N-(2-Acetylamino-ethyl)-4-[3-((R)-1-naphthalen-1-yl-ethylamino)-cyclohexyl]-benzamide (compound 1092),
N-Ethyl-4-[3-((R)-1-naphthalen-1-yl-ethylamino)-cyclohexyl]-benzamide (compound 1093),
N-(2-Hydroxy-ethyl)-4-[3-((R)-1-naphthalen-1-yl-ethylamino)-cyclohexyl]-benzamide (compound 1094),
N-(2-Hydroxy-1-hydroxymethyl-1-methyl-ethyl)-4-[3-((R)-1-naphthalen-1-yl-ethylamino)-cyclohexyl]-benzamide (compound 1095),
N-(2-Methoxy-ethyl)-4-[3-((R)-1-naphthalen-1-yl-ethylamino)-cyclohexyl]-benzamide (compound 1096),
N-(2-Mercapto-ethyl)-4-[3-((R)-1-naphthalen-1-yl-ethylamino)-cyclohexyl]-benzamide (compound 1097),
{4-[3-((R)-1-Naphthalen-1-yl-ethylamino)-cyclohexyl]-benzoylamino}-acetic acid ethyl ester (compound 1098),
N,N-Dimethyl-4-[3-((R)-1-naphthalen-1-yl-ethylamino)-cyclohexyl]-benzamide (compound 1099),
N-(2-Hydroxy-ethyl)-N-methyl-4-[3-((R)-1-naphthalen-1-yl-ethylamino)-cyclohexyl]-benzamide (compound 1100),
N-Ethyl-N-(2-hydroxy-ethyl)-4-[3-((R)-1-naphthalen-1-yl-ethylamino)-cyclohexyl]-benzamide (compound 1101),
N,N-Bis-(2-hydroxy-ethyl)-4-[3-((R)-1-naphthalen-1-yl-ethylamino)-cyclohexyl]-benzamide (compound 1102),
N-(2-Dimethylamino-ethyl)-4-[3-((R)-1-naphthalen-1-yl-ethylamino)-cyclohexyl]-benzamide (compound 1103),
N-(3-Dimethylamino-propyl)-4-[3-((R)-1-naphthalen-1-yl-ethylamino)-cyclohexyl]-benzamide (compound 1104),
{4-[3-((R)-1-Naphthalen-1-yl-ethylamino)-cyclohexyl]-phenyl}-piperidin-1-yl-methanone (compound 1105),
(4-Methyl-piperazin-1-yl)-{4-[3-((R)-1-naphthalen-1-yl-ethylamino)-cyclohexyl]-phenyl}-methanone (compound 1106),
[4-(2-Hydroxy-ethyl)-piperazin-1-yl]-{4-[3-((R)-1-naphthalen-1-yl-ethylamino)-cyclohexyl]-phenyl}-methanone (compound 1107),
Morpholin-4-yl-{4-[3-((R)-1-naphthalen-1-yl-ethylamino)-cyclohexyl]-phenyl}-methanone (compound 1108),
(4-Hydroxy-piperidin-1-yl)-{4-[3-((R)-1-naphthalen-1-yl-ethylamino)-cyclohexyl]-phenyl}-methanone (compound 1109),
N-(3-Imidazol-1-yl-propyl)-4-[3-((R)-1-naphthalen-1-yl-ethylamino)-cyclohexyl]-benzamide (compound 1110),
3-((R)-1-naphthalen-1-yl-ethylamino)-cyclopentanecarboxylic acid (compound 1111),
{4-[(1S,3S)-3-((R)-1-Naphthalen-1-yl-ethylamino)-cyclohexyl]-benzoylamino}-acetic acid (compound 1115), (S)-3-{4-[(1S,3S)-3-((R)-1-Naphthalen-1-yl-ethylamino)-cyclohexyl]-benzoylamino}-succinic acid 4-tert-butyl ester 1-methyl ester (compound 1116), (S)-2-{4-[(1S,3S)-3-((R)-1-Naphthalen-1-yl-ethylamino)-cyclohexyl]-benzoylamino}-succinic acid 4-tert-butyl ester (compound 1117),
(R)-2-{4-[(1S,3S)-3-((R)-1-Naphthalen-1-yl-ethylamino)-cyclohexyl]-benzoylamino}-3-phenyl-propionic acid methyl ester (compound 1118),
(R)-2-{4-[(1S,3S)-3-((R)-1-Naphthalen-1-yl-ethylamino)-cyclohexyl]-benzoylamino}-3-phenyl-propionic acid (compound 1119),
(S)-2-{4-[(1S,3S)-3-((R)-1-Naphthalen-1-yl-ethylamino)-cyclohexyl]-benzoylamino}-3-phenyl-propionic acid methyl ester (compound 1120),
(S)-2-{4-[(1S,3S)-3-((R)-1-Naphthalen-1-yl-ethylamino)-cyclohexyl]-benzoylamino}-3-phenyl-propionic acid; hydrochloride (compound 1121),
(S)-3-(1H-Indol-3-yl)-2-{4-[(1S,3S)-3-((R)-1-naphthalen-1-yl-ethylamino)-cyclohexyl]-benzoylamino}-propionic acid methyl ester (compound 1122),
(S)-3-(1H-Indol-3-yl)-2-{4-[(1S,3S)-3-((R)-1-naphthalen-1-yl-ethylamino)-cyclohexyl]-benzoylamino}-propionic acid (compound 1123),
(R)-3-(1H-Indol-3-yl)-2-{4-[(1S,3S)-3-((R)-1-naphthalen-1-yl-ethylamino)-cyclohexyl]-benzoylamino}-propionic acid methyl ester (compound 1124),
(R)-3-(1H-Indol-3-yl)-2-{4-[(1S,3S)-3-((R)-1-naphthalen-1-yl-ethylamino)-cyclohexyl]-benzoylamino}-propionic acid (compound 1125),
(Cyclohexyl-{4-[3-(1-naphthalen-1-yl-ethylamino)-cyclohexyl]-benzoyl}-amino)-acetic acid ethyl ester (compound 1126),
2-{4-[3-((R)-1-Naphthalen-1-yl-ethylamino)-cyclohexyl]-benzoylamino}-malonic acid diethyl ester (compound 1127),
(S)-3-Hydroxy-2-{4-[(1S,3S)-3-((R)-1-naphthalen-1-yl-ethylamino)-cyclohexyl]-benzoylamino}-propionic acid tert-butyl ester (compound 1128),
5-{4-[(1S,3S)-3-((R)-1-Naphthalen-1-yl-ethylamino)-cyclohexyl]-benzoylamino}-nicotinic acid (compound 1129),
4-{4-[(1S,3S)-3-((R)-1-Naphthalen-1-yl-ethylamino)-cyclohexyl]-benzoylamino}-benzoic acid (compound 1130),
4-Methoxy-3-{4-[(1S,3S)-3-((R)-1-naphthalen-1-yl-ethylamino)-cyclohexyl]-benzoylamino}-benzoic acid methyl ester; hydrochloride (compound 1131),
2-{4-[(1S,3S)-3-((R)-1-Naphthalen-1-yl-ethylamino)-cyclohexyl]-benzoylamino}-benzoic acid; hydrochloride (compound 1132),
(Carboxymethyl-{4-[(1S,3S)-3-((R)-1-naphthalen-1-yl-ethylamino)-cyclohexyl]-benzoyl}-amino)-acetic acid; hydrochloride (compound 1133),
1-({4-[(1S,3S)-3-((R)-1-Naphthalen-1-yl-ethylamino)-cyclohexyl]-benzoylamino}-methyl)-cyclopentanecarboxylic acid (compound 1134),
1-{4-[(1S,3S)-3-((R)-1-Naphthalen-1-yl-ethylamino)-cyclohexyl]-benzoylamino}-cyclopentanecarboxylic acid; hydrochloride (compound 1135),
3-{4-[(1S,3S)-3-((R)-1-Naphthalen-1-yl-ethylamino)-cyclohexyl]-benzoylamino}-propionic acid; hydrochloride (compound 1136),
(1-{4-[(1S,3S)-3-((R)-1-Naphthalen-1-yl-ethylamino)-cyclohexyl]-benzoylamino}-cyclohexyl)-acetic acid; hydrochloride (compound 1137),
1-{4-[(1S,3S)-3-((R)-1-Naphthalen-1-yl-ethylamino)-cyclohexyl]-benzoylamino}-cyclopropanecarboxylic acid ethyl ester (compound 1138), 1-{4-[(1S,3S)-3-((R)-1-Naphthalen-1-yl-ethylamino)-cyclohexyl]-benzoylamino}-cyclopropanecarboxylic acid (compound 1139), 1-({4-[(1S,3S)-3-((R)-1-Naphthalen-1-yl-ethylamino)-cyclohexyl]-benzoylamino}-methyl)-cyclopropanecarboxylic acid (compound 1140), 2-Methyl-2-{4-[(1S,3S)-3-((R)-1-naphthalen-1-yl-ethylamino)-cyclohexyl]-benzoylamino}-propionic acid (compound 1141), 1-{4-[(1S,3S)-3-((R)-1-Naphthalen-1-yl-ethylamino)-cyclohexyl]-benzoyl}-azetidine-3-carboxylic acid (compound 1142), (Methyl-{4-[(1S,3S)-3-((R)-1-naphthalen-1-yl-ethylamino)-cyclohexyl]-benzoyl}-amino)-acetic acid (compound 1143), 4-{4-[(1S,3S)-3-((R)-1-Naphthalen-1-yl-ethylamino)-cyclohexyl]-benzoylamino}-butyric acid (compound 1144), 1-{4-[(1S,3S)-3-((R)-1-Naphthalen-1-yl-ethylamino)-cyclohexyl]-benzoyl}-piperidine-4-carboxylic acid ethyl ester (compound 1145), 1-{4-[(1S,3S)-3-((R)-1-Naphthalen-1-yl-ethylamino)-cyclohexyl]-benzoyl}-piperidine-4-carboxylic acid (compound 1146), (Cyclohexyl-{4-[3-((R)-1-naphthalen-1-yl-ethylamino)-cyclohexyl]-benzoyl}-amino)-acetic acid ethyl ester (compound 1147), (Cyclohexyl-{4-[3-((R)-1-naphthalen-1-yl-ethylamino)-cyclohexyl]-benzoyl}-amino)-acetic acid (compound 1148), 4-[(1S,3S)-3-((R)-1-Naphthalen-1-yl-ethylamino)-cyclohexyl]-N—((R)-2-oxo-tetrahydro-furan-3-yl)-benzamide (compound 1149), N-Cyanomethyl-4-[(1S,3S)-3-((R)-1-naphthalen-1-yl-ethylamino)-cyclohexyl]-benzamide (compound 1150), N-(4-Cyano-1H-pyrazol-3-yl)-4-[(1S,3S)-3-((R)-1-naphthalen-1-yl-ethylamino)-cyclohexyl]-benzamide (compound 1151), (R)-3-Hydroxy-2-{4-[(1S,3S)-3-((R)-1-naphthalen-1-yl-ethylamino)-cyclohexyl]-benzoylamino}-propionic acid benzyl ester (compound 1152), (S)-3-Hydroxy-2-{4-[(1S,3S)-3-((R)-1-naphthalen-1-yl-ethylamino)-cyclohexyl]-benzoylamino}-propionic acid benzyl ester (compound 1153), (S)-3-Hydroxy-2-{4-[(1S,3S)-3-((R)-1-naphthalen-1-yl-ethylamino)-cyclohexyl]-benzoylamino}-propionic acid methyl ester (compound 1154), (R)-3-Hydroxy-2-{4-[(1S,3S)-3-((R)-1-naphthalen-1-yl-ethylamino)-cyclohexyl]-benzoylamino}-propionic acid methyl ester (compound 1155), (S)-3-Hydroxy-2-{4-[(1S,3S)-3-((R)-1-naphthalen-1-yl-ethylamino)-cyclohexyl]-benzoylamino}-propionic acid ethyl ester; hydrochloride (compound 1156), 3-Hydroxy-2-{4-[3-((R)-1-naphthalen-1-yl-ethylamino)-cyclohexyl]-benzoylamino}-propionic acid; hydrochloride (compound 1157), (R)-4-Hydroxy-2-{4-[(1S,3S)-3-((R)-1-naphthalen-1-yl-ethylamino)-cyclohexyl]-benzoylamino}-butyric acid (compound 1158), N-tert-Butoxy-4-[(1S,3S)-3-((R)-1-naphthalen-1-yl-ethylamino)-cyclohexyl]-benzamide; formiate (compound 1159), N-tert-Butoxy-4-[3-((R)-1-naphthalen-1-yl-ethylamino)-cyclohexyl]-benzamide; formiate compound 1160), N-Methoxy-4-[(1S,3S)-3-((R)-1-naphthalen-1-yl-ethylamino)-cyclohexyl]-benzamide; formiate (compound 1161), N-Methoxy-4-[3-((R)-1-naphthalen-1-yl-ethylamino)-cyclohexyl]-benzamide; formiate (compound 1162), 4-[(1S,3S)-3-((R)-1-Naphthalen-1-yl-ethylamino)-cyclohexyl]-N-(tetrahydro-furan-3-ylmethoxy)-benzamide (compound 1163), 4-[3-((R)-1-Naphthalen-1-yl-ethylamino)-cyclohexyl]-N-(tetrahydro-furan-3-ylmethoxy)-benzamide (compound 1164), N-Methoxy-N-methyl-4-[(1S,3S)-3-((R)-1-naphthalen-1-yl -ethylamino)-cyclohexyl]-benzamide; bis formate (compound 1165), N-Methoxy-N-methyl-4-[3-((R)-1-naphthalen-1-yl-ethylamino)-cyclohexyl]-benzamide (compound 1166), N-Benzyloxy-4-[(1S,3S)-3-((R)-1-naphthalen-1-yl-ethylamino)-cyclohexyl]-benzamide (compound 1167), N-Benzyloxy-4-[3-((R)-1-naphthalen-1-yl-ethylamino)-cyclohexyl]-benzamide (compound 1168), N-Hydroxy-4-[3-((R)-1-naphthalen-1-yl-ethylamino)-cyclohexyl]-benzamide (compound 1169), N-Hydroxy-4-[(1S,3S)-3-((R)-1-naphthalen-1-yl-ethylamino)-cyclohexyl]-benzamide (compound 1170), N-(2-Morpholin-4-yl-2-oxo-ethoxy)-4-[(1S,3S)-3-((R)-1-naphthalen-1-yl-ethylamino)-cyclohexyl]-benzamide (compound 1171), N-(2-Morpholin-4-yl-2-oxo-ethoxy)-4-[3-((R)-1-naphthalen-1-yl-ethylamino)-cyclohexyl]-benzamide (compound 1172), N-{4-[(1S,3S)-3-((R)-1-Naphthalen-1-yl-ethylamino)-cyclohexyl]-benzoyl}-methanesulfonamide (compound 1173), 4R-Hydroxy-1-{4-[(1S,3S)-3-((R)-1-naphthalen-1-yl-ethylamino)-cyclohexyl]-benzoyl}-pyrrolidine-2S-carboxylic acid methyl ester (compound 1174), 4R-Hydroxy-1-{4-[(1S,3S)-3-((R)-1-naphthalen-1-yl-ethylamino)-cyclohexyl]-benzoyl}-pyrrolidine-2S-carboxylic acid (compound 1175), N-{4-[3-((R)-1-Naphthalen-1-yl-ethylamino)-cyclohexyl]-benzoyl}-methanesulfonamide; hydrochloride (compound 1176), {4-[3-((R)-1-Naphthalen-1-yl-ethylamino)-cyclopentyl]-phenoxy}-acetic acid ethyl ester (compound 1177/1178), {4-[3-((R)-1-Naphthalen-1-yl-ethylamino)-cyclopentyl]-phenoxy}-acetic acid ethyl ester (compound 1179/1180), 3-{4-[(3S)-3-((R)-1-Naphthalen-1-yl-ethylamino)-cyclopentyl]-phenyl}-propionic acid methyl ester (compounds 1181/1182/1183/1184), {4-[3-((R)-1-Naphthalen-1-yl-ethylamino)-cyclopentyl]-phenoxy}-acetic acid (compound 1185), {4-[(1R,3S)-3-((R)-1-Naphthalen-1-yl-ethylamino)-cyclopentyl]-phenoxy}-acetic acid (compound 1186), {4-[3-((R)-1-Naphthalen-1-yl-ethylamino)-cyclopentyl]-phenoxy}-acetic acid (compound 1187), {4-[3-((R)-1-Naphthalen-1-yl-ethylamino)-cyclopentyl]-phenoxy}-acetic acid (compound 1188), 3-{4-[3-((R)-1-Naphthalen-1-yl-ethylamino)-cyclopentyl]-phenyl}-propionic acid (compound 1189), 3-{4-[(1S,3S)-3-((R)-1-Naphthalen-1-yl-ethylamino)-cyclopentyl]-phenyl}-propionic acid; hydrochloride (compound 1190), 3-{4-[3-((R)-1-Naphthalen-1-yl-ethylamino)-cyclopentyl]-phenyl}-propionic acid (compound 1191), 3-{4-[3-((R)-1-Naphthalen-1-yl-ethylamino)-cyclopentyl]-phenyl}-propionic acid (compound 1192),
{3-[3-((R)-1-Naphthalen-1-yl-ethylamino)-cyclopentyl]-phenoxy}-acetic acid ethyl ester (compounds 1193/1194/1195/1196),
3-{3-[3-((R)-1-Naphthalen-1-yl-ethylamino)-cyclopentyl]-phenyl}-propionic acid ethyl ester (compounds 1197/1198/1198/1200),
{3-[3-((R)-1-Naphthalen-1-yl-ethylamino)-cyclopentyl]-phenoxy}-acetic acid hydrochloride (compound 1201),
{3-[3-((R)-1-Naphthalen-1-yl-ethylamino)-cyclopentyl]-phenoxy}-acetic acid (compound 1202),
{3-[3-((R)-1-Naphthalen-1-yl-ethylamino)-cyclopentyl]-phenoxy}-acetic acid (compound 1203),
3-{3-[3-((R)-1-Naphthalen-1-yl-ethylamino)-cyclopentyl]-phenyl}-propionic acid hydrochloride (compound 1204),
3-{3-[3-((R)-1-Naphthalen-1-yl-ethylamino)-cyclopentyl]-phenyl}-propionic acid (compound 1205),
3-{3-[3-((R)-1-Naphthalen-1-yl-ethylamino)-cyclopentyl]-phenyl}-propionic acid (compound 1206),
3-{3-[3-((R)-1-Naphthalen-1-yl-ethylamino)-cyclopentyl]-phenyl}-propionic acid (compound 1207),
3-{3-[3-((R)-1-Naphthalen-1-yl-ethylamino)-cyclopentyl]-phenyl}-propionic acid hydrochloride (compound 1208),
[3-(4-Iodo-phenyl)-cyclohexyl]-((R)-1-naphthalen-1-yl-ethyl)-amine (compound 1209),
1-{4-[3-((R)-1-Naphthalen-1-yl-ethylamino)-cyclohexyl]-phenyl}-pyrrolidin-2-one (compound 1210),
3-{4-[3-((R)-1-Naphthalen-1-yl-ethylamino)-cyclohexyl]-phenyl}-oxazolidin-2-one (compound 1211),
N-{4-[3-((R)-1-Naphthalen-1-yl-ethylamino)-cyclohexyl]-phenyl}-acetamide (compound 1212),
4-{4-[3-((R)-1-Naphthalen-1-yl-ethylamino)-cyclohexyl]-phenyl}-tetrahydro-pyran-4-ol (compound 1213),
[3-(4-Imidazol-1-yl-phenyl)-cyclohexyl]-((R)-1-naphthalen-1-yl-ethyl)-amine (compound 1214),
1-{4-[3-((R)-1-Naphthalen-1-yl-ethylamino)-cyclohexyl]-phenyl}-cyclopentanol (compound 1215),
1-{4-[3-((R)-1-Naphthalen-1-yl-ethylamino)-cyclohexyl]-phenyl}-ethanone (compound 1216),
4-{4-[3-((R)-1-Naphthalen-1-yl-ethylamino)-cyclohexyl]-phenyl}-tetrahydro-pyran-4-ol hydrochloride (compound 1217),
{4-[3-((R)-1-Naphthalen-1-yl-ethylamino)-cyclohexyl]-phenyl}-methanol (compound 1218),
1-{4-[3-((R)-1-Naphthalen-1-yl-ethylamino)-cyclohexyl]-phenyl}-cyclobutanol (compound 1219),
2-{4-[3-((R)-1-Naphthalen-1-yl-ethylamino)-cyclohexyl]-phenyl}-malonic acid diethyl ester (compound 1220),
{4-[3-((R)-1-Naphthalen-1-yl-ethylamino)-cyclohexyl]-phenyl}-acetic acid ethyl ester (compound 1221),
{4-[3-((R)-1-Naphthalen-1-yl-ethylamino)-cyclohexyl]-phenyl}-acetic acid (compound 1222),
3-{4-[3-((R)-1-Naphthalen-1-yl-ethylamino)-cyclohexyl]-phenyl}-oxetan-3-ol (compound 1223),
{3-[4-(3-Fluoro-oxetan-3-yl)-phenyl]-cyclohexyl}-((R)-1-naphthalen-1-yl-ethyl)-amine (compound 1224),
{3-[4-(3-Amino-3-methyl-but-1-ynyl)-phenyl]-cyclohexyl}-((R)-1-naphthalen-1-yl-ethyl)-amine (compound 1225),
{3-[4-(5-Cyclopropyl-[1,2,4]oxadiazol-3-yl)-phenyl]-cyclohexyl}-((R)-1-naphthalen-1-yl-ethyl)-amine (compound 1226),
{3-[4-(5-Cyclopentyl-[1,2,4]oxadiazol-3-yl)-phenyl]-cyclohexyl}-((R)-1-naphthalen-1-yl-ethyl)-amine (compound 1227),
{3-[4-(5-Methyl-[1,2,4]oxadiazol-3-yl)-phenyl]-cyclohexyl}-((R)-1-naphthalen-1-yl-ethyl)-amine (compound 1228),
{3-[4-(5-Isopropyl-[1,2,4]oxadiazol-3-yl)-phenyl]-cyclohexyl}-((R)-1-naphthalen-1-yl-ethyl)-amine (compound 1229),
{3-[4-(5-tert-Butyl-[1,2,4]oxadiazol-3-yl)-phenyl]-cyclohexyl}-((R)-1-naphthalen-1-yl-ethyl)-amine (compound 1230),
{3-[4-(5-Cyclohexyl-[1,2,4]oxadiazol-3-yl)-phenyl]-cyclohexyl}-((R)-1-naphthalen-1-yl-ethyl)-amine (compound 1231),
(3-{4-[5-(3-Methyl-butyl)-[1,2,4]oxadiazol-3-yl]-phenyl}-cyclohexyl)-((R)-1-naphthalen-1-yl-ethyl)-amine (compound 1232),
5-(3-{4-[3-((R)-1-Naphthalen-1-yl-ethylamino)-cyclohexyl]-phenyl}-[1,2,4]oxadiazol-5-ylmethyl)-imidazolidine-2,4-dione (compound 1233),
(3-{4-[5-(4-Methyl-oxazol-5-yl)-[1,2,4]oxadiazol-3-yl]-phenyl}-cyclohexyl)-((R)-1-naphthalen-1-yl-ethyl)-amine (compound 1234),
(3-{4-[5-(2,5-Dimethyl-oxazol-4-yl)-[1,2,4]oxadiazol-3-yl]-phenyl}-cyclohexyl)-((R)-1-naphthalen-1-yl-ethyl)-amine (compound 1235),
2-Methyl-2-{4-[3-((R)-1-naphthalen-1-yl-ethylamino)-cyclohexyl]-phenyl}-propionitrile (compound 1236/1237),
2-Methyl-2-{4-[3-((R)-1-naphthalen-1-yl-ethylamino)-cyclohexyl]-phenyl}-propionic acid (compound 1238),
2-Methyl-2-{4-[3-((R)-1-naphthalen-1-yl-ethylamino)-cyclohexyl]-phenyl}-propionic acid (compound 1239),
[3-(4-Methanesulfonyl-phenyl)-cyclohexyl]-((R)-1-naphthalen-1-yl-ethyl)-amine (compounds 1240),
2-Fluoro-4-[3-((R)-1-naphthalen-1-yl-ethylamino)-cyclohexyl]-benzoic acid methyl ester (compound 1241),
{4-[3-((R)-1-Naphthalen-1-yl-ethylamino)-cyclohexyl]-phenyl}-methanol (compound 1242),
N-{4-[3-((R)-1-Naphthalen-1-yl-ethylamino)-cyclohexyl]-benzyl}-methanesulfonamide (compound 1243),
{3-[4-(Morpholine-4-sulfonyl)-phenyl]-cyclohexyl}-((R)-1-naphthalen-1-yl-ethyl)-amine (compound 1244/1245),
N-{4-[3-((R)-1-Naphthalen-1-yl-ethylamino)-cyclohexyl]-benzyl}-acetamide (compounds 1246/1247),
3-Fluoro-4-[3-((R)-1-naphthalen-1-yl-ethylamino)-cyclohexyl]-benzoic acid methyl ester (compound 1248),
N-{4-[3-((R)-1-Naphthalen-1-yl-ethylamino)-cyclohexyl]-phenyl}-methanesulfonamide (compound 1249/1250),
N-{3-[3-((R)-1-Naphthalen-1-yl-ethylamino)-cyclohexyl]-phenyl}-methanesulfonamide (compound 1251),
N-(2-Hydroxy-ethyl)-4-[3-((R)-1-naphthalen-1-yl-ethylamino)-cyclohexyl]-benzenesulfonamide (compounds 1252/1253),
3-{4-[3-((R)-1-Naphthalen-1-yl-ethylamino)-cyclohexyl]-phenyl}-propionic acid (compound 1254),
{4-[3-((R)-1-Naphthalen-1-yl-ethylamino)-cyclohexyl]-phenoxy}-acetic acid (compound 1255),
[3-(4-Methanesulfonyl-phenyl)-cyclopentyl]-((R)-1-naphthalen-1-yl-ethyl)-amine (compounds 1256/1257), N-{3-[3-((R)-1-Naphthalen-1-yl-ethylamino)-cyclopentyl]-phenyl}-methanesulfonamide (compounds 1258/1259),
N-{4-[3-((R)-1-Naphthalen-1-yl-ethylamino)-cyclopentyl]-phenyl}-acetamide (compounds 1260/1261),
N-{4-[3-((R)-1-Naphthalen-1-yl-ethylamino)-cyclopentyl]-benzyl}-acetamide (compound 1262/1263),
N-{4-[3-((R)-1-Naphthalen-1-yl-ethylamino)-cyclopentyl]-benzyl}-methanesulfonamide (compounds 1264/1265),
N-{4-[3-((R)-1-Naphthalen-1-yl-ethylamino)-cyclopentyl]-phenyl}-methanesulfonamide (compounds 1266/1267),
[3-(4-Methanesulfonyl-phenyl)-cycloheptyl]-((R)-1-naphthalen-1-yl-ethyl)-amine (compound 1268),
2-Fluoro-4-[3-((R)-1-naphthalen-1-yl-ethylamino)-cycloheptyl]-benzoic acid methyl ester (compound 1269),
N-{3-[3-((R)-1-Naphthalen-1-yl-ethylamino)-cycloheptyl]-phenyl}-methanesulfonamide (compound 1270),
N-{4-[3-((R)-1-Naphthalen-1-yl-ethylamino)-cycloheptyl]-phenyl}-acetamide (compound 1271/1272),
N-{4-[3-((R)-1-Naphthalen-1-yl-ethylamino)-cycloheptyl]-benzyl}-acetamide (compounds 1273/1274),
N-{4-[3-((R)-1-Naphthalen-1-yl-ethylamino)-cycloheptyl]-benzyl}-methanesulfonamide (compounds 1275/1276),
{4-[3-((R)-1-Naphthalen-1-yl-ethylamino)-cycloheptyl]-phenoxy}-acetic acid ethyl ester (compound 1277),
3-{4-[3-((R)-1-Naphthalen-1-yl-ethylamino)-cycloheptyl]-phenyl}-propionic acid methyl ester (compounds 1278/1279),
N-{4-[3-((R)-1-Naphthalen-1-yl-ethylamino)-cycloheptyl]-phenyl}-methanesulfonamide (compounds 1280/1281),
{3-[4-(Morpholine-4-sulfonyl)-phenyl]-cycloheptyl}-((R)-1-naphthalen-1-yl-ethyl)-amine (compound 1282),
{4-[3-((R)-1-Naphthalen-1-yl-ethylamino)-cycloheptyl]-phenyl}-methanol (compound 1283),
4-[3-((R)-1-Naphthalen-1-yl-ethylamino)-cyclohexyl]-benzoic acid methyl ester (compound 1284),
4-[3-((R)-1-Naphthalen-1-yl-ethylamino)-cyclohexyl]-benzoic acid ethyl ester (compound 1285),
4-[3-((R)-1-Naphthalen-1-yl-ethylamino)-cyclohexyl]-benzoic acid 2-morpholin-4-yl-ethyl ester dihydrochloride (compound 1286),
4-[3-((R)-1-Naphthalen-1-yl-ethylamino)-cyclohexyl]-benzoic acid 2-(2-methoxy-ethoxy)-ethyl ester hydrochloride (compound 1287),
4-[3-((R)-1-Naphthalen-1-yl-ethylamino)-cyclohexyl]-benzoic acid 2-[2-(2-methoxy-ethoxy)-ethoxy]-ethyl ester hydrochloride (compound 1288),
4-[3-((R)-1-Naphthalen-1-yl-ethylamino)-cyclohexyl]-benzoic acid 2-[2-(2-ethoxy-ethoxy)-ethoxy]-ethyl ester hydrochloride (compound 1289),
4-[3-((R)-1-Naphthalen-1-yl-ethylamino)-cyclohexyl]-benzoic acid 2,3-dihydroxy-propyl ester hydrochloride (compound 1290),
4-[3-((R)-1-Naphthalen-1-yl-ethylamino)-cyclohexyl]-benzoic acid tetrahydro-furan-2-ylmethyl ester hydrochloride (compound 1291),
4-[(1R,3S)-3-((R)-1-Naphthalen-1-yl-ethylamino)-cyclopentyl]-phenol (compound 1292),
2-{4-[(1R,3S)-3-((R)-1-Naphthalen-1-yl-ethylamino)-cyclopentyl]-phenoxy}-butyric acid ethyl ester (compound 1293),
2-{4-[(1R,3S)-3-((R)-1-Naphthalen-1-yl-ethylamino)-cyclopentyl]-phenoxy}-butyric acid (compound 1294),
2-{4-[(1R,3S)-3-((R)-1-Naphthalen-1-yl-ethylamino)-cyclopentyl]-phenoxy}-propionic acid (compound 1295),
3-{4-[(1R,3S)-3-((R)-1-Naphthalen-1-yl-ethylamino)-cyclopentyl]-phenoxy}-dihydro-furan-2-one (compound 1296),
(S)-{3R-[4-(2-Ethoxy-ethoxy)-phenyl]-cyclopentyl}-((R)-1-naphthalen-1-yl-ethyl)-amine (compound 1297),
3-{4-[(1R,3S)-3-((R)-1-Naphthalen-1-yl-ethylamino)-cyclopentyl]-phenoxy}-propionic acid ethyl ester (compound 1298),
4-{4-[(1R,3S)-3-((R)-1-Naphthalen-1-yl-ethylamino)-cyclopentyl]-phenoxymethyl}-benzonitrile (compound 1299),
(S)—((R)-1-Naphthalen-1-yl-ethyl)-{3R-[4-(pyridin-3-ylmethoxy)-phenyl]-cyclopentyl}-amine (compound 1300),
(S)—((R)-1-Naphthalen-1-yl-ethyl)-{3R-[4-(2-pyrazol-1-yl-ethoxy)-phenyl]-cyclopentyl}-amine (compound 1301),
(S)-(3R-{4-[2-(1H-Indol-3-yl)-ethoxy]-phenyl}-cyclopentyl)-((R)-1-naphthalen-1-yl-ethyl)-amine (compound 1302),
2-Methyl-2-{4-[(1R,3S)-3-((R)-1-naphthalen-1-yl-ethylamino)-cyclopentyl]-phenoxy}-propionic acid hydrochloride (compound 1303),
4-Hydroxy-2-{4-[(1R,3S)-3-((R)-1-naphthalen-1-yl-ethylamino)-cyclopentyl]phenoxy}-butyric acid (compound 1304),
2-{4-[(1R,3S)-3-((R)-1-Naphthalen-1-yl-ethylamino)-cyclopentyl]-phenoxy}-propionic acid hydrochloride (compound 1305),
{4-[(1R,3S)-3-((R)-1-Naphthalen-1-yl-ethylamino)-cyclopentyl]-phenoxy}-phenyl-acetic acid hydrochloride (compound 1306),
2-Methyl-1-{4-[(1R,3S)-3-((R)-1-naphthalen-1-yl-ethylamino)-cyclopentyl]-phenoxy}-propan-2-ol (compound 1307),
3-{4-[(1R,3S)-3-((R)-1-Naphthalen-1-yl-ethylamino)-cyclopentyl]-phenoxymethyl}-pentan-3-ol (compound 1308),
Dimethyl-carbamic acid 4-[(1R,3S)-3-((R)-1-naphthalen-1-yl-ethylamino)-cyclopentyl]-phenyl ester (compound 1309),
3-Ethyl-1-{4-[(1S,3S)-3-((R)-1-naphthalen-1-yl-ethylamino)-cyclopentyl]-phenyl}-pentan-3-ol (compound 1310),
2-Methyl-4-{4-[(1S,3S)-3-((R)-1-naphthalen-1-yl-ethylamino)-cyclopentyl]-phenyl}-butan-2-ol (compound 1311),
3-{4-[(1R,3S)-3-((R)-1-Naphthalen-1-yl-ethylamino)-cyclopentyl]-phenoxy}-propane-1,2-diol (compound 1312),
(2-Fluoro-phenyl)-{4-[(1R,3S)-3-((R)-1-naphthalen-1-yl-ethylamino)-cyclopentyl]-phenoxy}-acetic acid hydrochloride (compound 1313),
2-{4-[(1R,3S)-3-((R)-1-Naphthalen-1-yl-ethylamino)-cyclopentyl]-phenoxy}-ethanol formiate (compound 1314),
(1-{4-[3-((R)-1-Naphthalen-1-yl-ethylamino)-cyclohexyl]-benzyl}-pyrrolidin-2-yl)-methanol (compound 1315),
1-{4-[3-((R)-1-Naphthalen-1-yl-ethylamino)-cyclohexyl]-benzyl}-pyrrolidin-3-ol (compound 1316), 1-{4-[3-((R)-1-Naphthalen-1-yl-ethylamino)-cyclo-hexyl]-benzyl}-piperidine-3-carboxylic acid ethyl ester (compound 1317),
[3-(4-{[Methyl-(tetrahydro-furan-2-ylmethyl)-amino]-methyl}-phenyl)-cyclohexyl]-((R)-1-naphthalen-1-yl-ethyl)-amine (compound 1318),
4-[3-((R)-1-Naphthalen-1-yl-ethylamino)-cyclopentyl]-benzoic acid ethyl ester (compound 1335/1336),
4-[3-((R)-1-Naphthalen-1-yl-ethylamino)-cyclopentyl]-benzoic acid (compound 1337),
4-[3-((R)-1-Naphthalen-1-yl-ethylamino)-cyclopentyl]-benzoic add (compound 1338),
3-{4-[3-((R)-1-Naphthalen-1-yl-ethylamino)-cyclopentyl]-benzoylamino}-propionic acid methyl ester (compound 1339),
1-{4-[3-((R)-1-Naphthalen-1-yl-ethylamino)-cyclopentyl]-benzoyl}-piperidine-4-carboxylic acid hydrochloride (compound 1340),
3-{4-[3-((R)-1-Naphthalen-1-yl-ethylamino)-cyclopentyl]-benzoylamino}-propionic acid hydrochloride (compound 1341),
4-[3-((R)-1-Naphthalen-1-yl-ethylamino)-cyclopentyloxy]-benzoic acid methyl ester (compound 1342),
4-[3R-((R)-1-Naphthalen-1-yl-ethylamino)-cyclopentyloxy]-benzoic acid formiate (compound 1343),
5-Methyl-3-[3-((R)-1-naphthalen-1-yl-ethylamino)-cyclopentyl]-3H-imidazole-4-carboxylic acid (compound 1344),
5-(4-ethoxy-phenyl)-2-propyl-cyclohexyl]-(R)-1-naphthalen-1-yl-ethyl)-amine (compound 1346), and
3-{4-[3-((R)-1-Naphthalen-1-yl-ethylamino)-cyclopentyl]-phenyl}-propan-1-ol (compound 1348).

18. A method for the treatment of hyperparathyroidism comprising administering an effective amount of the compound according to claim 1 or N-(3,5-bis(trifluoromethyl) benzyl)-3-((1-(napthalen-1-yl)ethyl)amino)cyclopentanecarboxamide.

19. A pharmaceutical composition comprising the compound according to claim 1 or a pharmaceutically acceptable salt, solvate, or in vivo hydrolysable ester thereof together with a pharmaceutically acceptable vehicle or excipient.

20. The compound according to claim 1 or 2, wherein

represents

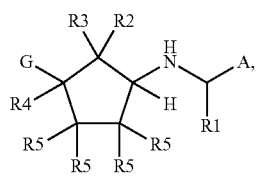

A represents 1-naphthyl;
$R_1$ represents methyl;
$R_2$ and $R_3$ represent hydrogen;
$R_4$ represents hydrogen;
$R_5$ represents hydrogen;
G represents phenyl optionally substituted with one or more, same or different substituents selected from —C(O)NH$_2$, halogen, carboxy, $C_{1-6}$alkyl, $C_{1-6}$amino, $C_{1-6}$haloalkyl, $C_{1-4}$alkoxy, $C_{1-4}$alkoxycarbonyl, $C_{1-4}$aminocarbonyl, $C_{3-6}$cycloalkyl, $C_{1-4}$alkylthio, $C_{1-4}$aminosulfonyl, $C_{1-4}$alkylsulfonylamino, $C_{1-6}$heteroaryl, $C_{1-4}$alkylcarbonylamino, $C_{3-6}$cycloalkylcarbonylamino, or $C_{1-4}$alkylsulfonyl,
wherein said $C_{1-6}$alkyl, $C_{1-6}$amino, $C_{1-4}$alkoxy, $C_{1-4}$aminocarbonyl, $C_{3-6}$cycloalkyl, $C_{1-4}$alkylthio, $C_{1-4}$aminosulfonyl, $C_{1-4}$alkylsulfonylamino, $C_{1-4}$alkylcarbonylamino, $C_{3-6}$cycloalkylcarbonylamino, or $C_{1-4}$alkylsulfonyl,
are optionally further substituted with one or more, same or different substituents selected from the group consisting of hydroxy, carboxy, halogen, oxo, $C_{1-6}$alkyl, $C_{3-6}$cycloalkyl, or $C_{1-10}$heteroaryl.

21. The compound according to claim 1 or 2, wherein

represents

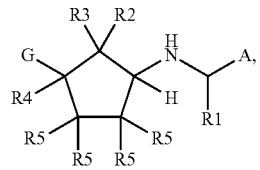

A represents 1-naphthyl;
$R_1$ represents methyl;
$R_2$ and $R_3$ represent hydrogen;
$R_4$ represents hydrogen;
$R_5$ represents hydrogen;
G represents phenyl optionally substituted with one or more, same or different substituents selected from —C(O)H, —C(O)NH$_2$, hydroxy, halogen, cyano, nitro, amidino, carboxy, trifluoromethyl, $C_{1-6}$alkyl, $C_{2-4}$alkenyl, $C_{2-4}$alkynyl, $C_{1-4}$hydroxyalkyl, $C_{1-6}$amino, aminoC$_{1-3}$alkyl, iminomethyl, hydroxyiminomethyl, $C_{1-6}$haloalkyl, $C_{1-4}$alkoxy, $C_{1-4}$alkoxycarbonyl, $C_{1-3}$alkoxycarbamoyl, $C_{1-4}$aminocarbonyl, $C_{1-3}$alkylsulfonylaminocarbonyl, hydroxyaminocarbonyl, $C_{1-6}$heterocycloalkyloxy, $C_{1-6}$heterocycloalkylaminocarbonyl, $C_{3-6}$cycloalkylaminocarbonyl, $C_{6-10}$arylaminocarbonyl, $C_{1-10}$heteroarylaminocarbonyl, $C_{3-6}$cycloalkyl, $C_{1-6}$heterocycloalkyl, $C_{1-6}$heterocycloalkenyl, $C_{1-6}$heterocycloalkylcarbonyl, $C_{1-4}$alkylcarbonyloxy, $C_{1-4}$alkoxycarbonyloxy, $C_{1-4}$alkoxysulfonyloxy, $C_{1-4}$alkylthio, $C_{3-6}$cycloalkenyl, $C_{1-4}$aminosulfonyl, $C_{1-4}$aminocarbonyloxy, $C_{1-4}$alkylsulfonylamino, $C_{1-6}$heteroaryl, $C_{6-10}$arylamino, $C_{6-10}$aryloxycarbonyl, $C_{6-10}$arylcarbonylamino, $C_{6-10}$arylsulfonylamino, $C_{1-4}$alkylcarbonylamino, $C_{1-4}$alkenylcarbonylamino, $C_{3-6}$cycloalkenylcarbonylamino, $C_{3-6}$cycloalkylcarbonylamino, $C_{1-4}$alkoxycarbonylamino, $C_{1-6}$heterocycloalkylcarbonylamino, $C_{1-4}$alkylsulfonyl or $C_{1-6}$heterocycloalkylsulfonyl, wherein said C(O)NH$_2$, $C_{1-6}$alkyl, $C_{2-4}$alkenyl, $C_{2-4}$alkynyl, $C_{1-4}$hydroxyalkyl, $C_{1-6}$amino, aminoC$_{1-3}$alkyl, iminomethyl, hydroxyiminomethyl, $C_{1-6}$haloalkyl, $C_{1-4}$alkoxy, $C_{1-4}$alkoxycarbonyl, $C_{1-3}$alkoxycarbamoyl, $C_{1-4}$aminocarbonyl, $C_{1-3}$alkylsulfonylaminocarbonyl, hydroxyaminocarbonyl, $C_{1-6}$heterocycloalkyloxy, $C_{1-6}$heterocycloalkylaminocarbonyl, $C_{3-6}$cycloalkylaminocarbonyl, $C_{6-10}$arylaminocarbonyl, $C_{1-10}$heteroarylaminocarbonyl, $C_{3-6}$cycloalkyl, $C_{1-6}$heterocycloalkyl, $C_{1-6}$heterocycloalkenyl, $C_{1-6}$heterocycloalkylcarbonyl, $C_{1-4}$alkylcarbonyloxy, $C_{1-4}$alkoxycarbonyloxy, $C_{1-4}$alkoxysulfonyloxy, $C_{1-4}$alkylthio, $C_{3-6}$cycloalkenyl, $C_{1-4}$aminosulfonyl, $C_{1-4}$aminocarbonyloxy, $C_{1-4}$alkylsulfonylamino, $C_{1-6}$heteroaryl, $C_{6-10}$arylamino, $C_{6-10}$aryloxycarbonyl, $C_{6-10}$arylcarbonylamino, $C_{6-10}$arylsulfonylamino, $C_{1-4}$alkylcarbonylamino, $C_{1-4}$alkenylcarbonylamino, $C_{3-6}$cycloalkenylcarbonylamino, $C_{3-6}$cycloalkylcarbonylamino, $C_{1-4}$alkoxycarbonylamino, $C_{1-6}$heterocycloalkylcarbonylamino, $C_{1-4}$alkylsulfonyl, or $C_{1-6}$heterocycloalkylsulfonyl are optionally further substituted with one or more, same or different substituents selected from the group consisting of hydroxy, —$NH_2$, $C_{1-6}$amino, iminomethyl, hydroxyiminomethyl, carboxy, trifluoromethyl, halogen, oxo, mercapto, cyano, —$C(O)NH_2$, nitro, $C_{1-6}$alkyl, $C_{2-4}$alkenyl, $C_{2-4}$alkynyl, $C_{1-4}$hydroxyalkyl, $C_{1-6}$haloalkyl, $C_{1-3}$alkoxy, $C_{1-4}$alkoxycarbonyl, $C_{1-6}$heterocycloalkylcarbonyl, $C_{3-6}$cycloalkyl, $C_{3-6}$cycloalkenyl, $C_{1-6}$heterocycloalkyl, $C_{6-12}$aryl, $C_{1-10}$heteroaryl, $C_{1-3}$alkoxy$C_{6-10}$aryl, $C_{1-10}$heterocycloalkylaryl, $C_{1-6}$heterocycloalkenyl, —$S(O)_2NH_2$, —$S(O)_2$OH, $C_{1-6}$ureido, $C_{1-6}$thioureido, $C_{1-4}$alkylcarbonyloxy, $C_{1-4}$alkoxycarbonyloxy, $C_{1-4}$alkoxysulfonyloxy, $C_{1-4}$alkoxycarbamoyl, $C_{1-4}$aminocarbonyl, $C_{1-4}$alkylthio, $C_{1-4}$aminosulfonyl, $C_{1-4}$aminocarbonyloxy, $C_{1-4}$alkylsulfonylamino, $C_{6-12}$arylsulfonyl, $C_{6-10}$arylsulfonylamino, $C_{1-4}$alkylcarbonylamino or $C_{1-4}$alkylsulfonyl, wherein said $C_{3-6}$cycloalkyl, $C_{1-6}$alkyl, $C_{1-3}$alkoxy, $C_{1-4}$alkoxycarbonyl, $C_{1-6}$heterocycloalkyl, $C_{6-10}$aryl or $C_{1-10}$heteroaryl may be further substituted with carboxy, halogen, hydroxy, cyano, $C_{1-6}$heterocycloalkyl, one or more $C_{1-6}$alkyl, $C_{1-3}$alkoxy; $C_{1-3}$alkoxy$C_{1-3}$alkoxy, $C_{1-4}$alkoxycarbonyl, $C_{1-3}$hydroxyalkyl or $C_{6-10}$aryl.

22. The compound according to claim 1 selected from the group consisting of:
{4-[(1S,3S)-3-((R)-1-Naphthalen-1-yl-ethylamino)-cyclohexyl]-benzoylamino}-acetic acid (compound 1115),
3-{4-[(1S,3S)-3-((R)-1-Naphthalen-1-yl-ethylamino)-cyclohexyl]-benzoylamino}-propionic acid; hydrochloride (compound 1136),
1-{4-[(1S,3S)-3-((R)-1-Naphthalen-1-yl-ethylamino)-cyclohexyl]-benzoylamino}-cyclopropanecarboxylic acid (compound 1139),
2-Methyl-2-{4-[(1S,3S)-3-((R)-1-naphthalen-1-yl-ethylamino)-cyclohexyl]-benzoylamino}-propionic acid (compound 1141),
(Methyl-{4-[(1 S,3S)-3-((R)-1-naphthalen-1-yl-ethylamino)-cyclohexyl]-benzoyl}-amino)-acetic acid (compound 1143),
4-{4-[(1S,3S)-3-((R)-1-Naphthalen-1-yl-ethylamino)-cyclohexyl]-benzoylamino}-butyric acid (compound 1144),
{4-[3-((R)-1-Naphthalen-1-yl-ethylamino)-cyclopentyl]-phenoxy}-acetic acid (compound 1185),
{4-[(1R,3S)-3-((R)-1-Naphthalen-1-yl-ethylamino)-cyclopentyl]-phenoxy}-acetic acid (compound 1186),
{4-[3-((R)-1-Naphthalen-1-yl-ethylamino)-cyclopentyl]-phenoxy}-acetic acid (compound 1187),
{4-[3-((R)-1-Naphthalen-1-yl-ethylamino)-cyclopentyl]-phenoxy}-acetic acid (compound 1188),
3-{4-[3-((R)-1-Naphthalen-1-yl-ethylamino)-cyclopentyl]-phenyl}-propionic acid (compound 1189),
3-{4-[(1S,3S)-3-((R)-1-Naphthalen-1-yl-ethylamino)-cyclopentyl]-phenyl}-propionic acid; hydrochloride (compound 1190),
3-{4-[3-((R)-1-Naphthalen-1-yl-ethylamino)-cyclopentyl]-phenyl}-propionic acid (compound 1191),
3-{4-[3-((R)-1-Naphthalen-1-yl-ethylamino)-cyclopentyl]-phenyl}-propionic acid (compound 1192),
{3-[3-((R)-1-Naphthalen-1-yl-ethylamino)-cyclopentyl]-phenoxy}-acetic acid hydrochloride (compound 1201),
{3-[3-((R)-1-Naphthalen-1-yl-ethylamino)-cyclopentyl]-phenoxy}-acetic acid (compound 1202),
{3-[3-((R)-1-Naphthalen-1-yl-ethylamino)-cyclopentyl]-phenoxy}-acetic acid (compound 1203),
3-{3-[3-((R)-1-Naphthalen-1-yl-ethylamino)-cyclopentyl]-phenyl}-propionic acid hydrochloride (compound 1204),
3-{3-[3-((R)-1-Naphthalen-1-yl-ethylamino)-cyclopentyl]-phenyl}-propionic acid (compound 1205),
3-{3-[3-((R)-1-Naphthalen-1-yl-ethylamino)-cyclopentyl]-phenyl}-propionic acid (compound 1206),
3-{3-[3-((R)-1-Naphthalen-1-yl-ethylamino)-cyclopentyl]-phenyl}-propionic acid (compound 1207),
3-{3-[3-((R)-1-Naphthalen-1-yl-ethylamino)-cyclopentyl]-phenyl}-propionic acid hydrochloride (compound 1208),
{4-[3-((R)-1-Naphthalen-1-yl-ethylamino)-cyclohexyl]-phenyl}-acetic acid (compound 1222),
2-Methyl-2-{4-[3-((R)-1-naphthalen-1-yl-ethylamino)-cyclohexyl]-phenyl}-propionic acid (compound 1238),
2-Methyl-2-{4-[3-((R)-1-naphthalen-1-yl-ethylamino)-cyclohexyl]-phenyl}-propionic acid (compound 1239),
3-{4-[3-((R)-1-Naphthalen-1-yl-ethylamino)-cyclohexyl]-phenyl}-propionic acid (compound 1254),
{4-[3-((R)-1-Naphthalen-1-yl-ethylamino)-cyclohexyl]-phenoxy}-acetic acid (compound 1255),
2-{4-[(1R,3S)-3-((R)-1-Naphthalen-1-yl-ethylamino)-cyclopentyl]-phenoxy}-butyric acid (compound 1294),
2-{4-[(1R,3S)-3-((R)-1-Naphthalen-1-yl-ethylamino)-cyclopentyl]-phenoxyl}-propionic acid (compound 1295),
2-Methyl-2-{4-[(1R,3S)-3-((R)-1-naphthalen-1-yl-ethylamino)-cyclopentyl]-phenoxy}-propionic acid hydrochloride (compound 1303),
2-{4-[(1R,3S)-3-((R)-1-Naphthalen-1-yl-ethylamino)-cyclopentyl]-phenoxyl}-propionic acid hydrochloride (compound 1305), and
3-{4-[3-((R)-1-Naphthalen-1-yl-ethylamino)-cyclopentyl]-benzoylamino}-propionic acid hydrochloride (compound 1341).

\* \* \* \* \*